US011753681B2

United States Patent
Chiu et al.

(10) Patent No.: US 11,753,681 B2
(45) Date of Patent: Sep. 12, 2023

(54) DIGITAL NUCLEIC ACID AMPLIFICATION USING ENCODED PARTICLES

(71) Applicant: UNIVERSITY OF WASHINGTON, Seattle, WA (US)

(72) Inventors: Daniel T. Chiu, Seattle, WA (US); Jiangbo Yu, Bothell, WA (US); Jason E. Kreutz, Marysville, WA (US); Jiasi Wang, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 180 days.

(21) Appl. No.: 16/761,235

(22) PCT Filed: Nov. 1, 2018

(86) PCT No.: PCT/US2018/058803
§ 371 (c)(1),
(2) Date: May 1, 2020

(87) PCT Pub. No.: WO2019/089996
PCT Pub. Date: May 9, 2019

(65) Prior Publication Data
US 2020/0362391 A1 Nov. 19, 2020

Related U.S. Application Data

(60) Provisional application No. 62/581,429, filed on Nov. 3, 2017.

(51) Int. Cl.
*C12Q 1/686* (2018.01)

(52) U.S. Cl.
CPC ....... *C12Q 1/686* (2013.01); *C12Q 2527/107* (2013.01); *C12Q 2531/125* (2013.01); *C12Q 2537/143* (2013.01)

(58) Field of Classification Search
CPC .............. C12Q 1/686; C12Q 2527/107; C12Q 2537/143; C12Q 2563/155; C12Q 2563/159; C12Q 2565/101
See application file for complete search history.

(56) References Cited

U.S. PATENT DOCUMENTS

| 11,266,990 B2 | 3/2022 | Fiorini et al. |
| 2002/0034747 A1* | 3/2002 | Bruchez, Jr. ......... C12Q 1/6818 435/6.11 |

(Continued)

FOREIGN PATENT DOCUMENTS

| CN | 105934498 A | 9/2016 |
| CN | 106086173 A | 11/2016 |

(Continued)

OTHER PUBLICATIONS

Alcaide et al., "Multiplex Droplet Digital PCR Quantification of Recurrent Somatic Mutations in Diffuse Large B-Cell and Follicular Lymphoma," Clinical Chemistry, vol. 62, No. 9, pp. 1238-1247. (Year: 2016).*

(Continued)

*Primary Examiner* — Young J Kim
(74) *Attorney, Agent, or Firm* — CHRISTENSEN O'CONNOR JOHNSON KINDNESS PLLC

(57) ABSTRACT

Methods, devices, and systems for performing digital assays are provided. In certain aspects, the methods, devices, and systems can be used for the detection of nucleic acids and proteins. Also provided are methods, devices, systems, and compositions for improved detection and quantification of target molecules using encoded probes. In certain aspects, the methods, devices, and systems provided herein are useful in multiplexed digital assays. In certain aspects, the methods, devices, and systems can be used for the recognition, detection, and sizing of compartmentalized volumes in (Continued)

a volume. Also provided are compositions and kits suitable for use with the methods and devices of the present disclosure.

15 Claims, 27 Drawing Sheets

(56) References Cited

U.S. PATENT DOCUMENTS

| | | |
|---|---|---|
| 2002/0155442 A1 | 10/2002 | Mirkin et al. |
| 2005/0059042 A1 | 3/2005 | Rothberg et al. |
| 2008/0102036 A1 | 5/2008 | Poss et al. |
| 2014/0087962 A1 | 3/2014 | Keys |
| 2015/0167067 A1 | 6/2015 | Spier |
| 2017/0003293 A1* | 1/2017 | Chiu ............ C09K 11/02 |
| 2017/0175174 A1 | 6/2017 | Chiu et al. |

FOREIGN PATENT DOCUMENTS

| | | |
|---|---|---|
| JP | 2010524430 A | 7/2010 |
| JP | 2014500891 A | 1/2014 |
| JP | 2015107113 A | 6/2015 |
| JP | 2017507191 A | 3/2017 |
| JP | 2017519484 A | 7/2017 |
| WO | 2008/143646 A2 | 11/2008 |
| WO | 2016166295 A1 | 10/2016 |
| WO | 2016191533 A1 | 12/2016 |
| WO | 2017112025 A2 | 6/2017 |

OTHER PUBLICATIONS

Alcaide et al., "Multiplex Droplet Digital PCR Quantification of Recurrent Somatic Mutations in Diffuse Large B-Cell and Follicular Lymphoma," Clinical Chemistry, Supplemental Method, pp. 1-3 (Year: 2016).*
Cheng et al., "Real-time PCR genotyping using displacing probes," Nucleic Acids Research, vol. 32, No. 7, e61, pp. 1-10 (Year: 2004).*
Shamirian et al., "QD-Based FRET Probes at a Glance," Sensors, vol. 15, pp. 13028-13051. (Year: 2015).*
Deerinck et al.., "The Application of Fluorescent Quantum Dots to Confocal, Multiphoton, and Electron Microscopic Imaging," Toxicol Pathol., vol. 36, No. 1, pp. 112-116. (Year: 2008).*
Search Report and Written Opinion dated Feb. 5, 2019, for International Patent Application No. PCT/US2018/058803. (14 pages).
Wang, Jiasi et al., "SD-Chip Enabled Quantitative Detection of HIV RNA using Digital Nucleic Acid Sequence-Based Amplification (dNASBA)," Lab Chip, 18(22):3501-3506, Nov. 6, 2018. (14 pages).
Wu, Changfeng et al., "Highly Fluorescent Semiconducting Polymer Dots for Biology and Medicine," Angew. Chem. Int. Ed. Engl., 52(11):3086-3109, Mar. 11, 2013. (55 pages).
Chinese Office Action dated Nov. 15, 2021, issued in CN Application No. 201880085447.X filed on Nov. 1, 2018, 42 pages.
Extended European Search Report dated May 30, 2022, issued in corresponding European Application No. EP 18872752, filed Nov. 1, 2018, 8 pages.
Stefan Rödiger et al: "Nucleic acid detection based on the use of microbeads: a review", Microchimica Acta, vol. 181, No. 11-12, Apr. 11, 2014 (Apr. 11, 2014), pp. 1151-1168, XP055608312, Vienna ISSN: 0026-3672, DOI: 10.1007/s00604-014-1243-4.
Chinese Office Action dated May 9, 2022, issued in CN Application No. 201880085447.X filed on Nov. 1, 2018, 26 pages (English Translation Provided).
Japanese Office Action dated Sep. 6, 2022, issued in corresponding Japanese Application No. 2020-524560, filed on Nov. 1, 2018, and its English translation thereof.
Adegoke, O and E. Y. Park, "The use of nanocrystal quantum dot as fluorophore reporters in molecular beacon-based assays," Nano Convergence, (2016) 3:32, 13 pages.
Resch-Genger, U. et al., "Quantum dots versus organic dyes as fluorescent labels," Nature Methods, Vo. 5: No. 9, Sep. 2008, 763-775.
Whale, A. et al., "Fundamentals of muiltiplexing with digital PCR," Biomolecular Detection and Quantification: Elsevier, 10: 2016: pp. 15-23.
Angew, Chem Int Ed Engl. 2013, vol. 52, No. 11, p. 3086-3109 (p. 1-55), doi: 10. 1002/anie. 201205133.
Japanese Notification of Reasons for Refusal dated Feb. 7, 2023, issued in corresponding Japanese App. No. 2020-524560, filed on Nov. 1, 2018, 10 pages, and its English translation thereof.

* cited by examiner

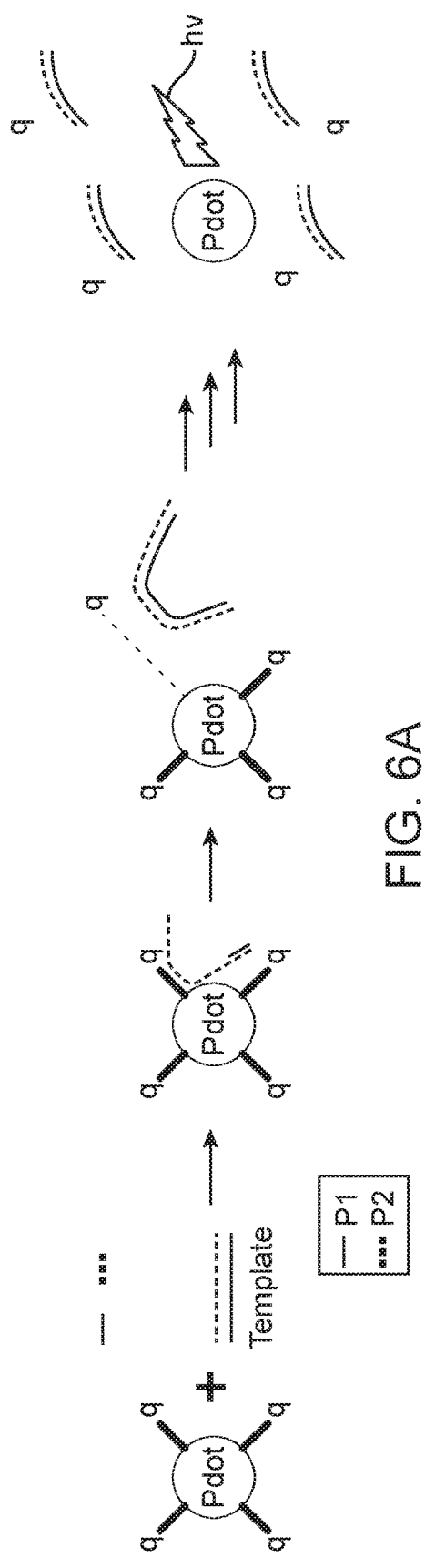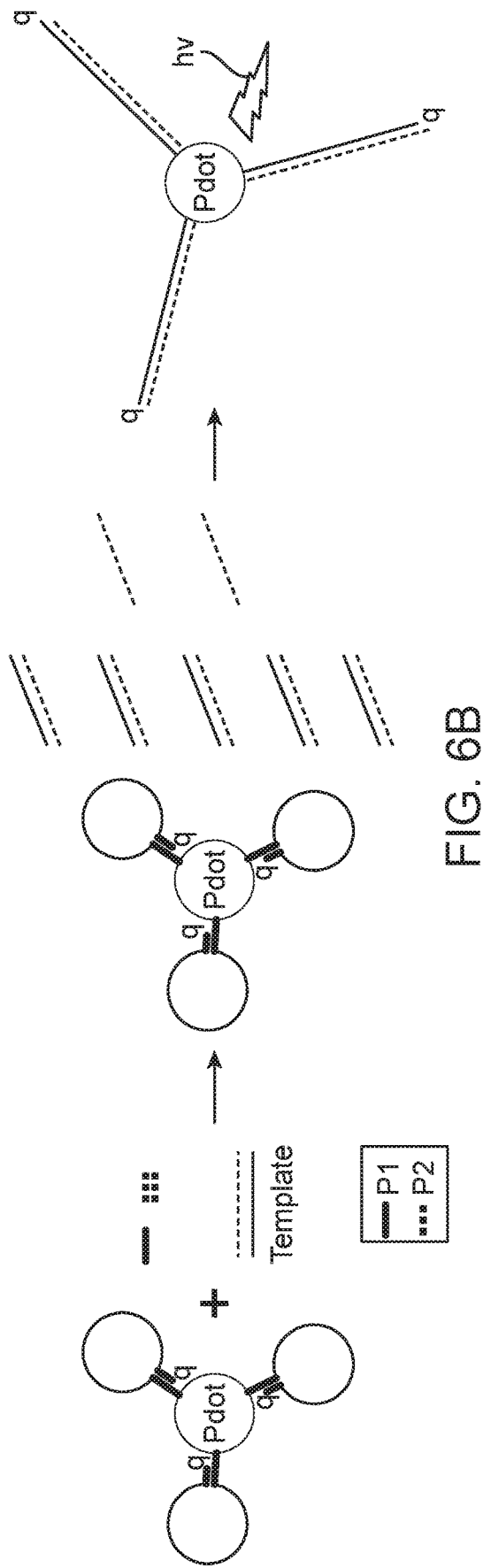
FIG. 6A
FIG. 6B

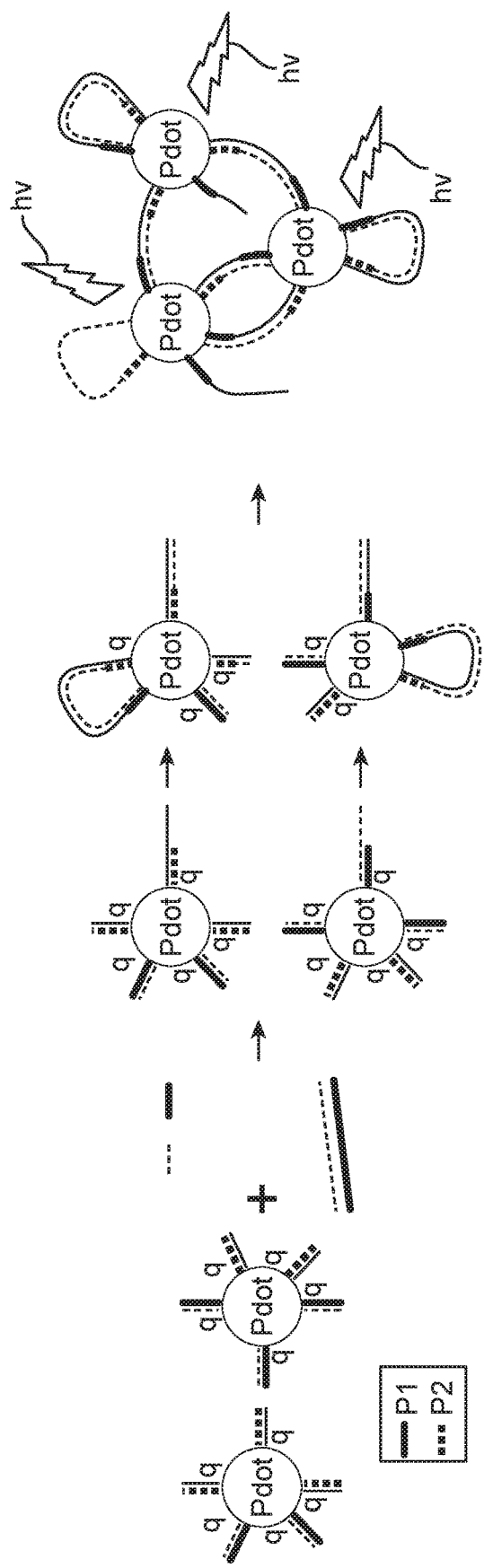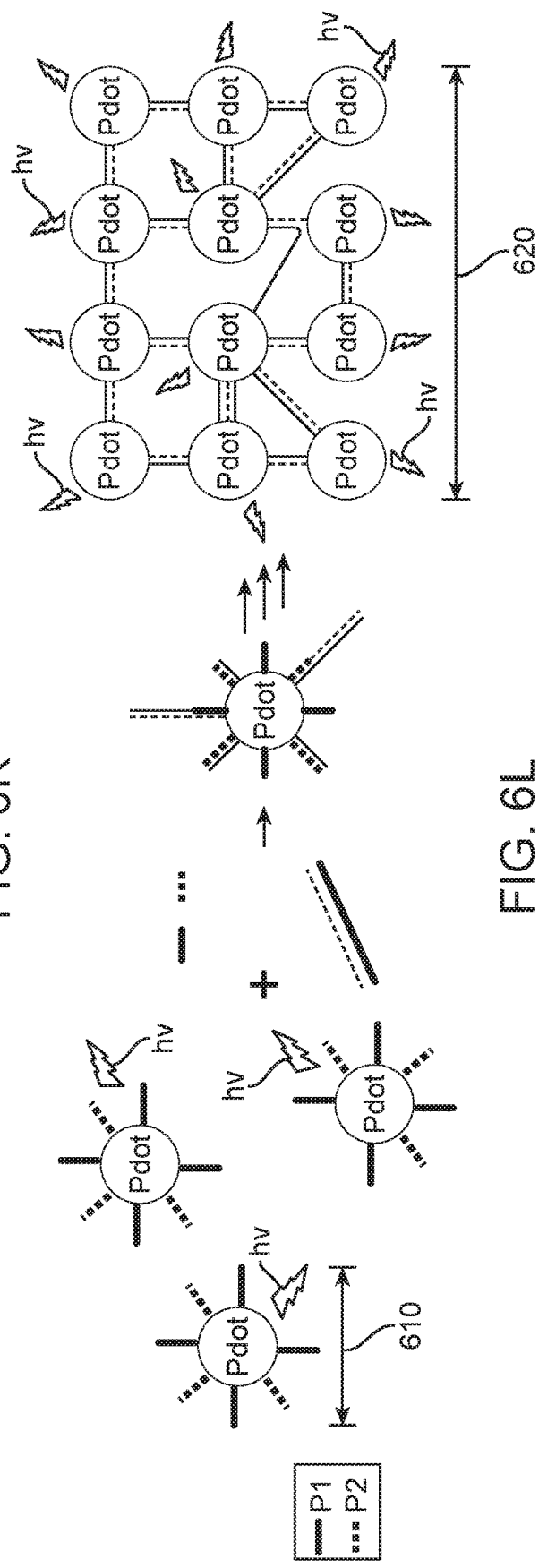
FIG. 6K
FIG. 6L

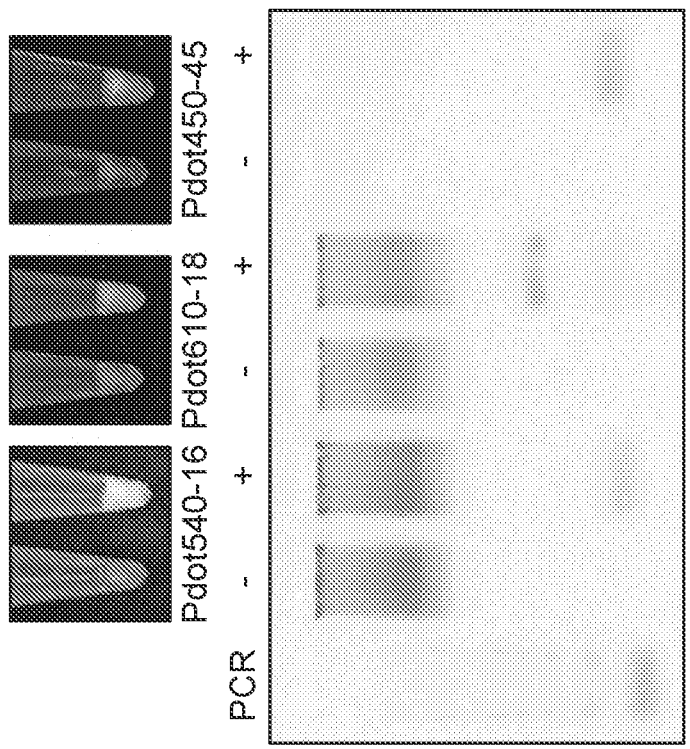
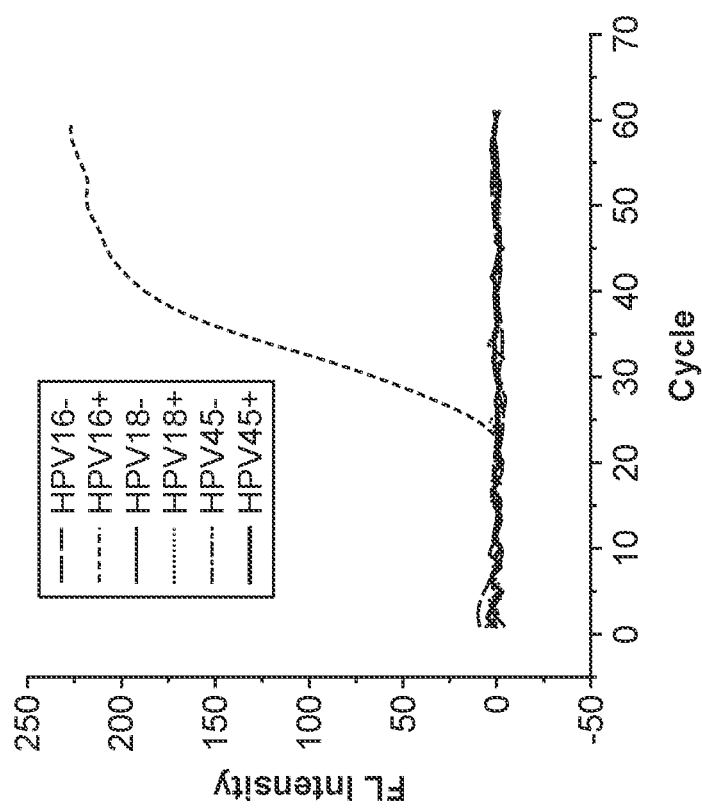
FIG. 12F
FIG. 12E

DIGITAL NUCLEIC ACID AMPLIFICATION USING ENCODED PARTICLES

CROSS-REFERENCE

This application is a national stage entry of International Application No. PCT/US2018/058803, filed Nov. 1, 2018, which claims the benefit of U.S. Provisional Application No. 62/581,429, filed Nov. 3, 2017, the applications of which are incorporated herein by reference in their entirety for all purposes.

BACKGROUND

Digital measurements can play an important role in certain biological assays because they can increase the sensitivity, accuracy, and robustness of a given assay. Furthermore, analog measurements can require calibration through additional analysis of calibration standards whereas digital measurements, which can be based on tabulation of binary values, can reduce the technical complexity of performing a given biological assay.

Amplification methods, such as polymerase chain reaction (PCR) can be used to detect target molecules, such as a nucleic acids (e.g., DNA or RNA molecules), in a sample. In the case of PCR, a target molecule, such as a DNA molecule, is amplified in a temperature-sensitive reaction catalyzed by a DNA-polymerizing enzyme. By cycling the DNA through a series of temperatures, which often range from about 60° C. to about 95° C., for a prescribed length of time at each temperature in the presence of a primer nucleic acid molecule and nucleoside triphosphate molecules, the number of copies of the DNA is increased. PCR is useful in a wide range of scientific areas, including basic biology, clinical diagnostics, genetic engineering, and forensics.

SUMMARY

Described herein are methods and systems for performing digital assays using compartmentalized volumes and probes comprising encoded particles. In particular, the present disclosure describes methods, systems, and devices for improved digital analysis of a molecule of interest in systems comprising a plurality of compartmentalized volumes. For example, the herein described methods and systems can be used to measure the volumes of compartmentalized volumes and the number of compartmentalized volumes in which a detectable signal or code can be detected, which can subsequently be used to determine the concentration of a sample. This invention further describes methods, systems, and devices capable of improving the speed, dynamic range, and reproducibility of molecular-level interrogation of a target molecule and increasing the quantity of target molecule species (e.g., the number of different types of target molecules) that can be analyzed in a single assay, as compared to traditional assays (e.g., analog assays). In particular, the methods, systems, and devices described herein can improve the speed, accuracy, and computational efficiency with which a target molecule's presence, absence, identity, or concentration is determined compared to conventional methods and systems of digital analysis. This is achieved through the amplification of the target molecule in a compartmentalized volume that is correlated with the presence of the target molecule. In addition, amplification of a molecule of interest can be used to modulate detection of a detectable signal or code in a digital assay and thereby improve speed, accuracy, and reliability of the digital assay.

In various aspects, the methods described herein comprise methods of performing a digital assay, the method comprising a plurality of compartmentalized volumes, wherein each compartmentalized volume in the plurality of compartmentalized volumes comprises a probe, and wherein each probe comprises an encoded particle and a binding region capable of binding to a target molecule or to a molecule that is correlated with the presence of the target molecule, and wherein the encoded particle has at least one dimension that is greater than 3 nm and at least some of the compartmentalized volumes in the plurality of compartmentalized volumes comprise the target molecule. Also described herein are methods for amplifying the target molecule, and detecting an optically detectable code emitted by an encoded particle in the compartmentalized volume, wherein the detection of the optically detectable code indicates that the target molecule is present in the compartmentalized volume.

In various aspects, the methods described herein comprise a method comprising: providing a plurality of compartmentalized volumes, wherein: each compartmentalized volume in the plurality of compartmentalized volumes comprises a probe, wherein each probe comprises an encoded particle and a binding region capable of binding to a target molecule or to a molecule that is correlated with the presence of the target molecule, and wherein the encoded particle has at least one dimension that is greater than 3 nm; and at least some of the compartmentalized volumes in the plurality of compartmentalized volumes comprise the target molecule; amplifying a molecule that is correlated with the presence of the target molecule; and detecting an optically detectable code emitted by an encoded particle in the compartmentalized volume, wherein the detection of the optically detectable code indicates that the target molecule is present in the compartmentalized volume.

In various aspects, the methods and systems for performing digital assays comprise the optically detectable code comprising at least one of: (i) an emission peak wavelength; (ii) an emission peak intensity at a given wavelength; (iii) an emission peak spectral intensity; (iv) an emission lifetime; and (v) an absorbance peak wavelength. In other aspects, the optically detectable code comprises at least two of: (i) an emission peak wavelength; (ii) an emission peak intensity at a given wavelength; (iii) an emission peak spectral intensity; (iv) an emission lifetime; and (v) an absorbance peak wavelength. In other aspects, the optically detectable code comprises at least three of: (i) an emission peak wavelength; (ii) an emission peak intensity at a given wavelength; (iii) an emission peak spectral intensity; (iv) an emission lifetime; and (v) an absorbance peak wavelength. In some aspects, the optically detectable code comprises at least 4 of, at least 5 of, at least 6 of, at least 7 of, at least 8 of, at least 9 of, or at least 10 of: (i) an emission peak wavelength; (ii) an emission peak intensity at a given wavelength; (iii) an emission peak spectral intensity; (iv) an emission lifetime; and (v) an absorbance peak wavelength. In various aspects, the optically detectable code can be a single type of optically detectable code selected from (i), (ii), (iii), (iv), or (v) or a combination of types of optically detectable codes selected from (i), (ii), (iii), (iv), and (v).

In various aspects of this invention, the optically detectable code has at least 2 emission peaks, at least 3 emission peaks, at least 4 emission peaks, at least 5 emission peaks, at least 6 emission peaks, at least 7 emission peaks, at least 8 emission peaks, at least 9 emission peaks, or at least 10 emission peaks.

In various aspects of this invention, the methods and systems described herein comprise an encoded particle that is characterized by at least one of: (i) an emission peak wavelength; (ii) an emission peak intensity at a given wavelength; (iii) an emission peak spectral intensity; (iv) an emission lifetime; and (v) an absorbance peak wavelength. In other aspects, the encoded particle is characterized by at least two of: (i) an emission peak wavelength; (ii) an emission peak intensity at a given wavelength; (iii) an emission peak spectral intensity; (iv) an emission lifetime; and (v) an absorbance peak wavelength. In other aspects, the encoded particle is characterized by at least three of: (i) an emission peak wavelength; (ii) an emission peak intensity at a given wavelength; (iii) an emission peak spectral intensity; (iv) an emission lifetime; and (v) an absorbance peak wavelength. In other aspects, the encoded particle is characterized by at least 4 of, at least 5 of, at least 6 of, at least 7 of, at least 8 of, at least 9 of, or at least 10 of: (i) an emission peak wavelength; (ii) an emission peak intensity at a given wavelength; (iii) an emission peak spectral intensity; (iv) an emission lifetime; and (v) an absorbance peak wavelength.

In various aspects, the encoded particle is characterized by a single type of property selected from (i), (ii), (iii), (iv), or (v) or a combination of types of properties selected from (i), (ii), (iii), (iv), and (v). In other aspects, the encoded particle is characterized by at least 2 emission peaks, at least 3 emission peaks, at least 4 emission peaks, at least 5 emission peaks, at least 6 emission peaks, at least 7 emission peaks, at least 8 emission peaks, at least 9 emission peaks, or at least 10 emission peaks.

In various aspects, the optically detectable code of each probe comprises measuring a spectral intensity of the detectable code. In some aspects, the compartmentalized volumes comprise at least one encoded particle that comprises an optically detectable code distinct from at least one other encoded particle present in the plurality of compartmentalized volumes. In some aspects, the compartmentalized volumes comprise a plurality of encoded particles that each comprises an optically detectable code distinct from at least one other encoded particle present in the plurality of compartmentalized volumes.

In various aspects, detecting the presence of the target molecule in the compartmentalized volume can be based on the spectral intensity of the optically detectable code.

In various aspects, detected the emission peak intensity can comprise detecting a plurality of emission wavelengths. In some aspects, the emission peak intensity is measured at the peak maximum for the emission peak.

In various aspects of this invention, a spectral intensity of the detectable code comprises measuring at different emission wavelength ranges a ratio of emission intensities of between 0.01 and 100, 0.05 and 50, 0.1 and 10, 1 and 100, 1 and 50, 1 and 40, 1 and 30, 1 and 20, 1 and 10, 1 and 9, 1 and 8, 1 and 7, 1 and 6, 1 and 5, 1 and 4, 1 and 3, 1 and 2, 0 and 10, 0 and 9, 0 and 8, 0 and 7, 0 and 6, 0 and 5, 0 and 4, 0 and 3, 0 and 2, or between 0 and 1.

In some aspects, the optically detectable code can comprise a luminescent or a fluorescent signal.

In various aspects, the plurality of compartmentalized volumes comprise a plurality of probes; each compartmentalized volume comprises at least one probe; a first distinct probe of the plurality of probes comprises a binding region that is distinct from the binding region of a second distinct probe of the plurality of probes; and the first distinct probe of the plurality of probes comprises an encoded particle capable of emitting an optically detectable code that is distinct from the optically detectable code of the second distinct probe of the plurality of probes. In some aspects, the optically detectable code of each distinct probe comprises a unique set of: an emission peak spectral intensity, emission peak wavelength, absorption peak wavelength, excitation peak wavelength, emission lifetime, or a combination thereof. In some aspects, a plurality of distinct target molecules can be detected. In some aspects, the plurality of compartmentalized volumes comprises at least 2, 5, 10, 20, 50, 100, 200, 500, 1000 distinct probes.

In various aspects, an encoded particle can comprise a matrix. In some aspects, an encoded particle comprises a chromophore. In some aspects, an encoded particle comprises a plurality of chromophores. In some aspects, an encoded particle comprises at least three dye units. In certain aspects, an encoded particle comprises a polymer dot. In some aspects, the matrix of the encoded particle is a chromophore or a plurality of chromophores. In some aspects, the matrix of the encoded particle comprises an inorganic material, an organic material, or a combination thereof. In some aspects, the matrix comprises silica, a silicate, titanium dioxide, phosphate, a polymer, or a combination thereof.

In various aspects, the matrix comprises a semiconducting polymer. In some aspects, the matrix comprises polystyrene (PS) or poly(methyl methacrylate) (PMMA).

In various cases, the chromophore comprises an inorganic material, an organic material, or a combination thereof. In some aspects, the encoded particle comprises an interpenetrated network of organic and inorganic materials.

In various aspects, the chromophore comprises a dye, a small molecule dye, a polymer, a metal complex, a semiconducting nanocrystal, a semiconducting polymer, or a combination thereof. In some cases, the chromophore is a fluorescent or luminescent chromophore.

In various cases, the encoded particle has at least one dimension from 3 nm to 1000 nm, from 10 nm to 500 nm, from 25 nm to 250 nm, from 50 nm to 100 nm, from 10 nm to 50 nm, from 10 nm to 30 nm, from 10 nm to 20 nm, or from 5 nm to 15 nm.

In various aspects, a probe further comprises a quencher, wherein the quencher reduces the intensity of the optically detectable code in the absence of the target molecule or prior to amplification of the target molecule. In some aspects, the quencher is connected to a binding region of the probe. In some aspects, the quencher is capable of binding to a binding region of the probe. In some aspects, distance between the encoded particle and the quencher during or after the amplifying can be increased. In some aspects, the distance between the encoded particle and the quencher can be increased by cleaving the connection between the quencher and the encoded particle.

In various aspects, the amplifying comprises or is accompanied by cleaving the binding region of the probe. In some aspects, the amplifying comprises producing a plurality of copies. In some aspects, the amplifying comprises producing a plurality of copies of the molecule that is correlated with the presence of the target molecule. In some aspects, amplifying comprises creating an amplified product. In some aspects, the amplifying comprises or is accompanied by cleaving the binding region of the probe.

In various aspects, the binding region comprises a nucleic acid configured to hybridize to the target molecule or to the molecule that is correlated with the presence of the target molecule. In some aspects, a first portion of the binding region is capable of hybridizing with a second portion of the binding region.

In various aspects, each compartmentalized volume in the plurality of compartmentalized volumes comprises a plurality of probes, wherein at least one probe comprises: a binding region configured to bind to the same distinct target molecule or to the molecule that is correlated with the presence of the same distinct target molecule as at least one other probe in the compartmentalized volume; and an encoded particle capable of emitting the same optically detectable code as the at least one other probe in the compartmentalized volume. In some aspects, each compartmentalized volume in the plurality of compartmentalized volumes comprises a plurality of probes, wherein each probe comprises: a binding region configured to bind to a different distinct target molecule or to the molecule that is correlated with the presence of a different distinct target molecule from at least one other probe in the compartmentalized volume; and an encoded particle capable of emitting an optically detectable code different from the at least one other probe in the compartmentalized volume.

In various aspects, the methods and systems described herein comprise extending a first binding region of a probe, wherein extending the first binding region allows the probe to hybridize to a second binding region of the same probe. In some aspects, extending the binding region allows a first probe to bind to a binding region of a second probe and the first and second probe are capable of producing the same detectable optical code.

In various aspects, the methods and systems described herein comprise extending a binding region through the activity of an enzyme, wherein each compartmentalized volume of the plurality of compartmentalized volumes comprises the enzyme. In some aspects, the binding region extended through the activity of an enzyme is capable of binding to a binding region of the same probe or to a binding region of a different probe, wherein each probe bound to another probe is capable of producing the same optically detectable code as the probe to which it is bound. In some aspects, the enzyme is a polymerase.

In various aspects, the methods and systems described herein comprise linking a probe of the plurality of probes with another probe of the plurality of probes during or after the amplifying to form a probe network, wherein the linking occurs only in the presence of the target molecule or the presence of the molecule that is correlated with the presence of the target molecule.

In various aspects, each probe comprises a plurality of different binding regions. In some aspects, the ratio of a first binding region to a second binding region on a first probe is 1.0 times, 1.05 times, 1.1 times, 1.2 times, 1.3 times, 1.4 times, 1.5 times, 1.6 times, 1.7 times, 1.8 times, 1.9 times, 2 times, 2.5 times, 3 times, 4 times, 5 times, 6 times, 7 times, 8 times, 9 times, 10 times, 20 times, 30 times, 40 times, 50 times, 60 times, 70 times, 80 times, 90 times, or 100 times that of the first binding region to the second binding region on a second probe of the same type.

In various aspects, each compartmentalized volume of the plurality of compartmentalized volumes comprises a circularized nucleic acid comprising a region capable of binding to the target molecule or to the molecule that is correlated with the presence of the target molecule; and the quencher is capable of hybridizing with an amplified product of the circularized nucleic acid. In some aspects, the circularized nucleic acid is amplified through rolling circle amplification.

In various aspects, the digital assay is digital nucleic acid analysis. In some aspects, the digital nucleic acid analysis comprises digital PCR. In various aspects, the digital assay comprises at least 2, at least 5, at least 10, at least 15, at least 20, at least 25, at least 30, at least 35, at least 40, or at least 45 temperature cycles. In some aspects, the digital assay is an isothermal assay. In some aspects, the isothermal assay comprises isothermal nucleic acid amplification. In some aspects, the compartmentalized volume is maintained at 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., or 75° C. In some aspects, each of the compartmentalized volumes have a volume of less than 20 pL, less than 15 pL, less than 10 pL, less than 5 pL, less than 4 pL, less than 3 pL, less than 2 pL, or less than 1 pL.

In various aspects, the methods and systems described herein comprise a digital assay system comprising: a plurality of compartmentalized volumes, wherein each compartmentalized volume in the plurality of compartmentalized volumes comprises; an amplification reagent; a probe comprising an encoded particle and a binding region capable of binding to a target molecule or to a molecule that is correlated with the presence of the target molecule, and wherein the encoded particle has at least one dimension that is greater than 3 nm; and at least some of the compartmentalized volumes in the plurality of compartmentalized volumes comprise the target molecule; a detector configured to optically detect an optically detectable code produced by the encoded particle in one or more compartmentalized volume; and a computer comprising a processor and a memory device with executable instructions stored thereon, the instructions when executed causing the processor to: operate the detector to measure the optically detectable code; store the measured optically detectable code; and analyze the measured optically detectable code. In some aspects, the optically detectable code comprises an emission wavelength, an emission spectrum, an emission lifetime, an emission intensity, an emission intensity range, an emission wavelength range, an absorption spectrum, an absorption wavelength range, an excitation spectrum, and excitation wavelength range or a combination thereof. In some aspects, the optically detectable code comprises a spectral intensity. In some aspects, the encoded particle comprises a polymer dot.

In various aspects, the sample holder is capable of holding the plurality of compartmentalized volumes during the detection of the optically detectable code.

In various aspects, the systems and methods described herein further comprise a source of electromagnetic radiation. In some aspects, the systems and methods further comprise, a heating element capable of regulating the temperature of at least one compartmentalized volume of the plurality of compartmentalized volumes.

In various aspects, the methods and systems described herein comprise a method of performing a digital melt-curve assay, the method comprising: providing a plurality of compartmentalized volumes distributed into a plurality of containers, wherein at least some of the compartmentalized volumes in the plurality of the compartmentalized volumes comprise a target molecule; applying a thermal energy gradient to the plurality of compartmentalized volumes to yield a plurality of assay temperatures varying over an area; and determining the melting temperature of the target molecule or of a molecule that is correlated with the presence of the target molecule by performing the digital melt-curve assay of the target molecule or of the molecule that is correlated with the presence of the target molecule in the presence of a temperature gradient. In some aspects, a variable thermal energy is applied to the plurality of compartmentalized volumes to yield a plurality of assay temperatures varying over a time. In some aspects, the plurality of containers comprises a multi-chamber self-digitization chip, multiple droplets, multi-well microfluidic chip, or a multi-well plate.

In various aspects, the methods and systems described herein comprise a method of performing a digital melt-curve assay, the method comprising: providing a plurality of compartmentalized volumes, wherein: each compartmentalized volume in the plurality of compartmentalized volumes comprises a nucleic acid capable of hybridizing to a target molecule or to a molecule that is correlated with the presence of the target molecule; and at least some of the compartmentalized volumes in the plurality of the compartmentalized volumes comprise the target molecule; amplifying the target molecule to produce an amplified molecule; applying a thermal energy gradient to the plurality of compartmentalized volumes to yield a plurality of assay temperatures varying over an area, such that when the assay temperature in each compartmentalized volume is: below a target molecule or amplified molecule melting temperature, at least 50% of the target molecule or of the amplified molecule is hybridized; and above the target molecule or amplified molecule melting temperature, less than 50% of the target molecule or of the amplified molecule is hybridized; detecting an optically detectable signal produced by a chromophore associated with the hybridized target molecule or the amplified molecule, wherein the optically detectable signal is detected when the chromophore is associated with the hybridized target molecule or the amplified molecule; and determining the melting temperature for the target molecule or amplified molecule based on the presence or absence or magnitude of the optically detectable signal at each of the assay temperatures of the plurality of assay temperatures. In some aspects, the target molecule is a nucleic acid. In some aspects, applying a variable thermal energy comprises varying the thermal energy over time. In some aspects, the variable thermal energy varies cyclicly over time. In some aspects, the variable thermal energy comprises a plurality of discrete temperature changes. In some aspects, the variable thermal energy comprises a continuous temperature change. In some aspects, the assay temperature is the temperature present in the compartmentalized volumes of the plurality of compartmentalized volumes. In some aspects, applying a variable thermal energy to the plurality of compartmentalized volumes occurs over a time period from 1 minute to 90 minutes, from 5 minutes to 60 minutes, from 10 minutes to 30 minutes, or from 10 minutes to 20 minutes.

In various aspects, the assay temperature is selected from: 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., or 90° C.

In various aspects, the chromophore is a fluorescent chromophore. In some aspects, the chromophore comprises an intercalating dye.

In various aspects, each compartmentalized volume has a volume of no more than 100 nL, no more than 50 nL, no more than 25 nL, no more than 10 nL, no more than 9 nL, no more than 8 nL, no more than 7 nL, no more than 6 nL, no more than 5 nL, no more than 4 nL, no more than 3 nL, no more than 2 nL, or no more than 1 nL.

In various aspects, the presence of a mutation in the target molecule can be identified based on the melting temperature of the target molecule. In various aspects, a patient can be diagnosed based the melting temperature of the target molecule.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A shows a schematic diagram of steps in a digital nucleic acid amplification, such as digital PCR, comprising polymerase-induced cleavage (e.g., via the exonuclease activity of the polymerase) of a binding region of a probe, in accordance with embodiments.

FIG. 6B shows a schematic diagram of steps in a digital nucleic acid amplification, such as digital PCR, comprising increasing the distance between an encoded particle of a probe and a quencher through amplification and hybridization, in accordance with embodiments.

FIG. 6K shows a schematic diagram of steps in a digital nucleic acid amplification, such as digital PCR, comprising increasing the distance between a quencher and a probe through amplification and competitive hybridization, with boosted amplification from free primers, and intraprobe and inter-probe amplification and hybridization, in accordance with embodiments.

FIG. 6L shows a schematic diagram of steps in a digital nucleic acid amplification, such as digital PCR, comprising hybridization of the binding regions of a plurality of probes, in accordance with embodiments.

FIG. 12E shows raw data recorded during a PCR assay for the three types of $SiO_2$/Polymer-Pdot-DNA demonstrating high signal to noise in the detection of HPV16, HPV18, and HPV45 in accordance with embodiments.

FIG. 12F shows compartmentalized volumes (under UV illumination) of PCR assays prior to and after amplification for the three types of $SiO_2$/Polymer-Pdot-DNA in the detection of HPV16, HPV18, and HPV45, together with the gel electrophoresis results showing the presence of the respective amplified products.

DETAILED DESCRIPTION

Figure 1:
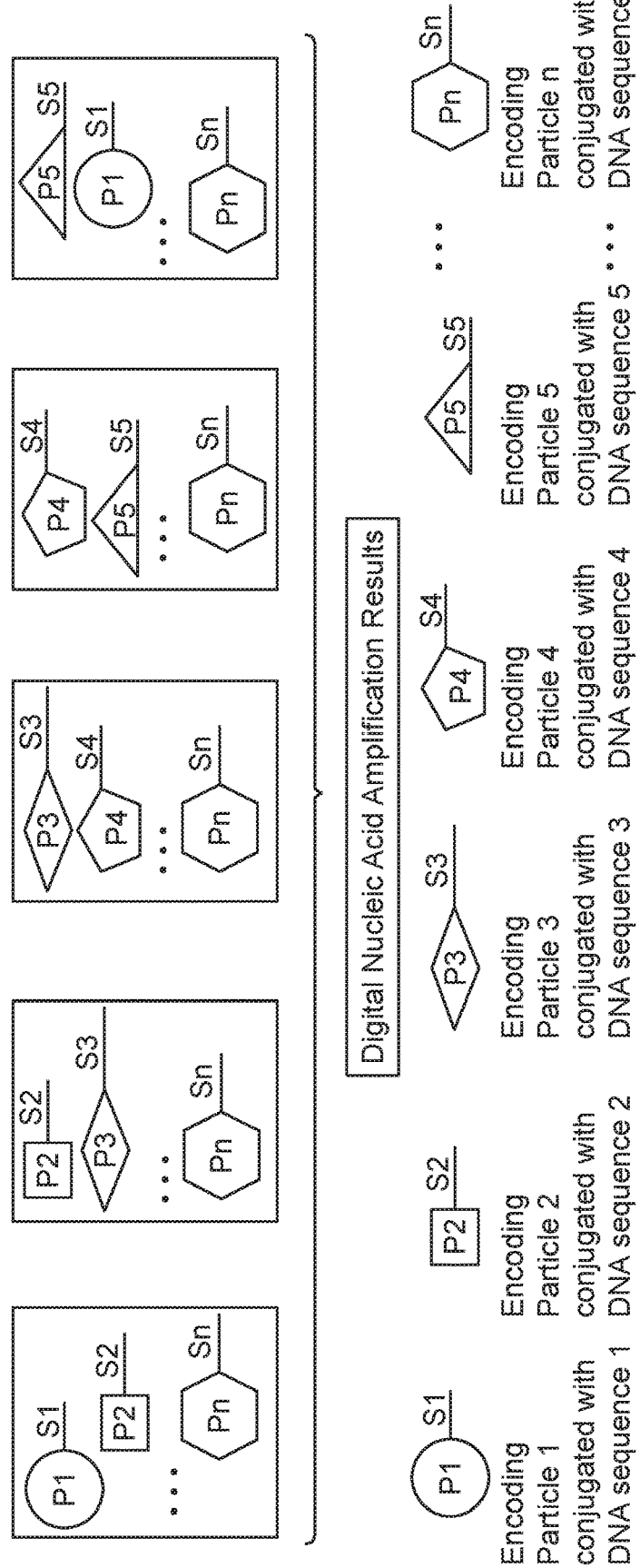
FIG. 1 shows a schematic diagram of a method of digital nucleic acid amplification, such as digital PCR, with encoded particles, in accordance with embodiments.
Figure 2:
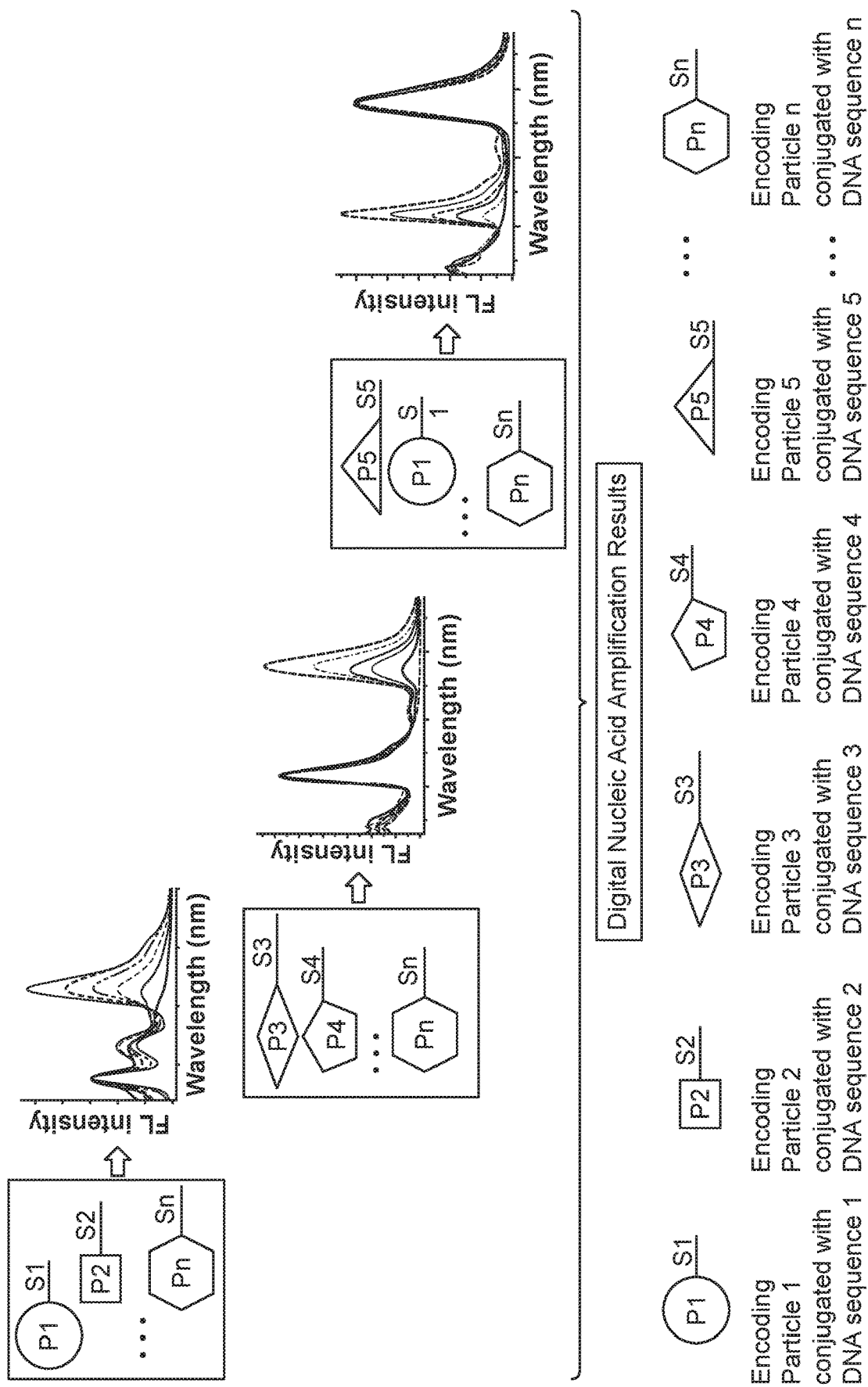
FIG. 2 shows a schematic diagram of a method of digital nucleic acid amplification, such as digital PCR, with particles encoded with respect to spectral intensity, in accordance with embodiments.
Figure 3:
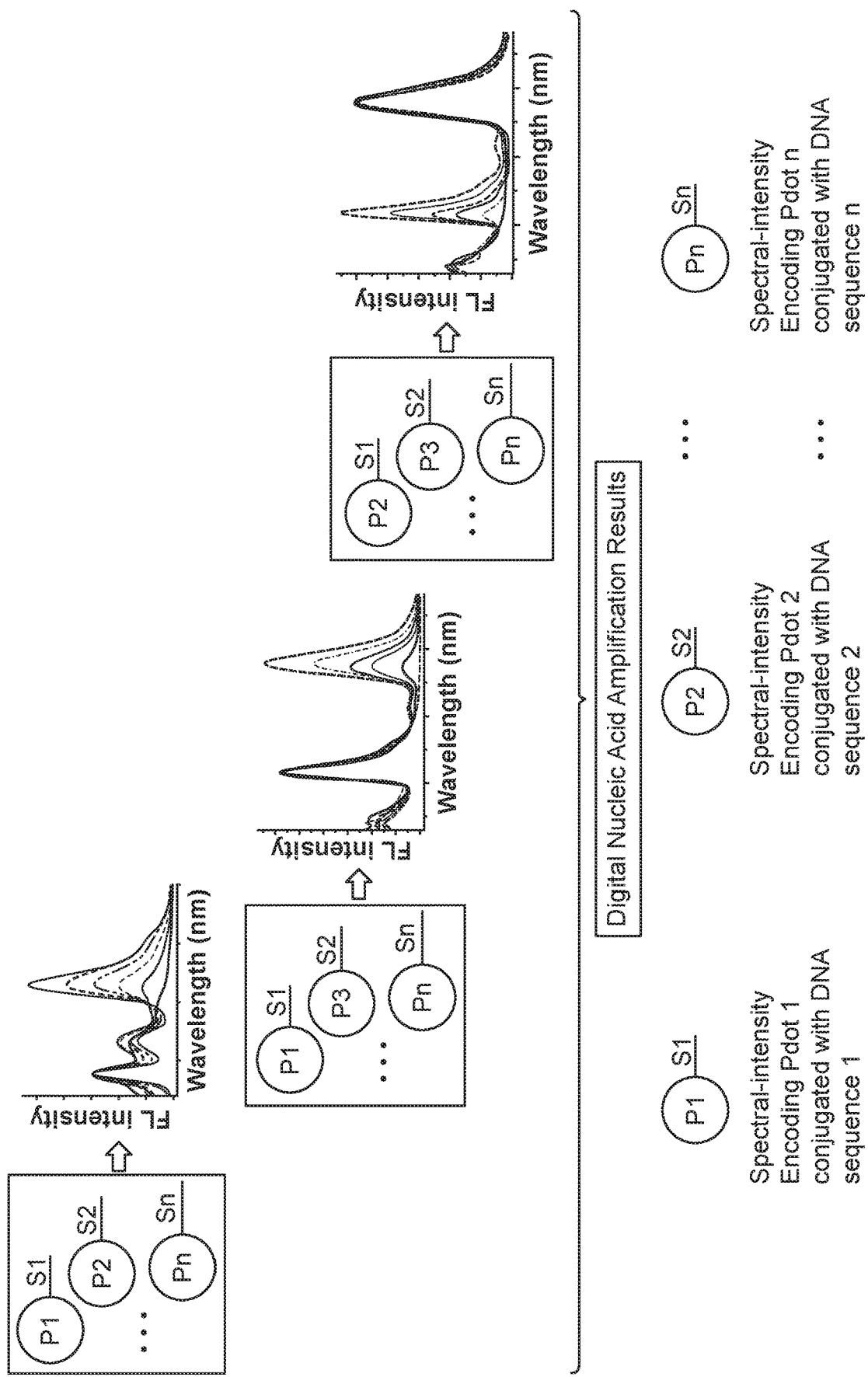
FIG. 3 shows a schematic diagram of a method of digital nucleic acid amplification, such as digital PCR, with polymer dots encoded with respect to spectral intensity, in accordance with embodiments.

The present disclosure relates to methods and systems for performing digital assays using compartmentalized volumes and probes comprising encoded particles. In particular, the present disclosure describes methods, systems, and devices for improved digital analysis of a target molecule (e.g., determining the presence, identity, or concentration of a molecule of interest or analyte) in systems comprising a plurality of compartmentalized volumes (e.g., droplets, aliquots, etc.) having identical sizes, approximately identical sizes, or different sizes. For example, the methods and systems can be used to determine (1) the volumes of compartmentalized volumes and (2) the number of compartmentalized volumes in which a detectable signal or code can be detected, which can subsequently be used to determine the concentration of a sample. The methods, systems, and devices for digital analysis described herein are capable of improving the speed, dynamic range, and reproducibility of molecular-level interrogation of a target molecule and increasing the quantity of target molecule species (e.g., the number of different types of target molecules) that can be analyzed in a single assay, as compared to traditional assays (e.g., analog assays). In particular, the present methods, systems, and devices can improve the speed, accuracy, and computational efficiency with which a target molecule's presence, absence, identity, or concentration is determined compared to conventional methods and systems of digital analysis through the amplification of the target molecule or a molecule in a compartmentalized volume that is correlated with the presence of the target molecule. As described herein, amplification of a target molecule (or of a molecule correlated with the presence of a target molecule in a compartmentalized volume, such as an amplification product of a target molecule) can be used to modulate detection of a detectable signal or code (e.g., an optically detectable signal or code) in a digital assay and thereby improve speed, accuracy, and reliability of the digital assay.

A digital assay, as described herein, can comprise partitioning, aliquoting, or otherwise separating a sample (or derivative thereof) into a plurality of compartmentalized volumes, evaluating the plurality of compartmentalized volumes individually for the presence or absence of a detectable signal or code (e.g., detecting a detectable signal or code produced by a chromophore or by an encoded particle of a probe), and assigning a binary value to each evaluated compartmentalized volume. In some cases, a value can be assigned to a compartmentalized volume based on the presence, absence, wavelength, intensity, and/or lifetime of a detectable signal or code (or portions thereof) in the compartmentalized volume. The values assigned to the evaluated compartmentalized volumes can be used to determine characteristics of target molecules in each compartmentalized volume. For example, detecting or failing to detect a detectable signal (e.g., a detectable code or aspects thereof) in a compartmentalized volume can indicate the presence or absence of a target molecule in the compartmentalized volume and can be used to determine the concentration of a target molecule in the sample. In some cases, detecting or failing to detect a detectable signal in a compartmentalized volume can be used to determine the nucleic acid sequence of a target molecule in the compartmentalized volume.

A detectable signal or code, as described herein, can be produced by a probe (or portion thereof) in a compartmentalized volume and can comprise various aspects, such as an emission intensity (e.g., an emission peak intensity or an emission intensity range), an emission wavelength (e.g., an emission peak wavelength or an emission wavelength range), an emission lifetime, an excitation wavelength (e.g., an excitation peak wavelength or an excitation wavelength range), an absorption wavelength (e.g., an absorption peak wavelength or an absorption wavelength range) or a spectral intensity. Thus, detecting a detectable signal or code (e.g., an optically detectable signal or code) can comprise measuring an emission intensity (e.g., an emission peak intensity or an emission intensity range), an emission wavelength (e.g., an emission peak wavelength or an emission wavelength range), an emission lifetime, an excitation wavelength (e.g., an excitation peak wavelength or an excitation wavelength range), an absorption wavelength (e.g., an absorption peak wavelength or an absorption wavelength range) a spectral intensity, or any combination thereof. In some cases, a spectral intensity can comprise a ratio, for example, of a plurality of emission peak intensities, emission peak wavelengths, range of emission intensities, range of emission wavelengths, emission wavelength spectra, excitation peak wavelengths, range of excitation wavelengths, absorption peak wavelengths, or range of absorption wavelengths. For example, detecting or determining the spectral intensity of a probe comprising two chromophores can comprise detecting or measuring the emission intensity of the detectable code produced by probe at two or more wavelengths (e.g., within two or more ranges of wavelengths) and, optionally, calculating a ratio of the intensities (e.g., intensity ranges) at the two or more wavelengths over which the intensities were detected or measured. The detectable signal or code can be an optically detectable signal or code (e.g., a luminescent or fluorescent detectable signal or code). In some cases, a detectable signal or code can comprise a wavelength or range of wavelengths that include at least one wavelength of 200 nm, 300 nm, 400 nm, 500 nm, 600 nm, 700 nm, 800 nm, 900 nm, 1000 nm, 2000 nm or within a range defined by any two values thereof. Disclosed herein are novel methods and systems of modulating a detectable signal or code of a probe in a digital assay. In some cases, the modulation of a detectable signal or code, as described herein, can depend on whether a target molecule is present in a compartmentalized volume containing a probe. For example, an amplification event capable of modulating the detectable code or signal of an encoded particle of a probe in a compartmentalized volume can, in some cases, require a target molecule to be present in the compartmentalized volume. Thus, a detectable code or signal or any aspect thereof (e.g., an emission peak intensity, an emission intensity range, an emission peak wavelength, an emission wavelength range, an excitation peak wavelength, an excitation wavelength range, an absorption peak wavelength, an absorption wavelength range, an emission lifetime, or a spectral intensity) can be used to determine the presence or absence of a target molecule. As a result, the methods and systems described herein can be used to facilitate digital assays as a means of determining or indicating the presence or absence of one or more distinct target molecules in a compartmentalized volume, for example, through the modulation of a detectable signal or code emitted by an encoded particle of a probe present in the compartmentalized volume.

The methods and systems of the present disclosure advantageously enable the performance of high-throughput analysis of samples through the use of compartmentalized volumes (e.g., digitized volumes), for example, in a digital assay. Since amplification-based methods of detection, such as PCR, can be affected by cross-talk (e.g., competition) between individual reactions occurring at the same time, the use of compartmentalized volumes (such as in digital PCR) can improve the efficiency of an amplification-based assay by segregating assay reagents and limiting cross-talk between reactions using the digital format. By employing high-throughput analysis of a plurality of compartmentalized volumes (e.g., through multiplexing of digitized volumes), statistically robust calculations can be made with respect to target molecule concentration in a sample without sacrificing reaction efficiency (e.g., as a result of cross-talk between reactions). This minimization of cross talk by segregating assay reagents and/or target molecules is further enhanced by utilizing very small compartmentalized volumes, that is, volumes less than 20 pL, less than 15 pL, less than 10 pL, less than 5 pL, less than 4 pL, less than 3 pL, less than 2 pL, or less than 1 pL.

High-throughput analysis, which can comprise the use of multiplexed systems as described herein, can be used to rapidly interrogate a plurality of distinct target molecules (e.g., a plurality of different types of target molecules) from patient samples as well. In some cases, each distinct target molecule of a plurality of distinct target molecules can be different from (e.g., can comprise a different nucleic acid sequence than) every other distinct molecule of the plurality of distinct molecules.

Such high-throughput screening of patient-derived target molecules can be useful for improving the efficiency of a clinical screening (e.g., for viral infection, genetic conditions, or numerical quantification of clinically relevant metabolites) both with respect to the number of target molecules that can be interrogated per sample and with respect to the number of subjects that can be compared across a common panel of examined target molecules. Thus, the methods and systems described herein can be useful in the diagnosis and/or treatment of a patient through the determination of whether one or more target molecule is present in a patient sample and, if so, the concentration of the target molecule in the patient sample.

As used herein, the term "distinct" refers to signals, codes, metrics, molecules, structures, components, or portions thereof that are non-identical. For example, a digital assay can comprise analysis of two distinct target molecules (e.g., a first target molecule that is structurally non-identical to a second target molecule). That is a two distinct molecules (or fragments thereof) can be different types of molecules or different species of molecules. By contrast, additional instances or copies of a single type or species of molecule are not necessarily distinct molecules.

Methods for Detecting a Target Molecule

As described herein, various characteristics related to a target molecule of a sample (or a plurality of distinct target molecules of a sample) can be determined via digital analysis of a plurality of compartmentalized volumes created from the sample, wherein at least some of the compartmentalized volumes comprise the target molecule. For example, by determining the presence or absence of each distinct target molecule in each compartmentalized volume of a plurality of compartmentalized volumes can allow for the efficient and accurate calculation of each distinct target molecule's concentration in the sample. In some cases, the determination of the presence or absence of a target molecule in a compartmentalized volume can comprise detecting a detectable signal or code of a probe contained in the compartmentalized volume. In some cases, the detectable signal or code produced (e.g., emitted) by a probe can be modulatable (e.g., through the conditional quenching of the detectable signal or code by a quencher contained in the compartmentalized volume). In other words, the detection of a target molecule in a sample or portion thereof (e.g., in a compartmentalized volume derived from a sample comprising a target molecule) can comprise detecting a modulatable, detectable signal or code produced by a probe present in the sample or portion thereof.

As described herein, a probe can comprise an encoded particle and a binding region. An encoded particle can comprise a chromophore, and a chromophore of an encoded particle is capable of emitting a detectable signal or code, as further described herein. In some cases, the detectable signal or code of an encoded particle can be modulated. In some cases, the ability of a detector to detect a detectable signal or code of an encoded particle can be decreased or eliminated. For example, if a quencher is adjacent to or in close proximity to an encoded particle, the quencher can reduce the intensity of the detectable signal or code that can be detected by a detector (e.g., via a dynamic quenching mechanism) compared to a situation in which the quencher was not present or was not in close proximity to the encoded particle. As a result, it is possible to modulate the degree to which a detectable signal or code can be detected from a probe, encoded particle, or chromophore in a compartmentalized volume by modulating the distance between a quencher and the probe, encoded particle, or chromophore. For example, the ability of a detector to detect or measure a detectable signal or code can be reduced or eliminated if a quencher is capable of hybridizing with or binding to a binding region of the probe capable of producing the detectable signal or code.

In some cases, a probe can comprise a quencher. A quencher can comprise a nucleic acid sequence capable of hybridizing with a binding region of a probe, a target molecule, an amplification product of a target molecule, or a portion thereof. In some cases, a quencher can be bound to or hybridized with a binding region of a probe. In some cases, the hybridization of a quencher to a probe or portion thereof (e.g., a binding region of a probe or portion thereof) can anchor the quencher in sufficiently close proximity to the probe or portion thereof (e.g., to the encoded particle of the probe) to decrease or to eliminate the ability of a detector to detect or measure the detectable signal or code of the probe or portion thereof (e.g., the detectable signal or code of the encoded particle).

Described herein are methods and systems useful for modulating the distance between a quencher and the source of a detectable signal or code (e.g., a probe, encoded particle, or chromophore) in a compartmentalized volume comprising a target molecule of a sample. In some cases, modulating the distance between a quencher in a compartmentalized volume and a source of a detectable signal or code in the same compartmentalized volume can depend on the presence or absence of a target molecule (or molecule correlated with the presence of a target molecule) in the compartmentalized volume. For example, in some cases, a quencher and a target molecule can each hybridize with or bind to the same binding region of a probe or to a portion of the same binding region of a probe. In such cases, the target molecule can compete with the quencher for the opportunity to bind to or hybridize with the binding region of a probe. Depending on the concentration of the target molecule in each compartmentalized volume, the intensity of the detectable signal or code from each compartmentalized volume can depend on the presence of the target molecule in a given compartmentalized volume. As used herein, a molecule correlated with the presence of a target molecule can be an amplification product of a target molecule or portion thereof, a fragment of the target molecule, a molecule or complex stabilized by a target molecule, or a molecule requiring the presence of a target molecule to be formed or expressed.

As described herein, the efficiency of quencher-mediated, target molecule-dependent signal modulation can be significantly improved if quencher-mediated signal modulation is coupled with amplification of molecules capable of displacing a quencher from the vicinity of a probe, encoded particle, or chromophore (e.g., through competitive binding). For example, thermal cycle amplification or isothermal amplification can be used to increase the number of moieties capable of competitively inhibiting quencher association with a binding region of a probe, an encoded particle, or a chromophore. As described herein, a moiety capable of competitively inhibiting quencher association with a binding region of a probe, an encoded particle, or a chromophore can comprise a target molecule, an amplification product created from a target molecule (which can, for example, comprise a nucleic acid sequence that is complementary to the nucleic acid sequence of the target molecule), a product of rolling circle amplification, or other molecule correlated with the presence of a target molecule. If the template molecule or trigger molecule for amplification is the target molecule or a molecule correlated with the presence of a target molecule, it is possible to greatly increase the speed with which competitive inhibition of quencher-binding region association is achieved. Thus, target-molecule amplification can efficiently increase the number of molecules in a compartmentalized volume capable of competitively inhibiting a quencher's association with a binding region of a probe, an encoded particle, or a chromophore. Compartmentalized volumes that do not contain a target molecule would not be expected to inhibit a quencher's association with a binding region of a probe, an encoded particle, or a chromophore to the same degree or with the same efficiency.

As a result, the use of target molecule-dependent amplification to increase the distance between a quencher and a probe, encoded particle, or chromophore capable of emitting a detectable signal or code can significantly improve the ability to detect the presence or absence of a target molecule in a compartmentalized volume of a digital assay. Therefore, using the methods and systems described herein, it is possible to improve digital assay efficiency and accuracy by incorporating the means for target molecule-dependent amplification.

Digital assay efficiency and robustness can also be increased by forming a network of probes or encoded particles. Increasing the spatial concentration of a plurality of similar detectable signals or codes can improve the efficiency with which the detectable signal or code can be detected in a digital assay. For example, a network of probes, wherein a plurality of the probes of the network each comprise an encoded particle capable of emitting the same detectable signal or code as one another, can be more readily detected in a compartmentalized volume than the detectable signal or code from a single probe comprising an encoded particle. In some cases, a network of probes can be formed through the association or hybridization of one or more binding region of a probe with a binding region of one or more other probes (e.g., as illustrated in FIG. 6F, FIG. 6G, FIG. 6H, FIG. 6J, FIG. 6K, or FIG. 6L). Increasing the efficiency of detecting a signal in a compartmentalized volume can, in some cases, increase the speed with which a plurality of compartmentalized volumes can be interrogated for the presence of a detectable signal or code. As a result, an assessment of the presence of a target molecule in a compartmentalized volume can be made more efficiently if a plurality of similar or identical detectable signals or codes are spatially concentrated in a compartmentalized volume, for example, as a result of aggregation or association of a plurality of probes (e.g., as in FIG. 6F, FIG. 6G, FIG. 6H, FIG. 6J, FIG. 6K, or FIG. 6L).

In some cases, forming a network of probes or encoded particles can comprise causing a plurality of probes or encoded particles to become associated with one another. In some cases, forming a network of encoded particles can comprise a target molecule-dependent amplification step, as described herein. In some cases, forming a network of probes or encoded particles can comprise association, binding, or hybridization of a binding region of a first probe with a binding region of a second probe (e.g., inter-probe hybridization).

Quenchers

A digital assay can comprise a quencher. In some cases, a detectable code (e.g., an optically detectable code) of a probe can be modulated by proximity to a quencher. A quencher can comprise a molecule capable of absorbing electromagnetic emissions produced by another molecule (e.g., through a dynamic quenching mechanism or through a dipole-dipole mechanism). For example, a quencher can comprise a chemical signal quencher, such as Black Hole Quencher® (e.g., BHQ-1, BHQ-2, or BHQ-3 from Sigma-Aldrich), capable of absorbing emitted energy in the fluorescent light spectrum. In some cases, a quencher can inhibit the detection of a broad range of wavelengths. For example, a quencher can, in some cases, inhibit detection of all of the wavelength peaks emitted by an encoded particle or a chromophore. In some cases, a quencher can inhibit the detection of only a portion of the emission wavelength peaks produced by an encoded particle or chromophore. In some cases, a quencher is not able to inhibit any wavelengths emitted by a chromophore or encoded particle of a probe. For example, a probe can comprise a plurality of chromophores, and a quencher may not inhibit detection of each chromophore comprising the probe.

A quencher can comprise a polynucleotide sequence (e.g., a nucleic acid chain). In some cases, a nucleic acid comprising a quencher (e.g., a quencher primer or quencher strand) can be able to hybridize with another molecule, such as a target molecule, an amplification product (e.g., an amplicon or amplified product, such as a nucleic acid PCR product), or a binding region of a probe. A quencher can also comprise a polypeptide sequence. In some cases, a polypeptide comprising a quencher (e.g., a quencher antibody) can hybridize with another molecule, such as a target molecule, an amplification product, or a binding region of a probe (e.g., a portion of a binding region of a probe).

In some cases, a quencher can associate with (e.g., bind to or hybridize with) a portion of a binding region of a probe. A quencher comprising a nucleic acid sequence can be capable of hybridizing with (e.g., complementary to) a portion of a binding region of a probe, wherein the binding region comprises a nucleic acid sequence. In some cases, the association of the quencher with the binding region of the probe can inhibit the detection of a detectable signal or detectable code of a probe, encoded particle, or chromophore.

In some cases, a quencher that is associated with (e.g., hybridized with or bound to) a portion of a binding region of a probe can be extended during an amplification step of a digital assay. In some cases, a quencher that is associated with (e.g., hybridized with or bound to) a portion of a binding region of a probe is not extended during an amplification step of a digital assay.

A quencher can be connected to or linked to an encoded particle. For example, a quencher can be bound to (e.g., tethered to) an encoded particle via a nucleic acid molecule, a binding region, a linker, an aptamer, or other such molecule. In some cases, a quencher can be covalently bound to an encoded particle via a nucleic acid molecule, a binding region, a linker, an aptamer, or another such molecule. It is possible, during a PCR amplification step, for a quencher to be disassociated from an encoded particle by the polymerase enzyme (e.g., TaqMan® polymerase) via the enzyme's exonuclease activity. For example, it is possible to cleave or destroy a portion of a binding region that connects a quencher to a probe through a polymerase-mediated mechanism (e.g., as illustrated in FIG. 6A).

It is possible for a quencher to absorb at least a portion of the energy emitted by an encoded particle (e.g., the optically detectable code produced by the encoded particle) if the quencher is adjacent to, associated with, or otherwise in close proximity to the encoded particle. A quencher comprising a nucleic acid quencher capable of hybridizing or binding to the binding region of the probe can reduce the detectable code of an encoded particle below the limits of detection of a digital assay system or below a threshold used for digital assay analysis. For example, a quencher in close proximity to an encoded particle can reduce the spectral intensity of an optically detectable code below a threshold used in a digital assay to indicate the presence of a target molecule in a compartmentalized volume.

In some cases, the distance between a quencher and an encoded particle can be increased (e.g., the quencher can be removed from the encoded particle's proximity) by producing another molecule capable of competing with the quencher for opportunity to associate with the binding region of the probe. For example, amplification of a molecule in the compartmentalized volume can inhibit a quencher's ability to associate with a binding region of a probe. In some cases, amplifying a molecule in the compartmentalized volume can cause the distance between a quencher and an encoded particle to increase by increasing competitive binding (e.g., competitive hybridization) for a binding region of the probe (e.g., as a result of the amplification product binding to the portion of the probe to which the quencher is capable of binding). PCR-related amplification comprising subjecting the compartmentalized volume to a plurality of thermal cycles can be used to increase the distance between a probe or encoded particle and a quencher, e.g., through competitive hybridization. Isothermal amplification can also be used to increase the distance between a probe or encoded particle and a quencher, e.g., through competitive hybridization.

Thus, quenchers can be used to decrease detection of an optically detectable code of a probe (e.g., of an encoded particle) in the absence of a target molecule or of a molecule correlated with the presence of a target molecule. Furthermore, embodiments of a digital assay featuring compositions and methods as described herein can be used to directly or indirectly cause an increase in the distance between an quencher and an encoded particle in the presence of a target molecule (e.g., when one or more probe, quencher, and target molecule are each contained in a compartmentalized volume).

Amplification in a Digital Assay

An amplification step can be useful in modulating the detection of a detectable signal or code in a compartmentalized volume of a digital assay. As described herein, amplification (e.g., an amplification step) can comprise nucleic acid synthesis, extension of a nucleic acid (e.g., lengthening of a nucleic acid through polymerase activity), annealing of a nucleic acid to another molecule (e.g., to another nucleic acid), or melting (e.g., separating a first nucleic acid from a second nucleic acid that are bound to or hybridized with one another through temperature modulation). In some cases, amplification (or an amplification step) can comprise producing one or more copy of a molecule or one or more copy of a portion of a molecule present in a compartmentalized volume. In some cases, amplification can comprise producing one or more copy of a target molecule. In some cases, amplification can comprise producing one or more copy of a portion of a target molecule. In some cases, amplification can comprise producing one or more copy of a molecule correlated with a target molecule, such as an amplification product of a target molecule. For example, amplification of a nucleic acid can comprise producing one or more molecule having a sequence complementary to a target molecule or portion thereof (e.g., an amplification product of a target molecule).

A target molecule-dependent amplification step or amplification event (e.g., extension of a polynucleotide by a polymerase) in a digital assay can cause the distance between a quencher and a binding region of a probe, encoded particle, or chromophore to increase. In some cases, increasing the distance between a quencher and a binding region of a probe, encoded particle, or chromophore can increase the ability of a detector to detect the detectable signal or code of an encoded particle or chromophore (e.g., by decreasing the quenching of the signal or code). As described herein, a variety of methods and compositions can be used to cause target molecule-dependent amplification and separation of a quencher and encoded particle or chromophore in a digital assay.

Amplification can also comprise modification of a molecule in a compartmentalized volume. For example, amplification (or an amplification step) can comprise extending a molecule in a compartmentalized volume. In some cases, extending a molecule can affect the molecule's ability to hybridize with, bind to, or associate with another molecule in the compartmentalized volume. For example, amplification can comprise extending one or more binding region of a probe such that the extended binding region is capable of binding to or hybridizing with a binding region (e.g., an extended binding region) of another probe. In some cases, binding or hybridization between a binding region of a first probe and a binding region of a second probe can cause the first and second probe to be associated with one another (e.g., tethered together or spatially associated with one another). In some cases, extending one or more binding region of a plurality of probes can cause the plurality of probes to become associated with one another in this fashion (e.g., inter-hybridized or latticed) to form a network of probes.

Amplification Comprising Polymerase Mediated Cleavage

In some cases, amplification (or an amplification step) can comprise cleavage or destruction of a molecule in a compartmentalized volume. In some cases, cleavage or destruction of a molecule in a compartmentalized volume can affect the molecule's ability to hybridize with, bind to, or associate with another molecule in the compartmentalized volume. For example, as illustrated in FIG. 6A, a probe (e.g., a fluorescent probe) can comprise a quencher connected (i.e., coupled through covalent linkage) to an encoded particle (e.g., a polymer dot (Pdot)). In some cases, the probe and the quencher can each be covalently bound to the same DNA sequence. In some cases, the quencher can be bound to the 5' end of the DNA sequence, and the probe can be bound to the 3' end of the DNA sequence. In some cases, the quencher can be bound to the 3' end of the DNA sequence, and the probe can be bound to the 5' end of the DNA sequence. In some cases, the encoded particle can be attached to one or more quencher through one or more identical DNA sequences (e.g., which can comprise a portion of a binding region of a probe). In some cases, the DNA sequences can be not identical and the use of more than one DNA sequence can be used to minimize false positives, such as by requiring a two-factor authentication, or can be used to aid in multiplexing. In some cases, one or more quencher can be in close enough proximity to the encoded particle to quench a significant portion of a detectable signal or code emitted from the encoded particle (e.g., when one or more quencher is covalently bound to the encoded particle). In some cases, the one or more quenchers can be of the same type with the same absorption spectrum. In some cases, the one or more quenchers can be of different types with different absorption spectrum. The use of quenchers of different types can be useful in aiding better quenching of the fluorescence emission if the emission from the fluorescent probes cover a broad range of emission wavelengths. A DNA sequence linking the quencher and encoded particle can be complementary to a portion of the target molecule (or an amplification product of the target molecule). In some cases, the complementary sequence of the target molecule (or an amplification product of the target molecule) can hybridize to the probe during amplification (e.g., PCR-related amplification). If the polymerase has exonuclease activity (e.g., Taqman® polymerase), the polymerase may cleave or degrade the DNA sequence linking the quencher to the encoded particle as it replicates (e.g., amplifies) the nucleic acid (e.g., DNA or RNA) from the primer that is also complementary to a different region of the target molecule. As a result, the exonuclease cleavage process can separate the quencher from the encoded particle. Once free in solution the quencher may not be in close enough proximity to the encoded particle to efficiently quench the detectable code (e.g., the fluorescent signal) of the encoded particle of the probe. As the quenchers are cleaved from the encoded particle during amplification, one or more aspect of the detectable code or signal of the encoded particle (e.g., an emission wavelength, an emission lifetime, an emission intensity, or a range of intensity ratios such as that described by the spectral intensity code) may become sufficiently detectable to a detector to surpass a threshold value level, indicating the presence of a target molecule.

Figure 6C:
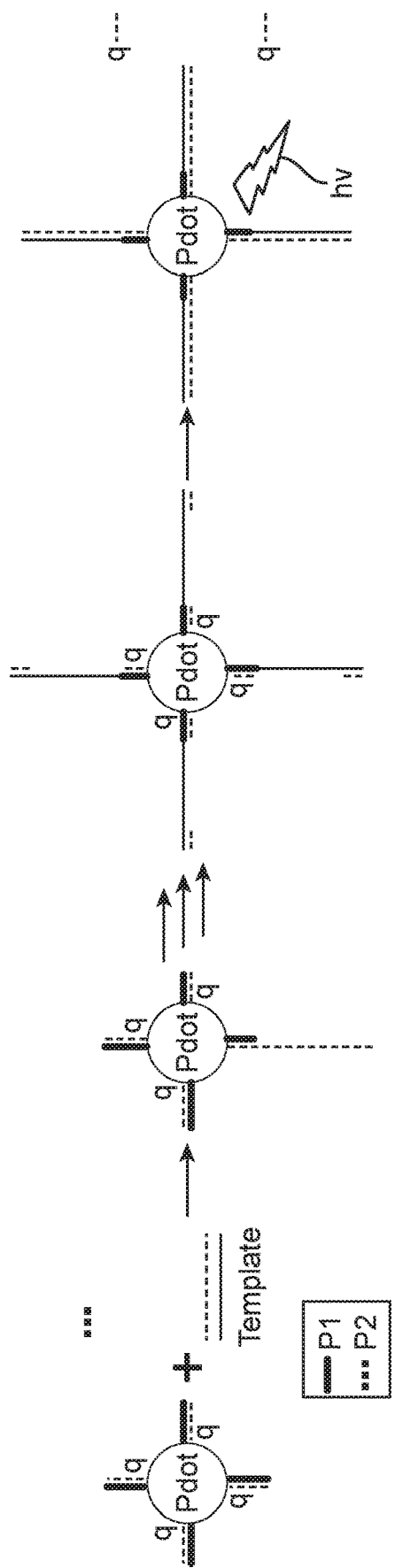
FIG. 6C shows a schematic diagram of steps in a digital nucleic acid amplification, such as digital PCR, comprising increasing the distance between a quencher and a probe through amplification and competitive hybridization, in accordance with embodiments.
Figure 6D:
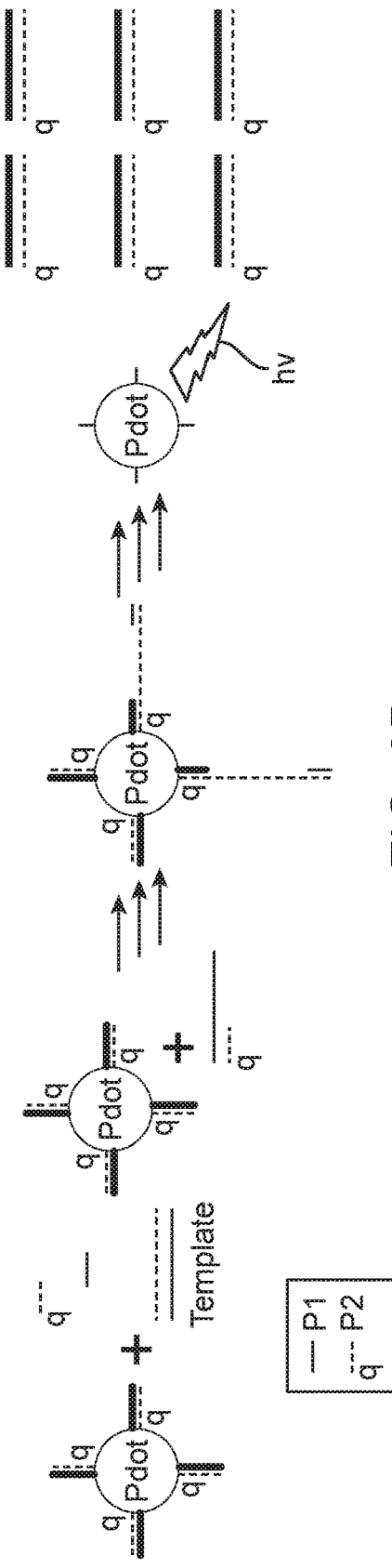
FIG. 6D shows a schematic diagram of steps in a digital nucleic acid amplification, such as digital PCR, comprising increasing the distance between a quencher and an encoded particle of a probe through amplification and competitive hybridization, in accordance with embodiments.

In some cases, separation of a quencher and encoded particle of a probe can comprise cleavage, even in the absence of a direct, covalent linkage between the quencher and the encoded particle or any other part of the probe. For example, as illustrated in FIG. 6I, the encoded particle and quencher comprise complementary DNA sequences (e.g., wherein the DNA sequence of a quencher (or portion thereof) can hybridize with a DNA sequence of a binding region of a probe (or portion thereof)). The hybridization of the DNA sequence of the quencher and the DNA sequence of the binding region can bring the quencher into close enough proximity with the encoded particle to induce reduction of (e.g., quenching of) of the detectable code (e.g., the fluorescence signal) of the encoded particle. In some cases, the DNA sequence of the binding region, the quencher, or both can be complementary to a portion of the target molecule (or to a portion of an amplification product of the target molecule). In some cases, the DNA sequence of the binding region may hybridize with the first portion of the target molecule (or amplification product of the target molecule), one strand of the target molecule, or one strand of the amplification product of the target molecule, and the DNA sequence of the quencher may hybridize with the first portion of the complementary strand of the target molecule, or the complementary strand of the amplification product. In some cases, the DNA sequence of the binding region may hybridize with a portion of the target molecule (or amplification product of the target molecule) that overlaps with the first portion of the target molecule, or a portion of the target molecule (or amplification product of the target molecule) sufficiently close to the first portion of the target molecule (or amplification product of the target molecule) to cause steric inhibition of hybridization of a molecule at the first portion of the target molecule (or amplification product of the target molecule). In some cases, the compartmentalized volume can comprise a first primer molecule (e.g., a first oligonucleotide PCR primer, such as "P1" of FIG. 6I) capable of hybridizing with a second portion of the target molecule (or amplification product of the target molecule), wherein the second portion can be located downstream (i.e., past the 3' end) of the first portion of the target molecule, which is complementary to the binding region. In some cases, the second portion of the target molecule can be located near the 5' end of the target molecule. In some cases, the second portion of the target molecule can be located near the 3' end of the target molecule. In some cases, the second portion of the target molecule can be located near the center 50% between the 5' and 3' end of the target molecule. In some cases, the primers can be complementary to the region of the target molecule or amplification product that is downstream (i.e., on the 3' end) of the region that is complementary to the binding region of the probe or the quencher. A compartmentalized volume can also comprise a second primer molecule (e.g., a second oligonucleotide PCR primer, such as "P2" of FIG. 6I) capable of hybridizing with a second portion of the target molecule (or amplification product of the target molecule), wherein the second portion can be located downstream (i.e., past the 3' end) of the first portion of the target molecule, which is complementary to the DNA sequence of the quencher. In some cases, the first and second primer molecules can facilitate replication of the target molecule and the amplification product of the target molecule via nucleic acid amplification (e.g., such as PCR amplification) using a polymerase enzyme. In some cases, an enzyme can have exonuclease activity (e.g., Taqman® polymerase). In some cases, amplification of a target molecule or amplification product that is hybridized with the binding region of the probe, or the DNA sequence of the quencher, (e.g., at the first region of the target molecule or amplification product) can cause polymerase-mediate cleavage or degradation of the binding region, or the DNA sequence of the quencher, or a portion thereof. Cleavage or destruction of the binding region, or the DNA sequence of the quencher or a portion thereof (e.g., through polymerase-mediated cleavage or degradation) can inhibit the ability of the quencher to associate with the encoded particle, which can, in turn, limit the efficiency with which the quencher can inhibit the detectable code or signal of the encoded particle. As disruption of the association between a quencher and an encoded particle can increase the ability of a detector to detect the detectable code or signal of the encoded particle, amplification comprising polymerase-mediated cleavage or degradation of a binding region can indicate the presence of a target molecule in a compartmentalized volume. As a result, the distance between a quencher and an encoded particle or chromophore of a probe can be increased through a target molecule-dependent amplification step in a digital assay. As would be understood by a person of skill in the art, the roles and binding specificities of the target molecule and amplification product of the target molecule described for this mechanism (and illustrated in FIG. 6I) can be switched to the same effect. Furthermore, and as would be understood by a person of skill in the art, polymerase-mediate cleavage of a nucleic acid portion of a quencher (e.g., a nucleic acid portion of a quencher that is complementary to a binding region of a probe) during amplification can also reduce the association of the quencher with the encoded particle.

Amplification Comprising Inhibiting Self-Association of Binding Regions

In some cases, it is possible to increase the distance between a quencher and an encoded particle in a reversible fashion, without the need for cleavage/degradation of a linker. It can be carried out through reversible conformational changes in the linker that connects the quencher and encoded particle. In some cases, the quencher can be covalently attached to the binding region of a probe, which can also be covalently attached to an encoded particle of the probe. In some cases, a first portion of the binding region of the probe can hybridize with a second portion of the binding region. In some cases, hybridization of the first portion of a binding region with the second portion of the binding region (e.g., self-association or self-hybridization of the binding region) can cause the quencher to be in sufficiently close proximity to the encoded particle that the quencher partially or completely quenches the detectable code or signal of the encoded particle (e.g., as illustrated in FIG. 6B). In some cases, a first and/or second portion of a binding region capable of hybridizing with one another can be approximately 6 base pairs long. In some cases, the first and second portions of the binding region that are capable of hybridizing with one another can be located at the proximal and distal (i.e., 5' and 3') ends of the binding region, or vice versa. A third portion of the nucleic acid binding region, which can be located between the first and second portions of the binding region, can be complementary to the target molecule (or to an amplification product of the target molecule), and, upon hybridization with the target molecule (or amplification product of the target molecule), may form a double helical structure capable of preventing the binding region from self-hybridizing (e.g., into a hairpin structure). In some cases, the third portion of the binding region of the probe can be sufficiently longer than the first or second portions of the binding region (e.g., so that hybridization between the target molecule and third portion of the binding region is more thermodynamically favorable than the hybridization of the first portion of the binding region and the second portion of the binding region). In some cases, the third portion of the binding region can overlap with the first and/or second portion. During amplification, a target molecule present in the compartmentalized volume can be amplified, and the amplification product of the target molecule can further be amplified to produce molecules that comprise nucleic acid sequences identical to that of the target molecule. Thus, it is possible to produce sufficient quantities of the target molecule and/or amplification product of the target molecule to cause extension of the binding region of the probe and to separate the quencher from the encoded particle. As a result, it is possible to drive opening of a hairpin structure in a binding region of a probe connecting a quencher to an encoded particle through nucleic acid amplification in order to separate the quencher from the encoded particle. In some cases, this target molecule-dependent extension of the binding region can separate the quencher and encoded particle (or chromophore) of the probe by a large enough distance that the quencher is no longer able to inhibit the detectable code or signal of the probe. In some cases, the detectable code or signal can then be detected and a binary value reflecting the presence of the target molecule can be assigned to the compartmentalized volume.

In some cases, asymmetric amplification can be used to produce a preponderance of single stranded nucleic acid molecules complementary to first or second portion of the binding region of the probe in order to inhibit hairpin conformation of the binding region. Other amplification methods can also be used to produce single stranded RNA (such as NASBA) for inhibition of binding region self-hybridization.

Amplification Comprising Competitive Inhibition of Quencher Hybridization

Association of a quencher with an encoded particle can be inhibited through competitive inhibition of hybridization between a nucleic acid sequence of a binding region of a probe having a sequence complementary to that of the quencher. For example, as illustrated in FIGS. 6C-6E and 6G, the probe can comprise an encoded particle covalently linked to one or more binding region having a DNA sequence complementary to a DNA sequence of a quencher. In some cases, when the complementary DNA sequences of the quencher and binding region hybridize with one another, the quencher, and encoded particle can be brought into close enough proximity with one another to enable partial or complete quenching of the detectable code or signal (e.g., the fluorescence signal) produced by the encoded particle. In some cases, an encoded particle can be covalently bound to a plurality of binding regions capable of hybridizing with the DNA sequence of the quencher, which could increase the number of quenchers in close proximity to the encoded particle and improve quenching efficiency. In some embodiments, a binding region of a probe (or a portion thereof) can hybridize with a portion of a target molecule (or amplification product of a target molecule) and/or serve as a primer for the PCR-based amplification of the target molecule (or amplification product of the target molecule). For example, as illustrated in FIG. 6C, hybridization of a biding region to a target molecule (or amplification product of the target molecule) prior to an amplification step, wherein the binding region comprises a PCR primer (e.g., P1), can result in the extension of the primer and/or the amplification of the target molecule (or amplification product of the target molecule). The extended binding region can, in some cases, hybridize with a second primer present in the compartmentalized volume (e.g., an oligonucleotide PCR primer such as "P2," as illustrated in FIG. 6C) at a location of the binding region that was synthesized during the extension of the binding region (e.g., a portion of the extended binding region that is complementary to a portion of the target molecule located at the opposite end of the target molecule as the portion capable of binding the unextended binding region of the probe) and thus, P2 can then be extended creating a complementary sequence to the extended binding region much longer, and thus more stable during hybridization, than the nucleic acid sequence of the quencher. In some cases, all or nearly all of the binding regions functioning as P1 can be extended and hybridized to the complementary portion of the target molecule or amplification product. In some cases, the quantity of amplification products (e.g., molecules comprising a DNA sequence identical to or complementary to a portion of a target molecule) produced in a digital assay can greatly outnumber the quenchers in the compartmentalized volume. Because the amplification product can comprise a significantly longer hybridization region than either the unextended binding region of the probe or the nucleic acid sequence of the quencher, the quencher may be preferentially displaced from the binding region of the probe, thus inhibiting the association of the quencher with the encoded particle and inhibiting the fluorescence quenching. As a result, target molecule-dependent extension of the binding region of the probe and amplification of the target molecule (and/or the amplification product of the target molecule) can result in a reduced quenching of the detectable code or signal of an encoded particle.

Figure 6E:
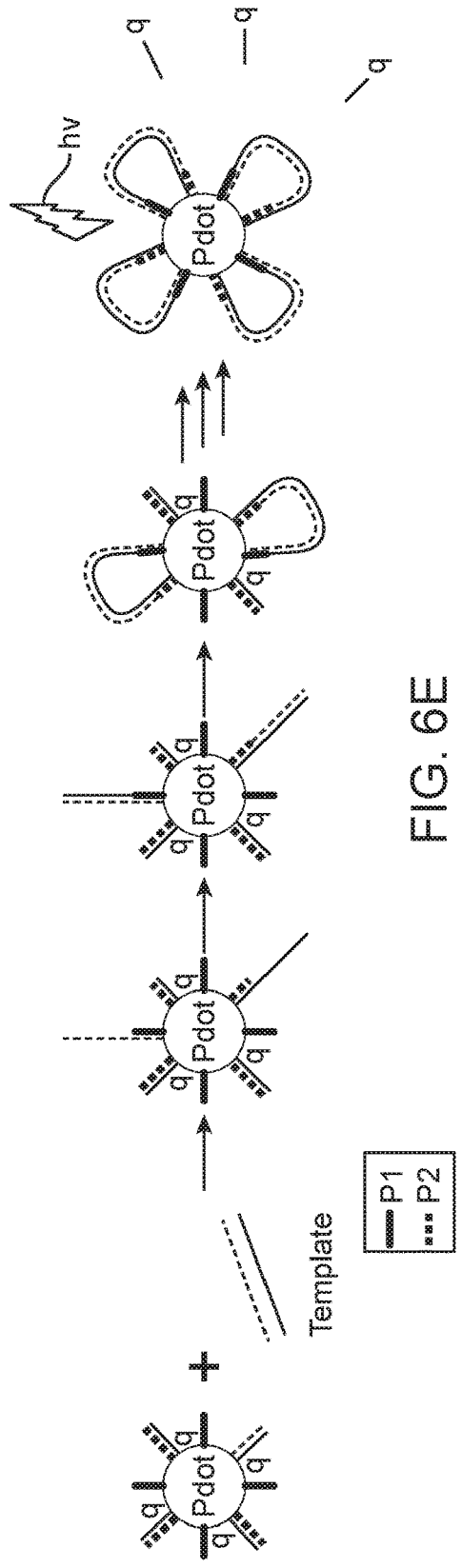
FIG. 6E shows a schematic diagram of steps in a digital nucleic acid amplification, such as digital PCR, comprising increasing the distance between a quencher and a probe through amplification and competitive hybridization, with intraprobe amplification and hybridization, in accordance with embodiments.

In some cases (e.g., as illustrated in FIG. 6E), the probe can comprise a plurality of distinct binding regions (e.g., unextended binding regions) that can each be PCR primer molecules (e.g., P1 and P2). In some cases, one or more of the binding regions can comprise a sequence complementary to a DNA sequence of a quencher. Each distinct binding region of the probe can also comprise a nucleic acid sequence complementary to a portion of the target molecule (or amplification product of the target molecule), which upon hybridization with the target molecule (or amplification product thereof), function as primers and be extended (e.g., during an amplification step of a digital assay). In some cases, an extended binding region (e.g., extended from P1) can now have a sequence that is complementary to the other type of binding region (e.g., P2). Upon hybridization, the P2 binding region can also be extended. Due to the close proximity of the different binding regions, this intraprobe hybridization can be efficient and lead to exponential intraprobe binding region extension and amplification. As a result, binding regions that are extended during an amplification step can comprise a nucleic acid sequence identical to or complementary to a portion of (e.g., a region or the entirety of) the target molecule or an amplification product of the target molecule. Therefore, an extended binding region of a probe can comprise a nucleic acid sequence complementary to a target molecule (or amplification product of a target molecule) that is longer than the nucleic acid sequence of the binding region that is complementary to the nucleic acid sequence of a quencher. As a result, the extended binding region of a probe can hybridize with the target molecule (or amplification products of the target molecule), which can inhibit quencher association with the encoded particle (e.g., through competitive inhibition). In this way, it is possible to increase the distance between a quencher and an encoded particle or chromophore of a probe by extending a binding region using a target molecule or amplification product thereof as a PCR template.

In some cases, the binding regions that function as primers can be the only sources of those primers (e.g., FIGS. 6C and 6E). In some cases, extra copies of the primers which are not covalently linked to the probe can also be in solution (e.g., FIG. 6G). In this case, the extra primer can facilitate amplification so that all probe molecules can be efficiently exposed to the target molecule or amplification product thereof.

In some cases, a quencher capable of associating with a binding region of a probe can comprise an oligonucleotide primer (e.g., a PCR primer). For example, and as illustrated in FIG. 6D, a quencher can associate with a binding region of a probe in a compartmentalized volume. The compartmentalized volume can also comprise a target molecule (or amplification product thereof), wherein a portion of a first end of a target molecule (or amplification product thereof) is capable of associating with the DNA sequence of the quencher. In some cases, the compartmentalized volume can also comprise a target molecule (or amplification product thereof), wherein a portion of a first end of a target molecule (or amplification product thereof) is capable of associating with the binding region of the probe. In some cases, and as further illustrated in FIG. 6D, an oligonucleotide primer (e.g., a PCR primer) capable of associating with a second end of the target molecule (or amplification product thereof) can be used to facilitate amplification of the target molecule. In this way, amplification products can be created during amplification steps of a digital assay capable of associating with the quencher. Because a great number of such amplification products can be created in this way during a digital assay, it is possible (e.g., through stoichiometrically competition) to cause the quenchers in a compartmentalized volume to associate with amplification products rather than the binding regions of a probe. Because the quencher itself can be a PCR primer, an amplification step of a digital assay can cause a quencher associated with an amplification product to extend using the amplification product as a template. By extending a quencher using an amplification product as a template, it is possible to further increase the proportion of quenchers associated with amplification products, as compared to those associated with the binding region of a probe. Thus, it is possible to increase the distance between a quencher and an encoded particle or chromophore of a probe in a target-molecule dependent fashion. In some cases, utilization of this method of target molecule-dependent modulation of a detectable signal or code can comprise providing excess quencher in a compartmentalized volume to ensure that the detectable signal or code is completely quenched in the absence of a target molecule or prior to amplification.

In some cases, a nucleic acid sequence of a quencher, a portion of a binding region of probe, or a free oligonucleotide in the compartmentalized volume can comprise a PCR primer for nucleic acid amplification in a digital assay. In some cases, any or all of these primer types may be present in the same compartmentalized volume and can comprise an identical or complementary nucleic acid sequence to one another.

Amplification Comprising Intra-Probe Hybridization or Inter-Probe Hybridization

Figure 6F:
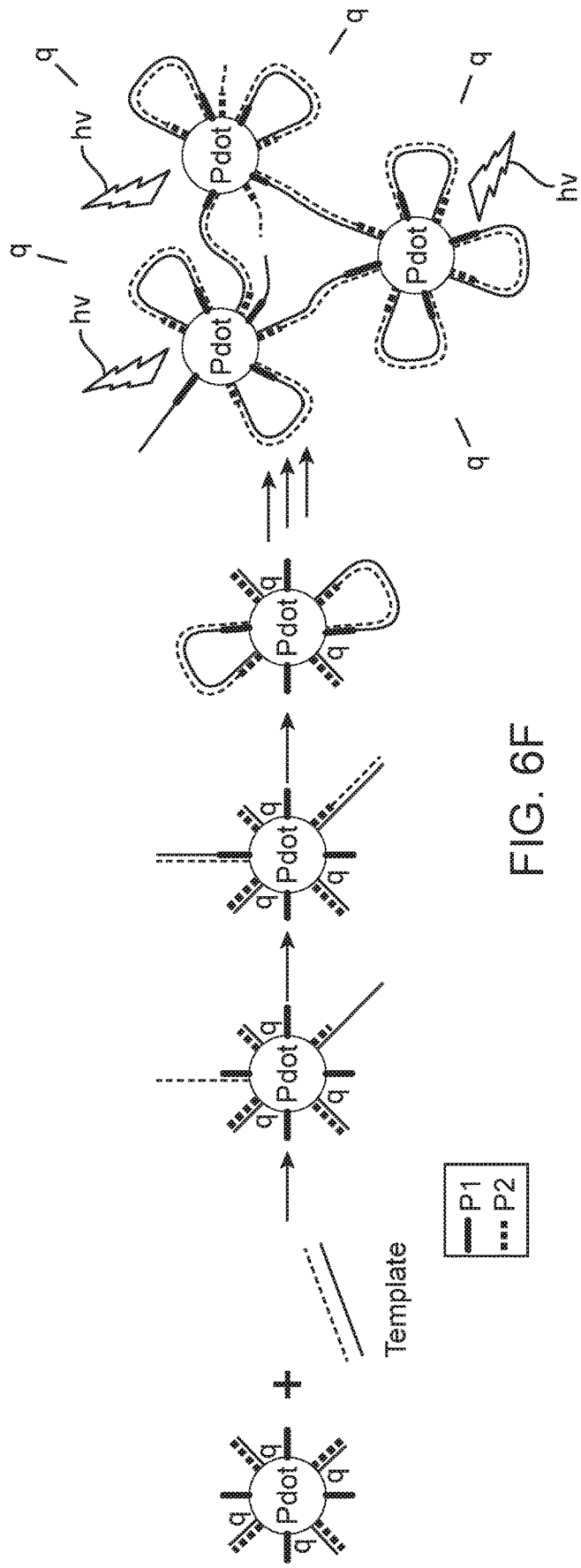
FIG. 6F shows a schematic diagram of steps in a digital nucleic acid amplification, such as digital PCR, comprising increasing the distance between a quencher and a probe through amplification and competitive hybridization, with intraprobe and inter-probe amplification and hybridization, in accordance with embodiments.

The distance between a quencher and an encoded particle or chromophore of a probe can be increased by associating a portion of a first binding region with a portion of a second binding region of the same probe. In some cases, the first binding region can have a different nucleic acid sequence as the second binding region (e.g., the probe can comprise two distinct binding regions). As described herein, a binding region of a probe (e.g., a first distinct binding region, a second distinct binding region, a third distinct binding region, etc.) can comprise a PCR primer. For example, as illustrated in FIG. 6E and FIG. 6F, a probe can comprise two distinct binding regions (e.g., two different types of binding regions). In some cases, the compartmentalized volume containing the probe can also comprise a plurality of quenchers. The plurality of quenchers of the compartmentalized volume can comprise one or more quencher capable of associating with each binding region of the probe. In some cases, the plurality of quenchers can comprise a plurality of distinct quenchers. In some cases, the compartmentalized volume can comprise a distinct quencher capable of associating with each distinct binding region of the probe. In some cases, a portion of a target molecule can associate with a first binding region of the probe. A portion of an amplification product of a target molecule can associate with a second binding region of the probe. In some cases, a first portion of a target molecule (or of an amplification product of the target molecule) is capable of associating with a first binding region of a probe and a second portion of the target molecule (or amplification product of the target molecule) is capable of associating with a second binding region of the probe. In some cases, the association of a target molecule or amplification product of a target molecule with a binding region of a probe can prevent a quencher from associating with the binding region. As illustrated in FIG. 6E and FIG. 6F, a target molecule or amplification product of a target molecule that is associated with a binding region of a probe can serve as a template (e.g., a PCR template) wherein the binding region can function as a primer and an extension of the binding region can occur. In some cases, a portion of a binding region extended during an amplification step (e.g., wherein the target molecule or the amplification product of the target molecule are used as the template for binding region extension) is capable of associating with another binding region of the same probe (e.g., as illustrated in FIG. 6E), resulting in intraprobe hybridization and amplification. In some cases, a portion of a binding region extended during an amplification step is capable of associating with a binding region, or extended binding region, of another probe (e.g., as illustrated in FIG. 6F), resulting in inter-probe hybridization. As further illustrated in FIG. 6F, a first portion of the plurality of binding regions of a first probe may associate with a second portion of the plurality of binding regions of the first probe, and a third portion of the plurality of binding regions of the first probe may associate with a portion of the binding regions of a second probe. In some cases, the binding regions of a probe can associate with (e.g., hybridize with or bind to) a plurality of other identical probes or a plurality of other distinct probes. In the mechanisms of target molecule-dependent amplification exemplified in both FIG. 6E and FIG. 6F, extension of a binding region using a target molecule (or amplification product thereof) can increase the distance between a quencher and an encoded particle or chromophore of a probe through competitive hybridization.

In some embodiments, inter-probe hybridization could occur spontaneously. For example, the conditions described above that are illustrated in 6E and 6G, could produce inter-probe hybridization (e.g., as illustrated in 6F and 6H respectively). This could occur because of stochastic variations in the exact number of each primer linked to each encoded particle and/or because of the stochastic variations regarding the exact pattern of internal hybridization of amplification products within a single encoded particle and the potential for some of the covalently linked amplification products not being able to pair with a complementary amplification product within the same encoded particle.

Figure 6G:
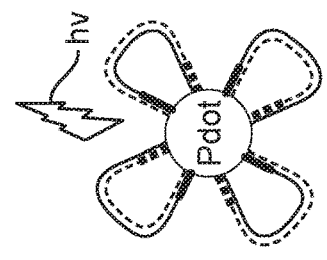
FIG. 6G shows a schematic diagram of steps in a digital nucleic acid amplification, such as digital PCR, comprising increasing the distance between a quencher and a probe through amplification and competitive hybridization, with boosted amplification from free primers, and intraprobe amplification and hybridization in accordance with embodiments.
Figure 6G:
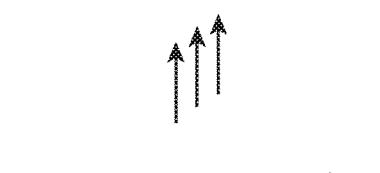
Figure 6G:
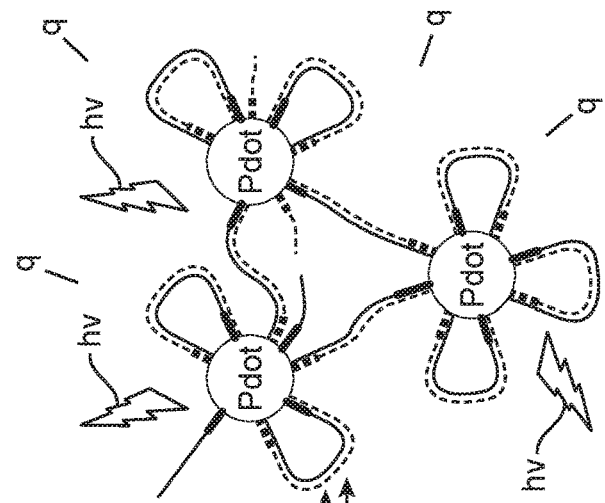
Figure 6G:
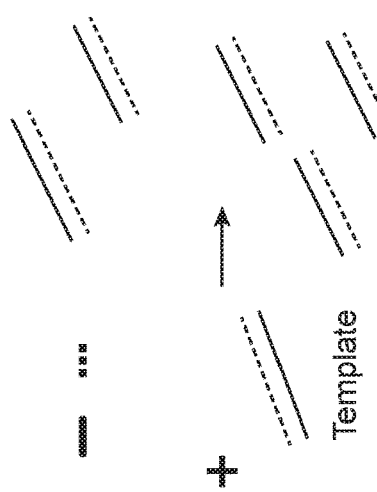
Figure 6G:
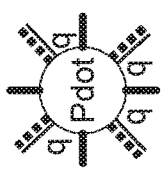
Figure 6H:
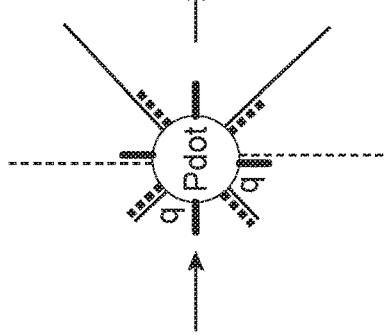
FIG. 6H shows a schematic diagram of steps in a digital nucleic acid amplification, such as digital PCR, comprising increasing the distance between a quencher and a probe through amplification and competitive hybridization, with boosted amplification from free primers, and intraprobe and inter-probe amplification and hybridization, in accordance with embodiments.
Figure 6H:
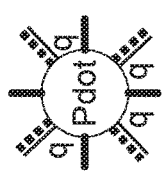
Figure 6I:
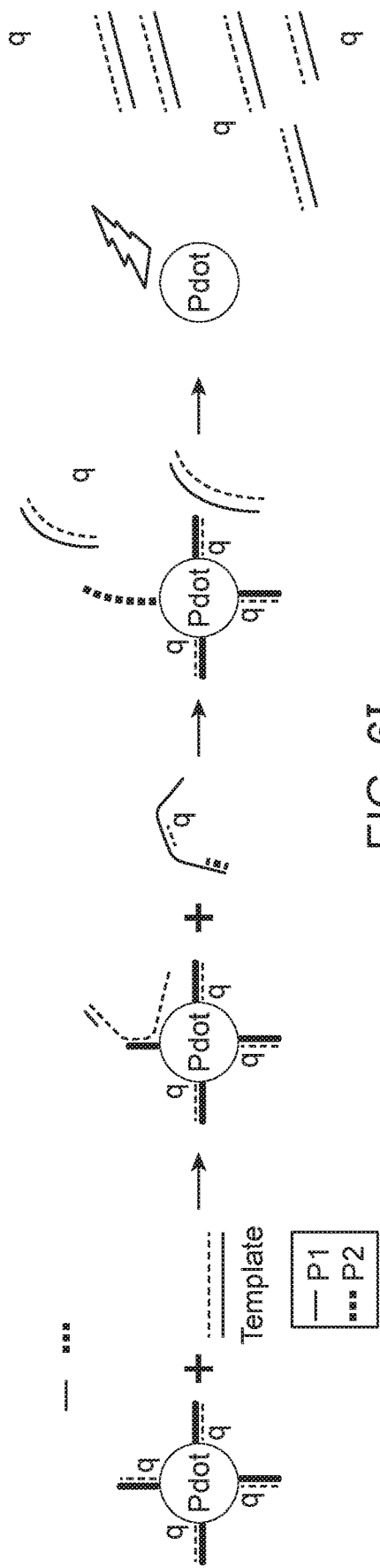
FIG. 6I shows a schematic diagram of steps in a digital nucleic acid amplification, such as digital PCR, comprising increasing the distance between a probe and a quencher through polymerase-induced molecular cleavage, in accordance with embodiments.

In some cases, additional forward and reverse PCR primers capable of recognizing and amplifying the target molecule can be provided in the compartmentalized volume in order to increase the efficiency with which the target molecule is amplified and the amplification product of the target molecule is produced (e.g., as illustrated in FIG. 6G and FIG. 6H). In some cases, the concentration of a target molecule can be increased through isothermal or thermal cycle amplification prior to association with a binding region of a probe and/or use as a template in binding region extension. By improving the efficiency with which copies of a target molecule or amplification product of the target molecule are produced, binding region extension can proceed more quickly, as the template for binding region extension is provided in the compartmentalized volume more efficiently. Therefore, "boosting" the production of binding region extension templates (e.g., copies of the target molecule and the amplification product of the target molecule) by increasing the concentration of PCR primers and/or pre-amplifying the target molecule can further improve the efficiency with which the binding regions of a probe are associated with one another or with the binding regions of one or more additional probe.

When inter-probe hybridization occurs, the production of signal can be based on a general increase in fluorescence signal, an increase in the size of the spot producing the fluorescent signal, or a combination of both. In some cases, where individual probes can be visualized, inter-probe hybridization can produce one, or a few, large aggregate signals, instead of many small signals generated from individual probe molecules.

Figure 6J:
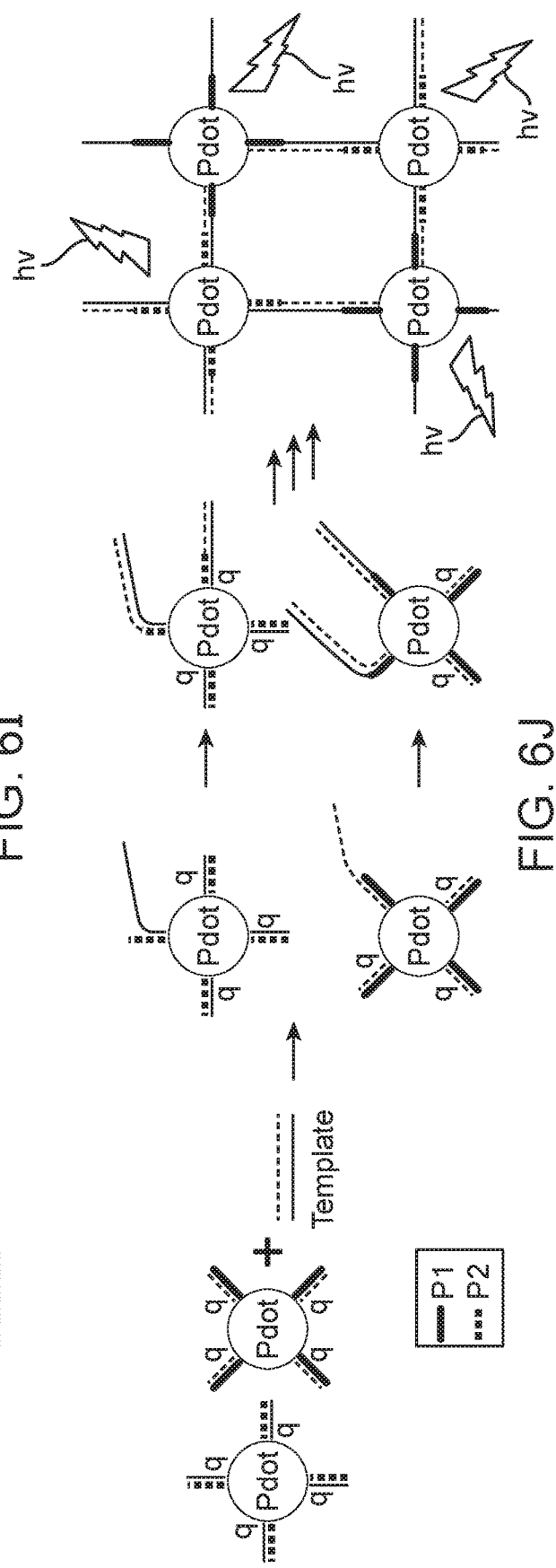
FIG. 6J shows a schematic diagram of steps in a digital nucleic acid amplification, such as digital PCR, comprising increasing the distance between a quencher and a probe through amplification and competitive hybridization, with inter-probe hybridization, in accordance with embodiments.

In some cases, a compartmentalized volume of a digital assay can comprise two distinct probes (e.g., a first distinct probe and a second distinct probe). The first distinct probe can comprise a binding region distinct from a binding region of the second distinct probe (e.g., a first distinct binding region and a second distinct binding region). In some cases, a binding region of a probe can comprise an amplification primer (e.g., a PCR primer). In some cases, a portion of a target molecule is capable of associating with (e.g., binding to or hybridizing with) the first distinct binding region. An amplification product of a target molecule can comprise a nucleic acid sequence, a portion of which can be capable of associating with the second distinct binding region. In either situation, a target molecule or amplification product thereof can serve as an amplification template for the extension of the first distinct binding region and/or the second distinct binding region of the first and second distinct probes, as illustrated in FIG. 6J. An amplification step of a digital assay can, therefore, comprise the extension of a first distinct binding region of a first distinct probe and/or the extension of a second distinct binding region of a second distinct probe. In some cases, a portion of the first distinct binding region synthesized during binding region extension of the first distinct probe can associate with a portion of the second distinct binding region. A portion of the second distinct binding region synthesized during binding region extension of the second distinct probe can, in some cases, associate with a portion of the first distinct binding region. If a compartmentalized volume also comprises a first quencher capable of associating with the first distinct binding region and/or a second quencher capable of associating with the second binding region (e.g., as illustrated in FIG. 6J), association of a first distinct binding region of a first probe and a second distinct binding region of a second probe following target molecule-dependent binding region extension, the first quencher and/or second quencher can be displaced from the first distinct binding region and/or the second distinct binding region. Therefore, the distance between a first quencher and the encoded particle of a first distinct probe or the distance between a second quencher and the encoded particle or chromophore of the second distinct probe can be increased via a target molecule-dependent amplification step. In some cases, the first quencher or second quencher can also be displaced by the association of a target molecule or an amplification product of the target molecule with the first distinct binding region or the second distinct binding region.

In some embodiments, the mechanism of inter-probe hybridization (e.g., the association or clustering of a plurality of probes or encoded particles) can be sufficient to produce a positive signal. In this case, as illustrated in FIG. 6L, no complementary sequences attached to quenching molecules are required. In some cases where individual probes can be imaged, the aggregation of probes through inter-probe hybridization results in a distinct clustering of the probes of interest. The size difference between many single probes, and one, or a few, large clusters/aggregates, in some cases, can provide a sufficient distinction to produce a positive signal, and no quenching is required.

In some cases, inter-probe hybridization can be preferentially induced by careful selection of the number and types of binding regions present on one or more probe in a compartmentalized volume (e.g., as illustrated in FIG. 6K). As described herein, a compartmentalized volume can comprise a plurality of distinct probes, and a probe can comprise a plurality of distinct binding regions. In some cases, a first distinct probe can differ from a second distinct probe in the ratio of distinct binding regions comprising each distinct probe, as illustrated in FIG. 6K. For example, a first distinct probe can comprise a 60:40 ratio of first distinct binding regions to second distinct binding regions while a second distinct probe can comprise a 40:60 ratio of first distinct binding regions to second distinct binding regions. In some cases, the ratio of a first distinct binding region to a second distinct binding region on a probe can be from about 1:1000 to about 1:100, from about 1:100 to about 1:10, from about 1:10 to about 1:5, from about 1:5 to about 1:4 (e.g., 20:80), from about 1:4 to about 1:3 (e.g., 25:75), from about 1:3 to about 1:1 (e.g., 50:50), from about 2:3 (e.g., 40:60) to about 3:2 (e.g., 60:40), from about 1:1 to about 3:1 (e.g., 75:25), from about 3:1 to about 4:1 (e.g., 80:20), from about 4:1 to about 5:1, from about 5:1 to about 10:1, from about 10:1 to about 100:1, or from about 100:1 to about 1000:1. In certain aspects, the ratio of a first binding region to a second binding region on a first distinct probe is about 1 times, about 1.05 times, about 1.1 times, about 1.2 times, about 1.3 times, about 1.4 times, about 1.5 times, about 1.6 times, about 1.7 times, about 1.8 times, about 1.9 times, about 2 times, about 4 times, about 5 times, about 6 times, about 7 times, about 8 times, about 9 times, about 10 times, about 20 times, about 30 times, about 40 times about 50 times, about 60 times, about 70 times about 80 times, about 90 times, or about 100 times that of the first binding region to the second binding region on a second distinct probe. As described herein, a quencher, a target molecule (or portion thereof), or amplification product of a target molecule (or portion thereof) can associate with a binding region of a probe. In some cases, a target molecule or amplification product of a target molecule can function as a PCR amplification template in the extension of a binding region during an amplification step of a digital assay. In some cases, an extended binding region of a probe can associate with a binding region of the same probe or of a different probe, as illustrated in FIG. 6J and FIG. 6K. In some cases, association of an extended binding region of a first probe with the binding region of a second probe can facilitate probe network formation. If, for example, a first distinct probe comprises first and second distinct binding regions at a ratio of 60:40, and a second distinct probe comprises the first and second distinct binding regions at a ratio of 40:60 the compartmentalized volume may comprise more binding region associations between probes (e.g., versus associations of binding regions on the same probe) as compared to a plurality of probes comprising a 50:50 ratio of first distinct binding regions to second distinct binding regions, following amplification in a digital assay. That is, it is possible to limit the number of probes that do not comprise probe-to-probe binding regions in a digital assay by controlling the ratio of distinct binding regions in a probe. Thus, the ratio of first distinct binding regions to second distinct binding regions on two probes of a compartmentalized volume can affect the detected intensity and spatial distribution of a detectable signal or code in the compartmentalized volume of a digital assay (e.g., as a result of different degrees of inter-probe association).

In some cases, a probe can comprise a first distinct binding region and a second distinct binding region. In some cases, the first distinct binding region is not capable of associating with the second distinct binding region. For example, a first distinct binding region may not be able to associate with any portion of a second binding region. That is, a first distinct binding region may comprise a nucleic acid sequence that is not complementary to any portion of the second distinct binding region. In some cases, however, a target molecule, an amplification product of a target molecule, or both may be able to associate with a portion of the first distinct binding region. That is, a target molecule, an amplification product of a target molecule, or both can comprise a nucleic acid sequence complementary to a portion of the first distinct binding region. A target molecule, an amplification product of a target molecule, or both may be able to associate with a portion of a second distinct binding region. That is, a target molecule, an amplification product of a target molecule or both can comprise a nucleic acid sequence complementary to a portion of the second distinct binding region. In some cases, a plurality of regions of a target molecule, an amplification product of a target molecule or both may be capable of associating with (e.g., binding to or hybridizing with) a first distinct binding region. In some cases, a plurality of regions of a target molecule, an amplification product of a target molecule or both may be capable of associating with (e.g., binding to or hybridizing with) a second distinct binding region. Thus, a target molecule, an amplification product of a target molecule, or both can facilitate the formation of a network of probes by associating with a first distinct binding region of two identical probes comprising a plurality of distinct binding regions, a second distinct binding region of two identical probes comprising a plurality of distinct binding regions, or a first distinct binding region of a first probe and a second distinct binding region of a second probe that is identical to the first probe. Such target molecule-dependent probe network formation can reflect the presence of a target molecule in a compartmentalized volume and can be measured or determined by an increase in signal or code intensity or in signal or code spatial size. In some cases, amplification of a target molecule in the compartmentalized volume can facilitate formation of such a probe network. In some cases, a portion of a first binding region can comprise a nucleic acid sequence complementary to that of a second binding region. In some cases, the formed network of probes does not contain quencher molecules or the mechanism does not involve quencher molecules (e.g., FIG. 6L).

The formation of a network of probes (e.g., inter-probe hybridization, such as illustrated in FIG. 6F, FIG. 6H, FIG. 6J, FIG. 6K, and FIG. 6L) can also improve the efficiency of signal detection in a digital assay. For example, inter-probe hybridization can result in clustering or spatial concentration of probes (and thus, the detectable code or signals of the probes) in a compartmentalized volume. Clustering or spatial concentration of detectable codes or signals in a compartmentalized volume can increase the ability of a detector to detect the detectable code or signal in a compartmentalized volume (e.g., by increasing the overall apparent intensity of the detectable code or signal within the compartmentalized volume as a whole). As a result, it can be advantageous to employ target molecule-dependent amplification methods that employ inter-probe hybridization, as described herein, in applications involving multiplexed digital assay approaches.

In some cases, a digital assay comprising nucleic acid amplification can comprise both intra-probe hybridization (e.g., hybridization of a first distinct binding region of a probe with a second distinct binding region of the probe) and inter-probe hybridization (e.g., hybridization of a binding region of a first distinct probe with a binding region of a second distinct probe).

Amplification Comprising Rolling Circle Amplification

Figure 6M:
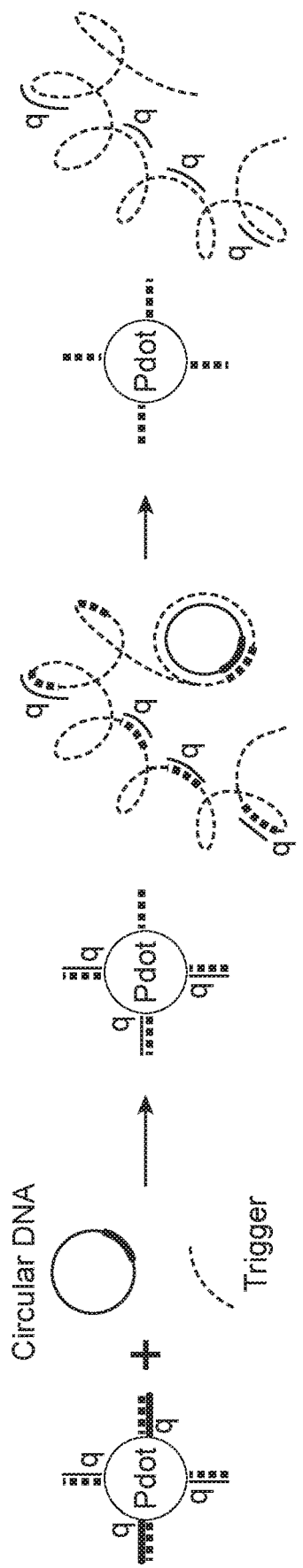
FIG. 6M shows a schematic diagram of steps in a digital nucleic acid amplification, such as digital PCR, comprising rolling circle amplification, in accordance with embodiments.
Figure 7A:
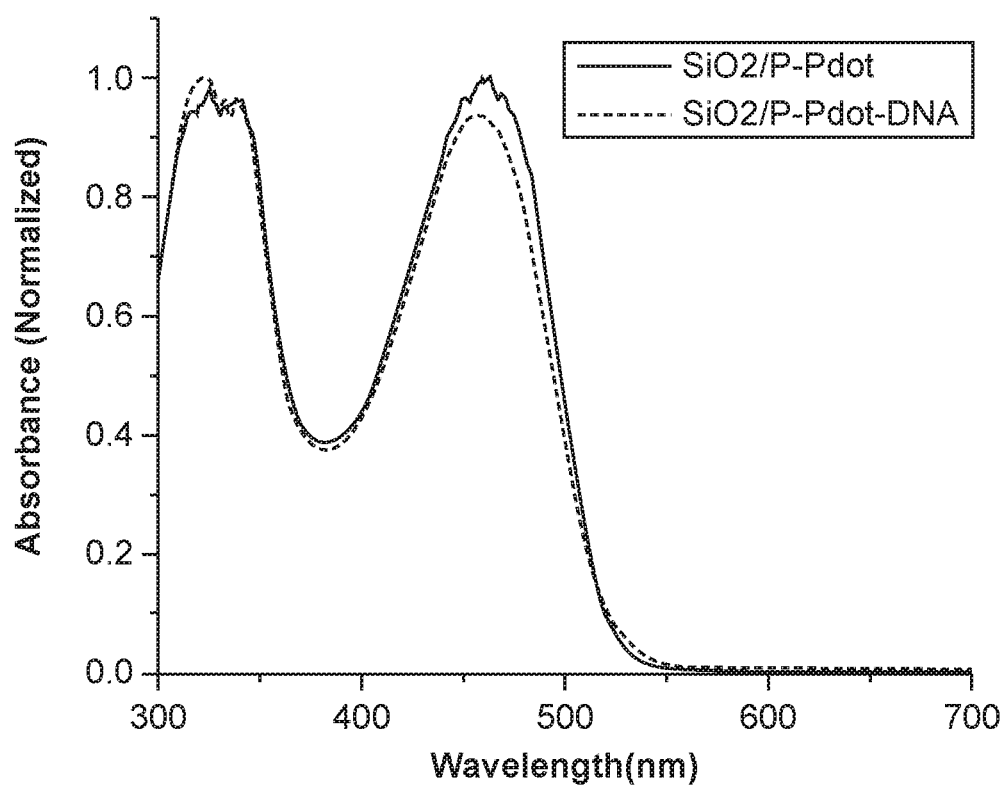
FIG. 7A shows absorption spectra of $SiO_2$/Polymer-Pdots (solid line) and $SiO_2$/Polymer-Pdot-DNA (dashed line), in accordance with embodiments.
Figure 7B:
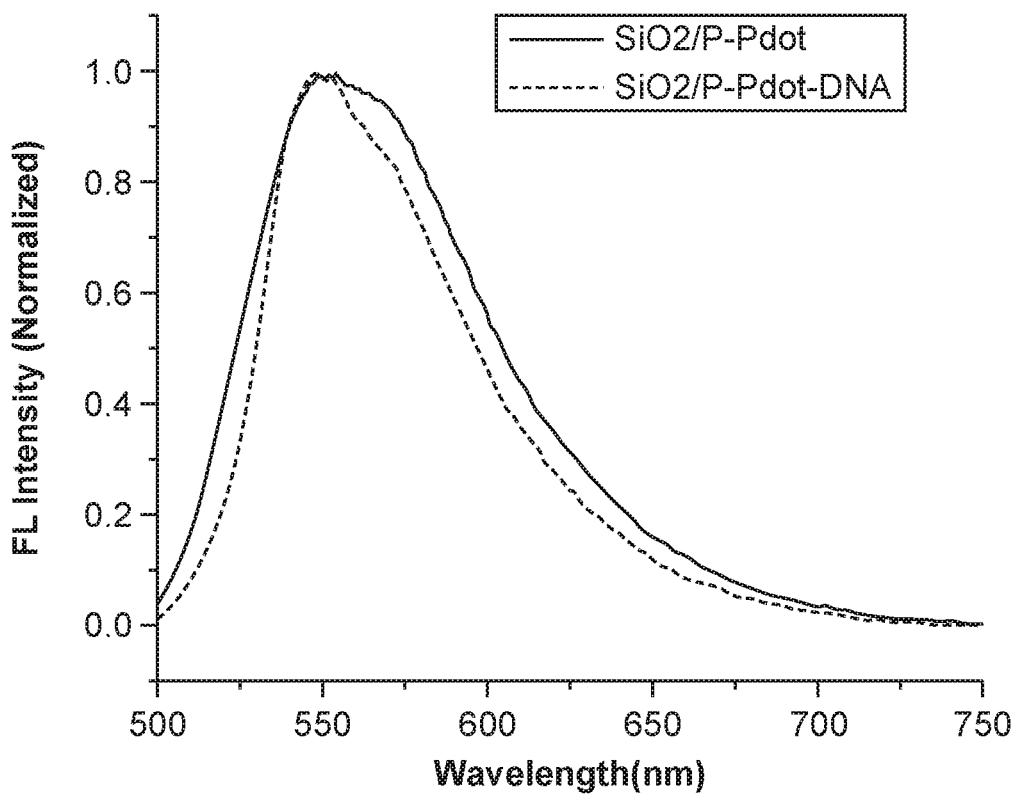
FIG. 7B shows emission spectra of $SiO_2$/Polymer-Pdots (solid line) and $SiO_2$/Polymer-Pdot-DNA (dashed line), in accordance with embodiments.
Figure 8A:
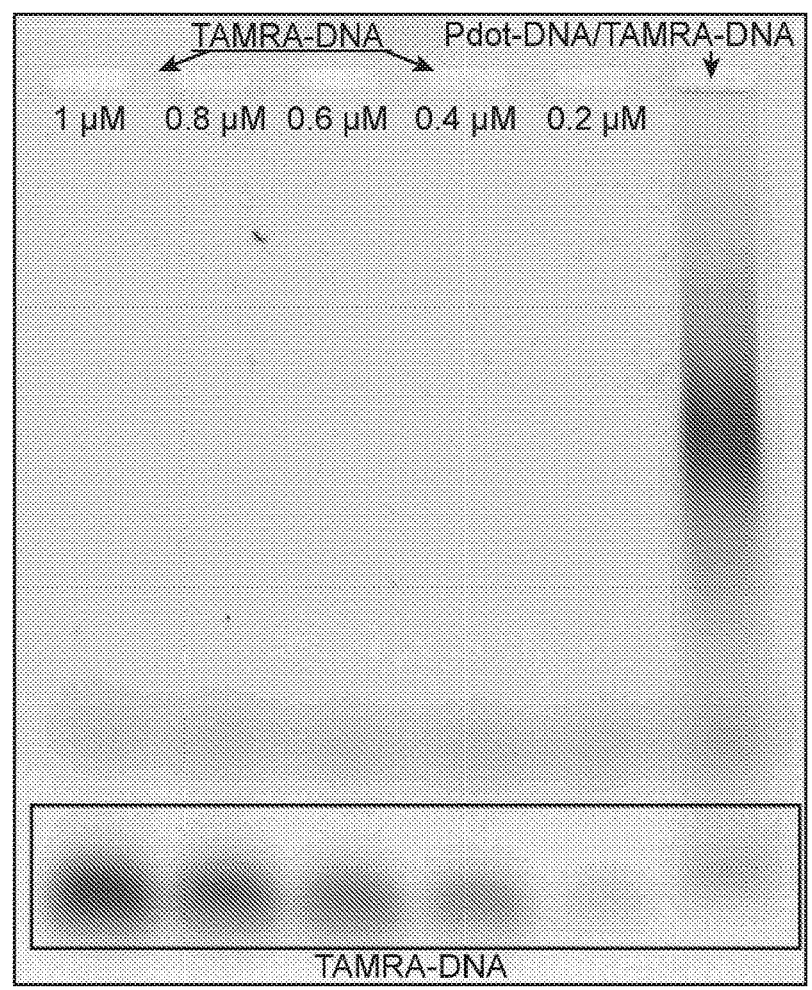
FIG. 8A shows a relationship of hybridized dye-conjugated DNA (TAMRA-DNA) concentration per $SiO_2$/Polymer-Pdot-DNA nanoparticle to detected fluorescent emission, in accordance with embodiments.
Figure 8B:
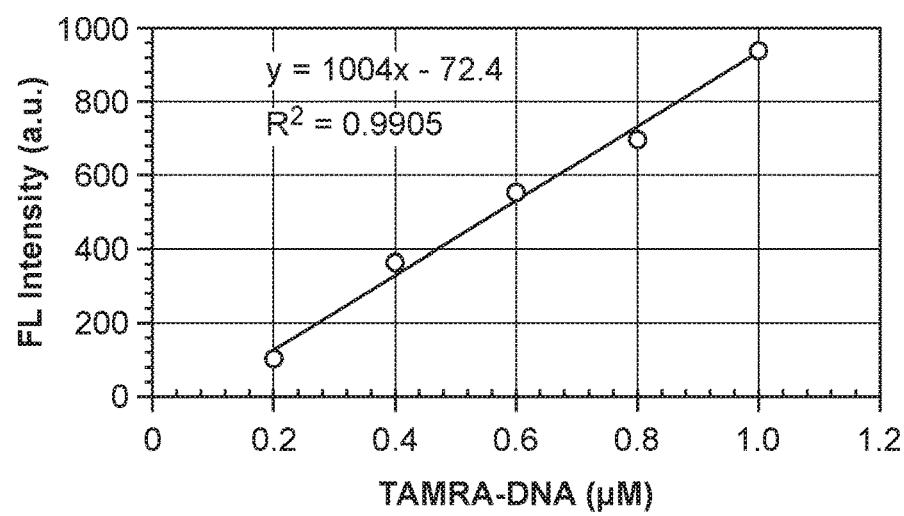
FIG. 8B shows calculated values illustrating a relationship of hybridized dye-conjugated DNA (TAMRA-DNA) concentration per $SiO_2$/Polymer-Pdot-DNA nanoparticle to detected fluorescent emission, in accordance with embodiments.
Figure 9C:
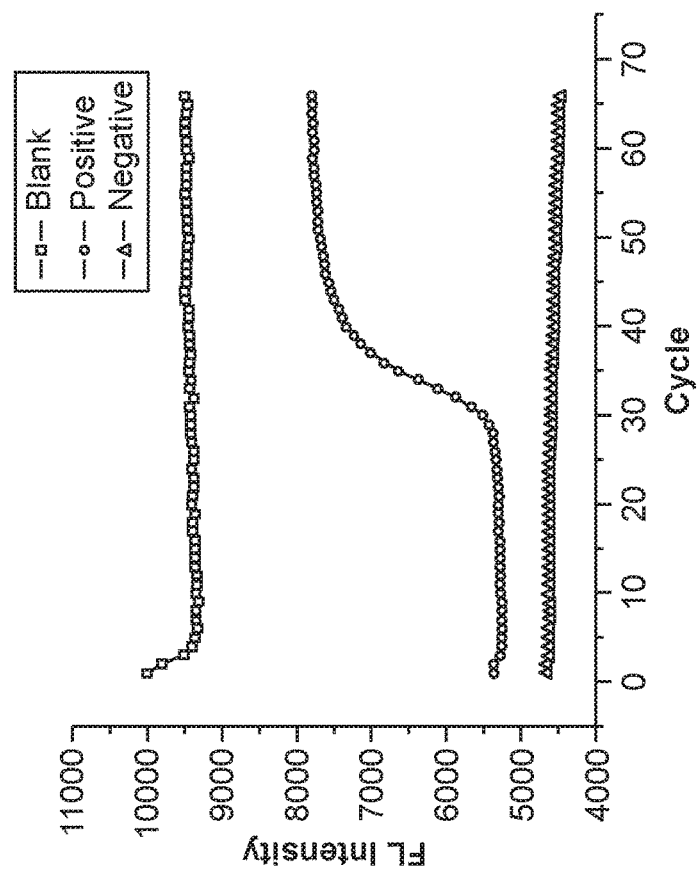
FIG. 9C shows raw data recorded during a PCR assay, in accordance with embodiments.
Figure 9A:
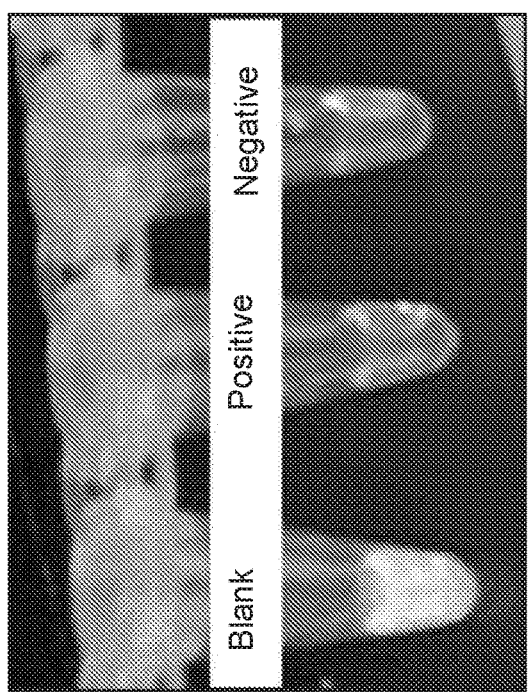
FIG. 9A shows compartmentalized volumes of a PCR assay prior to amplification, in accordance with embodiments.
Figure 9B:
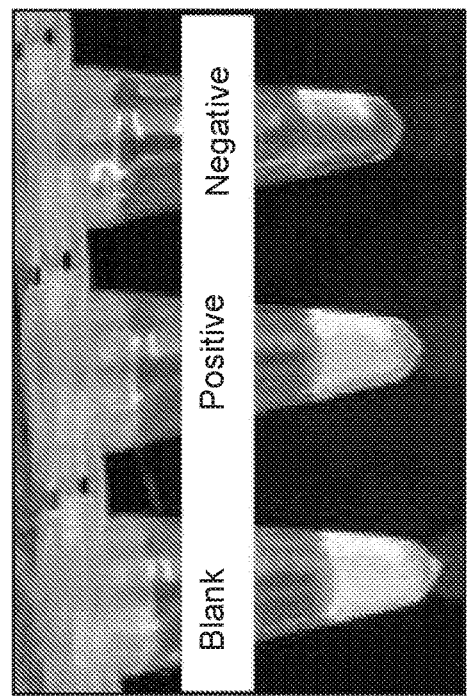
FIG. 9B shows compartmentalized volumes of a PCR assay after amplification, in accordance with embodiments.
Figure 9D:
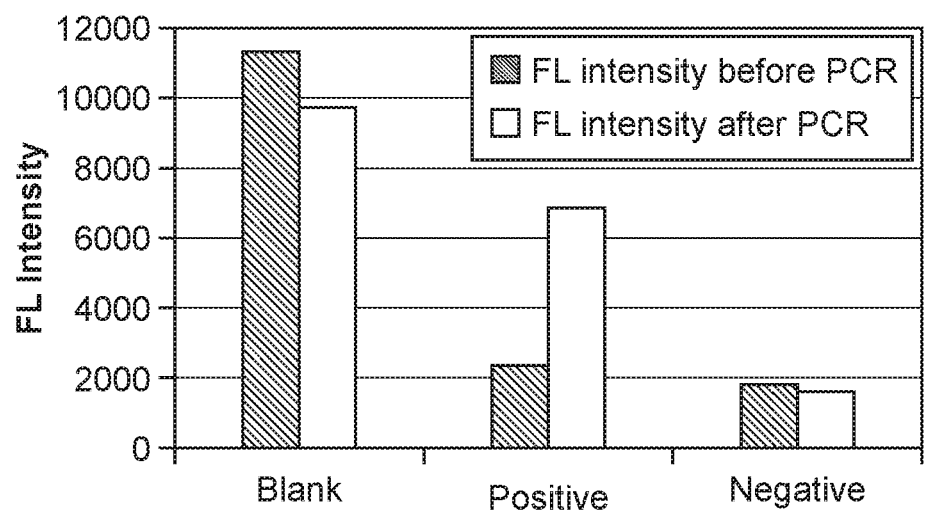
FIG. 9D shows analyzed data from PCR assays, in accordance with embodiments.
Figure 9E:
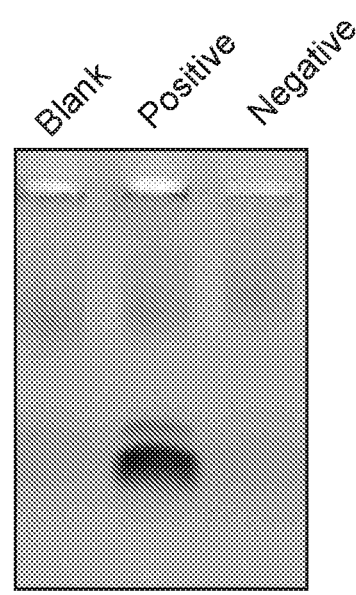
FIG. 9E shows a fluorescence image of a 1% agarose gel loaded with samples from a PCR assay, in accordance with embodiments.
Figure 10A:
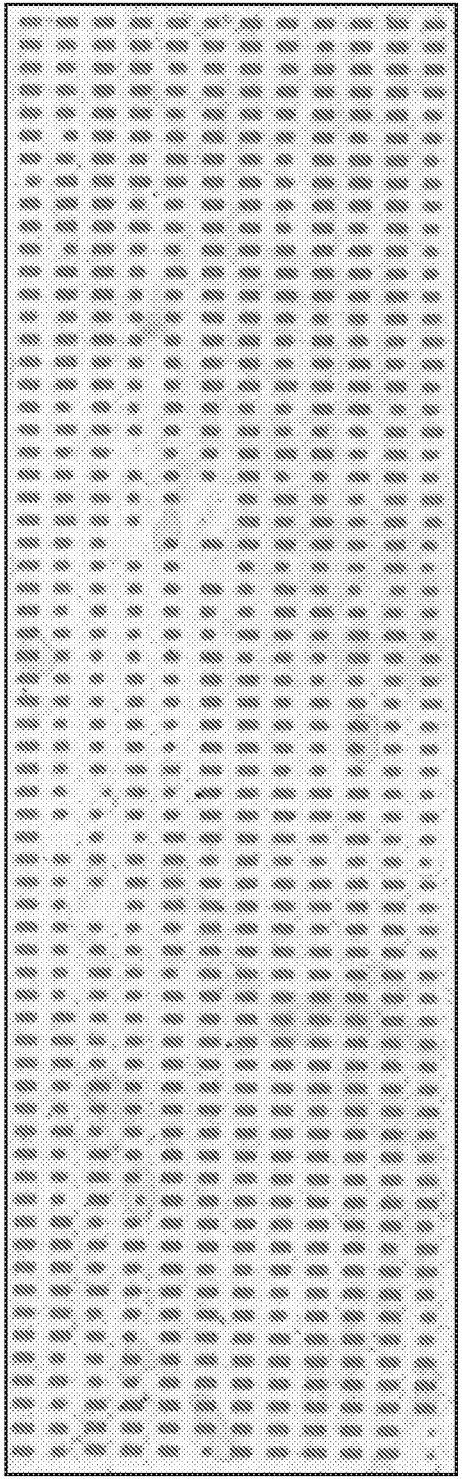
FIG. 10A shows compartmentalized volumes of a digital PCR assay prior to amplification, in accordance with embodiments.
Figure 10B:
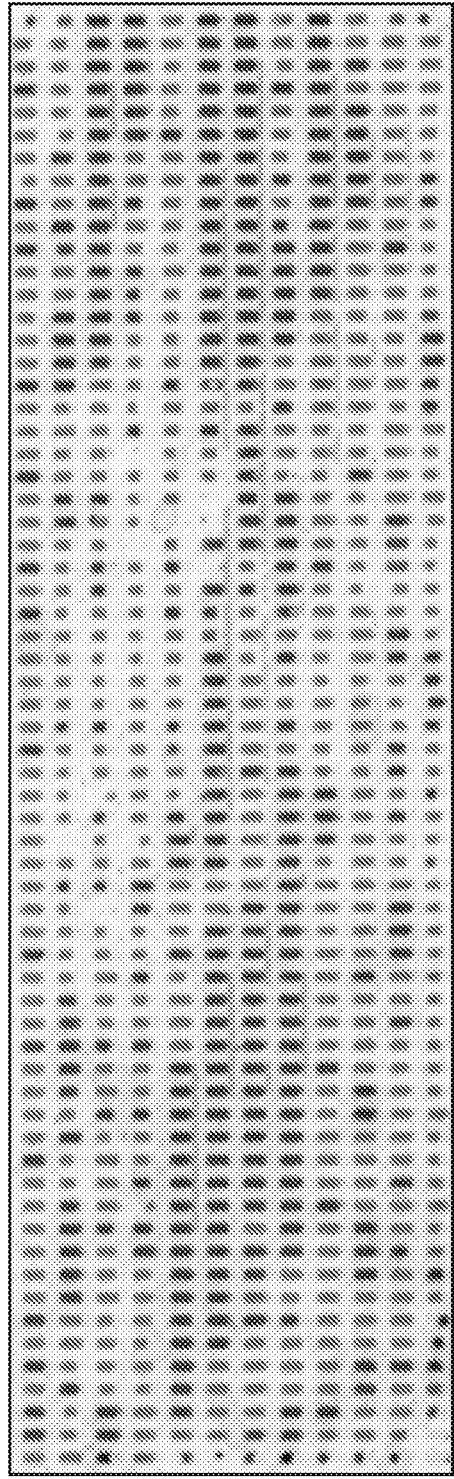
FIG. 10B shows compartmentalized volumes of a digital PCR assay after amplification, in accordance with embodiments.

A compartmentalized volume can comprise a circularized nucleic acid molecule. In some cases, each compartmentalized volume of a plurality of compartmentalized volumes comprises a circularized nucleic acid molecule. In some cases, the circularized nucleic acid molecule can comprise a nucleic acid sequence identical to a nucleic acid sequence of a quencher and complementary to a nucleic acid sequence of a binding region of a probe or portion thereof. In embodiments such as this, the quencher, having a nucleic acid sequence complementary to a portion of the binding region of the probe as well, can associate with the binding region of the probe. In some cases, detection of the detectable code or signal of the probe can be inhibited when the quencher is associated with (e.g., is bound to or is hybridized with) the binding region of the probe. In some cases, a trigger molecule, which can comprise a PCR primer capable of hybridizing with a portion of the circularized nucleic acid molecule, can be provided in the compartmentalized volume as well. The trigger molecule can be a target molecule or a portion thereof, an amplification product of a target molecule or a portion thereof, or another molecule associated with the presence of a target molecule. During an amplification step of a digital assay, the trigger molecule can facilitate rolling circle amplification of the circularized nucleic acid molecule. The amplification product of the rolling circle amplification can comprise a nucleic acid sequence complementary to the quencher. The amplification product of the rolling circle amplification can comprise a plurality of nucleic acid sequences complementary to the quencher. As a result, the quencher can associate with the amplification product of the rolling circle amplification reaction instead of the binding region of the probe, increasing the distance between the quencher and the encoded particle or chromophore of the probe. The amplification product of the rolling circle amplification reaction can also associate with the binding region of the probe, competitively inhibiting association of the quencher with the binding region of the probe. Thus, a target molecule-dependent rolling circle amplification reaction can be used in a digital assay to increase the distance between a quencher and an encoded particle or chromophore of a probe, as illustrated in FIG. 6M. Target molecule-dependent rolling circle amplification can, therefore, be used to indicate the presence or absence of a target molecule in a compartmentalized volume.

A digital assay can comprise increasing, decreasing or maintaining the temperature of a compartmentalized volume. In some cases, an amplification step of a digital assay can comprise increasing and decreasing, increasing and maintaining, or decreasing and maintaining the temperature of a compartmentalized volume. For example, an amplification step of a digital assay can comprise heating a compartmentalized volume from room temperature to a temperature of about 95° C. or from a temperature of about 68° C. to a temperature of about 95° C. An amplification step can also comprise decreasing the temperature of a compartmentalized volume from about 95° C. to a temperature within the range from about 45° C. to about 68° C. An amplification step can also comprise increasing the temperature of a compartmentalized volume from temperature value within the range from about 45° C. to about 68° C. to a temperature of about 95° C.

In some cases, the steps of increasing, decreasing, or maintaining the temperature of a compartmentalized volume can be repeated one or more times. That is, a digital assay can comprise one or more thermal cycle sequence (e.g., temperature cycle), wherein a thermal cycle sequence comprises a sequence of increasing, decreasing, or maintaining (or any sequence of any combination thereof) the temperature of a compartmentalized volume. In some cases, a digital assay can comprise a plurality of distinct thermal cycles. That is, a digital assay can comprise one or more instance of a first thermal cycle sequence and one or more instance of a second thermal cycle sequence. In some cases, a digital assay can comprise at least 2, at least 5, at least 10, at least 15, at least 20, at least 25, at least 30, at least 35, at least 40, or at least 45 temperature cycles. In some cases, a digital assay can comprise from 2 to 5, from 5 to 10, from 10 to 15, from 15 to 20, from 20 to 25, from 25 to 30, from 30 to 35, from 35 to 40, or from 40 to 45 temperature cycles.

Any digital assay comprising an amplification step can comprise providing PCR reagents in each compartmentalized volume of a plurality of volumes. In some cases, only a portion of the compartmentalized volumes of a plurality of compartmentalized volumes comprises PCR reagents. PCR reagents provided in a compartmentalized volume can include primers, nucleotides, a polymerase, and/or a buffer.

A digital assay can comprise a variety of methods of digital nucleic acid analysis. In various aspects, the present disclosure provides methods, devices, and systems for amplification by performing digital nucleic acid amplification. In various aspects, the present disclosure provides methods, devices, and systems for amplification by performing digital PCR (dPCR). Digital PCR is a method in which individual nucleic acid molecules present in a sample are distributed to many separate reaction volumes (e.g., compartmentalized volumes, which can be located in the chambers or wells or droplets of a microfluidic chip or multi-well plate) prior to PCR amplification of one or more target sequences. The concentration of individual molecules in the sample is adjusted so that at least some of the reaction volumes contain no target molecules and at least some of the reaction volumes contain at least one target molecule. Amplification of a target sequence results in a binary digital output in which each chamber is identified as either containing or not containing the PCR product indicative of the presence of the corresponding target sequence. A count of reaction volumes containing detectable levels of PCR end-product is a direct measure of the absolute nucleic acids quantity. In various aspects of the present disclosure, nucleic acid samples are distributed by partitioning them into separate reaction volumes (e.g., compartmentalized volumes). In some cases, the digitized samples can then be thermocycled (e.g., subjected to cyclical application of thermal energy) in the presence of PCR reagents, thereby facilitating the amplification of the nucleic acid sample.

In some aspects, the apparatus, devices, methods and systems of the present disclosure can be used to amplify a polynucleotide sample, such as with polymerase chain reaction (PCR), reverse transcriptase PCR (RT-PCR), ligase chain reaction (LCR), loop mediated amplification (LAMP), reverse transcription loop mediated amplification (RT-LAMP), helicase dependent amplification (HDA), reverse transcription helicase dependent amplification (RT-HDA), recombinase polymerase amplification (RPA), reverse transcription recombinase polymerase amplification (RT-RPA), catalytic hairpin assembly reactions (CHA), hybridization chain reaction (HCR), entropy-driven catalysis, strand displacement amplification (SDA), and/or reverse transcription strand displacement amplification (RT-SDA). In certain aspects, the apparatus, devices, methods and systems of the present disclosure can be used for nucleic acid sequence based amplification (NASBA), transcription mediated amplification (TMA), self-sustained sequence replication (3 SR), and single primer isothermal amplification (SPIA). Other techniques that can be used include, e.g., signal mediated amplification of RNA technology (SMART), rolling circle amplification (RCA), hyper branched rolling circle amplification (HRCA), exponential amplification reaction (EXPAR), smart amplification (SmartAmp), isothermal and chimeric primer-initiated amplification of nucleic acids (ICANS), and multiple displacement amplification (MDA). Other aspects, the apparatus, devices, methods, and systems of the present disclosure can include the manipulation and/or analysis of cells (e.g., rare cells or single cells), the manipulation and/or analysis of other biological particles (e.g., isolated mitochondria, bacteria, viral particles), or other biological or chemical components.

Isothermal Assays

In some cases, a digital assay or portion thereof can comprise an isothermal step, reaction, or assay. An isothermal step, reaction, or assay can comprise maintaining one or more compartmentalized volume of a plurality of compartmentalized volumes at a certain temperature, above a certain temperature, or below a certain temperature.

In a further aspect of the present disclosure, the methods, systems and devices described herein can be applied to isothermal amplification techniques, such as digital nucleic acid sequence-based amplification (NASBA) and loop-mediated isothermal amplification (LAMP). NASBA and LAMP are isothermal amplification schemes that have been developed to complement PCR.

In an isothermal amplification, temperature cycling can be not required or not permitted. Isothermal amplification can comprise isothermal nucleic acid amplification. There are several types of isothermal nucleic acid amplification methods such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification.

Nucleic acid sequence based amplification (NASBA) is an isothermal method of amplification that can be performed, for example, at about 40° C. NASBA can comprise: high amplification efficiency and fast amplification kinetics, wherein greater than a thousand-fold amplification can be achieved within an hour or two; low false positive rates; and a lesser need to control temperature and feedback needed compared to PCR. The fact that NASBA is an isothermal method makes it possible to run multiple samples simultaneously with the use of a temperature controlled oven, which is an important practical advantage in many applications.

Loop-mediated isothermal amplification (LAMP), is an isothermal amplification assay capable of amplifying DNA with high specificity, efficiency, and rapidity (e.g., at around 60° C.). Because of the characteristics of its amplification reaction, LAMP can allow the discrimination of single nucleotide differences during amplification. As a result, LAMP can distinguish between samples comprising molecules that are very similar to but different than the target molecule, such as genetic testing applications. LAMP has also been shown to have about 10 fold higher sensitivity then RT-PCR in the detection of viruses. In one aspect, the present disclosure provides a method for performing digital loop-mediated amplification of a sample. The method can include producing a plurality of compartmentalized volumes of the sample on a microfluidic device, wherein at least one compartmentalized volume in the plurality comprises a nucleic acid molecule (e.g., a DNA and/or a RNA molecule); and performing loop-mediated amplification in the at least one compartmentalized volume to produce amplified product of the nucleic acid molecule. The method can also include detecting the amplified product. In some aspects, the method includes determining a number of compartmentalized volumes in the plurality that comprise the amplified product; and calculating a concentration of the nucleic acid molecule in the sample using individual volumes of the compartmentalized volumes in the plurality and the number of compartmentalized volumes in the plurality that contain the nucleic acid molecule. The microfluidic device can include a plurality of chambers configured to form the plurality of compartmentalized volumes.

Rolling circle amplification (RCA) can be an isothermal nucleic-acid amplification method. RCA can differ from polymerase chain reaction (PCR) and other nucleic-acid amplification schemes in several respects. A target molecule can act as a trigger molecule and/or primer for a rolling circle amplification reaction. The trigger molecule or a portion thereof can anneal to a small circular DNA template, and a DNA polymerase can be added to extend the primer. The DNA polymerase can extend the primer continuously around the circular DNA template generating a long DNA product that can consist of many repeated copies of the circle. By the end of a reaction, the polymerase is capable of generating many thousands of copies of the circular template.

By using arrays of compartmentalized volumes of different sizes, the dynamic range of digital measurements employing NASBA, LAMP, and/or RCA can be increased. The methods and systems described herein can utilize these amplification schemes for measurement and quantitation of the presence of RNA and DNA in a compartmentalized sample (e.g., a sample separated into compartmentalized volumes). In another aspect, the method can be applied to specific molecule recognition based amplification.

Melt-Curve Analysis

Another aspect of the disclosure comprises methods and systems for determining the presence of genetic variations between target molecules through melt-curve analysis. A genetic variation can comprise a genetic mutation, a genetic polymorphisms, or an epigenetic difference between two molecules (e.g., between a control molecule and a target molecule). In some cases, melt-curve analysis can be used to detect, to validate, or to identify engineered or de novo mutations, to test for zygosity, to examine epigenetic state of a nucleic acid molecule, or to diagnose a patient's condition based on the presence of a genetic sequence. For example, melt-curve analysis testing can be used to rapidly identify the species, strain, or subtype of virus with which a patient has been suspected of been infected. Diagnosing a patient can be based on the presence, absence, identity, or sequence of a target molecule, as determined by melt-curve analysis or using any other method or system described herein. Melt-curve analysis can be temporal melt-curve analysis or spatial melt-curve analysis.

The principle of melt-curve analysis lies in the differences in melt-curve kinetics between two double-stranded nucleic acid pairs. As in PCR cycling, a hybridized pair of nucleic acids will begin to melt, or disassociate with one another, as they are heated in melt-curve analysis. The rate at which the nucleic acids disassociate with one another can depend on, e.g., the relative content of adenine-thymine (A-T) pairs and guanine-cytosine (G-C) pairs that comprise the hybridized nucleic acid pair. Since G-C pairs share more hydrogen bonds than A-T pairs, a G-C pair may take slightly longer to melt than an A-T pair, as observed during temporal melt-curve analysis, when melting is monitored at high resolution and in real time. In the case of spatial melt-curve analysis, a static temperature gradient (e.g., a spatial temperature gradient) can be established across an array of compartmentalized volumes (e.g., wells, cavities, chambers, digitized volumes, or droplets on a chip or tubes in a series). A temperature gradient across a plurality of compartmentalized volumes can result in a linear or nonlinear distribution of temperatures in the compartmentalized volumes (e.g., a linear or nonlinear distribution of assay temperatures). In this way, it is possible to compare the genetic sequences of two hybridized nucleic acid pairs based on the kinetics or spatial map of the melt-curve.

The temperature in any two compartmentalized volumes in a melt-curve assay can be the same at a given time. The temperature in any two compartmentalized volumes in a melt-curve assay can be different at a given time.

In some cases, the temperature of a compartmentalized volume (e.g., the assay temperature) can vary over time. Variable application of thermal energy over time can result in the variation of in the temperature of a compartmentalized volume over time. In some cases, the temperature of compartmentalized volume can vary cyclically over time. Cyclic variation of the temperature of a compartmentalized volume can, in some cases, cause amplification of a target molecule or molecule correlated with the presence of a target molecule (e.g., in the compartmentalized volume).

In both temporal and spatial melt-curve analysis, melting of the hybridized nucleic acid pair can be observed by monitoring a spectral intensity signal emitted from a compartmentalized volume. For example, the melting of a hybridized nucleic acid pair can release a detectable agent (e.g., a chromophore such as an intercalating dye or fluorophore) from between the strands of the nucleic acid pair. Release of a detectable agent during melting can lead to a decrease in spectral intensity signal. A spectral intensity signal can be produced by a detectable agent, such as an encoded particle (e.g., such as a polymer dot) of a probe, a particle (e.g., a chromophoric particle such as a polymer dot), an intercalating dye, or a fluorophore. A spectral intensity can be a fluorescent signal (e.g., a fluorescent emission signature, which can, for example, comprise an emission wavelength). The spatial or temporal melt-curve that is produced during melt-curve analysis can be referred to as a melt-curve signature. A melt-curve signature can indicate the composition (e.g., nucleic acid sequence) of the target molecule (e.g., as compared to a second target or analyte molecule). A melt-curve signature can, therefore, be used to diagnose a patient based on the composition of a target molecule.

During a digital assay, such as a melt-curve analysis, spectral intensity signals can be detected from between 1 and about 100,000, between 100 and about 100,000, between 500 and about 50,000, between 1,000 and about 30,000, between 5 and about 7,500, between about 10 and about 5,000, between about 25 and about 4,000, between about 50 and about 3,000, between about 10 and about 100, between about 50 and about 200, from about 100 and about 2,000, from about 250 and about 1,000, or from about 500 and about 800 compartmentalized volumes at one time.

A melt-curve analysis can be performed in a time of from about 1 minute to about 90 minutes, from about 5 minutes to about 60 minutes, from about 10 minutes to about 30 minutes, from about 10 minutes to about 20 minutes, or from about 1 minute to about 10 minutes.

The heating of a hybridized nucleic acid pair during temporal melt-curve analysis can be performed step-wise in order to provide better resolution as each portion of the nucleic acid pair melts. Each temperature step of the melt-curve analysis can be between about 0.01° C. and about 1.0° C., between about 0.05° C. and about 0.5° C., between about 0.1° C. and about 0.25° C. or between about 0.15° C. and about 0.3° C. A temporal melt-curve assay can include a pause before or after any temperature step, e.g., in order to more clearly distinguish changes in spectral intensity signal on the melt-curve signature. A temporal melt-curve assay can be performed across a temperature range from about 25° C. to about 100° C., from about 40° C. to about 95° C., from about 48° C. to about 90° C., or from about 60° C. to about 76° C. In some cases, a temporal melt-curve assay can comprise heating a compartmentalized volume to or maintaining a compartmentalized volume at a temperature of about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., or within a range defined by any two of those values.

A temporal melt-curve assay can be performed by applying a variable thermal energy (e.g., a variable quantity of thermal energy) across a plurality of compartmentalized volumes over time. The application of a variable thermal energy to a plurality of compartmentalized volumes over time can comprise a plurality of discrete temperature steps or a continuous temperature change.

A spatial melt-curve assay (e.g., static melt-curve assay) can be performed on compartmentalized volumes. A spatial melt-curve assay using compartmentalized volumes can be performed at a temperature falling within the range of about 25° C. to about 100° C., from about 40° C. to about 95° C., from about 48° C. to about 90° C., or from about 60° C. to about 76° C. In some cases, a static melt-curve assay can comprise heating a compartmentalized volume to or maintaining a compartmentalized volume at a temperature of about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69°

C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., or within a range defined by any two of those values.

In some cases, a spatial melt-curve can be performed on a plurality of compartmentalized volumes arranged in a two-dimensional array (e.g., such as the chambers of a microfluidic or self-digitization chip or the wells of a multi-well plate). In some cases, a first axis (e.g., a vertical column) of a two-dimensional array of a spatial melt-curve (or a portion thereof) can comprise a series of compartmentalized volumes that represent experimental repeats (e.g., for averaging during normalization or statistical analysis). In some cases, a second axis (e.g., a horizontal row) of a two dimensional array of a spatial melt-curve (or a portion thereof) can comprise a series of compartmentalized volumes that are subjected to application of different amounts of thermal energy. In some cases, the amount of thermal energy applied to a first compartmentalized volume can cause the temperature in the compartmentalized volume to be 0.05, 0.06, 0.07, 0.08, 0.09, 0.1° C., 0.2° C., 0.3° C., 0.4° C., 0.5° C., 0.6° C., 0.7° C., 0.8° C., 0.9° C., 1.0° C., 1.5° C., 2.0° C. (or a range defined by any two of those values) higher than the temperature in a second compartmentalized volume.

In some cases, a static melt-curve analysis can be performed on a single compartmentalized volume or other compartmentalized volume by creating a temperature gradient across the compartmentalized volume or other compartmentalized volume and characterizing a spatial melt-curve within a single compartmentalized volume.

Probes for Use in Digital Assays

A probe can be used to detect, identify, or quantify a target molecule in a digital assay. According to the methods and systems described herein, a compartmentalized volume of a digital assay can comprise a probe or a plurality of probes. A compartmentalized volume can also comprise a plurality of distinct probes. In some cases, a compartmentalized volume can comprise at least 2, at least 5, at least 10, at least 20, at least 50, at least 100, at least 200, at least 500, or at least 1000 distinct probes. In some cases, a compartmentalized volume can comprise about 2 distinct probes, about 5 distinct probes, about 10 distinct probes, about 20 distinct probes, about 50 distinct probes, about 100 distinct probes, about 200 distinct probes, about 500 distinct probes, about 1000 distinct probes, or a number of probes within a range defined by any two of the preceding quantities of probes.

In some cases, a probe can be located in a compartmentalized volume that comprises a target molecule. In some cases, a probe can be located in a compartmentalized volume that does not comprise a target molecule.

In some aspects, the methods described herein comprise contacting a sample comprising a target molecule with a suspension of probes. In some cases, the detection, identification, and/or quantification of a target molecule with a probe can comprise contacting the target molecule with a probe. In some cases, the detection, identification, and/or quantification of a target molecule with a probe can comprise contacting a molecule correlated with the presence of a target molecule.

A probe can comprise a chromophore or an encoded particle (e.g., polymer dot such as an encoded chromophoric polymer dot) capable of emitting a detectable signal or code. In some cases, a probe can comprise a plurality of chromophores or encoded particles (e.g., polymer dots). For example, a probe can comprise 2, 3, 4, 5, 6, 7, 8, 9, 10, from 10 to 20, from 20 to 50, from 50 to 100, or more than 100 different chromophores or encoded particles. In some cases, a first chromophore or encoded particle of a probe can produce a different detectable code or signal than that of a second chromophore or encoded particle of the probe. For example, a first chromophore or encoded particle of a probe can produce a signal with a different emission intensity but at the same wavelength or within the same wavelength range as the signal produced by a second chromophore or encoded particle of the probe. In some cases, a first chromophore or encoded particle of a probe may be capable of producing a signal having an emission intensity greater than a threshold value at a wavelength or within a wavelength range that is different from the wavelength or wavelength range at which or within which a second chromophore or encoded particle of the probe is capable of producing a signal having an emission intensity greater than the threshold value.

In some cases, the detectable signal or code of the chromophore or encoded particle of a probe can be an optically detectable signal. A detectable code or signal of a chromophore or encoded particle can be a fluorescent signal. For example, a detectable code or signal of a probe comprising a polymer dot can comprise a fluorescent signal emitted by the polymer dot.

The detectable code or signal that a probe is capable of producing can comprise the detectable code(s) or signal(s) (e.g., optically detectable code(s) or signal(s)) of one or more chromophore or encoded particle comprising the probe. In some cases, the detectable code or signal that a probe is capable of producing can depend on the number and types of chromophores or encoded particles that comprise the probe. In some cases, the detectable code or signal that a first probe is capable of producing can be different than the detectable code or signal that a second probe is capable producing. In some cases, the detectable code or signal that a first probe is capable of producing may be different from the detectable code or signal that a second probe is capable of producing because the first probe comprises a different set of chromophores or encoded particles than the second probe comprises. For example, a detectable code or signal produced by a first probe comprising a first and second type of chromophore (e.g., a first and second chromophore capable of producing a first and second optically detectable code or signal) can be different than the detectable code or signal produced by a second probe comprising a third and fourth type of chromophore (e.g., a third and fourth chromophore capable of producing a third and fourth optically detectable code or signal, respectively).

In some cases, a first probe capable of producing a first detectable code or signal can be distinguished from a second probe capable of producing a second detectable code or signal. For example, a first probe may, in some cases, be distinguished from a second probe if the detectable code produced by the first probe is different than the detectable code produced by the second probe. In some cases, the fact that a first probe can produce a first detectable code or signal and a second probe can produce a second detectable code or signal that is different than the first detectable code or signal can be used in digital assays to distinguish between the presence of a first target molecule and a second target molecule in a compartmentalized volume.

A detectable signal or code emitted by an encoded particle or chromophore of a probe can be modulated by a quencher. In some cases, the modulation of a detectable signal or code by a quencher can depend on the proximity of the quencher to the encoded particle or chromophore capable of emitting the detectable code or signal.

A probe can also comprise a quencher, which can decrease the intensity of a detectable signal or code produced by an encoded particle or other chromophore. A quencher can comprise a nucleic acid sequence. In some cases, the nucleic acid sequence can be complementary to (e.g., capable of hybridizing with, binding to, or associating with) one or more of: i) a binding region of a probe (or portion thereof), ii) a target molecule (or portion thereof), or iii) an amplification product of a target molecule (or portion thereof). In some cases, a quencher can be covalently bound to an encoded particle of a probe directly. In some cases, a quencher can be covalently bound to an encoded particle of a probe via a linker molecule.

A probe can also comprise a binding region. A probe can comprise a nucleic acid (e.g., a polynucleotide), a polypeptide, or a combination thereof. A probe can comprise a binding region configured to recognize a target molecule. That is, a binding region of a probe can be configured to bind to, hybridize with, or otherwise associate with a target molecule. A probe can comprise from 1 to about 5, from about 5 to about 20, from about 20 to about 50, from about 50 to about 75, from about 75 to about 100, from about 100 to about 150, from about 150 to about 200, from about 200 to about 250 binding regions, from about 250 to about 300 binding regions, from about 300 to about 350 binding regions, from about 350 to about 400 binding regions, from about 400 to about 450 binding regions, from about 450 to about 500 binding regions, or from about 500 to about 1,000 binding regions. A binding region of a probe can comprise a polynucleotide, a Taqman® sequence, a primer nucleic acid molecule, a template nucleic acid molecule, a protein, a linker, or an aptamer. A binding region of a probe can be connected (e.g., covalently or non-covalently) to another molecule. In some cases, a binding region of a probe can be connected covalently or non-covalently to a quencher. A binding region (or portion thereof) can also be associated with (e.g., bound to or hybridized with) a PCR primer, a target molecule, or an amplification product (e.g., an amplification product of a target molecule). In some cases, a binding region of a probe can be a PCR primer or a portion of a PCR primer. In some cases, a binding region of a probe can be a PCR template or a portion of a PCR template. In some cases, a first region of a binding region can be associated with (e.g., bound to or hybridized with) a second region of the same binding region. In some cases, a first binding region can be associated with (e.g., bound to or hybridized with) a second binding region on the same probe. In some cases, two distinct binding regions of a probe (e.g., a first distinct binding region and a second distinct binding region) can associate with one another. In some cases, a binding region of a first type of probe (e.g., a first distinct probe or a first species of probe) can be associated with (e.g., bound to or hybridized with) a binding region of a second type of probe (e.g., a second distinct probe or a second species of probe). In some cases, a first distinct binding region of a first probe can associate with a second distinct binding region of a second probe.

A probe can be used to detect, identify, or quantify a target molecule directly or indirectly. For example, in dPCR, a probe can indirectly indicate the presence of a target molecule by through hybridization with an amplification product (e.g., an amplicon) of the target molecule.

The present disclosure further provides methods of using the encoded particles described herein. For example, the present disclosure provides methods of fluorescence-based detection using an encoded particle as a class of fluorescent probe and their bioconjugates for a variety of applications. These include but are not limited to immunofluorescence, immunohistochemistry, fluorescence multiplexing, DNA and gene analysis, protein analysis, metabolite analysis, lipid analysis, Förster resonance energy transfer (FRET)-based sensors, high throughput screening, cell detection, bacteria detection, virus detection, biomarker detection, cellular imaging, in vivo imaging, bioorthogonal labeling, fluorescence-based biological assays such as immunoassays and enzyme-based assays, and a variety of fluorescence techniques in biological assays and measurements. In certain aspects, the encoded particles herein have a number of advantages for use as detection agents, e.g., for detection of proteins or peptides such as in the course of immunoassay analysis. Encoded particles according to the present disclosure can comprise any suitable polymer subunit or subunits that enable the detection of proteins or peptides, and in particular, proteins.

Detectable Agents

In various aspects, a digital assay can comprise a detectable agent. A detectable agent can comprise a chromophore, such as a fluorescent or luminescent molecule.

In certain aspects, the detectable agent can be associated with a target molecule for detection. For example, the detectable agent can be associated with a nucleic acid molecule (e.g., DNA or RNA), a peptide, a protein, a lipid, a metabolite, a drug, or other molecule (e.g., biomolecule) present in a sample. As defined herein, "associated" in the context of the detectable agent includes interaction with the molecule via covalent and/or non-covalent interactions. For example, the detectable agent can be associated with the target molecule through hybridization with the target molecule. Alternatively, the detectable agent can, for example, be an intercalation agent or a chromophore. In various aspects, the detectable agent can comprise a fluorescent molecule. In further aspects, the detectable agent is luminescent. In certain aspects, the detectable agent can be fluorescein, a derivative of fluorescein, rhodamine, a derivative of rhodamine, boron dipyrromethene (BODIPY), a derivative of BODIPY, a semiconducting polymer, a semiconducting polyelectrolyte, a semiconducting polymer dot, or a chromophoric polymer dot. In some cases, a chromophore can comprise an intercalating dye.

The detectable agent used can depend on the type of digital assay that is employed. In one aspect, a detectable signal or code can be generated by a non-sequence-specific fluorophore such as EvaGreen or SYBRgreen, where the fluorophore is quenched when in solution but can intercalate into double-stranded DNA where it exhibits much brighter fluorescence. Thus, a large amount of double stranded DNA generated during PCR can result in detectable levels of fluorescence in a melt-curve assay, for example. Increasing or maintaining the temperature of the sample of a compartmentalized volume at or above the melting point of certain nucleotide pairs or sequences can thus cause a double-stranded DNA molecule to separate, completely or only in part, thereby releasing the intercalating dye. Thus released, the intensity of a detectable signal or code from a compartmentalized volume in a melt-curve assay can decrease as the intercalating dye disperses into the compartmentalized volume.

In another aspect, sequence specific fluorescent probes can be used. In one aspect, this can consist of a molecular beacon such as a hairpin structure, whose fluorescence is highly quenched in its closed conformation and whose intensity is increased once it hybridizes with a target molecule or with a molecule correlated with the presence of a target molecule. In another aspect a specific fluorescent probe can comprise a probe capable of hybridizing with a quencher, wherein the portion of the quencher capable of binding or hybridizing with the probe undergoes polymerase-mediated cleavage during an amplification step comprising extension of the binding region.

Encoded Particles

According to the present disclosure, probes can comprise an encoded particle. Encoded particles may be encoded with a chemically or physically distinguishable characteristic or characteristics. Encoded particles according to the present disclosure are capable of being detected and identified or of producing a characteristic detectable signal or code. In some aspects, the encoded particle comprises a compound with two or more distinguishable properties. In certain aspects, the encoded particle comprises an aggregate of molecules, wherein the encoded particle has two or more distinguishable properties.

An encoded particle can comprise a chromophore. In some cases, an encoded particle can comprise a plurality of chromophores. An encoded particle can comprise a plurality of distinct chromophores. A chromophore of an encoded particle can be luminescent, fluorescent, or a combination thereof. As described herein, an encoded particle or chromophore thereof can comprise an inorganic material, an organic material, or a combination thereof. For example, a chromophore of an encoded particle can comprise a metal complex. In some cases, an encoded particle or chromophore thereof can comprise an interpenetrated network of organic and inorganic materials. In some cases, an encoded particle or chromophore thereof can comprise a semiconducting nanocrystal, such as a quantum dot. In other cases, an encoded particle or chromophore thereof can comprise a semiconducting polymer. In some cases, an encoded particle or chromophore thereof can comprise a polymer dot. In some cases, a chromophore of an encoded particle can comprise a dye or a small molecule dye. In some aspects, the encoded particle comprises an extended molecule with two or more dye units, three or more dye units, four or more dye units, or five or more dye units. In some aspects, the encoded particle comprises two or more distinct types of detectable components, for example, the encoded particle can comprises a dye molecule and a non-dye fluorophore. In further aspects, the encoded particle comprises three or more distinct types of detectable components, for example, the encoded particle can comprise a dye and two additional non-dye fluorophores.

An encoded particle can comprise a matrix. The matrix of an encoded particle can comprise an organic material. For example, the matrix of an encoded particle can comprise one or more polymers. In some cases, the matrix of an encoded particle can comprise one or more semiconducting polymers. In some cases, the matrix of an encoded particle can comprise one or more non-semiconducting polymers or molecules. For example, the matrix of an encoded particle can comprise polystyrene (PS) or poly(methyl methacrylate) (PMMA). In some cases, the matrix of an encoded polymer can comprise a chromophore. For example, the matrix of an encoded particle can comprise a chromophoric semiconducting polymer, such as a polymer dot. In some cases, the matrix of an encoded particle can comprise a plurality of chromophoric semiconducting polymers (e.g., a plurality of polymer chains of the same type or different types). The matrix of an encoded particle can also comprise an inorganic material. In some cases, the matrix of an encoded particle can comprise one or more of: silica, a silicate, titanium dioxide, phosphate, or a combination thereof. In some cases, the matrix of an encoded particle can comprise a combination of inorganic and organic materials (e.g., an organic-inorganic hybrid encoded particle).

In some respects, an encoded particle can be a nanoparticle. An encoded particle can be approximately spherical in shape. A measurement of a particle's size can be expressed in terms of the smallest dimension of the particle, which is also referred to as the "critical dimension" of the particle. For example, if an encoded particle consists of a nanosphere, the critical dimension of the encoded particle can be the particle's diameter. Some encoded particles, such as spheres and cubes, can be nanoscopic with respect to every dimension. Some encoded particles are nano-scale in some dimensions and greater than nano-scale in other dimensions. For example, a nano-cylinder may have a nano-scale diameter but a length that is on the micro-scale (e.g., a nano-cylinder that is greater than 1000 nanometers in length). In some cases, an encoded particle can comprise additional structures (e.g., a nucleic acid) or can be associated with additional structures (e.g., a nucleic acid or polymer chain of a nanoparticle can be associated with a nucleic acid primer, which, in turn, can be linked to a quencher), wherein the additional structure or structures are not on the nano-scale but the encoded particle retains a diameter on the nano-scale.

The critical dimension of a probe or encoded particle (e.g., the diameter of an encoded particle) can be from 3 nanometer to 1000 nanometers, from 1 nanometer to 500 nanometers, from 1 nanometer to 400 nanometers, from 1 nanometer to 300 nanometers, from 1 nanometer to 200 nanometers, from 1 nanometer to 100 nanometers, from 1 nanometer to 50 nanometers, from 1 nanometer to 40 nanometers, from 1 nanometer to 30 nanometers, from 1 nanometer to 20 nanometers, from 1 nanometer to 10 nanometers, from 10 nanometers to 500 nanometers, from 50 nanometers to 400 nanometers, from 100 nanometers to 300 nanometers, from about 25 nanometers to about 250 nanometers, from about 50 nanometers to about 100 nanometers, from about 10 nanometers to about 50 nanometers, from about 10 nanometers to about 30 nanometers, from about 10 nanometers to about 20 nanometers, or from about 5 nanometers to about 15 nanometers. In some cases, the critical dimension of a probe or encoded particle can be a hydrodynamic diameter.

An encoded particle can have at least one dimension that is greater than 3 nanometers. An encoded particle also can have at least one dimension that is greater than 4 nanometers, 5 nanometers, 10 nanometers, 15 nanometers, 20 nanometers, 25 nanometers, 30 nanometers, 35 nanometers, 40 nanometers, 45 nanometers, or 50 nanometers. For example, an encoded particle can comprise a chromophoric nanoparticle, such as a polymer dot. In other aspects, the encoded particle can have at least one dimension that is less than 4 nm or at least one dimension that is less than 3 nanometers. In certain aspects, the encoded particle has at least one dimension that is less than 3 nm and at least one dimension that is greater than 3 nanometers, 4 nanometers, 5 nanometers, 10 nanometers, 15 nanometers, 20 nanometers, 25 nanometers, 30 nanometers, 35 nanometers, 40 nanometers, 45 nanometers, or 50 nanometers. In some aspects, the encoded particle has at least one dimension that is less than 3 nanometers and at least one dimension that is greater than 3 nanometers.

In some cases, the size of an encoded particle can affect the function of the encoded particle. For example, the size of an encoded particle can affect the emission intensity of the nanoparticle or the emission spectrum of the encoded particle. In some cases, aggregation of chromophoric polymer encoded particle can cause a decrease in the emission intensity of the encoded particle or an alteration in the emission spectrum of the encoded particle.

The encoded particles of the present disclosure can be of various forms or shapes. For example, the shape of an encoded particle can be a sphere, a cylinder, an ellipsoid, a polyhedron, a prism, a rod, a cube, a sheet, pyramid, or a wire. The shape of a nanoparticle can contribute to the function of the nanoparticle. For example, the shape of a nanoparticle can contribute to the optical properties of the nanoparticle (e.g., nano-rods may have different optical properties than nano-spheres).

The encoded particles can comprise a plurality of materials, including detectable agents and other materials. For example, the encoded particles can comprise plastics, ceramics, glass, polystyrene, methylstyrene, acrylic polymers, metal, paramagnetic materials, thoria sol, graphitic carbon, titanium dioxide, latex or cross-linked dextrans such as Sepharose, cellulose, nylon, cross-linked micelles and teflon.

Chromophoric Polymer Compositions of Encoded Particles

Various types of chromophoric polymer particles are suitable for use as a platform for the optical encoding and/or biomolecular encoding approaches of the present disclosure. It shall be understood that any description herein referring to chromophoric polymer particles is applicable to the encoded particles of the present disclosure. Encoded particles can adopt a variety of configurations, including but not limited to, a monolithic polymer particle having a uniform, homogeneous composition or a polymer particle having a distinct core and cap structure. The encoded particles provided herein may be formed by any method known in the art, including, without limitation, methods relying on precipitation, methods relying on the formation of emulsions (e.g., mini or micro emulsion), and methods relying on condensation. Examples of additional encoded particle compositions (e.g., chromophoric polymer particle compositions) suitable for use with the techniques described herein can be found in, for example, PCT application numbers PCT/US2010/056079, PCT/US2012/071767, PCT/US2011/056768, PCT/US2013/024300, and PCT/US2013/063917, PCT/US2014/067471, and in U.S. patent application Ser. No. 13/687,813, each of which is incorporated herein by reference.

Any suitable number and combination of chromophoric polymer types can be incorporated in the encoded particles described herein, such as one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers. The mass concentration of the chromophoric polymers relative to the entire encoded particle mass can be varied from 1% to 100%, more preferably between 10% and 99%, more preferably between 20% and 99%, more preferably between 30% and 99%, more preferably between 40% and 99%, and more preferably between 50% and 99%.

In some aspects, the encoded particles described herein include a polymer matrix formed from one or more chromophoric polymers. The chromophoric polymer can be a homopolymer or a heteropolymer. In various aspects, the chromophoric polymer can be a semiconducting polymer, a non-semiconducting polymer, or a combination thereof. For example, a number of semiconducting polymers are suitable for use in encoded particles according to the present disclosure. Semiconducting polymers have been developed with emission wavelengths ranging from UV to infrared, including the entire visible spectrum. Example of semiconducting polymers include but are not limited to: polyfluorene polymers, including but not limited to poly(9,9-dihexylfluorenyl-2,7-diyl) (PDHF) based polymer and poly(9,9-dioctylfluorenyl-2,7-diyl) (PFO)) based polymer; fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2, 1,3}-thiadiazole)] (PFBT), poly[(9,9-dioctylfluorenyl-2,7-diyl)-co-(4,7-Di-2-thienyl-2,1,3-benzothiadiazole)] (PFTBT), and poly[(9,9-dioctylfluorenyl-2,7-diyl)-co-(4,7-Di-2-thienyl-2,1,3-benzothiadiazole)] (PF-0.1TBT); phenylene vinylene based polymers, including but not limited to, poly[2-methoxy-5-(2-ethylhexyloxy)-1,4-phenylenevinylene] (MEH-PPV) and poly[2-methoxy-5-(2-ethylhexyloxy)-1,4-(1-cyanovinylene-1,4-phenylene)] (CN-PPV); phenylene ethynylene polymers, including but not limited to, poly(2,5-di(3',7'-dimethyloctyl)phenylene-1,4-ethynylene (PPE); BODIPY (boron dipyrromethene) based polymers; Squaraine based polymers; PVK (poly vinylcarbazole) based polymers; or a combination thereof.

A wide variety of chromophoric polymer structures are suitable for use in accordance with various aspects of the present disclosure. In some aspects, the chromophoric polymer can be a linear polymer. In other aspects, the chromophoric polymer can be a branched polymer. In certain aspects, the chromophoric polymer can be a dendrimer. In certain aspects, the chromophoric polymer can be a brush polymer. In certain aspects, the chromophoric polymer can be a star polymer.

In some aspects, encoded particles can be used that contain a polystyrene-based, comb-like polymer. Non-limiting examples of polystyrene based comb-like polymers include polystyrene graft acrylic acid, polystyrene graft ethylene oxide, polystyrene graft butyl alcohol, and the like.

In some aspects, encoded particles can be used that contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like.

In some aspects, encoded particles can be used that contain a comb-like polymer comprising carboxyl, amine, thiol, ester, succinimidyl ester, azide, alkyne, cyclooctyne, or phosphine groups.

In some aspects, encoded particles can be used that contain a polymer functionalized on the terminal monomeric unit, for example with a carboxyl, amine, thiol, ester, succinimidyl ester, azide, alkyne, cyclooctyne, phosphine, or similar functional group. Examples of polymers that can be used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some aspects, encoded particles can be used that contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacryl amide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethyl aminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(-vinyl naphthalene)-based copolymers such as poly(-vinyl naphthalene-b-acrylic acid), poly (vinyl pyridine and N-methyl vinyl pyridinium iodide)-based copolymers such as poly(-vinyl pyridine-b-ethylene oxide), poly(-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(-vinyl pyridine-b-ethylene oxide) PEO end functional OH; and poly(vinyl pyrrolidone)-based copolymers such as poly(vinyl pyrrolidone-b-D/L-lactide); and the like.

In some aspects, the encoded particle used for the detection of nucleic acids, proteins, or peptides can include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, vinylcarbazole unit, boron-dipyrromethene unit, squaraine unit, units comprising Lanthanides, and derivatives thereof. The different chromophoric units can be segregated, as in a block copolymer, or intermingled. In some aspects, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

In certain aspects, the encoded particle can include a blend of semiconducting polymers. The blends can include any combination of homopolymers, copolymers, and oligomers. Polymer blends used to form encoded particles may be selected in order to tune the properties of the resulting polymer particles, for example, to achieve a desired excitation or emission spectra for the polymer particle.

For some assays, semiconducting encoded particles offer improved detection sensitivity in part because they exhibit higher quantum yields than other fluorescent reporters. In some aspects, the quantum yield of the chromophoric polymer particle used is more than 10%, is more than 20%, more than 30%, more than 40%, more than 50%, more than 60%, more than 70%, more than 80%, or more than 90%.

For some assays, semiconducting encoded particles offer improved detection sensitivity in part because they exhibit faster emission rates than other fluorescent reporters. In certain aspects, the emission rate of the encoded particle used is between about 100 picoseconds and about 50 nanoseconds.

In some aspects, the encoded particle used comprises polymers bearing units of small organic dye molecules, metal complexes, photochromic dye, and any combinations thereof, for example, optically inactive polymers such as polystyrene covalently linked or grafted with small organic dye, metal complexes, photochromic dyes and any combination thereof. These dyes or metal complexes may have protein sensing capability.

In some aspects, the encoded particles comprise semiconducting polymers covalently linked with small organic dye molecules, metal complexes, photochromic dyes, and any combinations thereof as emissive units. Such emissive units can tune the emission color, increase the quantum yield, and improve the photostability of the chromophoric polymer particle.

In some aspects, the small organic dyes, or metal complexes can have sensing functions, and therefore add additional functionalities to the encoded particle, such as protein sensing capability.

In some aspects, the encoded particle may comprise a semiconducting polymer physically mixed or chemically cross-linked with other chromophoric polymers such as optically inactive polymer covalently linked or grafted with small organic dye, metal complexes, photochromic dyes and any combination thereof, to have additional functionalities such as sensing.

In some aspects, the chromophoric polymer particle may comprise semiconducting polymers physically mixed or chemically cross-linked with other components such as fluorescent dyes, inorganic luminescent materials, magnetic materials, metal materials, and the like in order to tune emission color, improve quantum yield and/or photostability, and/or provide additional functionalities such as magnetic functions, plasmon resonance functions, and the like.

The optical properties, such as absorption wavelength, for a given chromophoric polymer particle can be tuned by modifying its composition and geometry. Semiconducting polymers have been developed with absorption wavelengths ranging from UV to infrared, including the entire visible spectrum. In some aspects, encoded particles having a peak absorption wavelength between about 200 nanometers and about 300 nanometers, about 250 nanometers and about 350 nanometers, about 300 nanometers and about 400 nanometers, about 350 nanometers and about 450 nanometers, between about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, or about 900 nanometers and about 1000 nanometers are used.

Semiconducting polymers have been developed with emission wavelengths ranging from UV to infrared, including the entire visible spectrum. In some aspects, encoded particles having a peak emission wavelength between about 200 nanometers and about 300 nanometers, about 250 nanometers and about 350 nanometers, about 300 nanometers and about 400 nanometers, about 350 nanometers and about 450 nanometers, about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, about 900 nanometers and about 1000 nanometers, about 950 nanometers and about 1050 nanometers, about 1000 nanometers and about 1100 nanometers, about 1150 nanometers and about 1250 nanometers, or about 1200 nanometers and about 1300 nanometers are used.

In some aspects, the present disclosure provides encoded particles with narrow-band emissions. Narrow-band emissions are advantageous for certain applications, including but not limited to multiplexing applications. The emission wavelength of the polymer particles can vary from ultraviolet to near infrared region. In some aspects, the full width at half maximum (FWHM) of the emission band is less than 70 nanometers. In some aspects, the FWHM is less than about 65 nanometers. In some aspects, the FWHM is less than about 60 nanometers. In some aspects, the FWHM is less than about 55 nanometers. In some aspects, the FWHM is less than about 50 nanometers. In some aspects, the FWHM is less than about 45 nanometers. In some aspects, the FWHM is less than about 40 nanometers. In some aspects, the FWHM is less than about 35 nanometers. In some aspects, the FWHM is less than about 30 nanometers. In some aspects, the FWHM is less than about 25 nanometers. In some aspects, the FWHM is less than about 20 nanometers. In some aspects, the FWHM is less than about 10 nanometers. In some aspects, the FWHM of the polymer particles described herein can range between about 5 nanometers to about 70 nanometers, from about 10 nanometers to about 60 nanometers, from about 20 nanometers to about 50 nanometers, or from about 30 nanometers to about 45 nanometers.

A wide variety of chromophoric polymer particles can be used for encoding, such as the examples described herein as well as others that are disclosed, e.g., in PCT/US2010/056079 and PCT/US2012/071767, each of which is incorporated by reference herein in its entirety and specifically with regard to the particular chromophoric polymer particle compositions and the respective methods of making them as described therein. As provided, e.g., in PCT/US2010/056079, the polymers in the chromophoric polymer particles can be physically blended or chemically bonded (or chemically crosslinked). For example, the physically blended polymer particles can include polymers that are blended in the chromophoric polymer particle and held together by non-covalent interactions. Chemically bonded chromophoric polymer particles can include polymers that are covalently attached to each other in the polymer particle. The chemically bonded polymers can be covalently attached to each other prior to formation of the polymer particles.

Organic-Inorganic Encoded Particles

An encoded particle can comprise an organic material or an inorganic material or a combination thereof. For example, an encoded particle can comprise an organic-inorganic hybrid. In some cases, an encoded particle can comprise an interpenetrated network of organic and inorganic materials. The present disclosure provides various embodiments of organic-inorganic hybrid encoded particles, also referred to herein as "hybrid encoded particles." In some cases, a hybrid encoded particle can be a polymer dot (e.g., a hybrid polymer dot). In some embodiments, an organic-inorganic hybrid encoded particle can comprise an organic network and an inorganic network. In certain embodiments, the organic network includes at least one organic species, such as one or more of the chromophoric polymers described herein. In some cases, an inorganic network can comprise at least one inorganic species, such as siloxane, aluminosiloxane, titanium-siloxane, titanium oxide, or a combination thereof. In certain embodiments, an inorganic network can be a siloxane network (e.g., including Si—O—Si linkages), an alumino-siloxane network (e.g., including Al—O—Si linkages), a titanium-siloxane network (e.g., including Ti—O—Si linkages), a titanium oxide network (e.g., including Ti—O—Ti linkages), or a combination thereof. The terms "siloxane network" and "silica ($SiO_2$) network" treated synonymously herein. Additional examples of silica and hybrid encoded particles (e.g., hybrid polymer dots) that can be used with the methods, compositions, and systems described herein can be found in PCT/US2017/037260, which is incorporated herein in its entirety.

In some embodiments, the organic network and inorganic network are interpenetrated with each other so as to form an organic-inorganic interpenetrated network. For example, a siloxane network can form an interpenetrated network with a chromophoric polymer. As used herein, an "organic-inorganic interpenetrated network" refers to the encoded particle comprising at least two networks that together form the interpenetrated network. In some cases, the organic-inorganic interpenetrated network can be mesh-like and/or an interlocking structure of the inorganic network interpenetrated with the polymer. In some cases, interpenetration can occur primarily through the physical association (e.g., hydrophobic interaction) of the at least two networks so as to form the interpenetrated network. In certain cases, interpenetration can occur through the physical association of the at least two networks without any chemical bonding (e.g., without covalent bonding between the two networks). In certain cases, interpenetration can occur primarily through the chemical bonding (e.g., covalent bonding) of the two networks to each other so as to form the interpenetrated network. Covalent bonding between the organic network and inorganic network can be used alternatively to or in combination with physical association in order to form the organic-inorganic interpenetrated network.

In certain embodiments, the present disclosure provides organic-inorganic hybrid encoded particles (e.g., hybrid polymer dots) that can be structurally distinct from other types of encoded particles and polymer dots, included but not limited to encoded particles formed by blending (e.g., encoded particles blended with amphiphilic polymers) and encoded particles without an inorganic network. For example, in some embodiments, the organic-inorganic interpenetrated network of the hybrid encoded particles described herein is distinct from a core-cap or core-shell structure that may be found in other types of encoded particles. In certain embodiments, the organic-inorganic hybrid encoded particles herein do not include a core-cap or core-shell structure.

As described in further detail herein, in some embodiments, the organic-inorganic interpenetrated network can be formed during formation of the organic-inorganic hybrid encoded particle. For example, in some embodiments, formation of an organic-inorganic hybrid encoded particle involves forming a siloxane network during hydrolysis of organic silane molecules. In some cases, one or more polymers can be collapsed, precipitated, or condensed simultaneously with hydrolysis of organic silane molecules and cross linking in order to simultaneously form an organic network and an inorganic network, which together form the organic-inorganic interpenetrated network.

The hybrid encoded particles of the present disclosure can be functionalized and/or bioconjugated, e.g., to a biological molecule. In some embodiments, a hybrid encoded particle includes an organic network (e.g., a semiconducting chromophoric polymer), an inorganic network (e.g., a siloxane network), and X, where X is a functional group suitable for bioconjugation. Examples of functional groups and/or linkers suitable for bioconjugation in accordance with the present disclosure are provided further below. The functional group X may be attached to the inorganic network, the organic network, or a combination thereof.

In some embodiments, a hybrid encoded particle includes at least two orthogonal reactive chemical groups. In certain embodiments, an orthogonally reactive chemical group is a chemical group that reacts only with its designated chemical reactive group, but not with another chemical reactive group that may be present. For example, reactive groups A and B can form a designated pair that reacts with each other, and reactive groups Y and Z can form another designated pair that reacts with each other. In such embodiments, reactive group A is considered to be orthogonal with respect to Y because A does not react with Z, and reactive group Y is orthogonal with respect to A because Y does not react with B. In some embodiments, reactive groups A can react with each other or with reactive groups B to form a siloxane network, and reactive groups Y do not react with either A or B, such that A and Y, and/or B and Y, are considered to be orthogonal reactive groups.

Organic-Inorganic Hybrid Encoded Particles with a Siloxane Network

An encoded particle, as described herein, can comprise a siloxane network, e.g., a network including a plurality of Si—O—Si linkages. A siloxane network can be formed by the full or partial hydrolysis of one or more silane and/or siloxane species.

The weight percent of the siloxane network and/or the components thereof (e.g., silicon) in an encoded particle can be varied as desired. In some embodiments, the weight percent of the siloxane network and/or the components thereof (e.g., silicon) is selected to avoid formation of a core-shell structure in the resulting hybrid encoded particle. In certain embodiments, the weight percent of silicon from the siloxane network in the hybrid encoded particle is less than or equal to about 1%, less than or equal to about 5%, less than or equal to about 10%, less than or equal to about 15%, less than or equal to about 20%, less than or equal to about 25%, less than or equal to about 30%, less than or equal to about 35%, less than or equal to about 40%, less than or equal to about 45%, or less than or equal to about 47%. In certain embodiments, the weight percent of silicon from the siloxane network in the hybrid encoded particle is greater than or equal to about 1%, greater than or equal to about 5%, greater than or equal to about 10%, greater than or equal to about 15%, greater than or equal to about 20%, greater than or equal to about 25%, greater than or equal to about 30%, greater than or equal to about 35%, greater than or equal to about 40%, or greater than or equal to about 45%. In certain embodiments, the weight percent of silicon from the siloxane network in the hybrid encoded particle is within a range from about 1% to about 45%, or within a range from about 1% to about 47%.

Organic-inorganic hybrid encoded particles can comprise at least two silane species, each having their own respective function. The hybrid encoded particle can comprise a siloxane network and at least one other network to form the interpenetrated organic-inorganic network. For example, in some embodiments, the present disclosure provides organic-inorganic hybrid encoded particles comprising a semiconducting chromophoric polymer and a siloxane network, wherein the semiconducting chromophoric polymer and the siloxane network form an organic-inorganic interpenetrated network. The interpenetrated network can be a mesh-like and/or interlocking structure of the siloxane network interpenetrated with the chromophoric polymer (e.g., without forming a core-cap or a core-shell structure).

An organic-inorganic hybrid encoded particle with a siloxane network can be formed in various ways. In certain embodiments, the hybrid encoded particle is formed through the physical association of the siloxane network with the chromophoric polymer so as to form an interpenetrated network. Alternatively or in combination, the siloxane network and chromophoric polymer can be chemically bonded (e.g., covalently bonded) to each other to form the interpenetrated network.

Hybrid Encoded Particles with Physical Association between a Siloxane Network and a Semiconducting Chromophoric Polymer In some embodiments, the present disclosure provides hybrid encoded particles in which the siloxane network is physically associated with the semiconducting chromophoric polymer, such as by hydrophobic interaction. In some embodiments, the siloxane network comprises an alkylene, alkoxy, alkenyl, alkenylene, alkynyl, alkynylene, alkyl amine, cycloalkyl, cycloalkylene, heterocycloalkyl, or heterocycloalkylene.

In some embodiments, the siloxane network includes one or more orthogonally cross-linked units. In certain embodiments, an orthogonally cross-linked unit includes a reactive group that cross-links only with its designated reactive group, but not with another reactive group that may also be present.

In some embodiments, the siloxane network can comprise a plurality of interconnected units.

In some embodiments, the chromophoric polymer is physically associated with but not covalently bonded to the siloxane network. For example, in various embodiments, the chromophoric polymer is not silane functionalized, and functionalization and formation of the interpenetrated network of the hybrid encoded particle is achieved by the physical association (e.g., hydrophobic interaction) of the chromophoric polymer with the siloxane network only. In alternative embodiments, the chromophoric polymer can also be covalently bonded with the siloxane network, as discussed in greater detail below herein.

Chromophoric Polymers for Use in Hybrid Encoded Particles

An encoded particle described herein can comprise various types of chromophoric polymers, such as one or more of the chromophoric polymer types described herein. Encoded particles can include one or more chromophoric polymers (e.g., semiconducting chromophoric polymers) that have been collapsed into a stable sub-micron sized particle.

In some embodiments, the hybrid encoded particles of the present disclosure comprise a plurality of polymers. For example, the hybrid encoded particles can comprise a blend of chromophoric polymers. In certain embodiments, the hybrid encoded particles include a blend of semiconducting chromophoric polymers. The blends can include any combination of homopolymers, copolymers, and oligomers. Polymer blends used to form hybrid encoded particles may be selected in order to tune the properties of the resulting polymer particles, for example, to achieve a desired excitation or emission spectra for the hybrid encoded particle.

The hybrid encoded particles can comprise polymers with one or more repeating units, which can be combined in fixed, ordered, or random configurations and ratios. A repeating unit can be a monomer or a chemical motif that occurs throughout the polymer, such as an aromatic or heterocyclic unit. The polymers can be halogenated, for example, fluorinated, chlorinated, brominated, or iodinated. A polymer, a repeating unit, or a monomer can be halogenated at one or multiple sites. A halogenated polymer, for example, a fluorinated polymer, can provide greater levels of fluorescence than can a non-halogenated analogous polymer.

Any suitable number and combination of chromophoric polymer types can be incorporated in the hybrid encoded particles described herein, such as one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers.

The chromophoric polymer can be a homopolymer or a heteropolymer. In various embodiments, the chromophoric polymer can be a semiconducting polymer, a non-semiconducting polymer, or a combination thereof. For example, a number of semiconducting polymers are suitable for use in hybrid encoded particles according to the present disclosure. Semiconducting polymers have been developed with emission wavelengths ranging from UV to infrared, including the entire visible spectrum. A wide variety of chromophoric polymer structures are suitable for use in accordance with various embodiments and embodiments of the present disclosure. In some embodiments, the chromophoric polymer is a linear polymer. In other embodiments, the chromophoric polymer is a branched polymer. In certain embodiments, the chromophoric polymer is a dendrimer. In certain embodiments, the chromophoric polymer is a brush polymer. In certain embodiments, the chromophoric polymer is a star polymer.

In some embodiments, the chromophoric polymers contain a polymer functionalized on the terminal monomeric unit, for example with a carboxyl, amine, thiol, ester, succinimidyl ester, azide, alkyne, cyclooctyne, phosphine, or similar functional group.

In some embodiments of the present disclosure, the hybrid encoded particles provided herein include the polymer CN-PPV, also known as poly[2-methoxy-5-(2-ethylhexyloxy)-1,4-(1-cyanovinylene-1,4-phenylene)], which is a bright, compact, and orange-emitting semiconducting polymer particle. In certain embodiments, CN-PPV has superior fluorescence properties, such as a large absorption cross-section, high quantum yield, and a fast emission rate. In some embodiments, the hybrid encoded particle comprises a polymer that consists essentially of CN-PPV. In some embodiments, the particle includes CN-PPV and at least one other material. For example, the CN-PPV can form part of a copolymer or be mixed with a copolymer or other material that provides an additional functionality.

In some embodiments, the hybrid encoded particles of the present disclosure include a semiconducting copolymer having at least two different chromophoric units. For example, a conjugated or semiconducting copolymer can contain both fluorene and benzothiazole chromophoric units present at a given ratio. Typical chromophoric units used to synthesize semiconducting copolymers include, but are not limited to fluorene units, phenylene vinylene units, phenylene units, phenylene ethynylene units, benzothiazole units, thiophene units, carbazole fluorene units, vinylcarbazole unit, borondipyrromethene units, squaraine units, Lanthanide containing units, and derivatives thereof. The different chromophoric units can be segregated, as in a block copolymer, or intermingled. In some embodiments, a chromophoric copolymer is represented by writing the identity of the major chromophoric species. For example, PFBT is a chromophoric polymer containing fluorene and benzothiazole units at a certain ratio. In some embodiments, a dash is used to indicate the percentage of the minor chromophoric species and then the identity of the minor chromophoric species. For example, PF-0.1 BT is a chromophoric copolymer containing 90% PF and 10% BT.

Lanthanide Compositions of Encoded Particles

In some aspects of the present disclosure, the encoded particles described herein include one or more lanthanide materials. The lanthanide materials can be lanthanide ions, lanthanide complexes, or lanthanide nanoparticles. In certain aspects, the lanthanide materials are lanthanide chromophores. In some aspects, the present disclosure utilizes the unique luminescent properties of lanthanide ions such as their narrow emission bandwidths, long lifetimes, and stable f-f transitions that are not easily influenced by the environment. Therefore, when integrating into conjugated polymer nanoparticles or other types of chromophoric polymer particles, lanthanide ions maintain their individual luminescence and their emission intensity can be independently or semi-independently tuned. Based on these unique properties, the present disclosure provides an improved encoding technology for high throughput bioanalysis.

In certain aspects, the lanthanide chromophores described herein have narrow emission properties, long luminescence lifetime, and distinct luminescence mechanisms as compared to organic fluorophores. For example, in a principle luminescence mechanism of lanthanide (III) ions (such as Ce (III), Pr(III), Nd(III), Pm(III), Sm(III), Eu(III), Gd(III), Tb(III), Dy(III), Ho(III), Er(III), Tm(III), or Yb(III)), whose 4f shells are not empty and not fully filled by electrons, transitions within the f shells can yield luminescence ranging from the UV region to near infrared region. In some aspects, because the inner shell f orbital electrons are shielded from the environment by the filled 5s5p sub-shells, their luminescence does not vary much with the environment. In some aspects, lanthanide ions exhibit Stokes luminescence, i.e., a short-wavelength photon excitation generates a long-wavelength photon emission. In certain aspects, one photon excitation can generate two or more photon emission (quantum cutting), e.g., the energy of one photon can be split to have two or more photon emission. In some aspects, lanthanide ions exhibit anti-Stokes luminescence (upconversion luminescence), e.g., two or more long-wavelength photons excitation generates a short-wavelength photon emission.

Various types of lanthanide chromophores are suitable for use with the present disclosure. A lanthanide chromophore can include any suitable type of lanthanide material, such as lanthanide ions, lanthanide complexes, lanthanide nanoparticles, or combinations thereof. In some aspects, a lanthanide chromophore includes a lanthanide selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), Lu(III), or a combination thereof. In some aspects, the lanthanide chromophores of the present disclosure are lanthanide derivatives, e.g., lanthanide derivatives selected from an alkyl derivative, aryl derivative, alkyne derivative, aromatic derivative, alkoxide derivative, aza derivative, an extended system thereof, or an analogue thereof. In certain aspects, the lanthanide chromophores are doped in an inorganic host material such as lanthanide oxide, lanthanide fluoride and related materials. The lanthanide ion can also coordinate with organic chromophores to form lanthanide chromophore complexes.

In some aspects, a lanthanide chromophore includes a rare earth metal selected from Sc, Y, La, Ce, Pr, Nd, Pm, Sm, Eu, Gd, Tb, Dy, Ho, Er, Tm, Yb, Lu, or a combination thereof. In certain aspects, the lanthanide chromophore includes a rare earth metal (e.g., a rare earth metal ion) that is used as a non-luminescent host material (e.g., Sc, Y, La, Gd, Lu, or a combination thereof) and one or more luminescent rare earth metal ions that are doped in the host (e.g., Eu(III), Tb(III), Ho(III), Er(III), Tm(III), Yb(III), or combinations thereof). In various aspects, the lanthanide chromophore includes at least one doped lanthanide ion that is preferable for downconversion luminescence, such as Pr(III), Sm(III), Eu(III), Tb(III), Dy(III), Yb(III), or a combination thereof. In various aspects, the lanthanide chromophore includes at least one doped lanthanide ion that is preferable for upconversion luminescence, such as Ho(III), Er(III), Tm(III), Yb(III), or a combination thereof. Any suitable number and combination of ions can be simultaneously doped into a single host material, such as two or more ions, three or more ions, four or more ions, five or more ions, six or more ions, seven or more ions, eight or more ions, nine or more ions, or ten or more ions.

In certain aspects, the encoded particles of the present disclosure can include at least one type of chromophoric polymer as described herein and at least one type of lanthanide chromophore, such as lanthanide ions, lanthanide complexes, or lanthanide nanoparticles. The optical properties of the chromophoric polymer and/or lanthanide chromophore can be varied as desired. In some aspects, the chromophoric polymer is fluorescent so that both the polymer fluorescence and lanthanide chromophore luminescence can be used for encoding. In some aspects, the chromophoric polymer is weakly fluorescent or significantly quenched so that only the lanthanide materials are used for encoding. In certain aspects, the peak emission wavelength of the lanthanide chromophore is longer than the peak emission wavelength of the chromophoric polymer. In other aspects, the peak emission wavelength of the lanthanide chromophore is shorter than the peak emission wavelength of the chromophoric polymer.

In some aspects, the encoded particle provides a flexible polymer matrix (e.g., formed from one or more chromophoric polymers) that can accommodate the lanthanide materials. Accordingly, in certain aspects, an encoded particle includes a polymer matrix and at least one lanthanide chromophore incorporated in the polymer matrix. Any suitable number and combination of lanthanide chromophore types can be incorporated in the polymer matrix, such as one or more lanthanide chromophores, two or more lanthanide chromophores, three or more lanthanide chromophores, four or more lanthanide chromophores, five or more lanthanide chromophores, six or more lanthanide chromophores, seven or more lanthanide chromophores, eight or more lanthanide chromophores, nine or more lanthanide chromophores, ten or more lanthanide chromophores, at fifty or more lanthanide chromophores, or one hundred or more lanthanide chromophores. The mass concentration of the lanthanide materials relative to the entire encoded particle mass can be varied from 1% to 99%, more preferably between 10% and 99%, more preferably between 20% and 99%, more preferably between 30% and 99%, more preferably between 40% and 99%, and more preferably between 50% and 99%.

In certain aspects, at least some of the lanthanide chromophores are distinct lanthanide chromophores (e.g., having different structures, compositions, and/or properties). For example, some or all of the lanthanide chromophores can have optical properties (e.g., emission spectra, emission wavelengths, emission intensities, emission lifetimes) that are distinguishable from one another. The concentrations of the lanthanide chromophores in the encoded particle can be varied as desired. In some aspects, the encoded particle comprises a first concentration of a first lanthanide chromophore and a second concentration of a second lanthanide chromophore. In certain aspects, the encoded particle comprises two or more lanthanide chromophores in a fixed ratio (e.g., fixed mass ratio) to each other.

In various aspects, the optical properties of the polymer matrix and one or more lanthanide chromophores incorporated in the polymer matrix are designed to generate the desired optical encoding for the chromophoric polymer particle. In some aspects, the optical properties (e.g., emission spectra) of the polymer matrix and the one or more lanthanide chromophores are distinguishable from one another. For example, in certain aspects, the emission peak(s) of the one or more lanthanide chromophores have longer wavelengths than the emission peak(s) of the polymer matrix. In other aspects, the emission peak(s) of the one or more lanthanide chromophores have shorter wavelengths than the emission peak(s) of the polymer matrix. In various aspects, the intensities of the emission peaks of the one or more lanthanide chromophores and the polymer matrix are independently or semi-independently controllable. In certain aspects, there is energy transfer between the polymer matrix and the one or more lanthanide chromophores. In alternative aspects, there is substantially no energy transfer between the polymer matrix and the one or more lanthanide chromophores.

In some aspects, the lanthanide chromophore incorporated in the polymer matrix is physically embedded or integrated into the polymer matrix. In some aspects, the lanthanide chromophore is chemically crosslinked and/or physically blended with the polymer matrix. In some aspects, a first lanthanide chromophore is crosslinked to the polymer matrix at a first concentration and a second lanthanide chromophore is crosslinked to the polymer matrix at a second concentration that is different from the first concentration. In some aspects, a first lanthanide chromophore is physically blended with the polymer matrix at a first concentration and a second lanthanide chromophore is physically blended with the polymer matrix at a second concentration that is different from the first concentration.

In some aspects, the encoded particles include at least one type of chromophoric polymer physically blended, chemically cross-linked with, or covalently bound to a lanthanide chromophore, such as luminescent lanthanide complexes. Exemplary luminescent lanthanide (III) complexes include La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) complexes. Because the majority of lanthanide complexes show luminescence from f-f transitions sensitized by the organic ligands, energy transfer from the chromophoric polymer to the lanthanide complexes can be controlled by varying the structure and/or composition of the polymer and/or the lanthanide complexes. In some aspects, the energy transfer from the polymers to the lanthanide complexes can be prevented or minimized. In some aspects, the energy transfer from the polymer to the lanthanide complexes can be allowed. The optical properties (e.g., emission intensities, emission wavelengths, emission lifetimes) of each set of emission peaks of the particle can be tuned and adjusted independently or semi-independently.

In some aspects, the encoded particle includes one type of chromophoric polymer physically blended or chemically cross-linked with at least one type of luminescent lanthanide complex such as terbium (Tb) complexes. In some aspects, the Tb complexes generally show bright green luminescence. The energy transfer from the chromophoric polymers to the Tb complexes can be controlled by varying the structure and/or composition of the polymers and/or the Tb complexes. In some aspects, the energy transfer from the polymers to the Tb complexes is prevented or minimized. In some aspects, the energy transfer from the polymers to the Tb complexes is allowed. Therefore the optical properties (e.g., emission intensities, emission wavelengths, emission lifetimes) of the Tb and the chromophoric polymer inside the particle can be tuned and adjusted independently or semi-independently.

In some aspects, the encoded particle includes at least one type of chromophoric polymer physically blended or chemically cross-linked with one type of luminescent lanthanide complex such as europium (Eu) complexes. In some aspects, the Eu complexes generally show bright red luminescence.

The energy transfer from chromophoric polymers to the Eu complexes can be controlled by varying the structure and/or composition of the polymer and/or the Eu complexes. In some aspects, the energy transfer from the polymer to the Eu complexes is prevented or minimized. In some aspects, the energy transfer from the polymer to the Eu complexes is allowed. Therefore the optical properties (e.g., emission intensities, emission wavelengths, emission lifetimes) of the Eu and the chromophoric polymer inside the particle can be tuned and adjusted independently or semi-independently.

In some aspects, the encoded particle includes at least one type of chromophoric polymer that is associated with lanthanide ions selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. The lanthanide ions can coordinate with the backbone, side chains, or terminal groups of the chromophoric polymer. The resulting encoded particles therefore include the luminescent ions. In some aspects, the encoded particles include one type of lanthanide ions. In some aspects, the encoded particles include two types of lanthanide ions. In some aspects, the encoded particles include three types of lanthanide ions. In some aspects, the encoded particles include three types of lanthanide ions. In some aspects, the encoded particles include four types of lanthanide ions. In some aspects, the encoded particles include five types of lanthanide ions. In some aspects, the encoded particles include more than six types of lanthanide ions. The energy transfer from chromophoric polymers to the lanthanide ions can be controlled by varying the structure and composition of the polymer and the lanthanide ions. In some aspects, the energy transfer from the polymer to the lanthanide ions is prevented or minimized. In some aspects, the energy transfer from the polymer to the lanthanide ions is allowed. Therefore the optical properties (e.g., emission intensities, emission wavelengths, emission lifetimes) of each species inside the particle can be tuned and adjusted independently or semi-independently.

In some aspects, the chromophoric polymer particle includes at least one type of chromophoric polymer physically blended or chemically cross-linked with at least one type of lanthanide nanoparticles. In certain aspects, a lanthanide nanoparticle is a nanoparticle comprising one or more lanthanide chromophores. The lanthanide nanoparticles of the present disclosure can be lanthanide ion-doped inorganic nanoparticles such as oxides, fluorides, sulfides, aluminates, silicates, phosphates, molybdates, titanates, bismuthates, other metal salts, or a combination thereof. In some aspects, the lanthanide ion-doped inorganic nanoparticles comprise one or more metal salts.

In one aspect, the lanthanide nanoparticles are doped with one type of lanthanide ions selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. In some aspects, the lanthanide nanoparticles are co-doped by two or more types of lanthanide ions, and therefore the resulting chromophoric polymer particles include two or more types of luminescent ions. The doped lanthanide ions can be any combinations selected from La(III), Ce(III), Pr(III), Nd(III), Pm(III), Sm(III), Sm(II), Eu(III), Eu(II), Gd(III), Tb(III), Dy(III), Ho(III), Er(III), Tm(III), Yb(III), Yb(II), or Lu(III) ions. The energy transfer from chromophoric polymers to the lanthanide nanoparticles can be controlled by varying the structure and composition of the polymer and the lanthanide nanoparticles. In some aspects, the energy transfer from the polymer to the lanthanide nanoparticles can be prevented or minimized. In some aspects, the energy transfer from the polymer to the lanthanide nanoparticles can be allowed. Therefore the optical properties (e.g., emission intensities, emission wavelengths, emission lifetimes) of each species inside the particle can be tuned and adjusted independently or semi-independently.

In some aspects, the encoded particle includes at least one type of chromophoric polymer physically blended or chemically cross-linked with at least one type of lanthanide upconversion nanoparticles. The lanthanide upconversion nanoparticles describe the nanoparticles that exhibit short-wavelength luminescence emissions by long-wavelength multiple-photon excitations. The lanthanide upconversion nanoparticles can be lanthanide ions doped inorganic nanoparticles such as oxides, fluorides, sulfides, aluminates, silicates, phosphates, molybdates, titanates, bismuthates, other metal salts, or a combination thereof.

Chromophoric Dye Compositions for Encoded Particles

In various aspects, the encoded particles of the present disclosure include one or more chromophoric dyes, such as fluorescent dyes, luminescent dyes, or combinations thereof. The chromophoric dye can be a small molecule dye. In certain aspects, the encoded particles of the present disclosure can include at least one type of chromophoric polymer as described herein and at least one type of chromophoric dye. The optical properties of the chromophoric polymer and/or chromophoric dye can be varied as desired. In some aspects, the chromophoric polymer is fluorescent so that both the polymer fluorescence and chromophoric dye luminescence can be used for encoding. In some aspects, the chromophoric polymer is weakly fluorescent or significantly quenched so that only the lanthanide materials are used for encoding. In certain aspects, the peak emission wavelength of the chromophoric dye is longer than the peak emission wavelength of the chromophoric polymer. In other aspects, the peak emission wavelength of the chromophoric dye is shorter than the peak emission wavelength of the chromophoric polymer.

In some aspects, the encoded particle provides a flexible polymer matrix (e.g., formed from one or more chromophoric polymers) that can accommodate the chromophoric dyes. Accordingly, in certain aspects, an encoded particle includes a polymer matrix and at least one chromophoric dye incorporated in the polymer matrix. Any suitable number and combination of chromophoric dye types can be incorporated in the polymer matrix, such as one or more chromophoric dyes, two or more chromophoric dyes, three or more chromophoric dyes, four or more chromophoric dyes, five or more chromophoric dyes, six or more chromophoric dyes, seven or more chromophoric dyes, eight or more chromophoric dyes, nine or more chromophoric dyes, ten or more chromophoric dyes, at fifty or more chromophoric dyes, or one hundred or more chromophoric dyes. The mass concentration of the chromophoric dyes relative to the entire encoded particle mass can be varied from 1% to 99%, more preferably between 10% and 99%, more preferably between 20% and 99%, more preferably between 30% and 99%, more preferably between 40% and 99%, and more preferably between 50% and 99%.

In certain aspects, at least some of the chromophoric dyes are distinct chromophoric dyes (e.g., having different structures, compositions, and/or properties). For example, some or all of the chromophoric dyes can have optical properties (e.g., emission spectra, emission wavelengths, emission intensities, emission lifetimes) that are distinguishable from one another. The concentrations of the chromophoric dyes in the encoded particle can be varied as desired. In some aspects, the encoded particle comprises a first concentration of a first chromophoric dye and a second concentration of a second chromophoric dye. In certain aspects, the encoded particle comprises two or more chromophoric dyes in a fixed ratio (e.g., fixed mass ratio) to each other.

In various aspects, the optical properties of the polymer matrix and one or more chromophoric dyes incorporated in the polymer matrix are designed to generate the desired optical encoding for the chromophoric polymer particle. In some aspects, the optical properties (e.g., emission spectra) of the polymer matrix and the one or more chromophoric dyes are distinguishable from one another. For example, in certain aspects, the emission peak(s) of the one or more chromophoric dyes have longer wavelengths than the emission peak(s) of the polymer matrix. In other aspects, the emission peak(s) of the one or more chromophoric dyes have shorter wavelengths than the emission peak(s) of the polymer matrix. In various aspects, the intensities of the emission peaks of the one or more chromophoric dyes and the polymer matrix are independently or semi-independently controllable. In certain aspects, there is energy transfer between the polymer matrix and the one or more chromophoric dyes. In alternative aspects, there is substantially no energy transfer between the polymer matrix and the one or more lanthanide chromophores.

In some aspects, the chromophoric dye incorporated in the polymer matrix is physically embedded or integrated into the polymer matrix. In some aspects, the chromophoric dye is chemically crosslinked and/or physically blended with the polymer matrix. In some aspects, a first chromophoric dye is crosslinked to the polymer matrix at a first concentration and a second chromophoric dye is crosslinked to the polymer matrix at a second concentration that is different from the first concentration. In some aspects, a first chromophoric dye is physically blended with the polymer matrix at a first concentration and a second chromophoric dye is physically blended with the polymer matrix at a second concentration that is different from the first concentration. In certain aspects, the chromophoric dye is chemically crosslinked and/or physically blended with a chromophoric polymer (e.g., a chromophoric polymer forming the polymer matrix).

A wide variety of chromophoric dyes are suitable for use with the encoded particles described herein. In certain aspects, the chromophoric dye is a fluorescent dye. In various aspects, the chromophoric dye is a small molecule organic dye. Examples of fluorescent dyes include but are not limited to: BODIPY and/or BODIPY derivatives, a squaraine and/or squaraine derivatives, a metal complex and/or metal complex derivatives, a porphyrin and/or porphyrin derivatives, a metalloporphyrin and/or metalloporphyrin derivatives, a phthalocyanine and/or phthalocynanine derivatives, a metal phthalocyanine and/or metal phthalocynanine derivatives, a lanthanide complex and/or lanthanide complex derivatives, a perylene and/or perylene derivatives, a cyanine and/or cyanine derivatives, a rhodamine and/or rhodamine derivatives, a coumarin and/or coumarin derivatives, and/or a xanthene and/or xanthene derivatives. In some aspects, the derivatives are selected from an alkyl derivative, aryl derivative, alkyne derivative, aromatic derivative, alkoxide derivative, aza derivative, or analogue thereof.

Polyelectrolyte-Coated Encoded Particles

In some aspects, the encoded particles provided herein can have a polyelectrolyte coating. Advantageously, a polyelectrolyte coating can, e.g., improve the colloidal stability of polymer particles in solutions that have high ionic strength, contain bivalent metal ions, or both. The improved colloidal stability as compared to some polymer particles without the polyelectrolyte coating, e.g., can allow polymer particles to be used in an assay without losing their functionality. In certain aspects, the compositional makeup of the polyelectrolyte coating can be tailored to reduce or eliminate aggregation of the polymer particles in solution, e.g., high ionic strength solutions. In addition, under certain conditions, ions (e.g., bivalent ions) in a solution can chelate groups on the surface of polymer particles, thereby affecting aggregation properties. In some aspects, polyelectrolyte coatings are used to reduce or eliminate aggregation of the polymer particles in solution.

The polyelectrolyte coatings can have a layer thickness ranging from about two to four nanometers, thereby adding about four to eight nanometers to the diameter of the nanoparticle including the polymer particle and the polyelectrolyte coating.

The polyelectrolytes in the coating can form on the surface of the polymer particles in a variety of ways. For example, if one type of polyelectrolyte is used, the polyelectrolyte polymer molecules can physically blend together to form the coating. If two or more types of polyelectrolytes are used, the polyelectrolyte polymer molecules can physically blend together to form the coating or, in some aspects, the different polyelectrolytes may form regions (or rafts) on the surface of the nanoparticle. In some aspects, the polyelectrolytes can be chemically crosslinked. For example, some or all of the polyelectrolytes in the coating can be chemically crosslinked using any crosslinking reaction generally well known in the art. The polyelectrolytes may also be chemically crosslinked with the condensed polymer(s) forming the polymer particle. In some aspects, the coating can include more than one layer of polyelectrolytes. For example, the coating can include two layers of polyelectrolytes, three layers of polyelectrolytes, or more layers of polyelectrolytes. The polyelectrolytes in the layers can include the same or different types of polyelectrolytes.

In some aspects, "polyelectrolytes" can include, e.g., polymers whose repeating units bear an electrolyte group having a charge. In some aspects, the polyelectrolytes can include polymers in which all the repeating units along the polymer bear an electrolyte group. In certain aspects, some of the repeating units of the polymer bear an electrolyte group. For example, polyelectrolytes of the present disclosure can include polymers in which at least 99%, 95%, 90%>, 85%, 80%, 75%, 70%, 65%, 60%, 55%, 50%, 45%, 40%, 35%, 30%, 25%, 20%, 15%, 10%, 5%, or 1% of the repeating units in the polymer bear an electrolyte group. In some aspects, polyelectrolytes of the present disclosure can include polymers in which at least 99%, 95%, 90%, 85%, or 80% of the repeating units in the polymer bear an electrolyte group.

In some aspects, the polyelectrolytes can include at least one type of electrolyte group. For example, the polyelectrolytes can include only one type of electrolyte group, or two or more types of electrolyte groups. The various electrolyte groups described herein can be included in a variety of different types of polyelectrolytes. Example polyelectrolytes in the present disclosure can include, but are not limited to, poly(styrene sulfonate), polyphosphate, polyacrylate, polymethacrylate, polyacrylate-co-maleate, polyacrylamide, chitosan, polysaccharide, polylysine, polyhistidine, and polypeptide. The electrolyte group described herein can be included in the polymer backbone, included in side chains attached to the polymer backbone, and/or included in a group that is attached to a side chain of a polymer.

A wide variety of electrolyte groups can be used in the present disclosure. Generally, any group that generates a charge under certain conditions can be used for the polyelectrolytes. For example, the electrolyte group can include an anion or a cation. In some aspects, the electrolyte group can include one anion or one cation. Alternatively, the electrolyte group can include more than one anion and/or cation such that the electrolyte group includes an overall negative or positive charge. The charge on the electrolyte groups can be a permanent charge or a charge generated according to a specific pH of a solution (e.g., a hydrogen can dissociate to form the charged electrolyte group). In some aspects, the electrolyte group can be a salt (e.g., neutralized with a counterion) prior to being dissolved in an aqueous solution. In some aspects, the electrolyte groups can include, but are not limited to, a carboxyl group, a sulfonate group, a phosphate group, an amino, a hydroxyl group, and a mercapto group. In some aspects, the charges of the electrolyte groups can be generated depending on acidic or basic solution characteristics. For example, a carboxyl group, sulfonate group, phosphate group, hydroxyl group, or mercapto group can be negatively charged, e.g., according to a pH of the solution and the pKa of the respective electrolyte group. In aqueous solutions, the electrolyte groups on polymers can dissociate to form charged groups and thereby making the polymers charged, forming the polyelectrolyte. In some aspects, the electrolyte groups can be substituted with substituents to place a permanent charge on the electrolyte group. For example, an amino group can include a quaternary ammonium cation that has a permanent positive charge. Substituents for the electrolyte groups can be varied, such as alkyl, aryl, CN, amino, sulfide, aldehyde, ester, ether, acid, hydroxyl or halide. In certain aspects, the substituents on the electrolyte groups can provide the charge to the electrolyte.

One aspect of the present disclosure includes modifying the zeta potential of the polymer particles by providing a polyelectrolyte coating. This coating can be used to modify, e.g., the surface charge of the nanoparticles and prevent aggregation in solutions. Depending on the solution, the zeta potential can be tailored to prevent aggregation. In some aspects, zeta potential is a parameter to evaluate whether the particles dispersed in a solution can resist aggregation. For example, particles (e.g., polymer particles coated with polyelectrolytes) will be stable (e.g., resist aggregation) when the particles have a zeta potential more positive than +30 mV or more negative than −30 mV. Higher value zeta potentials can provide more stability against aggregation. For example, a dispersion of particles with +/−60 mV can provide excellent stability. Depending on the selected polyelectrolyte(s) described herein, the present disclosure includes particle dispersions (e.g., polymer particles having a polyelectrolyte coating) having zeta potentials that are more positive than about +30 mV, more positive than about +40 mV, more positive than about +50 mV, or move positive than about +60 mV. The present disclosure includes particle dispersions (e.g., polymer particles having a polyelectrolyte coating) having zeta potentials that are more negative than about −30 mV, more negative than about −40 mV, more negative than about −50 mV, or move negative than about −60 mV. The particles having a polymer particle with a polyelectrolyte coating can be prepared using the methods described herein for the wide variety of polyelectrolytes. The zeta potential of particle dispersions can then be determined using a variety of techniques, such as by using instruments designed to measure zeta potential, e.g., by a Malvern Zetasizer.

In certain aspects, the present disclosure includes nanoparticles that include a polymer particle having a coating including more than one polyelectrolyte polymer. For example, the coatings can include two different polyelectrolytes, three different polyelectrolytes, four different polyelectrolytes, or more and at any desired ratio.

Functionalization and Bioconjugates of Encoded Particles

In some aspects, the present disclosure provides functionalized encoded particles for biomolecular encoding. The functionalized particle includes an encoded particle and a functional group that is physically or chemically attached to the particle.

In some aspects, this invention provides encoded particle functionalized with a functional group. In some aspects, the term "functional group" refers to any chemical unit that can be attached, such as by any stable physical or chemical association, to the encoded particle, thereby rendering the surface of the chromophoric polymer particle available for conjugation or bioconjugation. In some aspects, functional groups can be hydrophobic functional groups. Examples of hydrophobic functional groups include but not limited to alkyne, strained alkyne, azide, diene, alkene, cyclooctyne, and phosphine groups (for click chemistry). In some aspects, functional groups can be hydrophilic functional groups. Examples of hydrophilic functional groups include but not limited to carboxylic acid or salts thereof, amino, mercapto, azido, diazo, aldehyde, ester, hydroxyl, carbonyl, sulfate, sulfonate, phosphate, cyanate, succinimidyl ester, substituted derivatives thereof. Such functional groups can be found by one of ordinary skill in the art, for example in Bioconjugate Techniques (Academic Press, New York, 1996 or later versions) the content of which is herein incorporated by reference in its entirety for all purposes. Examples of methods of functionalization and suitable moieties for bioconjugation for use with the methods and systems described herein can be found in, for example, PCT application numbers WO 2015/081126, which is incorporated herein by reference.

Methods for Preparing Encoded Particles

In some aspects, methods of preparing encoded particles are disclosed. In some aspects, the chromophoric polymer particles can be formed using nanoprecipitation. The nanoprecipitation method involves the introduction of a solution of a polymer in a good solvent into a poor solvent, where the change in solubility collapses the polymer into a particle form. In certain aspects, the chromophoric polymer particles can be prepared using the mini-emulsion method, the solvent mixing method, methods using emulsions, or the precipitation method. Examples of these and other methods for preparing encoded particles for use with the methods and systems described herein can be found in, for example, PCT application numbers WO 2015/081126, which is incorporated herein by reference.

Detectable Codes and Signals

As used herein, "a detectable code" can refer to an identifiable or quantifiable signal produced by a molecule (e.g., an encoded particle or chromophore) on its own or in response to a stimulus, such as excitation by a source of electromagnetic radiation. A detectable code produced by an encoded particle can comprise an optically detectable code. In some cases, an optically detectable code can be a fluorescent signal (e.g., as produced by a fluorescent molecule such as a polymer dot, quantum dot, or fluorophore). In some cases, an optically detectable code can be a luminescent signal. In some cases, a detectable code can be a colorimetric signal, such as can be produced by an enzymatic dye.

One or more aspects of a detectable code (e.g., emission wavelength, an emission lifetime, an emission intensity, a spectral intensity, or any combination thereof) can be measured and/or quantified during a digital assay. Any aspect of a detectable code (or combination thereof) can be used to assign a compartmentalized volume a value. For example, the detection, measurement, or determination (e.g., the calculation) of a spectral intensity signal produced by an encoded particle of a probe in a compartmentalized volume containing a target molecule can be used to assign the compartmentalized volume a value.

In some cases, detecting a detectable code or signal can comprise detecting the intensity of the radiation emitted by a chromophore or encoded particle at a wavelength or over a range or spectrum of wavelengths. For example, detecting a detectable code or signal can comprise detecting a fluorescent signal having an intensity higher than a threshold value or within a defined range of intensities within a range of wavelengths. A non-limiting example of detecting a detectable code could comprise the use of a detector and a band-pass filter to detect a fluorescent signal within a range of wavelengths defined by the band-pass filter. In some cases, detecting a detectable code or signal can comprise detecting a signal intensity at an emission peak wavelength of a chromophore or encoded particle or within a range comprising the emission peak wavelength of the chromophore or encoded particle.

In some cases, detecting a detectable code or signal can comprise detecting a spectral intensity. Detecting, measuring, or calculating a spectral intensity of a detectable code or signal produced by a probe can comprise detecting or measuring emission intensities at a plurality of emission wavelengths or within a plurality of emission wavelength ranges. In some cases, detecting, measuring, or calculating a spectral intensity can comprise determining or calculating a ratio between a plurality of detected emission intensities. For example, a spectral intensity of a detectable code or signal can be the ratio of a first wavelength or first wavelength range at which or in which a first emission intensity is detected (e.g., an emission intensity greater than or equal to a threshold value, or within a defined range of intensities) to a second wavelength or second wavelength range at which or in which a second emission intensity is detected (e.g., a second emission intensity greater than or equal to a threshold value, or within a defined range of intensities). In some cases, the ratio comprising a spectral intensity can uniquely identify a type of probe in a compartmentalized volume. For example, a first probe capable of producing a spectral intensity with a first ratio of signal wavelengths can be distinguished from a second probe capable of producing a spectral intensity with a second ratio of signal wavelengths. As a result, it is possible to detect and to distinguish between the presence of a first and second target molecule in a compartmentalized volume (e.g., via a method comprising a target molecule-dependent amplification step as described herein) by detecting, measuring, and/or calculating a first and second spectral intensity produced by a first and second probe, respectively, wherein the first and second probes are capable of producing the first and second spectral intensities in the presence of the first and second target molecules, respectively.

In some cases, wherein a plurality of distinct probes (e.g., a plurality of probes comprising different sets of chromophores or encoded particles) are used in a digital assay, the optically detectable code of each distinct probe can differ from another distinct probe with respect to its emission peak intensity, emission peak wavelength, an emission intensity range, an emission wavelength range or spectrum characteristic of that distinct probe type, emission lifetime, spectral intensity, or combination thereof. That is, in a digital assay comprising a plurality of distinct probes, distinct encoded particles, or distinct chromophores, each distinct probes, distinct encoded particle, or distinct chromophore can have a different set of emission peak intensity, emission peak wavelength, emission lifetime, spectral intensity, or combination thereof.

An optically detectable code can comprise a representation of the apparent spatial size of the encoded particle. That is, a difference in the diameter of an optically detectable code signal, as one example, can be an indication of the presence of a target molecule. For example, as shown in FIG. 6L, a PCR-related amplification event can cause multiple probes to associate with one another, increasing the apparent spatial size of the signal. An increase in the apparent spatial size of a signal can be caused by the increase in the emitted fluorescent or luminescent signal (e.g., an increase in the number of encoded particles). For example, a difference in the diameter of the chromophoric particle from the diameter of a single particle 610 to the diameter of associated (e.g., aggregated, inter-hybridized, or latticed) particles 620. Because the aggregated, inter-hybridized, or latticed particles contain more emitters, aggregated, inter-hybridized, or latticed particles can be or appear brighter (e.g., as measured by a detector). However, it is noted that, depending on the length of the binding regions connecting the probes, a slight decrease in maximum signal intensity detected from the encoded particle can also accompany the increase in apparent size (e.g., as a result of the increased proximity of encoded polymer dots to one another) of the optically detectable code signal. Furthermore, the encoded particles of the probes associating with one another may produce identical or a non-identical optically detectable codes as compared to the other encoded particle with which they are associating in this matter.

Optical Properties of Encoded Particles

In some aspects, the present disclosure provides an optical encoding system. In certain aspects, the optical encoding system includes a first encoded particle and a second encoded particle having optically detectable codes that are distinguishable from each other. In certain aspects, the system includes a plurality of encoded particles at least some of which have optically detectable codes that distinguishable from each other.

Certain aspects of the present disclosure provide chromophoric polymer particles suitable for use as an encoding platform. In some aspects, the present disclosure provides chromophoric polymer particles capable of optical encoding and/or biomolecular encoding, also referred to herein as "encoded particles" or "encoded polymer particles." In some aspects, an encoded particle has an optically detectable code, also referred to herein as an "optical code" or "optical encoding," which enables the particle to be optically distinguished from particles having a different code. Various types of optical encoding schemes are suitable for use with the encoded particles described herein. In certain aspects, the optically detectable code includes one or more optical properties of the polymer particle, such as a predetermined emission spectrum of the polymer particle (e.g., emission wavelength, emission intensity), a predetermined emission lifetime of the polymer particle, a predetermined emission rate, a predetermined absorption wavelength, or a combination thereof. Accordingly, an encoded particle can be uniquely identified by measuring its optical properties in order to determine the corresponding code.

In various aspects of the present disclosure, the optically detectable code is defined by the chromophores of the encoded particle. The encoded particle can include any suitable number and combination of the various chromophore compositions provided herein. For instance, exemplary chromophores suitable for use with the present disclosure include but are not limited to chromophoric polymers (e.g., one or more chromophoric polymers forming the polymer matrix of the particle, such as narrow-band chromophoric polymers), lanthanide chromophores (e.g., lanthanide ions, lanthanide complexes, lanthanide nanoparticles, or other lanthanide materials), or chromophoric dyes (e.g., fluorescent dyes, luminescent dyes), as described further herein.

In some aspects, because of the unique feature that chromophoric polymers are used as the polymer matrix, the present disclosure provides chromophoric particles for encoding where the entire particle is composed of chromophores (e.g., fluorescent and/or luminescent materials such as chromophoric polymers, lanthanide chromophores, or chromophoric dyes). In some aspects, up to 90% of the mass of each particle is composed of chromophores. In some aspects, up to 80% of the mass of each particle is composed of chromophores. In some aspects, up to 70% of the mass of each particle is composed of chromophores. In some aspects, up to 60% of the mass of each particle is composed of chromophores. In some aspects, up to 50% of the mass of each particle is composed of chromophores. In some aspects, up to 40% of the mass of each particle is composed of chromophores. In some aspects, up to 30% of the mass of each particle is composed of chromophores. In some aspects, up to 20% of the mass of each particle is composed of chromophores. In some aspects, up to 10% of the mass of each particle is composed of chromophores. In some aspects, the encoded particle includes a plurality of distinct chromophores and the combined mass of the plurality of distinct chromophores is between 1% and 99%, 10% and 99%, 20% and 99%, 30% and 99%, 40% and 99%, or 50% and 99% of the total mass of the polymer particle. In certain aspects, the chromophores can be chromophoric polymers alone. In other aspects, the chromophores can include chromophoric polymers physically blended or chemically cross-linked with other chromophore types, e.g., lanthanide materials such as lanthanide ions, lanthanide complexes, lanthanide nanoparticles, chromophoric dyes such as fluorescent dyes, or combinations thereof.

In some aspects, the encoded particle includes one or more distinct chromophores (e.g., chromophores having different structures, compositions, and/or properties) that are used to define the optically detectable code. The encoded particle can include any suitable number and combination of distinct chromophore types, such as only a single distinct chromophore, two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores. In some aspects, the encoded particle comprises a fixed mass ratio between any of the distinct chromophores in the plurality of distinct chromophores, such as a fixed mass ratio between two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores.

In certain aspects, distinct chromophores have one or more optical properties (e.g., emission spectra, emission intensities, emission wavelengths, emission lifetimes, emission rates, absorbance wavelengths, etc.) that are distinguishable from one another. For example, an encoded particle can include a polymer matrix (e.g., formed from at least one chromophoric polymer) and one or more chromophores (e.g., lanthanide chromophores) having optical properties that are distinguishable from the optical properties of the polymer matrix. In some aspects, an encoded particle includes two or more, three or more, four or more, five or more, six or more, seven or more, eight or more, nine or more, or ten or more distinct chromophores having emission spectra that are distinguishable from each other. In some aspects, the encoded particle includes two or more, three or more, four or more, five or more, six or more, seven or more, eight or more, nine or more, or ten or more distinct chromophores having emission intensities that are distinguishable from each other. In some aspects, the encoded particle includes two or more, three or more, four or more, five or more, six or more, seven or more, eight or more, nine or more, or ten or more distinct chromophores having emission wavelengths that are distinguishable from each other. In some aspects, the encoded particle includes two or more, three or more, four or more, five or more, six or more, seven or more, eight or more, nine or more, or ten or more distinct chromophores having emission lifetimes that are distinguishable from each other.

In certain aspects, distinct chromophores have one or more optical properties (e.g., emission spectra, emission intensities, emission wavelengths, emission lifetimes, etc.) that are independently or semi-independently controllable. In some aspects, the encoded particle includes two or more, three or more, four or more, five or more, six or more, seven or more, eight or more, nine or more, or ten or more distinct chromophores having emission spectra that are independently or semi-independently controllable. In some aspects, the encoded particle includes two or more, three or more, four or more, five or more, six or more, seven or more, eight or more, nine or more, or ten or more distinct chromophores having emission intensities that are independently or semi-independently controllable. In some aspects, the encoded particle includes two or more, three or more, four or more, five or more, six or more, seven or more, eight or more, nine or more, or ten or more distinct chromophores having emission wavelengths that are independently or semi-independently controllable. In some aspects, the encoded particle includes two or more, three or more, four or more, five or more, six or more, seven or more, eight or more, nine or more, or ten or more distinct chromophores having emission lifetimes that are independently or semi-independently controllable.

In certain aspects, various optical properties of the chromophores, which may be referred to herein as "optical coding parameters," are tunable so as to allow for a plurality of distinct optical codes (e.g., optical codes that are optically distinguishable from each other). As described further herein, the tunable optical coding parameters of a chromophore can include one or more optical properties of the chromophore, such as an emission peak intensity, an emission peak intensity range, an emission peak wavelength (e.g., an emission peak wavelength or an emission wavelength range), an emission lifetime, an emission rate, an absorption wavelength (e.g., an absorption peak wavelength or an absorption wavelength range), or combinations thereof. In certain aspects, the tunable optical coding parameters for each distinct chromophore are predetermined (e.g., have a value, profile, characteristic, etc. that is predetermined based on the structure and/or composition of the chromophore) in order to provide a defined optically detectable code for the polymer particle.

Various numbers and combinations of tunable optical coding parameters are suitable for use with the approaches described herein. In some aspects, a set of tunable optical coding parameters of a chromophore includes only a single tunable optical coding parameter. In other aspects, a set of tunable optical coding parameters includes at least two unique tunable optical coding parameters, at least three unique tunable optical coding parameters, at least four unique tunable optical coding parameters, at least five unique tunable optical coding parameters, at least six unique tunable optical coding parameters, at least seven unique tunable optical coding parameters, at least eight unique tunable optical coding parameters, at least nine unique tunable optical coding parameters, at least ten unique tunable optical coding parameters, at least twenty unique tunable optical coding parameters, at least fifty unique tunable optical coding parameters, or at least one hundred unique tunable optical coding parameters.

In certain aspects, each distinct chromophore is associated with a set of tunable optical coding parameters and at least some the sets of tunable optical coding parameters are independently or semi-independently tunable or modulatable. In some aspects, "tuned independently" means that one tunable optical coding parameter is not affected by another tunable optical coding parameter (e.g., one set of emission peaks is not affected by another set of emission peaks). In some aspects, "tuned semi-independently" means that one tunable optical coding parameter can be affected by another tunable optical coding parameter (e.g., one set of emission peaks can be affected by another set of emission peaks). Examples of optical coding parameters that are "tuned semi-independently" include cases where energy transfer is employed to adjust and tune the emission intensity of the polymer particles, where the polymer particles comprise donor molecules and acceptor molecules. For example, in some aspects, the sets of tunable optical coding parameters of two or more distinct chromophores, three or more or more distinct chromophores, four or more distinct chromophores, five or more distinct chromophores, six or more distinct chromophores, seven or more distinct chromophores, eight or more distinct chromophores, nine or more distinct chromophores, ten or more distinct chromophores, twenty or more distinct chromophores, fifty or more distinct chromophores, or one hundred or more distinct chromophores are independently or semi-independently tunable or modulatable.

The optically detectable code of an encoded particle can be defined based on any suitable number and combination of tunable optical coding parameters. In some aspects, the optically detectable code is defined according to a single tunable optical coding parameter (e.g., emission peak wavelength ("wavelength encoding"), emission peak intensity ("intensity encoding"), emission lifetime ("lifetime encoding"), etc.). Emission peaks comprise various peak intensities over a range of wavelengths generally centered around a peak maximum. Where the optically detectable code comprises emission peak intensity, it can be at the point of maximum emission intensity or a point of lesser emission intensity for the corresponding emission peak. Therefore, the emission peak intensity corresponds to the emission intensity at a given wavelength for any portion of the emission peak.

In some aspects, the optically detectable code is defined according to two tunable optical coding parameters (e.g., emission peak wavelength and emission peak intensity ("wavelength-intensity encoding") or emission peak wavelength and emission lifetime ("wavelength-lifetime encoding")). In alternative aspects, the optically detectable code is defined according to three tunable optical coding parameters (e.g., emission peak wavelength, emission peak intensity, and emission lifetime ("wavelength-intensity-lifetime encoding"). In some aspects, the optically detectable code is defined according to four tunable optical coding parameters, five tunable optical coding parameters, six tunable optical coding parameters, seven tunable optical coding parameters, eight tunable optical coding parameters, nine tunable optical coding parameters, ten tunable optical coding parameters, or more than ten tunable optical coding parameters.

In certain aspects, the optically detectable code includes a predetermined set of emission peaks of the encoded particle. In some aspects, the chemical composition and structure of the encoded chromophoric particle comprise at least two distinct chromophores (e.g., at least one type of chromophoric polymer and one type of lanthanide chromophore, at least one type of chromophoric polymer and one type of fluorescent dye) which are tuned to obtain at least two sets of emission peaks for the polymer particle. In some aspects, the encoded particles have at least two sets, at least three sets, at least four sets, at least five sets, at least six sets, at least seven sets, at least eight sets, at least nine sets, or at least ten sets of emission peaks generated by tuning a corresponding number of chromophores.

In one preferable aspect, the chromophoric polymer particle can have multiple, e.g., 2-10, sets of well-resolved emission peaks, in which any two neighboring emission peaks do not have spectral overlap. The intensity levels of each emission peak can be tuned independently by adjusting the particle composition and/or polymer structure. However, in certain aspects, the chromophoric polymer particle can have multiple emission peaks, and there may be some spectral overlap between two neighboring emission peaks. In some aspects, the overlapped area is less than 1% of the integrated area of any one of the two neighboring peaks. In some aspects, the overlapped area is less than 5% of the integrated area of any one of the two neighboring peaks. In some aspects, the overlapped area is less than 10% of the integrated area of any one of the two neighboring peaks. In some aspects, the overlapped area is less than 20% of the integrated area of any one of the two neighboring peaks. In some aspects, the overlapped area is less than 30% of the integrated area of any one of the two neighboring peaks. In some aspects, the overlapped area is less than 40% of the integrated area of any one of the two neighboring peaks.

In another preferable aspect, the encoded particle can have multiple, e.g., 2-10, sets of emission peaks, and each peak originates from one chromophore (e.g., a fluorescent species) in the particle. In certain aspects, the intensity levels of each emission peak can be tuned independently, e.g., by adjusting the particle composition and/or polymer structure. In certain aspects, the chromophoric polymer particle can have multiple emission peaks, but two or more than two emission peaks can originate from one chromophore species and the other emission peaks are from different species. The intensity levels of the emission peaks from one chromophore species can be correlated and tuned by adjusting the particle composition and polymer structure.

In some aspects, the chromophoric polymer particle shows multiple, e.g., 2-10, sets of emission peaks under one-wavelength excitation. In some aspects, the chromophoric polymer particle shows multiple sets of emission peaks under two-wavelength excitation. In some aspects, the chromophoric polymer particle shows multiple sets of emission peaks under three-wavelength excitation. In some aspects, the chromophoric polymer particle shows multiple sets of emission peaks under four- or more-wavelength excitation. However, the emission intensity of each set of emission peaks can be independently or semi-independently tuned by varying the particle composition and polymer structure, e.g., the relative intensity of one set of emission peak or peaks versus any of other peaks can be changed independently or semi-independently.

In certain aspects, the emission intensities and/or emission wavelengths of the set of emission peaks of an encoded particle can be modulated, thereby allowing for encoding based on peak wavelength and/or intensity. For example, in some aspects, a wavelength encoding scheme provides a plurality of optically detectable codes defined by varying the emission wavelength of the emission peaks of the encoded particle. The emission wavelength of the polymer particles can vary from the UV region to the near infrared region. In some aspects, the emission wavelength of each set of emission peak or peaks of the polymer particle is capable of being modulated independently or semi-independently. The emission intensity of each set of emission peak or peaks of the particle can be tuned and adjusted independently or semi-independently. In some aspects, the chromophoric polymer particles include two sets of emission peaks where their wavelengths can be independently or semi-independently tuned. In some aspects, the chromophoric polymer particles include three sets of emission peaks where their wavelengths can be independently or semi-independently tuned. In some aspects, the chromophoric polymer particles include four sets of emission peaks where their wavelengths can be independently or semi-independently tuned. In some aspects, the chromophoric polymer particles include five sets of emission peaks where their wavelengths can be independently or semi-independently tuned. In some aspects, the chromophoric polymer particles include six sets of emission peaks where their wavelengths can be independently or semi-independently tuned. In some aspects, the chromophoric polymer particles include more than six sets of emission peaks where their wavelengths can be independently or semi-independently tuned. In some aspects, the chromophoric polymer particles include up to ten sets of emission peaks where their wavelengths can be independently or semi-independently tuned. In some aspects, the chromophoric polymer particles include more than ten sets of emission peaks where their wavelengths can be independently or semi-independently tuned.

In some aspects, an intensity encoding scheme provides a plurality of optically detectable codes defined varying the emission intensity levels of the emission peaks of the encoded particle. In some aspects, the chromophoric polymer particles include two sets of emission peaks where their intensity levels can be independently or semi-independently tuned. In some aspects, the chromophoric polymer particles include three sets of emission peaks where their intensity levels can be independently or semi-independently tuned. In some aspects, the chromophoric polymer particles include four sets of emission peaks where their intensity levels can be independently or semi-independently tuned. In some aspects, the chromophoric polymer particles include five sets of emission peaks where their intensity levels can be independently or semi-independently tuned. In some aspects, the chromophoric polymer particles include six sets of emission peaks where their intensity levels can be independently or semi-independently tuned. In some aspects, the chromophoric polymer particles include more than six sets of emission peaks where their intensity levels can be independently or semi-independently tuned. In some aspects, the chromophoric polymer particles include up to ten sets of emission peaks where their intensity levels can be independently or semi-independently tuned. In some aspects, the chromophoric polymer particles include more than ten sets of emission peaks where their intensity levels can be independently or semi-independently tuned.

In some aspects, a wavelength-intensity encoding scheme provides a plurality of optically detectable codes by varying the emission wavelength and the emission intensity level of the emission peaks of the encoded particle. The wavelength-intensity encoding scheme can be any suitable combination of the wavelength encoding schemes and intensity encoding schemes provided herein.

In some aspects, the present disclosure provides encoded particles that are capable of lifetime encoding, e.g., have optically detectable codes defined based on the emission lifetime of the polymer particle. In some aspects, the fluorescence lifetime is defined as the average time the molecule (or the particle) stays in its excited state before emitting a photon. Fluorescence lifetime can be experimentally determined from the time constant of a single exponential decay function or the average time constant of a multiexponential decay function of the fluorophore. In certain aspects, the encoded particles are capable of wavelength-intensity-lifetime encoding, also known as wavelength-intensity-lifetime multiplexing. As the color and intensity coding can be limited by spectral overlap and background interference, the lifetime coding provides an additional coding dimension. Distinguishable lifetime codes can be generated by varying the compositions of the encoded particles. For each single-color emission band, a large number of encoded particles can be generated and used as lifetime codes with distinct lifetimes ranging from 10 picoseconds to 1 millisecond.

In some aspects, the encoded particles have multiple, e.g., 2-10, sets of emission peaks, and each set of emission peak or peaks have a fluorescence or luminescence lifetime different from others. The lifetime can vary from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond.

In some aspects, the encoded particle can include at least one type of chromophoric polymer with distinct lifetimes ranging from 10 picoseconds to 1 millisecond. In some aspects, the encoded particle can include at least one type of chromophoric polymer and at least one type of dye molecule, with either the chromophoric polymer or the dye molecules having distinct lifetimes ranging from 10 picoseconds to 1 millisecond. In some aspects, the encoded particle can include at least one type of chromophoric polymer and at least two types of dye molecules, either the chromophoric polymer or the dye molecules have distinct lifetimes ranging from 10 picoseconds to 1 millisecond. In some aspects, the encoded particle can include at least one type of chromophoric polymer and at least one type of lanthanide material (e.g., lanthanide chromophore), either the chromophoric polymer or the lanthanide material have distinct lifetimes ranging from 10 picoseconds to 1 millisecond. In some aspects, the encoded particle can include at least one type of chromophoric polymer, at least one type of dye molecule, and at least one type of lanthanide material. Any of the chromophoric polymer, the dye molecule, and the lanthanide material can have distinct lifetimes ranging from 10 picoseconds to 1 millisecond.

In some aspects, the encoded particle can include at least one type of chromophoric polymer for lifetime encoding. The monomer structure, monomer species, and concentration can be varied to tune the lifetimes of the encoded particles. The encoded particles can include two or more types of chromophoric polymers to generate multiple emission colors and each emission color can be independently used to produce lifetime codes. Energy transfer between the chromophoric polymers can be used to tune the lifetimes of the encoded particles.

In some aspects, the encoded particle can include at least one type of chromophoric polymer and at least one type of chromophoric dye for lifetime encoding. Either the polymer's emission or the dye's emission can be used independently to produce lifetime codes ranging from 10 picoseconds to 1 millisecond. Energy transfer between the chromophoric polymers and the dye molecules can be used to tune the lifetimes of the encoded particles. The dye molecules can be physically associated or chemically linked with the chromophoric polymer. The structure, composition, and concentration of the dyes and the polymers can be varied to tune the lifetimes of the encoded particles. The encoded particles can include two or more types of dye molecules to generate multiple emission colors and each emission color can be independently used to produce lifetime codes.

For each single-color emission band, a number of chromophoric polymer particles can be generated and used as lifetime codes with distinct lifetimes ranging from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. The dye doped chromophoric polymer particles can be used to produce a number of lifetime codes.

In yet another aspect, the present disclosure provides encoded particles with controlled inter-particle energy transfer. Because each particle possesses multiple sets of emission peaks from different fluorescent or luminescent materials, it is desirable in some aspects to control the inter-particle energy transfer so that the intensity levels of each peak or set of peaks can be tuned. In some aspects, the inter-particle energy transfer is completely prevented so that each set of emission peaks can be independently tuned. In some aspects, the inter-particle energy transfer is partially allowed to produce different emission colors and intensity levels.

In some aspects, there is less than 50%, less than 40%, less than 30%, less than 20%, less than 10%, less than 5%, less than 4%, less than 3%, less than 2%, or less than 1% energy transfer between two or more distinct chromophores of the encoded particle. In some aspects, there is substantially no energy transfer between two or more distinct chromophores of the encoded chromophoric polymer particle. In some aspects, there is less than 50% percent energy transfer between any of the chromophores present. In some aspects, there is less than 40% percent energy transfer between any of the chromophores present. In some aspects, there is less than 30% percent energy transfer between any of the chromophores present. In some aspects, there is less than 20% percent energy transfer between any of the chromophores present. In some aspects, there is less than 10% percent energy transfer between any of the chromophores present. In some aspects, there is less than 5% percent energy transfer between any of the chromophores present. In some aspects, there is less than 4% percent energy transfer between any of the chromophores present. In some aspects, there is less than 3% percent energy transfer between any of the chromophores present. In some aspects, there is less than 2% percent energy transfer between any of the chromophores present. In some aspects, there is less than 1% percent energy transfer between any of the chromophores present. In some aspects, there is substantially no energy transfer between any of the chromophores present. In some aspects, there is no detectable energy transfer between any of the chromophores present.

In some aspects, the encoded particles comprise at least one type of chromophoric polymer for biomolecular encoding. The encoded particles can comprise one or more types of conjugated polymers (e.g., semiconducting polymers). The encoded particles have at least two sets of emission peaks. The emission wavelength of the polymer particles can vary from UV to near infrared region. The emission intensity of each set of emission peak or peaks of the particle can be tuned and adjusted independently or semi-independently. Exemplary chromophoric polymer compositions are described further herein.

In some aspects, the encoded particles include two sets of emission peaks; one set of emission peaks is from the energy donor and the other set of emission peaks is from the energy acceptor, and their intensity levels can be semi-independently tuned by energy transfer. In some aspects, the emission intensities of the donor are greater than those of the acceptor. In some aspects, the emission intensities of the donor are less than those of the acceptor.

In certain aspects, the encoded particle can be characterized by their stability. The optical properties (e.g., emission spectrum, emission band width, fluorescence or luminescence quantum yield, fluorescence or luminescence lifetime, emission intensity at a particular wavelength) are stable for over 1 day, or 1 week, or 2 weeks, or 1 month, or 2 months, or 3 months, or 6 months, or 1 year, or longer. The stable fluorescence or luminescence quantum yield means that the fluorescence or luminescence quantum yield of the particles does not change by more than 5%, or 10%, or 20%, or 50%, or higher. The stable emission spectrum means that intensity ratio of the each peak relative to other emission peaks doesn't change by more than 5%, or 10%, or 20%, or 50%, or higher.

In some aspects, the encoded particle possess some or all of the following characteristics: (1) multiple sets of, e.g., 2-10, well-resolved emission peaks with minimal spectral overlap; (2) intensity levels of each sets of emission peaks is tuned by adjusting the particle composition and polymer structure; (3) high fluorescence or luminescence quantum yield that is greater than 5%, preferably greater than 10%, preferably greater than 20%, greater than 30%, greater than 40%, greater than 50%, greater than 60%, greater than 70%, greater than 80%, or greater than 90%; (3) each set of emission peaks has a fluorescence or luminescence lifetime different from others; (4) have high stability over at least 2 weeks, preferably 1 month, 2 month, 3 month, 6 months, 1 year, or longer.

As described further herein, the encoded particles exhibit multiple sets of emission peaks with their emission intensities tuned independently or semi-independently by varying the compositions of the polymer and lanthanide materials (lanthanide ions, lanthanide complexes, or lanthanide nanoparticles). In some aspects, the mass concentration of the lanthanide materials relative to the entire particle mass is higher than 10%. In some aspects, the mass concentration of the lanthanide materials is higher than 20%. In some aspects, the mass concentration of the lanthanide materials is higher than 30%. In some aspects, the mass concentration of the lanthanide materials is higher than 40%. In some aspects, the mass concentration of the lanthanide materials is higher than 50%. In some aspects, the mass concentration of the lanthanide materials is higher than 60%. In some aspects, the mass concentration of the lanthanide materials is higher than 70%. In some aspects, the mass concentration of the lanthanide materials is higher than 80%. In some aspects, the mass concentration of the lanthanide materials is higher than 90%.

In some aspects, the emission peak(s) of the one or more lanthanide chromophores have shorter wavelengths than the emission peak(s) of the polymer matrix. In some aspects, the emission peak(s) of the one or more lanthanide chromophores have longer wavelengths than the emission peak(s) of the polymer matrix.

In some aspects, the encoded particles exhibit multiple sets of emission peaks with their emission lifetime (e.g., fluorescence or luminescence emission lifetime or spectral intensity lifetime). In some cases, the emission lifetime tuned independently or semi-independently by varying the compositions of the polymer and lanthanide materials (lanthanide ions, lanthanide complexes, or lanthanide nanoparticles). Each set of emission peak or peaks have an emission lifetime different from others. The lifetime can vary from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. Based on these properties, the encoded particles can be used for wavelength-intensity-lifetime encoding. For example, we can separate the chromophoric polymers' fluorescence from the lanthanides' luminescence with time-gated detection or imaging.

In some aspects, the encoded particle can include at least one type of chromophoric polymer and at least one type of lanthanide materials for lifetime encoding. The lanthanide materials include lanthanide complexes, lanthanide ions, and lanthanide nanoparticles. Either the polymer's emission or the lanthanide's emission can be used independently to produce lifetime codes ranging from 10 picoseconds to 1 millisecond. Energy transfer between the chromophoric polymers and the lanthanide materials can be used to tune the lifetimes of the encoded particles. Energy transfer between different lanthanide ions can also be used to tune the lifetimes of the encoded particles. Energy transfer inside lanthanide nanoparticles can also be used to tune the lifetimes of the encoded particles. The lanthanide materials can be physically associated or chemically linked with the chromophoric polymer. The structure, composition, and concentrations of the lanthanide materials and the polymers can be varied to tune the lifetimes of the encoded particles. The encoded particles can include two or more types of lanthanide materials to generate multiple emission colors and each emission color can be independently used to produce lifetime codes. For each single-color emission band, a number of chromophoric polymer particles can be generated and used as lifetime codes with distinct lifetimes ranging from 10 picoseconds to 1 millisecond.

In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond.

In some aspects, an encoded particle can include at least one type of chromophoric polymer, at least one type of dye molecules, and at least one type of lanthanide materials for lifetime encoding. The lanthanide materials include lanthanide complexes, lanthanide ions, and lanthanide nanoparticles. Either the polymer's emission, or the dye's emission, or the lanthanide's emission can be used independently to produce lifetime codes ranging from 10 picoseconds to 1 millisecond. Energy transfer between the chromophoric polymers and the lanthanide materials can be used to tune the lifetimes of the encoded particles. Energy transfer between the polymers and the dyes can also be used to tune the lifetimes of the encoded particles. Energy transfer between the lanthanide materials and the dyes can also be used to tune the lifetimes of the encoded particles. Energy transfer inside lanthanide nanoparticles can also be used to tune the lifetimes of the encoded particles. The dye molecules, lanthanide materials, and chromophoric polymers can be physically associated or chemically linked with each other. The structure, composition, and concentrations of the polymers, the dyes, and lanthanide materials can be varied to tune the lifetimes of the encoded particles. The encoded particles can include two or more types of lanthanide materials and two or more types of dyes to generate multiple emission colors and each emission color can be independently used to produce lifetime codes.

For each single-color emission band, a number of chromophoric polymer particles can be generated and used as lifetime codes with distinct lifetimes ranging from 10 picoseconds to 1 millisecond. In some aspects, the lifetime varies from 10 picoseconds to 100 picoseconds. In some aspects, the lifetime varies from 100 picoseconds to 1 nanosecond. In some aspects, the lifetime varies from 1 nanosecond to 10 nanoseconds. In some aspects, the lifetime varies from 10 nanoseconds to 100 nanoseconds. In some aspects, the lifetime varies from 100 nanoseconds to 1 microsecond. In some aspects, the lifetime varies from 1 microsecond to 10 microseconds. In some aspects, the lifetime varies from 10 microseconds to 100 microseconds. In some aspects, the lifetime varies from 100 microseconds to 1 millisecond. Encoded particles comprising dye molecules and lanthanide complexes can be used to produce a number of lifetime codes.

In some aspects, other tunable optical properties of the encoded particle can be used as a basis for optical encoding. For example, the optically detectable code can be based on the overall fluorescence or luminescence quantum yield of the polymer particle. The overall fluorescence or luminescence quantum yield of the encoded particle at a given wavelength of excitation can vary from 100% to 1%. In some aspects, the quantum yield is greater than about 90%. In some aspects, the quantum yield is greater than about 80%. In some aspects, the quantum yield is greater than about 70%. In some aspects, the quantum yield is greater than about 60%. In some aspects, the quantum yield is greater than about 50%. In some aspects, the quantum yield is greater than about 40%. In some aspects, the quantum yield is greater than about 30%. In some aspects, the quantum yield is greater than about 20%. In some aspects, the quantum yield is greater than about 10%. In some aspects, the quantum yield is greater than about 5%. In some aspects, the quantum yield is greater than about 1%.

In other aspects, the optically detectable code can be based on the emission rate of a chromophore of the encoded particle. In certain aspects, the emission rate of a chromophore ranges from about 10 picoseconds to about 100 picoseconds, from about 100 picoseconds to about 1 nanosecond, from about 1 nanosecond to about 10 nanoseconds, or from about 10 nanoseconds to about 100 nanoseconds.

In other aspects, the optically detectable code can be based on the absorption properties of the encoded particle. The absorption peak can shift from the UV region to near infrared region. In some aspects, the encoded particle has one absorption peak. In some aspects, the encoded particle has two absorption peaks. In some aspects, the encoded particle has three absorption peaks. In some aspects, the encoded particle has more than three absorption peaks. The absorption peak of the encoded particle can be tuned to a certain laser wavelength. In some aspects, for example, the absorption peak is around 266 nanometers. In some aspects the absorption peak is around 355 nanometers. In some aspects, the absorption peak is around 405 nanometers. In some aspects, the absorption peak is around 450 nanometers. In some aspects, the absorption peak is around 488 nanometers. In some aspects, the absorption peak is around 532 nanometers. In some aspects, the absorption peak is around 560 nanometers. In some aspects, the absorption peak is around 635 nanometers. In some aspects, the absorption peak is around 655 nanometers. In some aspects, the absorption peak is around 700 nanometers. In some aspects, the absorption peak is around 750 nanometers. In some aspects, the absorption peak is around 800 nanometers. In some aspects, the absorption peak is around 900 nanometers. In some aspects, the absorption peak is around 980 nanometers. In some aspects, the absorption peak is around 1064 nanometers.

In some aspects, the encoded particle has an absorption peak between about 200 nanometers and about 300 nanometers. In some aspects, the encoded particle has an absorption peak between about 300 nanometers and about 400 nanometers. In some aspects, the encoded particle has an absorption peak between about 400 nanometers and about 500 nanometers. In some aspects, the encoded particle has an absorption peak between about 500 nanometers and about 600 nanometers. In some aspects, the encoded particle has an absorption peak between about 600 nanometers and about 700 nanometers. In some aspects, the encoded particle has an absorption peak between about 700 nanometers and about 800 nanometers. In some aspects, the encoded particle has an absorption peak between about 800 nanometers and about 900 nanometers. In some aspects, the encoded particle has an absorption peak between about 900 nanometers and about 1000 nanometers. In some aspects, the encoded particle has an absorption peak between about 1000 nanometers and about 1100 nanometers. In some aspects, the encoded particle has an absorption peak between about 1100 nanometers and about 1200 nanometers.

Digital Analysis of a Sample

Compartmentalized Volumes

In certain aspects, the present methods and systems can be used to analyze samples in compartmentalized volumes. The term "digitized volumes" refers to the volumes produced after obtaining an initial sample and separating it into physically distinct smaller volumes in preparation for an assay.

As used herein, the term "compartmentalized volume" refers to a volume of liquid that is defined by spatial boundaries such that the contents of two compartmentalized volumes do not readily mix. A compartmentalized volume can be a digitized volume. Non-limiting examples of spatial boundaries of a compartmentalized volume include solid structures (e.g., the walls of a test tube or of a well of a microtiter plate), the interface of insoluble liquids (e.g., an oil-water interface), or a gas-liquid interface (e.g., a liquid compartmentalized volume on a flat surface). Compartmentalized volumes, aliquots, digitized volumes, and liquid in wells or chambers can all be compartmentalized volumes. Compartmentalized volumes can be the same size (monodisperse) or they can be different sizes (polydisperse).

The present disclosure provides devices, systems and apparatuses that can be used in the generation, manipulation, analysis, and modeling of compartmentalized volumes. Related methods are also provided. The disclosure also includes methods and systems for high-throughput analysis of compartmentalized volumes using digital quantification platforms. While enabling of digital assays using polydisperse systems, the disclosure can also be applied to the digital assays using monodisperse systems. The disclosure also includes methods for emulsion distribution modeling, data acquisition and emulsion generation.

Some embodiments of the present invention include producing compartmentalized volumes in immiscible fluids. As is well known in the art, a wide variety of immiscible fluids can be combined to produce compartmentalized volumes of varying volumes. As described further herein, the fluids can be combined through a variety of ways, such as by emulsification. For example, aqueous solution (e.g., water) can be combined with an non-aqueous fluid (e.g., oil) to produce compartmentalized volumes in a container, such as a microfluidic chip. Aqueous solutions suitable for use in the present invention can include a water-based solution that can further include buffers, salts, and other components generally known to be used in detection assays, such as PCR. Thus, aqueous solutions described herein can include, e.g., primers, nucleotides, and probes. Suitable non-aqueous fluids can include, but are not limited to, an organic phase fluid such as a mineral oil (e.g., light mineral oil), a silicone oil, a fluorinated oil or fluid (e.g., a fluorinated alcohol or Fluorinert), other commercially available materials (e.g., Tegosoft®), polybutene, or a combination thereof.

In addition to aqueous solutions and non-aqueous fluids, surfactants can also be included to, e.g., improve stability of the compartmentalized volumes and/or to facilitate compartmentalized volume formation. Suitable surfactants can include, but are not limited to, non-ionic surfactants, ionic surfactants, silicone-based surfactants, fluorinated surfactants or a combination thereof. Non-ionic surfactants can include, for example, sorbitan monostearate (Span 60), octylphenoxyethoxyethanol (Triton X-100), polyoxyethylenesorbitan monooleate (Tween 80) and sorbitan monooleate (Span 80). Silicone-based surfactants can include, for example, ABIL WE 09 surfactant. Other types of surfactants generally well known in the art can similarly be used. In some embodiments, the surfactant can be present at a variety of concentrations or ranges of concentrations, such as approximately 0.01%, 0.1%, 0.25%, 0.5%, 1%, 5%, or 10% by weight.

Formation of Compartmentalized Volumes for Digital Assays

Compartmentalized volumes can be created in various ways, either randomly or through controlled application of microfluidics. In some cases, compartmentalized volumes can be generated by flowing a fluid (e.g., aqueous phase) through a microfluidic device, which can comprise a network of channels and compartments. For example, a method of generating a compartmentalized volume can comprise flowing aqueous phase through a microfluidic device comprising a self-digitization device (e.g., such as a microfluidic chip comprising an array of chambers or wells) prefilled with oil phase and subsequently flowing additional oil phase through the device. Flowing the aqueous phase can displace the oil phase from the compartments. In some cases, flowing additional oil phase through the device can displace the remaining aqueous phase from the channels. In some cases, flowing additional oil phase through the device after flowing aqueous phase through the device can "cap" and compartmentalize the aqueous phase within one or more chamber of the device. For example, flowing additional oil phase through the device after flowing aqueous phase through the device can trap the aqueous phase in a portion of a chamber of the device.

In some cases, compartmentalized volumes can be generated by flowing a fluid (e.g., aqueous phase) through a microfluidic device, which can comprise an array of apertures or channels. For example, a method of generating a compartmentalized volume can comprise flowing aqueous phase through a microfluidic device comprising an array of apertures or channels connected to a chamber that has a different height than the array of apertures or channels, with both prefilled with oil phase. Flowing of aqueous phase through the array of apertures or channels will result in the formation of droplets at or around the interface between the aperture/channel and the chamber. The formed droplets can be polydisperse in size, that is, vary in volume by more than a factor of two or more than 100%. The formed droplets can be monodisperse in size, that is, vary in volume by less than a factor of 0.3 or less than 30%.

Compartmentalized volumes can also be generated at flow junctions (e.g., where an aqueous phase and an oil phase meet). For example, compartmentalized volumes can be formed within a microfluidic device at a T-junction where a first fluid (e.g., such as an aqueous phase) flows from a first channel (e.g., a side channel) of the microfluidic device into a second channel (e.g., a main channel) of the microfluidic device, in which a second fluid (e.g., an oil phase) may be located or through which the second fluid may be flowing. In some cases, convergent flow (e.g., joint flow) at a junction can produce compartmentalized volumes (e.g., droplets or plugs) of the first fluid within the second fluid. In some cases, a first fluid (e.g., aqueous phase) can contact or converge with a plurality of fluids at a junction of a microfluidic device. One or more of the plurality of fluids contacted by or with which the first fluid converges at a junction can be an oil phase. For example, compartmentalized volumes can be formed when an aqueous fluid contacts or converges with two oil phases (e.g., in a "flow focusing" fashion) at a cruciform junction (e.g., a plus-shaped or cross-shaped junction).

In some cases, a first and second fluid (e.g., an aqueous phase and an oil phase) can meet at a coaxial junction, which can be an interface in which a first fluid from a first channel (e.g., an inner channel) is surrounded by a sheath flow of a second fluid (e.g., an oil phase) from a second channel (e.g., an outer channel that surrounds the first channel), resulting in the formation of a plurality of compartmentalized volumes (e.g., a plurality of droplets).

A first fluid (e.g., such as an aqueous phase) can be dispersed into a second fluid (e.g., an oil phase), for example, by flowing the first fluid through a hole or channel and into the second fluid, thereby forming a plurality of compartmentalized volumes comprising the first fluid within the second fluid. In some cases, a plurality of compartmentalized volumes (e.g., droplets) can be generated simultaneously by flowing a first fluid through a plurality of holes or channels and into a second fluid. For example, a plurality of compartmentalized volumes can be formed by flowing a first fluid through a porous membrane or a microfluidic filter and into a second fluid. In some cases, a plurality of compartmentalized volumes can be formed by flowing a first fluid through a parallel step junction or a splitting channel and into a second fluid.

In some cases, a first fluid (e.g., an aqueous phase) and a second fluid (e.g., an oil phase) contained within a container (e.g., a tube, a microtube, or microcentrifuge tube) can be subjected to shear forces (e.g., through agitation or vortexing) to produce a plurality of compartmentalized volumes (e.g., an emulsion comprising a plurality of droplets of the aqueous phase within the oil phase) inside of the container. In some cases, the shear forces can be introduced in the first and/or second fluid through sonication. In some cases, an emulsion (e.g., a plurality of droplets of a first fluid inside of a second fluid) can be formed by forcing flow of the first and second fluid through a constriction (e.g., by rapidly and/or repeatedly pipetting a mixture of the first and second fluids). Compartmentalized volumes can also be formed by causing an object or structure (stainless steel ball) to move within a container comprising a first and second fluid. Various methods can be used to move the object or structure within the container to cause formation of compartmentalized volumes, such as stirring, oscillating magnetic forces, physical shaking/agitation of the container, or any other method described herein.

In some embodiments, fluid flow in or through a device (e.g., a microfluidic device) can be induced by creating a pressure difference between an inlet or proximal end of the device and an outlet or distal end of the device. A pressure difference can be created by applying a positive pressure to the inlet and/or vacuum pressure applied to the outlet. In some cases, devices can be subjected to centrifugal forces (e.g., by spinning all or a portion of the device, for example, on a spinning rotor) to aid in inducing fluid flow. Using methods such as these to induce fluid flow can cause a more dense fluid through a lower density fluid within a device. In some cases, the higher density fluid can be an aqueous phase. In some cases, the lower density fluid can be an oil phase.

Compartmentalized volumes of different sizes (e.g., diameters, volumes, etc.) can be generated using a wide range of methods. In some aspects, compartmentalized volumes can be created using valves, wells, or chambers. Compartmentalized volumes of a defined size can be generated using microfluidics (e.g., with T-channel or flow focusing as well known in the art). In some cases, compartmentalized volumes of different sizes can be formed by varying the shear rate or channel dimension. Compartmentalized volumes of different sizes can also be generated by emulsification with the aid of different surfactants. In some cases, the compartmentalized volumes of different volumes can be stabilized and controlled with the use of different surfactants.

A variety of methods can be used to produce a plurality of compartmentalized volumes having a continuous volume distribution. For example, the methods herein can include producing a plurality of compartmentalized volumes having a volume distribution. In some aspects, the plurality of compartmentalized volumes of the sample can be produced in an emulsion that includes combining immiscible fluids, as further described herein. In one example, a sample can include an aqueous solution that includes a molecule of interest (e.g., a nucleic acid molecule). The sample can be mixed with an oil to form compartmentalized volumes of the sample suspended in the oil. Depending on the method used, the volumes of the plurality of compartmentalized volumes in the emulsion can be randomly distributed along a continuous volume distribution. Furthermore, the ranges of volumes can be controlled by the method used to form the emulsions. For example, intensity of vortexing, shaking, sonicating, and/or extrusion can be controlled to produce a desired volume distribution, or by varying the composition of the surfactant and/or oil.

Microfluidic generation of constant volume compartmentalized volumes can be accomplished by using a T-junction or flow-focusing device. In these systems, the size of the compartmentalized volume can be controlled by the shear rate and channel dimensions. If, for a given T-junction geometry, the shear rate is continuously varied, compartmentalized volumes of different volumes can be generated. These methods can be realized, e.g., by computer-controlled syringe pumps or modulated air pressure, which adjusts the relative flow speeds of the aqueous phase and the oil carrier fluid.

A digital assay can comprise a plurality of compartmentalized volumes. In some cases, the plurality of compartmentalized volumes can comprise 2, 3, 4, 5, 6, 10, 100, 200, 250, 300, 384, 500, 1000, 5000, 10,000, 20,000, 30,000, 50,000, 100,000, 200,000, 300,000, 400,000, 500,000, 1,000,000, or 10,000,000 compartmentalized volumes. The number of compartmentalized volumes in a digital assay can also be a number from 2 to about 96, from about 100 to about 5,000, from about 5,000 to about 15,000, from about 15,000 to about 30,000, from about 30,000 to about 50,000, from about 50,000 to about 100,000, from about 100,000 to about 500,000, from about 500,000 to about 1,000,000, from about 1,000,000 to about 10,000,000, or more than 10,000,000 compartmentalized volumes.

As described further herein, the volumes used for digital measurements can be generated and analyzed by a variety of ways. A container (e.g., a sample holder) can be used to hold the compartmentalized volumes so that the contents of the compartmentalized volumes can be further processed and/or analyzed. A container can include test tubes, microcentrifuge tubes, arrays of wells in a standard multi-well plate, arrays of wells or chambers on a microarray or in a microfluidic chip, a microfluidic chip configured to generate compartmentalized volumes, as well as other devices capable of holding discrete volumes of a sample (e.g., wells, chambers, or tubes).

In some aspects, compartmentalized volumes of various sizes can be generated randomly, by emulsification in a container (e.g., a test tube), or semi-randomly through extrusion in the microfluidic device. An emulsion of compartmentalized volumes can be produced between two or more immiscible fluids. As used herein, the term "immiscible fluids" means two or more fluids that, under a given set of experimental conditions, do not undergo mixing or blending to an appreciable degree to form a homogeneous mixture, even when in physical contact with one another.

Compartmentalized volume randomness (or semi-randomness) can simplify a digital assay by reducing or eliminating the effort needed to control the size of compartmentalized volumes. During emulsification, compartmentalized volumes of different volume can be stabilized with the use of any suitable surfactants. The emulsification approach is particularly useful for several reasons: (1) the method is compatible with basic instrumentation found in every biomedical laboratory, (2) compartmentalized volume generation is simple; it does not require complex chip design or sophisticated equipment for flow control, (3) the compartmentalized volumes do not necessarily need to be confined in individual wells or chambers, which minimizes the space required to accommodate a large number of compartmentalized volumes and (4) the assay can be simple because the same container can be used for compartmentalized volume generation and compartmentalized volume storage during amplification. Advantageously, using this method, sample transfer between compartmentalized volume generation and the amplification reaction is not required.

Some aspects of the present disclosure include producing compartmentalized volumes in immiscible fluids. As is well known in the art, a wide variety of immiscible fluids can be combined to produce compartmentalized volumes of varying volumes. As described further herein, the fluids can be combined through a variety of ways, such as by emulsification. For example, an aqueous solution (e.g., water) can be combined with a non-aqueous fluid (e.g., oil) to produce compartmentalized volumes in a container, such as a microfluidic chip. Aqueous solutions suitable for use in the present disclosure can include a water-based solution that can further include buffers, salts, and other components generally known to be used in detection assays, such as PCR. Thus, aqueous solutions described herein can include, e.g., primers, nucleotides, and probes. Suitable non-aqueous fluids can include, but are not limited to, an organic phase fluid such as a mineral oil (e.g., light mineral oil), a silicone oil, a fluorinated oil or fluid (e.g., a fluorinated alcohol or Fluorinert), other commercially available materials (e.g., Tegosoft), polybutene, or a combination thereof.

Emulsions can be generated in a variety of ways. According to certain aspects of the present disclosure, an emulsion can be generated by agitation, which is typically physical agitation. Some methods of physical agitation for emulsion generation include, but are not limited to, shaking, vortexing (that can include vortexing individual tubes or entire well plates or other devices), sonicating, mixing with magnets, rapid pipetting or some other extrusion method, or via flow focusing within microfluidic devices, among other methods. The agitation used according to the present disclosure can be any suitable agitation means that is sufficient to give rise to an emulsion. For example, the speed, degree, and time used for vortexing, sonicating, pipetting, extrusion or other agitation methods can readily be adjusted such that it is sufficient to give rise to an emulsion system of the present disclosure. The particular characteristics of the emulsion can be tuned by adjusting the chemical components in the system and the agitation conditions that the system is subjected to. Emulsions also can be generated through extrusion, such as through the opening of a microstructure.

In some aspects, the compartmentalized volumes comprise a plurality of emulsions. In certain aspects, the plurality of emulsions is prepared by combining three or more immiscible fluids.

A variety of fluids or liquids can be used to prepare an emulsion according to the present disclosure. In some aspects, the system includes two or more immiscible fluids, that when mixed under appropriate conditions, separate into a dispersed compartmentalized volume phase and a continuous carrier phase. For example a first fluid, which will become the dispersed compartmentalized volume phase, can contain a sample. In some aspects, this first fluid will be an aqueous solution. In some aspects, this first fluid will remain a liquid, in other aspects, it can be, or become, a gel or a solid.

Possible aqueous fluids that can be used as one phase of a compartmentalized volume emulsion include, but are not limited to, various PCR and RT-PCR solutions, isothermal amplification solutions such as for LAMP or NASBA, blood samples, plasma samples, serum samples, solutions that contain cell lysates or secretions or bacterial lysates or secretions, and other biological samples containing proteins, bacteria, viral particles and/or cells (eukaryotic, prokaryotic, or particles thereof) among others. In certain aspects, the aqueous fluids can also contain surfactants or other agents to facilitate desired interactions and/or compatibility with immiscible fluids and/or other materials or interfaces they may come in contact with. In certain aspects, the aqueous solutions loaded on the devices can have cells expressing a malignant phenotype, fetal cells, circulating endothelial cells, tumor cells, cells infected with a virus, cells transfected with a gene of interest, or T-cells or B-cells present in the peripheral blood of subjects afflicted with autoimmune or autoreactive disorders, or other subtypes of immune cells, or rare cells or biological particles (e.g., exosomes, mitochondria) that circulate in peripheral blood or in the lymphatic system or spinal fluids or other body fluids. The cells or biological particles can, in some circumstances, be rare in a sample and the discretization can be used, for example, to spatially isolate the cells, thereby allowing for detection of the rare cells or biological particles.

In some aspects, the second fluid, which would become the continuous phase, will be a fluid that is immiscible with the first fluid. The second fluid is sometimes referred to as an oil, but does not need to be an oil. Potential fluids that can serve as the second fluid include but are not limited to, fluorocarbon based oils, silicon compound based oils, hydrocarbon based oils such as mineral oil and hexadecane, polybutene, vegetable based oils, ionic liquids, an aqueous phase immiscible with the first aqueous phase, or that forms a physical barrier with the first phase, supercritical fluids, air or other gas phases.

In certain aspects of the present disclosure, the compartmentalized volumes can comprise a fluid interface modification. Fluid interface modification elements include interface stabilizing or modifying molecules such as, but not limited to, surfactants, lipids, phospholipids, glycolipids, proteins, peptides, nanoparticles, polymers, precipitants, microparticles, a molecule with a hydrophobic portion and a hydrophilic portion, or other components. In some aspects, one or more fluid interface modification elements can be present in a fluid that will be comprised in a disperse compartmentalized volume phase fluid. In other aspects, one or more fluid interface modification elements can be present in a fluid that will be comprised in a continuous carrier phase fluid. In still other aspects one or more fluid interface modification elements can be present in both disperse compartmentalized volume phase fluids and continuous carrier phase fluids. The fluid interface modification elements present in a fluid that will be comprised in one phase of the emulsion can be the same or different from the fluid interface modification elements present in a fluid that will be comprised in another phase of the emulsion.

In some aspects, of the present disclosure, the fluid interface modification element can be used to prevent coalescence of neighboring emulsion compartmentalized volumes, leading to long-term emulsion stability. In some aspects, fluid interface modification elements can have some other or additional important role, such as providing a biocompatible surface within compartmentalized volumes, which may or may not also contribute to emulsion stability. In some aspects, the components can play a role in controlling transport of components between the fluids or between compartmentalized volumes. Some non-limiting examples of fluid interface modification elements include without limitation ABIL WE 09, ABIL EM90, TEGOSOFT DEC, bovine serum albumin (BSA), sorbitans (e.g., Span 80), polysorbates (e.g., PEG-ylated sorbitan such as TWEEN 20 and TWEEN 80), sodium dodecylsulfate (SDS), 1H,1H,2H,2H-perfluorooctanol (PFO), Triton-X 100, monolein, oleic acid, phospholipids, and Pico-Surf, as well as various fluorinated surfactants, among others.

In some aspects, the emulsion system will consist of a dispersed aqueous phase, containing the sample of interest, surrounded by a continuous oil phase. Other aspects can be variations or modifications of this system, or they can be emulsions of completely different composition or construction. Alternative emulsion systems include multiple emulsions such as water in oil in water (water/oil/water, or w/o/w) emulsions, or oil in water in oil (oil/water/oil, or o/w/o) emulsions. These multiple emulsion systems would then have inner, middle and outer phases. In some aspects, the inner and outer phases can have the same composition. In other aspects, the inner and outer phases can be similar—for example, both aqueous, or both the same oil—but with different sub-components. In other aspects, all three emulsion phases can have different, and sometimes very different, compositions.

In certain aspects, the emulsion system can comprise two immiscible fluids that are both aqueous or both non-aqueous. In further aspects, both emulsion fluids can be oil based where the oils are immiscible with each other. For example, one of the oils can be a hydrocarbon-based oil and the other oil can be a fluorocarbon based oil. In other emulsion systems, both fluids can be primarily aqueous but still be immiscible with each other. In some aspects, this occurs when the aqueous solutions contain components that phase separate from each other. Some examples of solutes that can be used include, but are not limited to, systems containing dextran, ficoll, methylcellulose, polyethylene glycol (PEG) of varying length, copolymers of polyethylene glycol and polypropylene glycol, polyvinyl alcohol (PVA), polyvinyl pyrrolidone (PVP), Reppal PES, $K_3PO_4$, sodium citrate, sodium sulfate, $Na_2HPO_4$, and $K_3PO_4$.

In addition to aqueous solutions and non-aqueous fluids, surfactants can also be included to, e.g., improve stability of the compartmentalized volumes and/or to facilitate compartmentalized volume formation. Suitable surfactants can include, but are not limited to, non-ionic surfactants, ionic surfactants, silicone-based surfactants, fluorinated surfactants or a combination thereof. Non-ionic surfactants can include, for example, sorbitan monostearate (Span 60), octylphenoxyethoxyethanol (Triton X-100), polyoxyethylenesorbitan monooleate (Tween 80) and sorbitan monooleate (Span 80). Silicone-based surfactants can include, for example, ABIL WE 09 surfactant. Other types of surfactants generally well known in the art can similarly be used. In some aspects, the surfactant can be present at a variety of concentrations or ranges of concentrations, such as approximately 0.01%, 0.1%, 0.25%, 0.5%, 1%, 5%, or 10% by weight.

According to certain aspects of the present disclosure, compartmentalized volumes can be formed and assayed in a chip. According to further aspects, amplification and digital measurements can take place in a digitization chip.

According to one exemplary aspect, the present disclosure provides arrays of compartmentalized volumes of different sizes, where patterned surfaces are used to create arrays of volumes of different sizes. According to this aspect, seven sets of arrays are created, where each array contains 900 compartmentalized volumes (30×30). The array is formed by creating hydrophilic circular patches in a background of a hydrophobic surface. As a result, when the surface is exposed to aqueous solution and oil, the hydrophilic patches will be covered by an aqueous drop surrounded by oil. The compartmentalized volume can be hemi-spherical, but the shape can change (either more pancaked or more rounded) depending on the exact surfaces we use and the oil and aqueous solution used. In one aspect, a heavy oil is used, and the drop is more pancaked because the oil will push on the drop.

The circles that define each set of the 900 hydrophilic patches have different sizes, ranging from 1 µm in diameter to 5 µm to 10 µm to 50 µm to 100 µm to 500 µm and finally to 1 mm in diameter. Because the volume of the drop scales roughly as cubic to the diameter of the drop, increasing the diameter of the patch by ten times increases the volume by about 1,000 times. As a result, using compartmentalized volumes of varying sizes is more efficient in terms of space and readout than simply using more compartmentalized volumes of the same size. In one aspect, 900 compartmentalized volumes for each set of the array is used because this number is suitable for arriving at a statistically robust digital readout. However, depending on the particular application and the needed robustness of the readout, either more compartmentalized volumes within each set of array or less compartmentalized volumes can be designed. According to this aspect, a large array of compartmentalized volumes can be produced with varying sizes due to the ease of surface patterning hydrophilic patches of different sizes. This aspect can be useful for applications such as digital PCR where a wide dynamic range is often desired, it is highly beneficial to perform PCR in drops that are created using patterned surfaces.

Devices and Methods for Performing Digital Measurements

Another aspect of the disclosure comprises a device for carrying out the methods of the disclosure. According to this aspect, the present disclosure provides a means for producing an plurality of compartmentalized volumes having a volume distribution, a means for measuring the volume of a given compartmentalized volume in the plurality of compartmentalized volumes, a means for determining the presence or absence of sample in the compartmentalized volume, and the concentration of sample in the plurality of compartmentalized volumes. The present methods enable the performance of digital measurements over a large dynamic range and methods and systems for increasing the dynamic range. Specifically, the device increases the dynamic range of digital measurements of a sample by, inter alia, creating sample volumes of different sizes.

In some aspects, the present methods are performed concurrently on a plurality of compartmentalized volumes. In further aspects, the plurality of compartmentalized volumes comprises an array of compartmentalized volumes. In yet further aspects, the array of compartmentalized volumes is disposed in a multi-well plate.

In some aspects, the concentration of the detectable agent is determined over a dynamic range of at least three orders of magnitude or over a dynamic range of at least six orders of magnitude.

In some aspects, the plurality of compartmentalized volumes comprises a first fluid and a second fluid, wherein the first fluid is immiscible in the second fluid. In certain aspects, the emulsion of compartmentalized volumes is formed by agitating a solution comprising a first fluid and a second fluid, wherein the first fluid is immiscible in the second fluid. In further aspects, the agitating comprises vortexing.

In various aspects, the present disclosure provides methods comprising: forming an emulsion of compartmentalized volumes by agitating a solution comprising a first fluid and a second fluid, wherein the first fluid is immiscible in the second fluid; and agitating the emulsion in a third fluid, wherein the third fluid is immiscible in the second fluid, thereby forming a double emulsion.

In some aspects, the present disclosure provides methods that comprise fluid agitation, wherein the agitating can be shaking, vortexing, sonicating, mixing with magnets, extrusion, via flow focusing or a combination thereof. In further aspects, the agitating is sufficient to form an emulsion. In further aspects, extrusion comprises pipetting the fluid, wherein the pipetting is sufficient to produce an emulsion. In certain aspects, the agitating occurs in a microfluidic device.

In various aspects, the first fluid comprises water, the second fluid comprises oil and the third fluid comprises water.

In various aspects, the compartmentalized volumes comprise a plurality of emulsions. In further aspects, the plurality of emulsions is prepared by combining three or more immiscible fluids.

In some aspects the first fluid is aqueous. In certain aspects, first fluid comprises a sample. In further aspects, the second fluid is an oil. In certain aspects, the second fluid is an oil, and the second fluid is immiscible with the first fluid and the third fluid. In some aspects, the first fluid is different from the third fluid. In certain aspects, the third fluid is an oil, and wherein the third fluid is immiscible with the first fluid and the second fluid.

In some aspects, the emulsion comprises an aqueous phase and a non-aqueous phase. In further aspects, the first fluid comprises water and the second fluid comprises oil.

In certain aspects, the plurality of compartmentalized volumes further comprises a fluid interface modification element. In further aspects, the fluid interface modification element is a surfactant. In yet further aspects, the fluid interface modification element is selected from a lipid, phospholipid, glycolipid, protein, peptide, nanoparticle, polymer, precipitant, microparticle, a molecule with a hydrophobic portion and a hydrophilic portion, or a combination thereof.

In some aspects, the present methods further comprise converting one or more of the immiscible fluids to a gel or solid. In certain aspects, the immiscible fluid is converted to a gel or solid before amplifying the sample, during amplifying the sample, or after amplifying the sample.

As used herein, the term "dynamic range" is defined as the ratio between the largest and smallest possible values of a changeable quantity.

The term "digital assay" means an assay in which measurements are made based on a counting of smaller measurements, wherein each smaller measurement is binary, having a value that is one of exactly two possible values that can be assigned to it. The digital assays described herein comprise measurements of a sample present in a fluid based on a counting of binary measurements obtained from individual volumes of the fluid.

Reactions (e.g., amplification) can be carried out in volumes with different sizes, before or during analysis of the volumes to determine in which volumes have undergone reaction (e.g., have amplified product). In certain examples, the volumes (e.g., compartmentalized volumes) can be sized and the number of occupied compartmentalized volumes (e.g., compartmentalized volumes containing a detectable agent) counted. All or just some of the compartmentalized volumes can be analyzed. Analysis can, for example, be achieved by flowing the compartmentalized volumes in a single file through a flow cytometer or similar device, where the size of the compartmentalized volume can be determined and the presence of amplification can be detected. The size of the compartmentalized volume can, for example, determined based on the scattering signal from the compartmentalized volume and the presence of amplification can be indicated by a fluorescence signal from the compartmentalized volume. Alternatively, the diameter of compartmentalized volumes can be determined by microscopy. Compartmentalized volumes can be extracted (before, during, or after completion of a reaction, e.g., amplification) from a container (e.g., a sample holder) and imaged in widefield with a CCD camera. The compartmentalized volumes, e.g., can be spread out on a surface or embedded between two glass slides and placed under a widefield microscope. By using appropriate excitation and emission filters the fluorescence within the compartmentalized volume can be quantified to reveal the presence or absence of amplification. By noting both the size of the compartmentalized volume and the presence or absence of amplification product in each compartmentalized volume, it is possible to back-calculate the original concentration of the analyte present in the sample after interrogating a sufficient number of compartmentalized volumes of different sizes. Because the compartmentalized volumes are of different sizes, for a given dynamic range, the analysis is much faster than if the compartmentalized volumes are all of similar size. In some aspects, the methods herein further include using a number of compartmentalized volumes in a plurality and the individual volumes of the compartmentalized volumes in the plurality to conduct digital measurements. For example, a sample concentration of a molecule of interest can be determined using the number of compartmentalized volumes in the plurality, the number of compartmentalized volumes in the plurality with one or more molecules of interest, and by measuring the volume of some or all of the compartmentalized volumes in the plurality.

In some aspects, the present disclosure provides methods for performing a digital assay, comprising: producing a plurality of compartmentalized volumes, wherein at least some of the compartmentalized volumes comprise a sample; amplifying the sample; labeling the sample with a detectable agent; flowing the plurality of compartmentalized volumes through a flow cytometry channel; determining the volume of a compartmentalized volume as it flows through the flow cytometry channel; determining the presence or absence of the detectable agent in the compartmentalized volume; and determining the concentration of the sample in the plurality of compartmentalized volumes based on the presence or absence of the detectable agent in a plurality of compartmentalized volumes.

In certain aspects, determining the concentration of the sample comprises detecting light scattered from a compartmentalized volume.

The present disclosure can be used for any technique in which digital measurements provide useful information about a sample. As such, the methods, systems and devices provided herein can include a volume containing a detectable agent. In certain aspects, the volume can be a well or chamber in a microfluidic chip or a compartmentalized volume (e.g., a water compartmentalized volume formed in an emulsion or on the surface of a chip) that contains the detectable agent. It will be generally understood that the detectable agent can include a single detectable molecule or a plurality of detectable molecules. Other types of detectable agents can be used, e.g., beads, quantum dots, nanoparticles, and the like. Furthermore, the detectable agent can, for example, be a molecule of interest present in a sample to be analyzed (e.g., a nucleic acid molecule in blood, serum, saliva or other solutions). Alternatively, a detectable agent can be a molecule that associates with a molecule of interest (e.g., the nucleic acid molecule) in the sample, thereby allowing the molecule to be detected. In some aspects, the methods and systems of the present disclosure can be used for amplification-related techniques (e.g., digital PCR) involving digital measurements. For amplification measurements, a volume (e.g., a compartmentalized volume) can include a single DNA molecule, for example, but the volume will also contain necessary components that are generally well known to be used for amplification and detection. In some aspects, the detectable agent is fluorescent and, thus, can be detected by fluorescence-based detection methods known in the art. However, other detection methods (e.g., absorbance, chemiluminescence, turbidity, and/or scattering) can be used to analyze the contents of a volume. A variety of detectable agents suitable for the present disclosure are generally well known in the art and can, for example, be found in The Molecular Probes Handbook, $11^{th}$ Edition (2010).

In some aspects, the methods of the present disclosure comprise measuring a volume of a compartmentalized volume only if the compartmentalized volume comprises a sample. In further aspects, the methods comprise excluding from measurement any compartmentalized volumes determined to not comprise the sample. In some aspects, sample concentrations are determined according to methods disclosed herein by identifying, sizing or enumerating only those compartmentalized volumes, which are determined to comprise a sample. In some aspects, sample concentration is determined by measuring or knowing the total volume of the sample and by identifying, sizing and enumerating only those compartmentalized volumes, which are determined to comprises sample. In further aspects, the concentrations of analytes in a sample is determined by measuring or knowing the total volume of the sample and by enumerating all the positive compartmentalized volumes and determining the volume of each positive compartmentalized volume. Advantages of this method include reducing the number of compartmentalized volumes scanned and thereby reducing the analysis time for determining sample concentration.

As further described herein, the present disclosure provides various aspects for digital measurements that cannot be achieved by existing methods and systems. For example, the present disclosure can provide the ability to measure sample concentration over a wide dynamic range. In some aspects, the dynamic range can be at least three orders of magnitude, at least four orders of magnitude, at least five orders of magnitude, or at least six orders of magnitude. In some aspects, the dynamic range can be between about 10 and $10^{10}$ molecules/mL, about $10^2$ and $10^7$ molecules/mL, about $10^4$ and $10^{10}$ molecules/mL, about $10^5$ and $10^9$ molecules/mL. In certain aspects, determining sample concentration within a dynamic range can be performed by detecting a detectable agent that is associated with a molecule of interest in the sample. Dynamic range can be dependent on a variety of factors, such as the range of volumes that are produced in an emulsion and/or the range of volumes that are analyzed and detected. In certain aspects, the volume distributions include continuously varying compartmentalized volume sizes.

In some aspects, the present methods are performed on a chip using concentration gradients. By integrating dPCR with on-chip gradient generation, or by using compartmentalized volumes of varying sizes, or the combination of both these methods, the disclosure effectively increases the dynamic range of our dPCR chip by one order to six orders of magnitude, which is comparable to the dynamic range offered by RT-PCR. By using a greater range of concentration gradients or arrays of compartmentalized volumes with larger size differences, the dynamic range can be increased even further if desired. This method for carrying out quantitative PCR (qPCR) offers several key advantages over existing technologies: (1) it is more accurate; (2) it obviates the need for running the type of calibration samples that are needed for RT-PCR and thus is higher throughput; and (3) it removes the need for real-time sensitive fluorescence detection, which is responsible for the relatively higher cost (~10×) of RT-PCR versus standard PCR devices.

Another aspect of the disclosure comprises a device for carrying out the methods of the disclosure, wherein the device creates arrays of digitized and discrete volumes of different sizes. In another aspect, the device carries out the method for increasing the dynamic range of digital measurements of a sample, comprising creating a sample concentration gradient and creating sample volumes of different sizes.

In some aspects, the present disclosure provides methods for using digital measurements to determine a concentration of a sample. The methods can include producing a plurality of compartmentalized volumes having a volume distribution, wherein at least one of the compartmentalized volumes of the plurality contains contents from the sample; determining the volume of the compartmentalized volumes; determining the presence of absence of sample in the compartmentalized volumes; and using the volumes of the compartmentalized volumes and the number of compartmentalized volumes found to contain the detectable agent to determine the concentration of the sample.

In some aspects, the present disclosure includes methods to increase the dynamic range of digital measurements that are based on creating arrays of digitized and discrete volumes of varied sizes (i.e., volumes). This method is better than simply increasing the number of compartmentalized volumes so as to increase dynamic range. This is because simply increasing the number of compartmentalized volumes increases the area the volumes occupy as well as increase the likelihood of having defects on the chip where some compartmentalized volumes do not form properly or have other defects. Simply increasing the number of compartmentalized volumes also decreases throughput by increasing the time required to analyze all the compartmentalized volumes. In certain aspects, dynamic range can be increased by creating arrays of compartmentalized volumes of different sizes rather than simply increasing the number of compartmentalized volumes. The arrays of compartmentalized volumes of different sizes can be a random array (e.g., compartmentalized volumes of different diameters all present and distributed randomly in a container) or can be a regular array.

In certain aspects, the compartmentalized volumes can then be flowed in a single-file format through a flow cytometer or other similar device where the size of the compartmentalized volume can be determined and the fluorescence from the compartmentalized volume can be interrogated. When using flow cytometry or other flow-through methods, the presence of amplification product in each compartmentalized volume is determined based on fluorescence and the size (volume) of each compartmentalized volume is determined based on the scattering signal from the compartmentalized volume. Alternatively, the size can be determined by taking an image as the compartmentalized volume passes through the apparatus in a manner similar to image-based flow cytometry. In this way, by noting both the size of each compartmentalized volume and the presence or absence of amplification product in each compartmentalized volume of a given size, it is possible to back-calculate the original concentration of the analyte present in the sample after interrogating a sufficient number of compartmentalized volumes of different sizes. Because the compartmentalized volumes are of different sizes, for a given dynamic range, the analysis is much faster than if the compartmentalized volumes are all of a similar size for reasons discussed previously.

Furthermore, an emulsion of compartmentalized volumes may be formed by agitating a solution comprising a first fluid and a second fluid. The first fluid may be immiscible in the second fluid. And, the emulsion may be agitated in a third fluid. The third fluid may be immiscible in the second fluid, thereby forming a double emulsion. The first fluid may comprise water, the second fluid may comprises oil, and the third fluid may comprises water. The fluid(s) may be agitated in many ways such as by shaking, vortexing, sonicating, mixing with magnets, extruding, flow focusing or a combination thereof. The agitation may be sufficient to form an emulsion. The extrusion, for example, may comprise pipetting the fluid, wherein the pipetting is sufficient to produce an emulsion. The agitating may occur in a microfluidic device.

The emulsion may comprise an aqueous phase and a non-aqueous phase. The compartmentalized volumes may comprise a plurality of emulsions. The compartmentalized volumes may comprise a plurality of emulsions. The plurality of emulsions may be prepared by combining three or more immiscible fluids. The three or more immiscible fluids may comprise a first fluid, a second fluid, and a third fluid. The first fluid may be aqueous. The second fluid may comprise an oil. The second fluid may be immiscible with the first fluid and the third fluid. The immiscible first, second, and/or third fluid(s) may be converted into a gel or solid. The first fluid may be different from the third fluid. The third fluid may comprise an oil. The third fluid may be immiscible with the first fluid and the second fluid. The immiscible third fluid may be converted into a solid or gel. The first fluid may comprise a sample for detection. The refractive index of the first fluid may differs from the refractive index of the second fluid by less than 200%, less than 100%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

The systems of the present disclosure further include a detection system configured to analyze the volumes and the presence or absence of sample in the plurality of compartmentalized volumes. The detection systems can include detectors for analyzing the contents of the volumes, determining volumes of compartmentalized volumes, and/or other characteristics of interest. The methods described herein will be generally compatible with any known systems capable of detecting and analyzing volumes (e.g., compartmentalized volumes and/or wells).

Digital Assay Systems

The systems described herein can comprise a container (e.g., a sample holder) containing a plurality of compartmentalized volumes, a sample, a target molecule, an encoded particle or indicator contained in at least one compartmentalized volume of the plurality of compartmentalized volumes, or a computer comprising a memory device. Optionally, the system also can comprise a detector for detecting the size of a compartmentalized volume (i.e., volume of the compartmentalized volume). A system for performing digital assays can also comprise a heating element configured to apply thermal energy to one or more compartmentalized volume.

Samples of a Digital Assay

A sample, as used herein, can be a component of a digital assay. A sample or a portion there of can be aliquoted, divided, or otherwise separated into a compartmentalized volume (e.g., a digitized volume). A sample can comprise a homogeneous solution or a heterogeneous mixture. A sample can comprise a tissue, a cell, a fluid, a target molecule, or a combination thereof from a subject (e.g., an animal, a plant, or a single-celled organism). For example, the sample can comprise blood, serum, plasma, urine, stool, lymph, saliva, or cerebrospinal fluid. In some cases, a sample can be processed (e.g., filtered, purified, homogenized, concentrated, diluted, or compartmentalized) or augmented (e.g., via the addition of other reagents, such as a molecule, an enzyme, a quencher, a probe, an internal standard, a detectable agent, or amplification reagents).

A sample can comprise one or more target molecule (e.g., a plurality of target molecules, molecules of interests, or analytes, etc.). A sample can also comprise more than one type of target molecule (e.g., more than one distinct target molecule, more than one species of target molecule or more than one set of target molecules), a plurality of types of target molecules (e.g., a plurality of distinct target molecules, a plurality of species of target molecules, or a plurality of sets of target molecules). In some cases, a sample may not comprise a target molecule. Non-limiting examples of a target molecule include a polypeptide, a polynucleotide (e.g., genomic DNA, complementary DNA, recombinant DNA, cell free DNA, an oligonucleotide, RNA molecules such as messenger RNA, ribosomal RNA, transfer RNA, non-coding RNA, small nuclear RNA, small nucleolar RNA, guide RNA, microRNA, CRISPR RNA, piwi-interacting RNA, small interfering RNA, viral RNA, or a fragment thereof), a cell, a rare cell, a cellular fraction, organelles, a virus, a drug, a toxin, a carbohydrate, a sugar, a lipid, a fatty acid, a metabolite, or a fragment or derivative thereof. The sample may be amplified. A molecule of a sample (e.g., a target molecule) may be labeled with a detectable agent, such as an encoded particle or other chromophore.

A sample or portion thereof can lack a target molecule or type of target molecule (e.g., a portion of a sample can lack one or more distinct molecule of a plurality of distinct molecules). A sample can be aliquoted, partitioned, or otherwise separated into compartmentalized volumes such that one compartmentalized volume or a plurality of compartmentalized volumes contain a portion of the sample but do not contain a target molecule found in the sample prior to separation of the sample into compartmentalized volumes. In some cases, the entire sample lacks a target molecule. For example, a sample can comprise a blank sample (e.g., a control sample). A blank sample can be a fluid that shares chemical or physical properties with a patient sample but lacks a target molecule that is present in the patient sample.

In some aspects, the target molecule can be a polypeptide, a polynucleotide, a cell, a virus, a small molecule, a drug, a toxin, a carbohydrate, a sugar, a lipid, or a fatty acid. In some aspects, the target molecule can be a polypeptide, such as a protein, and a binding region of a probe can be configured to bind to or hybridize with the target molecule. In other aspects, a target molecule can be a biotinylated protein of interest, and the binding region of the probe is an avidin (e.g., streptavidin) that specifically binds to the biotinylated protein.

Containers for Compartmentalized Volumes

A compartmentalized volume can be located in a container. A container can comprise a vessel capable of maintaining the compartmentalized volume as a discrete volume. The container may be configured for holding a compartmentalized volume or a plurality of compartmentalized volumes (e.g., during detection of a detectable signal or code). For example, a container can comprise a test tube, a sample tube, a capillary tube, a pipet or pipette tip, a well of a multi-well plate (e.g., a microtiter plate), or a chamber in a self-digitization chip, which can be a microfluidic chip. In some cases, a container contains a plurality of compartmentalized volumes. For example, a self-digitization chip or microfluidic chip can comprise a plurality of chambers, each chamber of which can comprise a compartmentalized volume. A multi-well plate can also comprise a plurality of wells, each well of which can comprise a compartmentalized volume. A tube, channel, or length of tubing can contain multiple compartmentalized volumes that are separated by, for example, hydrophobic forces. In some respects, a container can comprise a chip, or comprise a region of a chip, such as a chamber in a chip. A chip can comprise a self-digitization chip. Examples of containers, such as self-digitization chips, that can be used with the methods and systems described herein can be found in WO 2012/100198, which is incorporated by reference in its entirety.

Temperature Control Apparatus

The methods and systems of this disclosure can comprise a temperature control apparatus (which can comprise a temperature-control device) for regulating the temperature of the compartmentalized volume and/or any molecules or reagents used in the methods and systems described herein. Thus a controlled (e.g., regulated) temperature can be applied to the compartmentalized volume and/or its contents by defining a target temperature, or temperature set point. By controlling the temperature of the compartmentalized volume (e.g., cells, molecules, or detectable agents), the extent and efficiency of amplification (e.g., any step or process of a digital process comprising synthesis, extension, annealing, or melting of a nucleic acid) can be improved or optimized.

In some embodiments, a plurality of temperature control devices can be used, for example, to improve uniformity of temperature across the individual compartmentalized volumes of a digital assay (e.g., wells or chambers of a container, such as a multi-well plate or microfluidic chip). A temperature control device can be used to maintain consistent experimental conditions between samples, groups, assays, and experiments. By increasing the temperature of a compartmentalized volume or molecule contained therein during the processes of amplification or extension, it is possible to cause, modulate, or stop amplification or extension of a molecule in a compartmentalized volume.

A temperature control device can comprise a heating element for increasing the temperature in or around a compartmentalized volume. A heating element can comprise an electrical heating element, a convective heating element, an air heating element, a Peltier heating element, a resistive heating element, a combustion heating element, an induction heating element (which can be used with a container that comprises an induction coil or the like), a chemical heating element, or light heating element (e.g., infrared light). Selection of a heating element mechanism can be made based on the impact to applied voltages or electric fields created in the vicinity, capacity to precisely and accurately induce a prescribed temperature in a compartmentalized volume (or contents thereof) with little or no variation or noise, and considerations regarding suitability for a given application.

A temperature control device can also comprise a cooling element for decreasing the temperature around a compartmentalized volume (or the contents thereof). A cooling element, for example, can comprise a Peltier device.

A temperature control device can comprise a system capable of varying temperature over time. The temperature control device or plurality of temperature control devices can be prescribed (manually or digitally) to vary the temperature of a compartmentalized volume, portion of a compartmentalized volume (or the contents thereof), container, or portion of a container over time, independently or in concert with other experimental conditions. In this way, heating and/or cooling of a compartmentalized volume or the contents thereof (e.g., a probe or target molecule) can be cyclical.

A temperature control device can also comprise a heat sink or cooling element, such as a refrigeration unit.

The temperature control device can comprise a thermocouple and/or a Peltier heat pump. The temperature control device can be used (e.g., manually or by a program executable with a computer processor) to control the temperature of a compartmentalized volume or contents thereof (e.g., a probe or target molecule) by incorporating the temperature control device (which can comprise a means of increasing temperature, a means of detecting temperature, and/or a means of reducing temperature) into the container or by positioning the temperature control device in proximity to the compartmentalized volume or by controlling the temperature around the container or compartmentalized volume. Through the control feedback loop of the computer processor, a temperature detecting element such as a thermocouple, and the heating element or cooling element, the temperature of the compartmentalized volume or contents thereof can be controlled with a variation of no more than 0.25° C., no more than 0.5° C., no more than 0.75° C., no more than 1° C., no more than 2° C., no more than 3° C., no more than 4° C., or no more than 5° C., which can be measured relative to a temperature set point.

A temperature set point can be a target temperature at which experimentation (e.g., amplification or extension, as described herein) is to be performed. A temperature set point can be stipulated by a programmed protocol stored in the computer's memory or it can be stipulated manually by the user (e.g., through an input interface such as a touchscreen or keyboard).

A system for performing digital assays, as described herein, can include a heating element capable of regulating the temperature of at least one compartmentalized volume of a plurality of compartmentalized volumes. A system for performing digital assays, as described herein, can include a heating element capable of heating a plurality of compartmentalized volumes or a portion thereof individually or in tandem. A heating element can be used in digital assays involving thermal cycling methods, wherein the temperature of a compartmentalized volume can be increased or decreased to a target temperature or series of preselected temperatures in sequence. In some cases, a heating element can apply thermal energy to one or more compartmentalized volume in discrete temperature steps. A heating element can also be configured to apply thermal energy to a compartmentalized volume at an increasing rate over time. In some cases, a heating element of a digital assay system can apply thermal energy to a plurality of compartmentalized volumes in tandem. A heating element can also be used in isothermal digital assay methods, wherein the temperature of a plurality of compartmentalized volumes (or a portion thereof) is raised to a target temperature and maintained at that temperature. For example, a heating element can be used to increase or decrease the temperature of a compartmentalized volume to or maintain the temperature of a compartmentalized volume at about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 970° C. or within a range defined by any two of those values. In some cases, a heating element is capable of heating a plurality of compartmentalized volumes to a plurality of target temperatures, individually or in groups. In some cases, a heating element can be configured to provide a continuous gradient of temperatures across a plurality of compartmentalized volumes, such as in an array of compartmentalized volumes.

Imaging Sources

The imaging source may comprise any of the imaging devices and sources described herein. The imaging source may comprise, for example, an optical imaging source. The imaging source may be configured to perform one or more of confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epifluorescent microscopy, bright field imaging, dark field imaging, oblique illumination, or a combination thereof.

The systems and methods described herein can include a source of radiation for imaging or detecting an encoded particle or molecule. A source of radiation can comprise a source of radiation of any wavelength, such as visible light, infrared light, ultraviolet light, microwaves, or X-rays (for use in X-ray diffraction). In some cases, a source of radiation used in digital assays can be used to excite a fluorophore or chromophore. By stimulating the contents of a compartmentalized volume (e.g., a probe, encoded particle, dye, fluorophore, chromophore, indicator, target molecule, etc.) it is possible to produce a detectable code or signal, which can then be used to assign the compartmentalized volume a digital value.

In some aspects, the source of electromagnetic radiation comprises a laser, a lamp, an LED, or a combination thereof. In some aspects, the system further comprises a spectral filter, a multichroic mirror, or a combination thereof. In some aspects, the detector comprises a microscope. In some aspects, the detector comprises a camera. In some aspects, the detector comprises a flow cytometer. In some aspects, the processor can direct the analyte to the flow cell of a flow cytometer or microfluidic device based on the measured emission property.

In some aspects, the system comprises a plurality of different analytes, such as two, three, four, five, six, seven, eight, nine, ten or more different analytes. In some aspects, the system comprises a plurality of different encoded chromophoric polymer particles, such as two, three, four, five, six, seven, eight, nine, ten or more different encoded chromophoric polymer particles, e.g., attached to two, three, four, five, six, seven, eight, nine, ten or more different biomolecules that each have a binding affinity for one of the two, three, four, five, six, seven, eight, nine, ten or more different analytes.

In some aspects, the system provides a source of electromagnetic radiation configured to act as a source of excitation for the suspension and sample containing encoded chromophoric polymer particles. In some aspects, the source of electromagnetic radiation includes a laser. In some aspects, the peak wavelength emitted by the laser is between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more lasers having distinct peak wavelengths can be used.

In some aspects, the source of electromagnetic radiation includes a light emitting diode (LED). An LED is a semiconducting light source. In some aspects, when an LED's anode lead has a voltage that is more positive than its cathode lead by at least the LED's forward voltage drop, current flows. Electrons are able to recombine with holes within the device, releasing energy in the form of photons. The color of the light (corresponding to the energy of the photon) is determined by the energy band gap of the semiconductor.

In some aspects, the peak wavelength emitted by an LED is between about 200 nanometers and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more LEDs having distinct peak wavelengths can be used.

Detection Systems

As discussed herein, the present disclosure includes detection systems configured to analyze the volumes and the presence or absence of a target molecule in a compartmentalized volume of a plurality of compartmentalized volumes. The detection system may comprise a computing device configured to be operated by a user, an imaging source configured to be operated by the computing device, and a multi-well plate configured to be imaged by the imaging platform or source and which may contain a compartmentalized volume system or emulsion system to be imaged and analyzed. The detection system may comprise a computing device configured to be operated by a user, an imaging source configured to be operated by the computing device, and a microfluidic chip configured to be imaged by the imaging platform or source and which may contain a compartmentalized volume system or emulsion system to be imaged and analyzed.

In some aspects of the present disclosure, the presence of one or more target molecules within a compartmentalized volume is indicated by an increase of fluorescence in a particular wavelength range. In some aspects, a PCR reaction product indicates the presence of the target molecule by an increase in the fluorescence in a particular wavelength range (indicator fluorescence). In some aspects, a reference agent can be utilized in parallel with the target molecule. According to this aspect, the compartmentalized volumes emit fluorescence (i.e., reference fluorescence) in a wavelength range separate from that of the target molecule regardless of whether the target molecule is present. For a given set of compartmentalized volumes, separate sets of images of the indicator fluorescence and reference fluorescence are obtained and the compartmentalized volumes in each are identified and measured. The indicator and reference fluorescence from a given compartmentalized volume can be compared. In some aspects, the ratio of the indicator to reference fluorescence can be used to indicate whether that particular compartmentalized volume contains the target molecule. In other aspects, the absolute intensity of the indicator fluorescence would be sufficient to indicate if the compartmentalized volume contained target. In some aspects, the average value of the background pixels or a multiple thereof can be subtracted from the pixel intensities within the compartmentalized volumes before the fluorescence intensities of the indicator and reference intensities are compared. By performing this analysis, a list of compartmentalized volume diameters is obtained, and for each measured compartmentalized volume, a binary measure is obtained defining whether the compartmentalized volume is occupied (contains one or more target molecules) or not. The list of compartmentalized volume sizes and the total number of occupied compartmentalized volumes can then be used to obtain the target concentration of the sample.

There are many possible ways to measure the size, contents, and/or other aspects of compartmentalized volumes in an emulsion while applying the methods of the present disclosure. In some aspects, compartmentalized volumes can be measured optically by an optical detector comprising a flow cytometer. According to this aspect, compartmentalized volumes can flow through a large flow channel where compartmentalized volume shapes are not distorted and their volumes can be determined by computer software, based on measurements of light scattering patterns acquired by an optical detector, such as a photomultiplier tube, as the compartmentalized volumes pass a source of light excitation. In other aspects, compartmentalized volumes can pass through a narrow flow channel where the compartmentalized volumes conform to the channel width. According to this aspect, the volume of the disperse compartmentalized volumes can be determined by using the channel width and the length of the individual compartmentalized volumes in the channel to define their volume.

A variety of signal detection methods can be used according to the present disclosure. In various aspects, the present methods and systems provide for detection of compartmentalized volume aspects using optical detection methods and optical detectors. In some aspects, the emulsion system can be measured optically by an optical detector comprising a fluorescence microscope and its associated components. Images can be acquired with, for example, a confocal laser scanning microscope, a spinning-disk (Nipkow disk) confocal microscope, or a microscope that uses programmable arrays of mirrors or spatial light modulators to acquire data from multiple focal depths. In other aspects, images can be acquired with an epifluorescence microscope. In some aspects, images acquired with an epifluorescence microscope can be processed subsequently using 3D deconvolution algorithms performed by computer software. In other aspects, images can be acquired with a multi-photon microscope, such a two-photon microscope. In other aspects images can be acquired using planar illumination microscopy, Bessel beam microscopy, differential interference contrast microscopy, phase contrast microscopy, bright field imaging, dark field imaging, or oblique illumination. In some aspects, images can be acquired using a combination of the imaging devices and methods listed herein, or any other suitable imaging devices and methods that can reasonably be applied to the present methods.

A detector of a digital assay system can be configured to detect various aspects of a compartmentalized volume or the contents thereof. For example, a detector can be configured to detect light scattered within the compartmentalized volume (e.g., as a result of being excited or irradiated by an imaging source or source of electromagnetic radiation). In some cases, a detector can detect a detectable signal or code from a probe, an encoded particle, or another particle comprising a chromophore. In some cases a detector can be configured to detect an optically detectable signal or code.

In some cases, a detector can be configured to detect or measure an emission intensity (e.g., an emission peak intensity), an emission wavelength (e.g., an emission peak wavelength), an emission lifetime, or a combination thereof. For example, a detector can be configured to detect or measure two or more aspects of a detectable signal or code selected from the group comprising an emission intensity (e.g., an emission peak intensity), an emission wavelength (e.g., an emission peak wavelength), or an emission lifetime. A detector can also be configured to detect or measure the spectral intensity of a detectable signal or code. In some cases, the detection of one or more aspect of a detectable signal or code (e.g., an emission peak intensity, an emission intensity range, an emission peak wavelength, an emission wavelength range or spectrum, an emission lifetime, an absorption peak wavelength, an excitation peak wavelength, and/or a spectral intensity) can indicate the presence of a target molecule in a compartmentalized volume. In some cases, detection of a detectable signal or code can comprise detecting a plurality of emission peak intensities, emission peak wavelengths, emission lifetimes, absorption peak wavelengths, excitation peak wavelengths, or spectral intensities. As a result, a detector can be configured to detect a plurality of emission peak intensities, emission intensity ranges, emission peak wavelengths, emission wavelength ranges or spectra, emission lifetimes, absorption peak wavelengths, excitation peak wavelengths, or spectral intensities.

In some cases, a detector can be configured to measure aspects of a compartmentalized volume. The systems of the present disclosure further include a detector and a computer configured to analyze the signal emitted by encoded particles. The detector can include detectors for analyzing the signal intensity, signal-to-noise ratio, and/or other characteristics of interest. The methods described herein will be generally compatible with any known systems capable of detecting and analyzing optical information such as images.

In some aspects, the system provides a detector that detects one or more signals emitted by encoded particles. In some aspects, the detector includes a microscope, such as a confocal microscope, spinning disk microscope, multi-photon microscope, planar illumination microscope, Bessel beam microscope, differential interference contrast microscope, phase contrast microscope, epifluorescent microscope, or a combination thereof. In some aspects, the detector includes a camera, such as a charge-coupled device camera, or a CMOS camera, that can integrate the signal into an image on a digital chip. In some aspects, the detector includes a photomultiplier tube. In some aspects, the detector includes a flow cytometer. In some cases, a detector can be configured to measure or determine the volume of a compartmentalized volume as it is flowed past the detector.

In some aspects, detectors and sources of electromagnetic radiation are optimized for performing multiplex analysis. In some aspects, the detectors and sources of electromagnetic radiation are configured to excite encoded particles and detect emitted signal (e.g., optically detectable codes) rapidly. In some aspects, the detectors and sources of electromagnetic radiation are configured to excite encoded particles and detect one or more emitted signals in less than 1 nanosecond, less than 10 nanoseconds, less than 100 nanoseconds, less than 1 microsecond, less than 10 microseconds, less than 100 microseconds, less than 1 millisecond, less than 10 milliseconds, less than 100 milliseconds, less than 1 second, less than 10 seconds, or less than 100 seconds. In some aspects, the detectors and sources of electromagnetic radiation are configured to excite encoded chromophoric polymer particles and detect two or more emitted signals simultaneously.

The dimensions or number of the compartmentalized volumes of a plurality of compartmentalized volumes can be detected by an optical detection method. Detection of an detectable signal or code from a compartmentalized volume can also be made using an optical detection method. Any detector, or component thereof, that operates by detecting a measureable optical property, such as the presence of light, can comprise an optical detector. Examples of optical detectors include, but are not limited to, cameras, photomultiplier tubes, photodiodes and photodiode arrays, and microscopes, and associated components thereof, such as objectives, optical filters, mirrors, and the like.

In certain aspects, the signal detected by an optical detector, or other suitable detector, is processed in order to interpret the signals being measured by the detector. In certain aspects, the measured information is processed by a device, apparatus, or component thereof that stores and/or processes information acquired by a detector, such as, e.g., an optical detector. Examples of an information processor include, but are not limited to, a personal computing device that stores information acquired by a detector, and software running on the personal computing device that processes the information. In other aspects, an information processor or component thereof can be embedded in a detector, such as in a chip embedded in a camera that stores optical information acquired by the camera either permanently or temporarily. In other aspects, an information processor and a detector can be components of a fully integrated device that both acquires and processes optical information to perform a digital assay.

In another aspect, systems are provided for analyzing volumes to detect and calculate information for a given compartmentalized volume. For example, a spectral intensity can comprise a ratio of a plurality of emission peak intensities, or emission intensity ranges, emission peak wavelengths, or emission wavelength ranges or spectra, and a system for digital assays can be capable of calculating a ratio of a plurality of emission peak intensities, or intensity ranges, emission peak wavelengths, or emission wavelength ranges or spectra. The system can include one or more processors, and a memory device including instructions executable by the one or more processors. When the instructions are executed by the one or more processors, the system at least can receive a user input to analyze volumes (e.g., a plurality of compartmentalized volumes). The instructions can cause the processor to operate the detector to measure a detectable signal or code, to store the measured detectable signal or code (e.g., in a non-transitory memory), and/or to analyze the measured detectable signal or code. The system can be configured to carry out aspects of the methods of the present disclosure, such as counting a number of volumes (e.g., compartmentalized volumes), determining volumes of a plurality of compartmentalized volumes in a volume distribution and use the number of the compartmentalized volumes containing one or more detectable agents to determine a concentration of the detectable agent in the sample. The system can also provide data to a user. The data provided to the user can include the concentration of the detectable agent in the sample or a sample concentration.

Image Analysis

In various aspects, the disclosure provides many methods for identification, selection, or analysis (e.g., determination of the dimensions or sizes of a compartmentalized volume) of compartmentalized volumes such as the Line Scan Method, the Simple Boundary Method, the Reverse Watershed Method, the Circle Detection Method, the Combined Reverse Watershed and Circle Detection Method, or combinations thereof described herein. In some aspects, the methods of detecting or recognizing the compartmentalized volumes may be independent of the methods to determine sample concentration. That is, the methods of detecting or recognizing the compartmentalized volumes may be used for many purposes other than performing digital assay described herein. Examples of image detection and image analysis methods for use with the systems and methods described herein can be found in WO 2015/157369 and WO 2012/100198, which are incorporated herein in their entireties.

In some cases, the optical imaging can be performed by confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epifluorescence microscopy, bright field imaging, dark field imaging, oblique illumination, or a combination thereof.

The set of instructions when executed by the processor can cause the processor to determine the presence or absence of a detectable agent in at least some of the plurality of compartmentalized volumes. The set of instructions when executed by the processor may further cause the processor to determine the concentration of a sample in the plurality of compartmentalized volumes based on the presence or absence of the detectable agent in the plurality of compartmentalized volumes and the determined plurality of volumes of the plurality of compartmentalized volumes.

Determination of Occupancy

In some aspects, after the compartmentalized volumes have been identified and their size determined, the detectable signal or code (e.g., the emission intensity, emission wavelength, emission lifetime, or spectral intensity) can be used to determine if a target molecule is or was present in the compartmentalized volume.

The presence of a target molecule in a compartmentalized volume can result in an increase in the detection of one or more aspects of the detectable signal or code of a probe in a compartmentalized volume. In those cases, an intensity cutoff or threshold standard can be imposed wherein a compartmentalized volume whose intensity exceeds the cutoff or threshold can be considered to be occupied by a target molecule. A compartmentalized volume in which no measured aspect of the detectable signal or code reaches the cutoff or threshold can, in some cases, be considered empty. A non-limiting list of values measured from a compartmentalized volume being compared to the cutoff or threshold value can include: the average intensity within the compartmentalized volume; the peak intensity within the compartmentalized volume, the lifetime of the signal or detectable code, the spectral intensity within the compartmentalized volume, or any user-chosen function of the detectable signal or code (or lack thereof) measured within the compartmentalized volume (for example the median of any measured value or a percentile of a measured value can be used).

In some cases, measurements in a digital assay can be normalized to a known value or a relative value. For example, a measurement of a detectable signal or code in a compartmentalized volume made after amplification can be compared to a measurement of the same compartmentalized volume prior to amplification. In some cases, a measurement of a detectable signal or code from a compartmentalized volume can be compared to a known value such as the measured detectable signal or code from a compartmentalized volume containing a blank or control sample.

Computing Devices

The computing device may be programmed to implement one or more of the methods described herein. The computing device may comprise a personal computer, a workstation, or a server, for example. The computing device includes a processor, computer processor, central processing unit, or CPU, which can be a single core or multi-core processor, or a plurality of processors for parallel processing.

The computing device may also include a memory (e.g., random-access memory, read-only memory, flash memory, a hard disk, or the like). The memory can store files, such as computer readable image files taken by the imaging source. The computing device in some cases can include one or more additional data storage units that are external to the computing device, such as located on a remote server that is in communication with the computing device through the one or more networks.

The computing device may further comprise an input/output or I/O system which can be used by the computing device to communicate with one or more of the user US, one or more other computing devices or systems, one or more networks (e.g., a local area network (LAN), an extranet, an intranet, the Internet, a telecommunications network, a data network, a cellular data network, or the like), or one or more peripheral devices including the imaging source, external memory, various adapters, etc. The I/O system may comprise a display, a user interface, and a communications interface. The display may comprise a touch screen display through which the user interface is projected to the user US, for example. The communications interface may comprise a network adaptor for the computing device to connect to the one or more networks. The user US, for example, may operate the computing device through the one or more networks remotely. For instance, the computing device may comprise a computing system based in the cloud such a distributed computing system which operates the imaging source which may be local to the user US. The computing device can be in communication with the imaging source through the one or more networks or by direct communication.

Methods as described herein can be implemented by way of machine (or computer processor) executable code (or software) stored on an electronic storage location of the computing device, such as, for example, on the memory or other electronic storage unit. During use, the code can be executed by the processor.

In yet another aspect, the systems can include a computer-readable storage medium for conducting digital measurements. The computer-readable storage medium can have stored thereon instructions that, when executed by one or more processors of a computer, cause the computer to: analyze a plurality of compartmentalized volumes having a volume distribution to determine a number of compartmentalized volumes in the plurality that contain the detectable agent; and use the number of compartmentalized volumes in the plurality of compartmentalized volumes, the volumes of some or all of the compartmentalized volumes in the plurality and the number of compartmentalized volumes in the second plurality containing one or more detectable agents to determine a concentration of the detectable agent in the sample.

The computer-readable storage medium can have stored thereon instructions that, when executed by one or more processors of a computer, cause the computer to operate any of the functions or methods described herein. For example, the instructions can operate the heating element in modulating the temperature of one or more compartmentalized volume (e.g., during an amplification step). The instructions can also operate fluid handling systems, substrate handling systems (e.g., the positioning or repositioning of containers like multi-well plates or chips), operation of imaging sources, detection systems, or software for image analysis.

Aspects of the systems and methods provided herein, such as the computing device, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Multiplexing and Automation

The method, systems, kits, and devices described herein can be further improved with respect to speed and efficiency through the use of multiplexing and automation strategies. In a multiplexed approach, a plurality of containers (e.g., test tubes, microtiter plates, digital assay chips, etc.) can be processed (e.g., loaded with reagents and target molecules, agitated to form compartmentalized volumes, cycled through rounds of amplification, subjected to melt-curve heating protocols, monitored for differences in spectral intensity, measured and counted on a drop-by-drop basis, assigned values on a drop-by-drop basis, etc., as described herein) in rapid succession. To facilitate multiplexing, substrates can be stacked and moved into position for individual steps of the amplification and imaging processes (e.g., loading, agitation, heating, labeling, detecting, quantifying, etc.) through a moveable sample tray capable of moving substrates individually into position for each step. This movement of substrates into position for each step can comprise a gear that operates the sample tray, and the gear can be operated by the computer processor as part of a pre-established program, which, in turn can be customized for individual protocols or detectable agents to be used in experimentation. In some embodiments, multiple steps in a given digital assay protocol can occur in the same location, without requiring the substrate to be moved between steps.

The processes of activating and deactivating flow cell(s) (e.g., to facilitate mixing and loading of reagents and samples), radiation source(s) (e.g., for imaging optically detectable codes, making measurements, intentional photobleaching, and/or stimulating detectable agents), temperature control device(s), moving microscope stage(s) and filter cube(s), and detector(s) can be automated such that all, some, or one of the steps of the methods described herein can be performed without additional intervention from a user. As these processes can be performed cyclically according to the assays described herein, multiple sets of probes or detectable agents can be detected in a short period of time by employing the methods and systems described herein. Therefore, in some embodiments, the system can comprise an open or enclosed system in which the user can initiate a program (e.g., a pre-programmed or user-defined program, executable on by a processor and storable on a non-transient computer readable medium, capable of commanding any of the method steps described herein to be performed) and all other steps of the program are performed automatically by the system. In some embodiments, user intervention is only required at the beginning (e.g., inserting the substrate and/or cells and/or detectable reagents, initiating the program or computer processor) and at the end (e.g., obtaining the results from the computer processor and removing the reagents/disposables from the system) of the experiment. In some cases, multiplexed or automated systems for performing digital assays as described herein can be designed to pause for user input or user intervention.

Multiplexed digital analysis assays utilizing encoded particles can be used to interrogate from 1 to about 1,000, 5 to about 500, from about 10 to about 200, from about 10 to about 150, from about 5 to about 125, from about 6 to about 100, from about 7 to about 90, from about 8 to about 80, from about 9 to about 75, from about 10 to about 60, from about 15 to about 50, from about 20 to about 45, from about 25 to about 40, or from about 10 to about 30 target molecules per compartmentalized volume (e.g., per well, compartmentalized volume, cavities, or patch).

In some cases, a container can comprise 1, 10, 100, 500, 1,000, 5,000, 10,000, 15,000, 20,000, 30,000, 50,000, 100,000, 200,000, 500,000, 1,000,000, 2,000,000, 5,000,000 or 10,000,000 compartmentalized volumes, or a number within a range defined by any two values from that list. In some cases, 1, 10, 100, 500, 1,000, 5,000, 10,000, 15,000, 20,000, 30,000, 50,000, 100,000, 200,000, 500,000, 1,000,000 compartmentalized volumes (or a number within a range defined by any two values from that list) can be analyzed (e.g., assayed or imaged) at a time during multiplexed digital analysis assays.

Detection of Detectable Signals and Codes During Multiplexing

The efficiency of multiplexed digital assays can be improved by evaluating each compartmentalized volume for the presence of a detectable signal or code as a whole rather than evaluating each probe or encoded particle located therein for a detectable signal or code individually. An imaging lens (e.g., a microscope objective) capable of resolving (e.g., detecting) a plurality of detectable codes or signals in a compartmentalized volume on a per-particle (or per cluster of particles or aggregates of particles) basis can be used during a detection step of a digital assay, as described herein. When a high-throughput, multiplexed workflow is used in a digital assay, as described herein, it can be advantageous to employ a detection scheme designed or optimized for evaluation of each compartmentalized volume as a whole. That is, rather than employing methods and systems required to resolve a plurality of detectable codes or signals in a compartmentalized volume individually (e.g., using high power objectives and/or software capable of resolving and/or quantifying detectable signals of individual probes, which can be expensive, monetarily, computationally, or temporally), methods and systems designed to image and evaluate (e.g., detect and analyze) a compartmentalized volume as a whole can be used. An individual compartmentalized volume can thus be evaluated as a whole and assigned a binary value based on whether a detectable code or signal in the compartmentalized volume meets or exceeds a threshold value (e.g., relative to a baseline value established through detecting the compartmentalized volume prior to an amplification step). In some cases, a plurality of compartmentalized volumes can be detected and/or analyzed at the same time. As a result, the overall efficiency of a multiplexed digital assay can be improved by detecting a detectable code or signal in a plurality of compartmentalized volumes by evaluating each compartmentalized volume as a whole.

In some cases, a plurality of detectable signals or detectable codes (e.g., produced by a plurality of probes in a compartmentalized volume comprising a target molecule, as described herein) can be detected more readily when the plurality of detectable signals or codes (or a portion thereof) are located in close proximity to one another (e.g., spatially concentrated). Spatial concentration of a plurality of detectable signals or codes can be accomplished by associating, aggregating, or spatially concentrating a plurality of probes producing the plurality of detectable signals or codes (e.g., through cross-hybridizing, cross-linking, latticing, or forming the plurality of probes into a network, as described herein). In some cases, spatial concentration of a plurality of detectable signals or codes in a compartmentalized volume can increase the apparent intensity of the overall detectable signal or code being produced within a compartmentalized volume. By increasing the apparent intensity of the overall detectable signal or code being produced within a compartmentalized volume, lower power objectives can be used and/or less time need be spent to detect the presence of a target molecule in a compartmentalized volume (e.g., a digitized volume). As a result, it is possible to determine the presence or absence of a target molecule in a plurality of compartmentalized more efficiently if probes can be spatially concentrated in each compartmentalized volume in the presence of a target molecule (e.g., as described herein and illustrated in FIG. 6F, FIG. 6H, FIG. 6J, FIG. 6K, and FIG. 6L).

Compositions and Kits for Performing Digital Assays

The present disclosure provides for compositions and kits for performing the digital assays as described herein. In certain aspects, kits and assays are provided for performing digital assays, such as digital nucleic acid analysis, digital PCR, melt-curve, or isothermal assays.

In various aspects, the present disclosure provides compositions and kits for performing a digital assay comprising: a first fluid; a second fluid, wherein the first fluid and the second fluid are immiscible in each other and are capable of forming an emulsion when agitated; a surfactant; and an amplification reagent.

In some aspects, the present disclosure provides compositions and kits for performing a digital assay. A digital assay composition or kit can comprise a first fluid and a second fluid, wherein the first fluid and the second fluid are immiscible in each other and are capable of forming an emulsion when physically agitated. A kit or composition can also comprise a surfactant and a digital assay reagent. In further aspects, digital assay reagents can include a polymerase (e.g., a thermostable DNA polymerase) or other enzyme suitable for the extension of a nucleic acid, a nucleotide, a circularized nucleic acid, a quencher, a primer, a probe, an encoded particle, a binding region, a fluorescent label or detectable agent (e.g., an intercalating dye) or a combination thereof.

In further aspects, the compositions and kits can further comprise suitable buffering and stabilizing agents that are compatible with PCR amplification.

Where a range of values is provided herein, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges can independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects, herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

While preferred aspects of the present disclosure have been shown and described herein, it is to be understood that the disclosure is not limited to the particular aspects of the disclosure described below, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims. In this specification and the appended claims, the singular forms "a," "an" and "the" include plural reference unless the context clearly dictates otherwise.

All publications, patents, and patent applications mentioned in this specification are herein incorporated by reference to the same extent as if each individual publication, patent, or patent application was specifically and individually indicated to be incorporated by reference.

EXAMPLES

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Example 1

Method for Detecting a Target Molecule with an Encoded Particle in Digital PCR This Example provides exemplary methods for the use of an encoded polymer dot nanoparticle in the detection of a target sequence of a target molecule using digital PCR, according to one aspect of the present disclosure.

Figure 4:
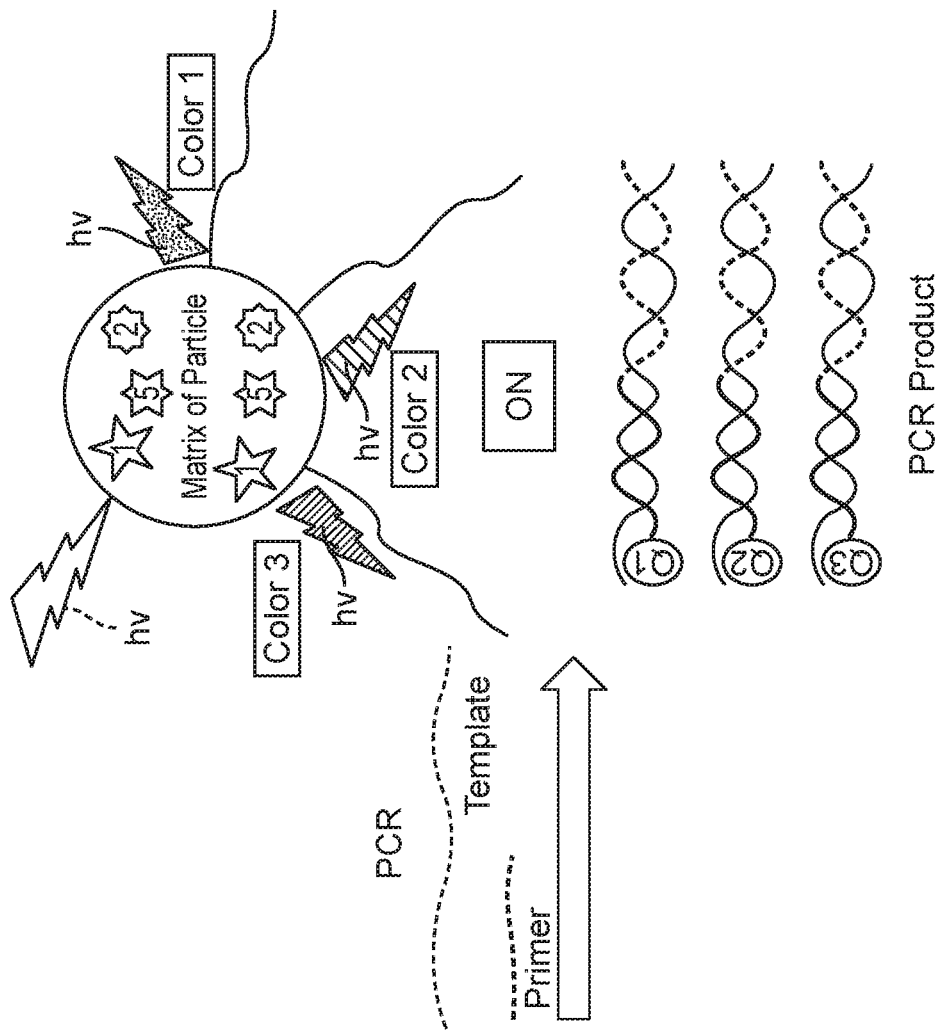
FIG. 4 shows a schematic diagram of a method of digital nucleic acid amplification, such as digital PCR, with particles encoded with respect to spectral intensity comprising one or more quenchers, in accordance with embodiments.
Figure 4:
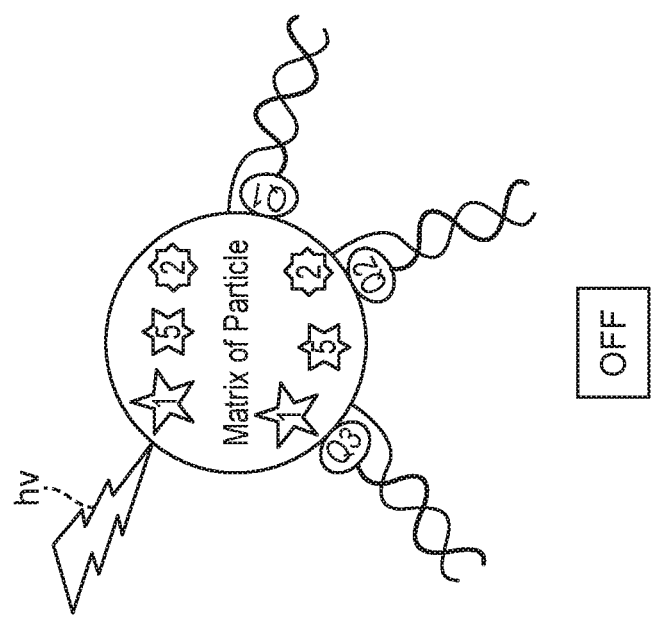
Figure 5:
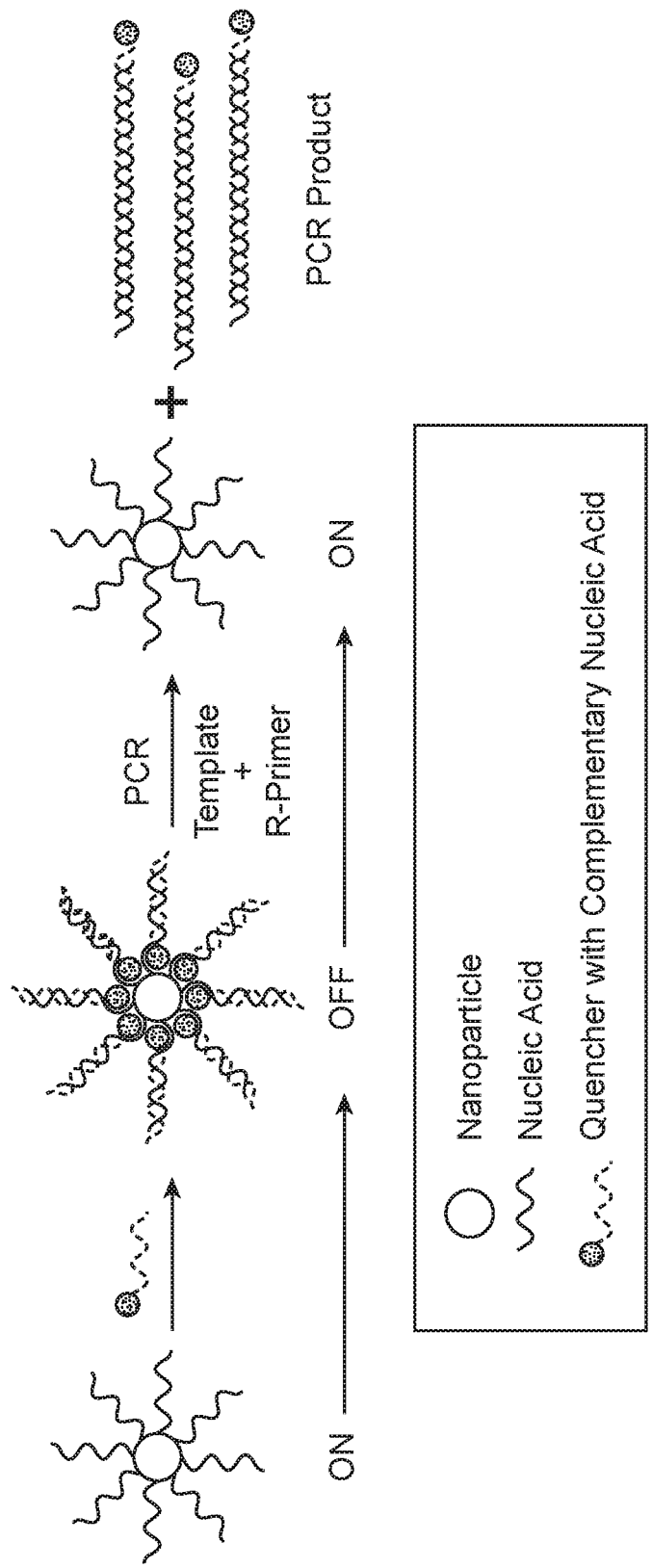
FIG. 5 shows a schematic diagram of a method of digital nucleic acid amplification, such as digital PCR, comprising $SiO_2$/Polymer-Pdots, in accordance with embodiments.

FIG. 4 depicts a probe comprising binding regions attached to an encoded polymer dot nanoparticle. Encoded polymer dot probes, comprising three individual types of fluorescent chromophores each, are provided in 1 nanoliter of reaction mix in each digitized volume (e.g., chamber) of a self-digitization (SD) chip. Prior to amplification, the encoded polymer dot probes, which each comprise nucleic acid binding regions are allowed to hybridize with the nucleic acid molecule region of the three types of provided quenchers. Each distinct quencher (e.g., type of quencher or each species of quencher) is attached to identical nucleic acid sequences that are capable of hybridizing with a specific sequence of the nucleic acid binding regions of the encoded polymer dot probes the combined quenchers are capable of quenching the fluorescence of the set of three fluorescent chromophores that are part of the encoded polymer dot. The reaction mix comprises TaqMan Fast Advanced Master Mix, the sample containing the target nucleic acid molecule (e.g., the template), TaqMan polymerase, a reaction buffer, the solution containing the encoded polymer molecules, and a solution containing the remaining custom PCR primers designed to recognize the target molecule.

Prior to amplification, encoded polymer dot probes that have been allowed to hybridize with quenchers are stimulated with laser light within the peak excitatory frequency range of the fluorescent chromophores, and it spectral intensity emission from the chambers is confirmed at background levels.

Digital PCR reactions are carried out in each digitized volumes of the chip using a Thermal Cycler, with a 3 minute hot start at 95° C., followed by 35 cycles of 30 seconds at 95° C., 30 seconds at 54° C., and 30 seconds at 72° C. each. The quencher bound primers are incorporated into amplification product during the PCR-based amplification and hybridize to the complementary amplification product instead of the binding regions of encoded polymer dot nanoparticles. Chambers are once again stimulated with excitatory laser light, and optically detectable codes resulting from the emissions of the encoded polymer dot probes are detected.

Chambers are assigned digital values based on spectral intensity measurements detected from each chamber, and the concentration of the target molecule in the sample is back-calculated using Poisson statistics as well as the number of chambers indicating the presence of the target molecule (through detectable emission of the encoded polymer dots' optically detectable code), the number of chambers indicating the absence of the target molecule (through a failure to detect the encoded polymer dots' optically detectable code), and volumes of each reaction volume.

Example 2

Method for Digital PCR Using a Quencher-Conjugated Polymer Dot Probe

This Example provides a method for detecting a target molecule using digital PCR and a quencher-conjugated polymer dot, according to one aspect of the present disclosure.

Compartmentalized volumes are generated by adding an aqueous and an oil phase to a small collection microtube containing a small stainless steel bead, wherein the aqueous phase contains reaction mix comprising TaqMan Fast Advanced Master Mix, the sample containing the target nucleic acid molecule (e.g., the template), TaqMan polymerase, a reaction buffer, custom PCR primer pairs designed to recognize the target molecule, and an encoded chromophoric polymer dot probe tethered to about 200 quenchers by a nucleic acid sequence capable of hybridizing with a portion of the complementary strand of target molecule. The quenchers are covalently linked to the distal end of the nucleic acid sequence, the proximal end of which is covalently linked to the polymer dot. The tube is subsequently shaken at 15-17 Hz for 20 seconds to generate an emulsion comprising a plurality of compartmentalized volumes. The quantity and individual sizes of the compartmentalized volumes are determined optically.

Compartmentalized volumes are subjected to a 95° C. hot start for 3 minutes followed by 35 cycles of 30 seconds at 95° C., 30 seconds at 54° C., and 30 seconds at 72° C. each. During amplification of the amplicon (e.g., the amplification product created from the template), the quencher-tethered nucleic acid sequence of the probe, which has annealed to a portion of the amplicon, is consumed by the TaqMan polymerase. The quencher is released from the probe after the nucleic acid tethering it to the probe is consumed by the TaqMan polymerase (as illustrated in FIG. 6A. After thermal cycling, compartmentalized volumes are excited with a 450 nm laser. The increased distance between the free quencher and the polymer dot allows the encoded polymer dot's optically detectable code to be detected. Emission spectra are optically detected from each compartmentalized volume, and a digital value is assigned to each compartmentalized volume based on whether the emission spectrum characteristic to the polymer dot probe is detected in the well. In compartmentalized volumes lacking a target molecule, amplicons are not produced during thermal cycling, and the nucleic acid sequence of the quencher is not consumed, leaving the quenchers to still hybridize to the polymer dots, remain in close proximity and continue to quench the optically detectable code of the polymer dot. These compartmentalized volumes that are negative for amplification and for the optically detectable code are assigned a value of "zero." The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

Example 3

Method of Digital PCR Using a Quencher-Conjugated Polymer Dot Probe with Self-Annealing Binding Regions This Example provides a method for determining a target molecule's concentration using digital PCR and a quencher-conjugated polymer dot with self-annealing binding regions, according to one aspect of the disclosure.

Compartmentalized volumes are generated by flowing aqueous phase through a microfluidic device consisting of a network of channels and compartments constituting a self-digitization device that was prefilled with oil phase, followed by flowing additional oil phase through the device. The encoded polymer dots in each compartmentalized volume are conjugated to quenchers through a DNA sequence. Each sequence has three binding regions. Short regions (e.g., 6 base pairs) at the proximal and distal ends of the DNA are complementary and thus bind to each other forming a hairpin structure (as illustrated in FIG. 6B). The intermediate region is capable of hybridizing with the amplicon (e.g., the amplification product of the target molecule). Also provided in the compartmentalized volume are a target nucleic acid molecule (e.g., the template), TaqMan polymerase, a reaction buffer, and a first and a second oligonucleotide primer, wherein the second oligonucleotide primer, capable of hybridizing with the template and serving as an initiation point for amplification of the template, is provided at a higher concentration than the first oligonucleotide primer, which is capable of hybridizing with the amplicon and serving as an initiation point for amplification of the amplicon (e.g., to produce additional copies of the target molecule).

Compartmentalized volumes are subjected to a 95° C. hot start for 3 minutes followed by 30 cycles of 30 seconds at 95° C., 30 seconds at 54° C., and 30 seconds at 72° C. each. Because of the higher relative concentration of the second oligonucleotide primer, more copies of the amplicon are produced than those of the target molecule. This produces single stranded DNA, which can then hybridize to the intermediate binding region of the polymer dot probes, causing the binding regions to extend out from the polymer dot and increasing the distance between the quencher and the polymer dot to the degree that the optically detectable code of the polymer dot is no longer quenched by the quenchers and can be detected. As described above, the optically detectable code is detected, and the compartmentalized volumes that comprise target molecules are assigned a value of "one." Compartmentalized volumes lacking target molecules fail to produce amplicons, and self-annealing nucleic acid binding regions are not extended, allowing the quenchers to continue to quench the optically detectable code of the polymer dot (not shown in FIG. 6B). These compartmentalized volumes in which the signal from the polymer dot is not detectable are assigned a value of "zero."

The digital values are matched with the corresponding measured compartmentalized volume sizes. The concentration of the target molecule is then back-calculated by fitting the measured and calculated data to a Poisson distribution curve.

Example 4

Method for Digital PCR Using Amplification-Mediated Quencher Competition

This Example provides a method for detecting and quantifying a target molecule using a method of digital PCR involving amplification-mediated quencher competition, according to one aspect of the present disclosure.

Compartmentalized volumes are generated in a microfluidic device at a T-junction where the aqueous phase flows from a side channel into a main channel where oil is flowing, and the joint flow produces droplet or plug based compartments of aqueous phase within the oil phase. The encoded polymer dots in each compartmentalized volume are conjugated to nucleic acid binding regions. These binding regions are both complementary to the nucleic acid binding region attached to quenchers, and to the target molecule for which they can serve as a primer. The quenchers are capable of absorbing the optically detectable code produced by the polymer dot when it is hybridized to the nucleic acid binding region of the polymer dot. The nucleic acid binding region attached to the polymer dot comprise primers capable of hybridizing with region near an end of the target molecule and serving as an initiation point for amplification of the target molecule during thermal cycling in the presence of PCR reagents. PCR reagents (e.g., PCR reaction buffer, Taq polymerase, and target molecule) are present in the compartmentalized volume. Also provided in the compartmentalized volumes are copies of a primer capable of hybridizing with the amplicon of the target molecule (e.g., the PCR amplification product of the target molecule) and serving as an initiation point for the amplification of the amplicon during thermal cycling in the presence of PCR reagents.

Compartmentalized volumes are subjected to a 95° C. hot start for 3 minutes followed by 35 cycles of 40 seconds at 95° C., 30 seconds at 54° C., and 30 seconds at 72° C. each. During cycling, copies of both the target molecule (e.g., the template) and the amplicon are produced via PCR reaction. As more copies of the target molecule are produced, the copies of the target molecule gain a stoichiometric advantage over the quencher with respect to hybridization with the nucleic acid binding region of the polymer dot. During cycling, the target molecule hybridizes with the nucleic acid binding region of the polymer dot, displacing the quencher, increasing the distance between the polymer dot and the quencher, and allowing the optically detectable code of the polymer dot to be detected.

As described above, the optically detectable code is detected, and the compartmentalized volumes that comprise target molecules are assigned a value of "one." Compartmentalized volumes lacking target molecules fail to produce amplicons and additional copies of the target molecule, and quenchers are not displaced from hybridizing with the nucleic acid binding region of the polymer dot, allowing the quenchers to continue to quench the optically detectable code of the polymer dot (not shown in FIG. 6C). These compartmentalized volumes in which the signal from the polymer dot is not detectable are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

Example 5

Method for Digital PCR Using Competitive Hybridization

This Example provides a method for detecting and quantifying a target molecule using digital PCR using decoy-mediated competitive hybridization, according to one aspect of the present disclosure.

Compartmentalized volumes are generated in a microfluidic device at a junction where the aqueous phase meets two converging oil phases at a plus (or cross) junction, in a "flow focusing" fashion to produce droplet compartments. The encoded polymer dots in each compartmentalized volume are conjugated to nucleic acid binding regions, which are capable of hybridizing with a nucleic acid primer sequence comprising the quenchers. Quenchers comprise a quencher capable of absorbing the optically detectable code produced by the polymer dot and a nucleic acid primer sequence and are provided in the compartmentalized volume in excess. As a primer itself, the nucleic acid primer sequence of the quencher is capable of being extended during PCR amplification steps. The nucleic acid binding regions comprise primers capable of hybridizing with region near an end of the target molecule and serving as an initiation point for amplification of the target molecule during thermal cycling in the presence of PCR reagents. PCR reagents (e.g., PCR reaction buffer, Taq polymerase, and target molecule) are present in the compartmentalized volume. Also provided in the compartmentalized volumes are copies of a primer capable of hybridizing with the amplicon of the target molecule (e.g., the PCR amplification product of the target molecule) and serving as an initiation point for the amplification of the amplicon during thermal cycling in the presence of PCR reagents.

Compartmentalized volumes are subjected to a 95° C. hot start for 3 minutes followed by 35 cycles of 30 seconds at 95° C., 30 seconds at 54° C., and 30 seconds at 72° C. each. During cycling, copies of both the target molecule (e.g., the template) and the amplicon are produced via PCR reaction. Furthermore, the quencher primer is extended during amplification, allowing it to hybridize with the entire length of the target molecule. As more copies of the target molecule are produced and the quencher primer sequences are extended during amplification, the quencher primer sequences begin to associate with copies of the target rather than the nucleic acid binding region of the polymer dot. The distance between the polymer dot and the quencher increases as a result of the association of the extended quencher primer sequence and copies of the target molecule, allowing the optically detectable code to be detected.

As described above, the optically detectable code is detected, and the compartmentalized volumes that comprise target molecules are assigned a value of "one." Compartmentalized volumes lacking target molecules fail to produce amplicons and additional copies of the target molecule, and quencher primers are not extended or displaced from hybridizing with the nucleic acid binding region of the polymer dot, allowing the quenchers to continue to quench the optically detectable code of the polymer dot (not shown in FIG. 6D). These compartmentalized volumes in which the signal from the polymer dot is not detectable are assigned a value of "zero."

The digital values are matched with the measured compartmentalized volume sizes. The concentration of the target molecule is then back-calculated by fitting the measured and calculated data to a Poisson distribution curve.

Example 6

Method for Digital PCR Using Intraprobe and/or Inter-Probe Amplification and Hybridization This Example provides a method for detecting and quantifying a target molecule using digital PCR and polymer dots conjugated to matched primer sets, according to one aspect of the present disclosure.

Compartmentalized volumes are generated in a device where the aqueous and oil phases meet at a coaxial junction in which the aqueous phase from the inner channel is surrounded in a sheath flow of oil phase from the outer channel and droplet compartments are formed. The encoded polymer dots in each compartmentalized volume are conjugated to a first set of nucleic acid binding regions, which are primers and are capable of hybridizing with a portion of an amplicon of the target molecule (e.g., a PCR amplification product of the target molecule) at the amplicon's 5' end. The polymer dots are also conjugated to a second set of nucleic acid binding regions, which are primers and are capable of hybridizing with a portion of the target molecule at the target molecule's 5' end. Quencher-conjugated oligonucleotides capable of hybridizing with nucleic acid binding regions of the first set of nucleic acid binding regions are provided in the compartmentalized volume in addition to the target molecule, PCR reaction buffer, nucleotides, and Taq polymerase.

Compartmentalized volumes are subjected to a 95° C. hot start for 3 minutes followed by 35 cycles of 30 seconds at 95° C., 30 seconds at 54° C., and 30 seconds at 72° C. each. During cycling, copies of the target molecule and its PCR amplification-generated amplicon hybridize with the second and first sets of nucleic acid binding regions, extending the length of members of each set of nucleic acid binding region (as seen in FIG. 6E). Both the target molecule and the amplicon are amplified in number each round, leading to a stoichiometric advantage for binding to the nucleic acid binding regions of the polymer dot over the quencher-conjugated oligonucleotides. PCR-extended nucleic acid binding regions of either the first or second set can hybridize with unextended primer regions of the second or first set, respectively, during subsequent rounds of PCR amplification. PCR-extended nucleic acid binding regions of the first set can hybridize with PCR-extended nucleic acid binding regions of the second set, as shown in FIG. 6E. PCR-extended nucleic acid binding regions of either set can also hybridize with those of neighboring polymer dot probes and with copies of the target molecule or its amplicon, as shown in FIG. 6F. The mechanisms illustrated in FIG. 6E and FIG. 6F may both occur in the same compartmentalized volume, and each is sufficient to competitively inhibit quencher-conjugated oligonucleotides from hybridizing with the nucleic acid binding regions of the polymer dot probes. Disassociation of quencher-conjugated oligonucleotides allows the optically detectable code produced by the polymer dots to be detected.

In a slight variation to the above description the ratio of the two binding regions do not need to be in a 1:1 ratio. There could in fact be two populations of the same polymer dots. One with, for example, a 6:4 ratio of the first and second binding regions, and another with a 4:6 ratio of the first and second binding region as illustrated in 6K. See Example 11 for more details.

As described above, the optically detectable code is detected, and the compartmentalized volumes that comprise target molecules are assigned a value of "one." In compartmentalized volumes lacking a target molecule, neither set of nucleic acid binding regions has a template on which to extend, and quencher-conjugated oligonucleotides remain closely associated with polymer dots. As a result, optically detectable codes in compartmentalized volumes remain quenched, and no optically detectable code is detected. These compartmentalized volumes, in which the signal from the polymer dot is not detectable, are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

In a slight variation to this method of performing digital PCR to determine the concentration of a target molecule, free oligonucleotide primers with the same sequence as the first and second nucleic acid binding regions are provided in the compartmentalized volume, as shown in FIG. 6G and FIG. 6H. The addition of free primer that is able to amplify the target molecule and amplicon provides more template for nucleic acid binding region extension at early cycles of PCR amplification, accelerating competitive inhibition of quencher-conjugated oligonucleotides. As discussed above and as shown in FIG. 6G and FIG. 6H, PCR-extended nucleic acid binding regions will bind to complementary binding regions on the same polymer dot (as shown in FIG. 6G), other polymer dots in the compartmentalized volume (as shown in FIG. 6H), or on copies of the target molecule or its amplicon (as shown in FIG. 6H). Detection and analysis of these variant mechanisms are performed in the same manner as described earlier in this Example.

Example 7

Method for Digital PCR Using Polymerase-Induced Molecular Cleavage

This Example provides a method for detecting and quantifying a target molecule using digital PCR and a quencher-conjugated polymer dot, according to one aspect of the present disclosure.

Compartmentalized volumes are generated in a microfluidic device in which the aqueous phase emerges into an oil phase through many parallel holes or channels, generating many droplets simultaneously. The encoded polymer dots in each compartmentalized volume are conjugated to nucleic acid binding regions. The nucleic acid binding regions is capable of hybridizing with a portion of the amplicon (e.g., the amplification product of the target molecule), as shown in FIG. 6I. Also provided in the compartmentalized volume are a target nucleic acid molecule (e.g., the template), TaqMan® polymerase, and a reaction buffer. Also provided in each compartmentalized volume are quencher-conjugated oligonucleotides that are capable of hybridizing with the nucleic acid binding region of the polymer dot and with a portion of the target molecule. Further provided in each compartmentalized volume are a first and a second oligonucleotide primer, wherein the second oligonucleotide primer, capable of hybridizing with the 5' end of the target molecule and serving as an initiation point for amplification of the target molecule. The first oligonucleotide primer is capable of hybridizing with the 5' end of the amplicon and serving as an initiation point for amplification of the amplicon (e.g., to produce additional copies of the target molecule).

Compartmentalized volumes are subjected to a 95° C. hot start for 3 minutes followed by 30 cycles of 30 seconds at 95° C., 30 seconds at 54° C., and 30 seconds at 72° C. each. As shown in FIG. 6I, nucleic acid binding regions of the polymer dots are destroyed during the extension phase of the PCR cycle if amplicons undergoing amplification with TaqMan® polymerase are concurrently associated with a nucleic acid binding region. Similarly, the oligonucleotide region of a quencher-conjugated oligonucleotide is destroyed during the extension phase of the PCR cycle if quencher-conjugated oligonucleotide is hybridized with a target molecule that is concurrently undergoing amplification by TaqMan polymerase and the second oligonucleotide primer. As a result of the destruction of both the nucleic acid binding region of the polymer dot and the destruction of the oligonucleotide region of the quencher-conjugated oligonucleotides during TaqMan®-mediated PCR amplification, the quenchers do not have the ability to associate with the polymer dots, and the optically detectable code can be detected. As described above, the optically detectable code is detected, and the compartmentalized volumes that comprise target molecules are assigned a value of "one." Compartmentalized volumes lacking target molecules fail to produce amplicons and neither the oligonucleotide region of the quencher-conjugated oligonucleotide nor the nucleic acid binding region of the polymer dot is destroyed. The quenchers are, therefore, able to quench the optically detectable code of the polymer dot in compartmentalized volumes lacking a target molecule. These compartmentalized volumes in which the signal from the polymer dot is not detectable are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

Example 8

Method for Digital PCR Using Inter-Probe Hybridization

This Example provides a method for detecting and quantifying a target molecule using digital PCR and complementary polymer dot probes, according to one aspect of the present disclosure.

Compartmentalized volumes are generated in a device in which the aqueous phase emerges into an oil phase through a porous membrane, generating many droplets simultaneously. A first set of encoded chromophoric polymer dots in each compartmentalized volume conjugated to a first set of nucleic acid binding regions, which are primers and are capable of hybridizing with a portion of an amplicon of the target molecule (e.g., a PCR amplification product of the target molecule) at the amplicon's 5' end. A second set of encoded chromophoric polymer dots are conjugated to a second set of nucleic acid binding regions, which are primers and are capable of hybridizing with a portion of the target molecule at the target molecule's 5' end.

A first set of quencher-conjugated oligonucleotides capable of hybridizing with nucleic acid binding regions of the first set of nucleic acid binding regions and a second set of quencher-conjugated oligonucleotides capable of hybridizing with nucleic acid binding regions of the second set of nucleic acid binding regions are provided in the compartmentalized volume in addition to the target molecule, PCR reaction buffer, nucleotides, primers, and Taq polymerase.

Compartmentalized volumes are subjected to a 95° C. hot start for 3 minutes followed by 35 cycles of 30 seconds at 95° C., 30 seconds at 54° C., and 30 seconds at 72° C. each. During cycling, copies of the target molecule and its PCR amplification-generated amplicon hybridize with the second and first sets of nucleic acid binding regions, extending the length of members of each set of nucleic acid binding region (as seen in FIG. 6J). Both the target molecule and the amplicon are amplified in number each round as well.

PCR-extended nucleic acid binding regions of the first set, on a polymer dot of the first type can hybridize with PCR-extended nucleic acid binding regions of the second set on a polymer dot of the second type, forming an aggregated structure and disassociating quencher-conjugated oligonucleotides from the nucleic acid binding regions of the polymer dots As described above, the optically detectable code is detected, and the compartmentalized volumes that comprise target molecules are assigned a value of "one." In compartmentalized volumes lacking a target molecule, spontaneous hybridization of nucleic acid binding regions of the first and second type on polymer dots of the first and second type will only occur at low levels. A background level of detection will be present in all compartmentalized volumes, and the threshold for assigning compartmentalized volume a value of "one" is evaluated by the system processor and adjusted automatically. Options for manual adjustment to the signal threshold are provided in the system software as well. As a result, low levels of detection of an optically detectable do not render the system inoperable. Instead, compartmentalized volumes failing to produce a detectable code with sufficient spectral intensity are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

As in Example 6, the efficiency of the reaction can be increased (e.g., "boosted") by providing a first and second set of oligonucleotide primers with the same sequence as the first and second set of nucleic acid binding regions attached to the polymer dots.

Example 9

Method for Digital PCR Using Unbalanced Inter-Probe Hybridization

This Example provides a method for detecting and quantifying a target molecule using digital PCR and a quencher-conjugated polymer dot with unbalanced binding region sets, according to one aspect of the present disclosure.

Compartmentalized volumes are generated in a device in which the aqueous phase emerges into an oil phase through a microfluidic filter or splitting channel, thereby generating many droplets simultaneously. The encoded polymer dots in each compartmentalized volume are conjugated to a first set of nucleic acid binding regions, which are primers and are capable of hybridizing with a portion of an amplicon of the target molecule (e.g., a PCR amplification product of the target molecule) at the amplicon's 5' end. The polymer dots are also conjugated to a second set of nucleic acid binding regions, which are primers and are capable of hybridizing with a portion of the target molecule at the target molecule's 5' end. The ratio of the first set of binding regions to the second set of binding regions on each polymer dot is 60:40 on a first group of polymer dots provided in each compartmentalized volume and 40:60 on a second group of polymer dots provided in each compartmentalized volume. Alternatively, ratios of 70:30 rather than 60:40 also can be used. Quencher-conjugated oligonucleotides capable of hybridizing with nucleic acid binding regions of the first set of nucleic acid binding regions are provided in the compartmentalized volume in addition to the target molecule, PCR reaction buffer, nucleotides, and Taq polymerase.

Compartmentalized volumes are subjected to a 95° C. hot start for 3 minutes followed by 35 cycles of 30 seconds at 95° C., 30 seconds at 54° C., and 30 seconds at 72° C. each. During cycling, copies of the target molecule and its PCR amplification-generated amplicon hybridize with the second and first sets of nucleic acid binding regions, extending the length of members of each set of nucleic acid binding region (as in Example 8). Both the target molecule and the amplicon are amplified in number each round, leading to a stoichiometric advantage for binding to the nucleic acid binding regions of the polymer dot over the quencher-conjugated oligonucleotides. PCR-extended nucleic acid binding regions of either the first or second set can hybridize with unextended primer regions of the second or first set, respectively, during subsequent rounds of PCR amplification. PCR-extended nucleic acid binding regions of the first set can hybridize with PCR-extended nucleic acid binding regions of the second set. However, PCR-extended nucleic acid binding regions of either group of polymer dots will more frequently hybridize with those of neighboring polymer dot probes than with binding regions of the same polymer dot, as shown in FIG. 6K, due to the unbalanced ratio of binding regions on each polymer dot. The inter-particle hybridization causes quencher-conjugated oligonucleotides to disassociate with the polymer dots. Disassociation of quencher-conjugated oligonucleotides allows the optically detectable code produced by the polymer dots to be detected. Since the polymer dots are smaller than the pixel resolution and/or the diffraction limited resolution, then in clusters the brightness of a single pixel should be significantly brighter for clustered polymer dots than of isolated polymer dots. This is in addition to the overall spot size for individual polymer dots being brighter.

As in Example 6, the efficiency of the reaction can be increased (e.g., "boosted") by providing a first and second set of oligonucleotide primers with the same sequence as the first and second set of nucleic acid binding regions attached to the polymer dots.

As further described above, the optically detectable code is detected, and the compartmentalized volumes that comprise target molecules are assigned a value of "one." In compartmentalized volumes lacking a target molecule, neither set of nucleic acid binding regions has a template on which to extend, and quencher-conjugated oligonucleotides remain closely associated with polymer dots. As a result, optically detectable codes in compartmentalized volumes remain quenched, and no optically detectable code is detected. These compartmentalized volumes, in which the signal from the polymer dot is not detectable, are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

Example 10

Method for Digital PCR Using Rolling-Circle Amplification

This Example provides a method for detecting a target molecule using digital PCR and a quencher-conjugated polymer dot, according to one aspect of the present disclosure.

Compartmentalized volumes are generated in a device in which the aqueous phase emerges into an oil phase through a parallel step junction, thereby generating many droplets simultaneously. In each compartmentalized volume is provided a polymer dot conjugated to oligonucleotides, an excess of quencher primers having a quencher and an oligonucleotide capable of hybridizing with the oligonucleotides of the polymer dot, a circularized single stranded DNA sequence designed to contain a sequence whose complement is capable of hybridizing with the oligonucleotide of the quencher primer, a target molecule (e.g., the trigger molecule) capable of hybridizing with a sequence of the circularized DNA and serving as a primer and initiator of amplification, reaction buffer (TrisHCl, pH8.5, $MgCl_2$, KCl, DTT, Dimethyl Sulfoxide), dNTPs, and Bst Polymerase.

Compartmentalized volumes are subjected to isothermal conditions at 60° C. During RCA isothermal amplification, the trigger molecule hybridizes with the circularized DNA, and the circularized DNA is then amplified. As the circularized DNA is amplified, hybridization sites complementary to the quencher primer oligonucleotide sequences are produced. The number of hybridization sites produced by rolling circle amplification create a stoichiometric advantage over the oligonucleotides of the polymer dots, and the quencher primers associate with the rolling circle amplification product instead of the polymer dot oligonucleotides, separating the quenchers from the polymer dots and allowing the optically detectable code of the polymer dots to be detected. As described above, the optically detectable code is detected, and the compartmentalized volumes that contain target molecules and are assigned a value of "one." Compartmentalized volumes lacking target molecules fail to initiate rolling circle amplification, and the quenchers are allowed to continue to quench the optically detectable code of the polymer dot. These compartmentalized volumes in which the signal from the polymer dot is not detectable are assigned a value of "zero."

The digital values are matched with the corresponding measured compartmentalized volume sizes to produce a relationship between the compartmentalized volume size distribution and the assigned values. The concentration of the target molecule is then back-calculated by fitting the measured and calculated data to a Poisson distribution curve.

Example 11

Method for Spatial Melt-Curve Analysis

This Example provides a method for determining the sequence of a target molecule using digital spatial melt-curve analysis, in accordance with one aspect of the present disclosure.

A sample containing a nucleic acid target molecule is transferred into a working buffer, which contains TrisHCl, pH 8.5, $MgCl_2$, KCl, DTT, and dimethyl sulfoxide. The sample-working buffer mixture is then diluted into reagent re-hydration buffer, which contains KCl, $MgCl_2$, DTT, and nucleoside triphosphates. Reverse transcriptase, T7 RNA polymerase, RNase H, amplification primers, a probe comprising an encoded polymer dot (Pdot) nanoparticle and a binding region, and a quencher primer nucleic acid with a complementary sequence to and capable of hybridizing with both the binding region of the probe and with the target molecule are added to the mixture containing the target molecule, and then the solution is fed into an inlet of a two-dimensional regular array of reaction chambers. The two-dimensional array of chambers is organized such that the vertical axis of the array contains identical replicates and successive chambers of the horizontal axis represent experimental conditions in which the temperature will be incrementally increased from one end to the other (e.g., "a" to "a'" in FIG. 11A and FIG. 11B) during application of thermal energy during melt-curve analysis.

Reaction chambers are stimulated with excitatory laser light with a wavelength of 470 nm prior to amplification, and light emitted from each reaction chamber is collected and analyzed.

Figure 11B:
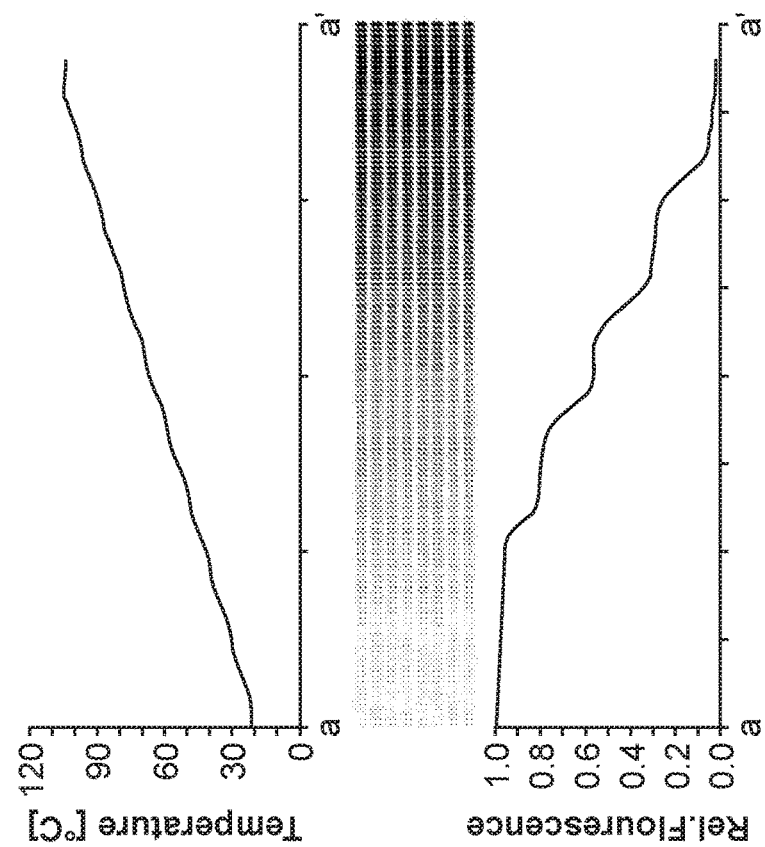
FIG. 11B shows simulated results from a digital spatial melt-curve assay, in accordance with embodiments.
Figure 11A:
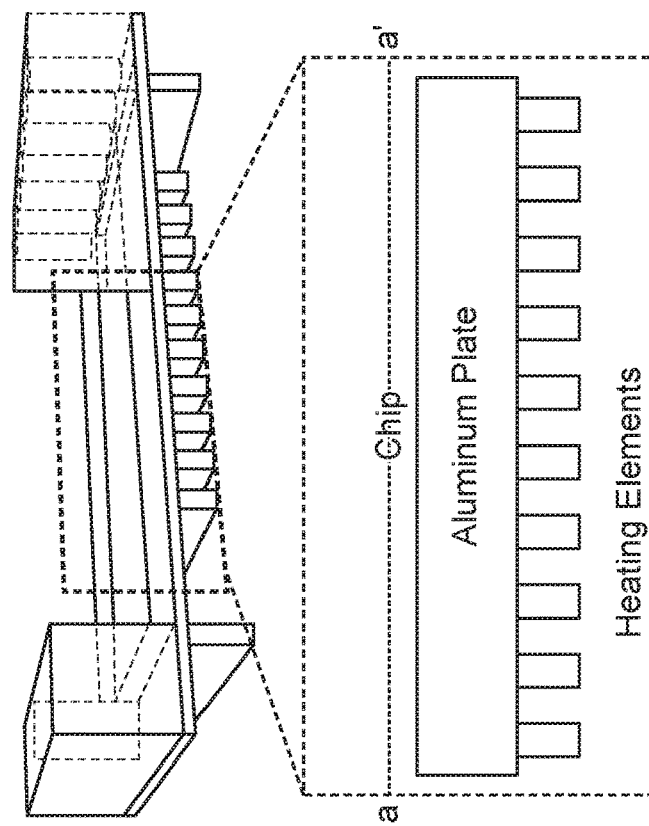
FIG. 11A shows elements of a system for performing digital melt-curve assays, in accordance with embodiments.

A heating element is placed in contact with or in close proximity with the chambers containing the target molecule and the isothermal amplification reagents, calibrated to heat the compartmentalized volumes of the reaction chambers to 41° C. and to maintain that temperature during isothermal amplification as illustrated in FIG. 11A and FIG. 11B.

After amplification a temperature gradient is created across the device from 50° C. to 90° C. producing a temperature step of 0.25° C. per compartment column. Probes will hybridize or dehybridize depending on their specific melting temperature (Tm) with the amplification product producing a sequence specific melt curve finger print. Reaction chambers are stimulated with excitatory light with a wavelength of 470 nm and light emitted from the reaction chambers is detected over a range of 500 nm to 700 nm.

Relative fluorescence values are recorded as a spatial melt-curve, relating normalized fluorescence emitted at each horizontal position of the array to the temperature at that position of the array. The sequence of the target molecule in the sample is then determined by relating changes in fluorescence over the spatial melt-curve to the presence of individual or multiple occurrences of adenine-thymine (A-T) base pairs or guanine-cytosine (G-C) base pairs, based on the magnitude of the change in fluorescence, the absolute temperature of the horizontal position at which the fluorescence change occurred, or the horizontal spatial interval in the array since the last change in fluorescence was detected.

Example 12

Method for Detecting Multiple Detectable Signals Individually in a Compartmentalized Volume This example provides exemplary methods for the quantification of a target molecule by individually detecting a plurality of detectable codes, according to one aspect of the present disclosure.

Encoded probes comprising a fluorescent polymer dot, a plurality of nucleic acid binding regions, and a plurality of quenchers capable of hybridizing with the binding regions of the probes are provided in 1 nanoliter (nl) of reaction mix in each of a plurality of compartmentalized volumes, which are located in a plurality of chambers of a self-digitization chip. The reaction mix comprises TaqMan Fast Advanced Master Mix, TaqMan polymerase, a reaction buffer, the encoded probes, and a portion of a sample, wherein the sample contains an unknown concentration of the target nucleic acid molecule (e.g., the template). The nucleic acid regions of the quenchers are allowed to hybridize with the nucleic acid binding regions prior to PCR amplification.

Figure 12A:
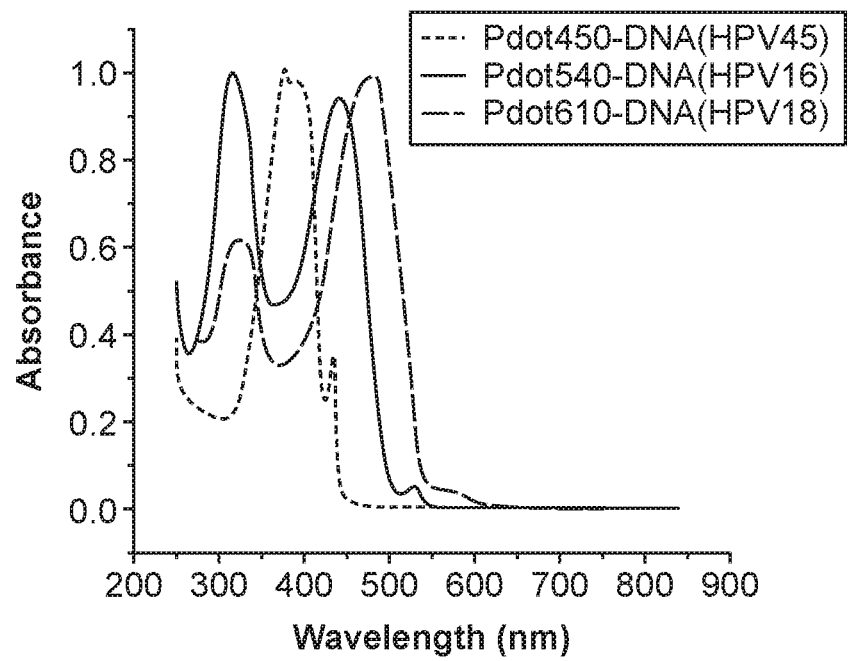
FIG. 12A shows the absorption spectra of three types of $SiO_2$/Polymer-Pdot-DNA for detecting HPV (human papilloma virus) 45, HPV16, and HPV18 in accordance with embodiments.
Figure 12B:
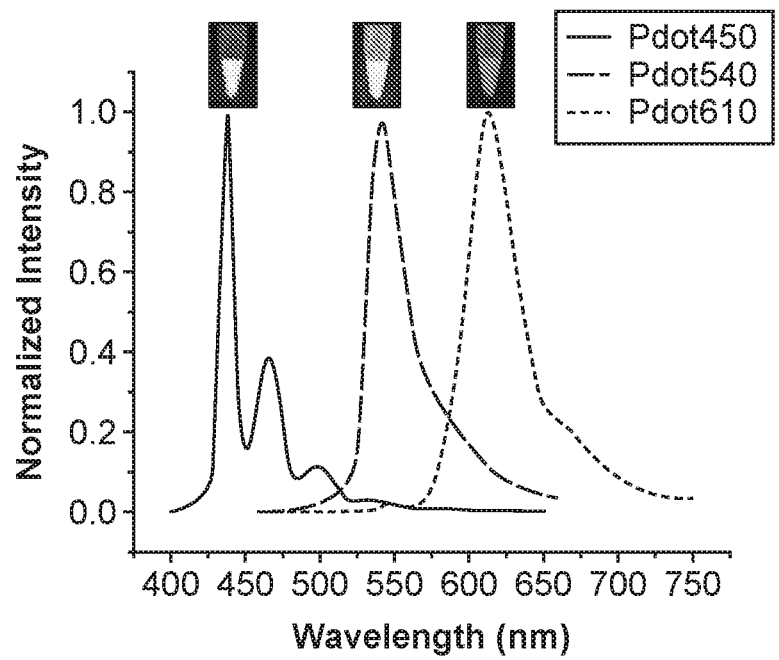
FIG. 12B shows the emission spectra of three types of $SiO_2$/Polymer-Pdot-DNA for detecting HPV (human papilloma virus) 45, HPV16, and HPV18 in accordance with embodiments.
Figure 12C:
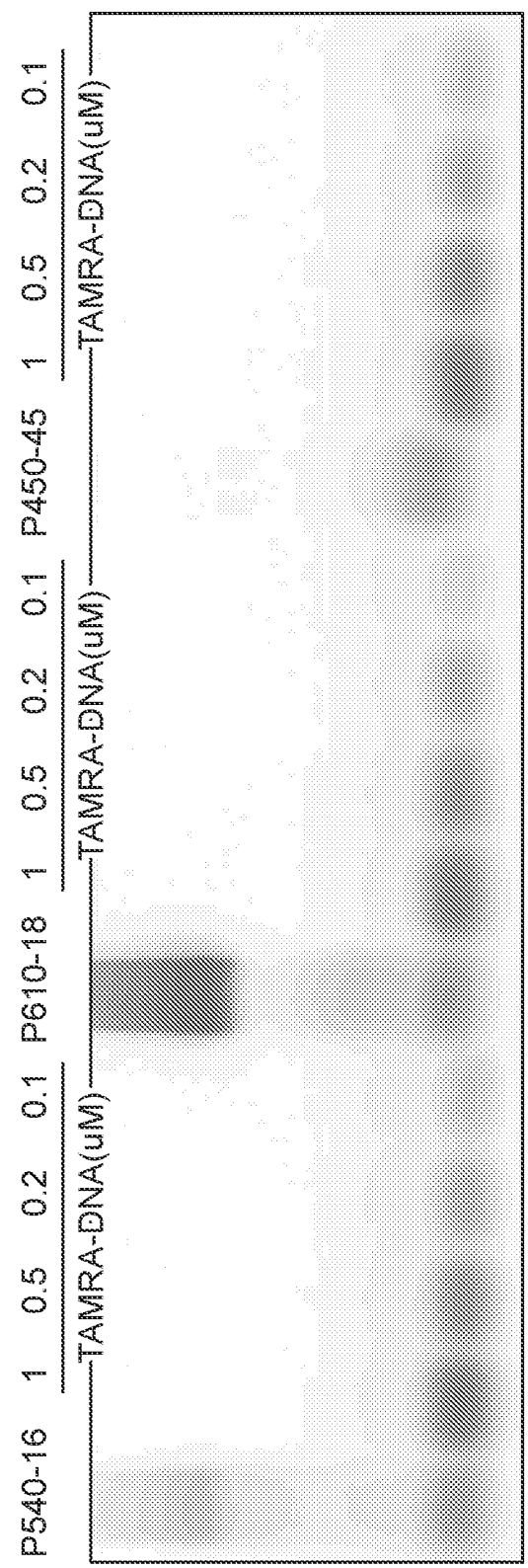
FIG. 12C shows gel electrophoresis characterization of the number of the respective nucleic acids (HPV45 or just 45; HPV16 or just 16; HPV18 or just 18) conjugated to the respective Pdots (Pdot540, Pdot610, Pdot450) for the three types of $SiO_2$/Polymer-Pdot-DNA in accordance with embodiments.
Figure 12D:
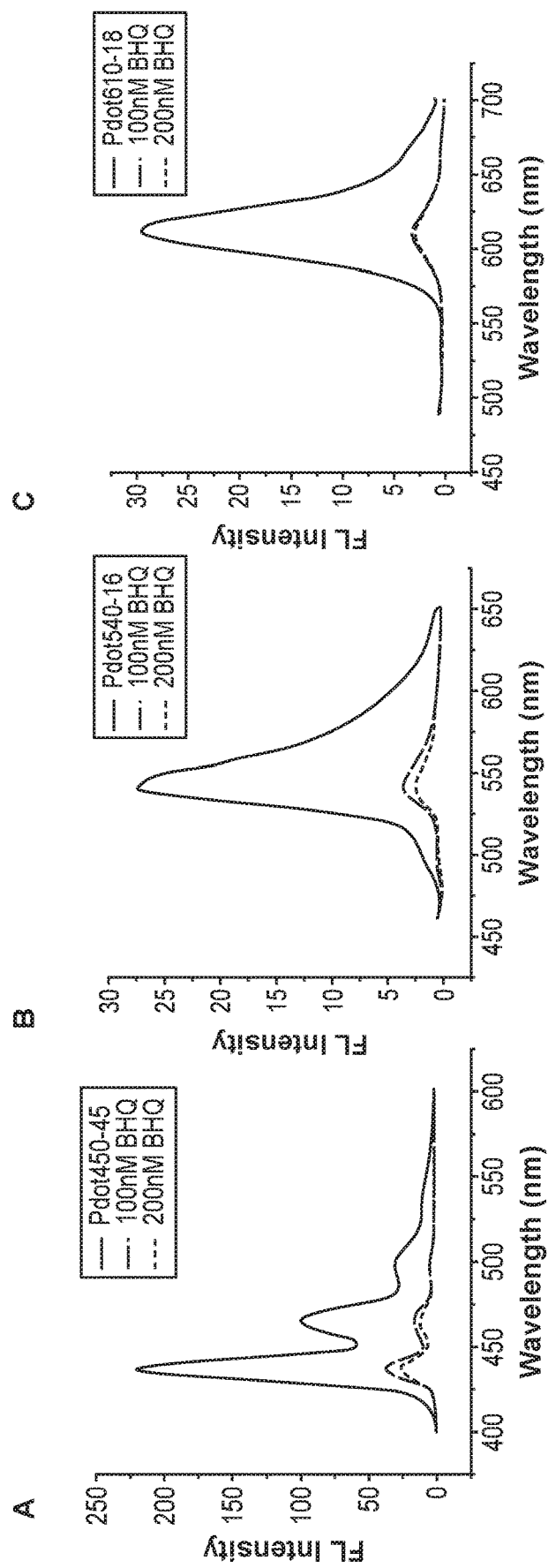
FIG. 12D shows characterization of the quenching by BHQ-DNA of the three types of $SiO_2$/Polymer-Pdot-DNA showing high levels of quenching and thus their ability to produced high signal-to-noise after digital nucleic acid amplification in accordance with embodiments.

The contents of each compartmentalized volume are stimulated with laser light within the peak excitatory frequency range of the fluorescent polymer dots prior to amplification, and the background fluorescence or spectral intensity of the detectable code emitted by each probe is measured. Prior to amplification, the presence of the quencher efficiently renders the probe non-fluorescent (FIG. 12D)

Digital PCR reactions are carried out in each compartmentalized volume of the chip using a thermal cycler, with a 3 minute hot start at 95° C., followed by 35 cycles of 30 seconds at 95° C., 30 seconds at 54° C., and 30 seconds 72° C. each. The quenchers disassociate with the binding regions of the probes during amplification by a mechanism as described in any of Examples 1-12.

Following amplification, the contents of each compartmentalized volume are once again stimulated with laser light within the peak excitatory frequency range of the fluorescent polymer dots, and the spectral intensity of the detectable code emitted by each probe is measured. Presence of the target nucleic acid result in significant increase in the fluorescence from the detectable codes (FIG. 12E) after PCR amplification. The spectral intensities measured for each probe are recorded and compared to a pre-determined threshold value or range of values. Chambers of the chip containing a compartmentalized volume with a detectable code having a value less than the threshold value is assigned a value of "zero" for that code, and chambers of the compartmentalized volume with a detectable code having a value greater than or equal to the threshold value or within the pre-determined range of values is assigned a value of "one." The digital values are matched with corresponding measured compartmentalized volume sizes to produce a relationship between the compartmentalized volume size distribution and the assigned values for the different detectable codes. The concentration of the target molecule corresponding to a detectable code is then back-calculated by fitting the measured and calculated data to a Poisson distribution curve.

Example 13

Method for Determining the Presence of a Detectable Signal in a Compartmentalized Volume This Example provides exemplary methods for the quantification of a target molecule by detecting detectable codes in a plurality of chambers of a self-digitization chip on a per-compartmentalized volume basis, according to one aspect of the present disclosure.

A plurality of encoded particles is provided in each of the plurality of chambers (e.g., compartment volumes) of the chip in 1 nanoliter (nl) of reaction mix. Each encoded particle comprises a fluorescent polymer dot, a plurality of nucleic acid binding regions, and a plurality of quenchers capable of hybridizing with the binding regions of the probes, and the reaction mix comprises TaqMan Fast Advanced Master Mix, TaqMan polymerase, a reaction buffer, the encoded probes, and a portion of a sample, wherein the sample contains an unknown concentration of the target nucleic acid molecule (e.g., the template). The nucleic acid regions of the quenchers are allowed to hybridize with the nucleic acid binding regions prior to PCR amplification.

The contents of each compartmentalized volume are stimulated with laser light within the peak excitatory frequency range of the fluorescent polymer dots prior to amplification. Spectral intensity values for each compartmentalized volume of the self-digitization chip are detected. The overall spectral intensity produced by each polymer dot in each compartmentalized volume is measured as a single value to establish a background spectral intensity value for each polymer dot in the compartmentalized volume.

Digital PCR reactions are carried out in each compartmentalized volume of the chip using a thermal cycler, with a 3 minute hot start at 95° C., followed by 35 cycles of 30 seconds at 95° C., 30 seconds at 54° C., and 30 seconds at 72° C. each. The quenchers dissociate with the binding regions of the probes during amplification by a mechanism as described in any of Examples 1-12.

Following amplification, the contents of each compartmentalized volume are once again stimulated with laser light within the peak excitatory frequency range of the fluorescent polymer dots, and the spectral intensity produced by each encoded polymer dot in the compartmentalized volume is measured. Spectral intensity values for each polymer dot in each compartmentalized volume of the chip are detected and recorded. The spectral intensity values measured after amplification is compared to a pre-determined threshold value or range of values. Pdots with chambers of the chip containing a compartmentalized volume with a spectral intensity value less than the threshold value are assigned a value of "zero," and Pdots within the compartmentalized volume with a spectral intensity value greater than or equal to the threshold value or within the pre-determined range of values are assigned a value of "one." The digital values are matched with corresponding measured compartmentalized volume sizes to produce a relationship between the compartmentalized volume size distribution and the assigned values for the different encoded Pdots. The concentration of the target molecule is then back-calculated by fitting the measured and calculated data to a Poisson distribution curve.

Example 14

Method for Generation of Probes Based on Hybrid Interpenetrated $SiO_2$—Pdot

This Example provides exemplary methods for the generation of probes using hybrid interpenetrated $SiO_2$—Pdots.

Three different types of Pdots, Pdot450, Pdot540, Pdot610 having different absorption and emission spectra (FIGS. 12A, 12B) are each conjugated to three different nucleic acid sequences, which were designed for the detection of HPV 16, 18, and 45. The three respective Pdots conjugated to nucleic acids, Pdot450-HPV45 (or Pdot450-45), Pdot540-HPV16 (or Pdot540-16), Pdot610-HPV18 (or Pdot610-18), were then characterized using dynamic light scattering showing a hydrodynamic diameter of around 30-40 nm, Zeta potential measurements, and Quantum Yield (QY) (see Table 1 below).

TABLE 1

Dynamic light scattering (DLS), zeta potential (ZP), and quantum yield (QY) characterization of the three types of $SiO_2$/Polymer-Pdot-DNA in accordance with embodiments of the present disclosure.

| | DLS-25C | ZP | QY |
|---|---|---|---|
| Pdot450-HPV45 | 33.9 ± 3.2 | −41.3 | 0.59 |
| Pdot540-HPV16 | 37.2 ± 4.3 | −43.7 | 0.37 |
| Pdot610-HPV18 | 39.9 ± 5.7 | −42.2 | 0.68 |

The respective Pdot-nucleic acids were characterized to quantify the number of nucleic acid molecules conjugated to each Pdot. FIG. 12C shows the electrophoresis results for quantification of the number of hybridized DNA per Pdot on Pdot450-45, Pdot540-16 and Pdot610-18. The different concentrations (0.1 to 1 µM) of TAMRA-DNA and the mixture of complementary TAMRA-DNA (1uM) and Pdot-DNA (Pdot450-45, Pdot540-16 or Pdot610-18, 2.8 nM) were loaded in 1 wt % Agarose gel. From the fluorescence intensity (532 nm LED excited) of the dye TAMAR with different concentrations, a function of TAMRA-DNA concentration to fluorescence intensity was obtained. From this function, it could be calculated that there were about an average of 106 DNA molecules hybridized on one Pdot450-45, about 81 DNA molecules hybridized on one Pdot540-16, and about 69 DNA molecules hybridized on one Pdot610-18.

To further prepare the three different types of Pdot-DNA probes for digital PCR, they were hybridized to their respective complementary BHQ-DNA quencher. FIG. 12D shows fluorescence of 2 ppm of Pdot450-45(A), Pdot540-16(B) and Pdot610-18(C), and the Pdots with various concentrations of complementary BHQ-DNA (100 nM, 200 nM) hybridized to the respective Pdot-DNA. Upon PCR or digital PCR in the presence of the target nucleic acid (HPV 16, 18, 45), each of the respective Pdot-DNA became fluorescent (FIG. 12E), because the quenchers disassociated with the binding regions of the respective probes during amplification by a mechanism as described in the above Examples. The presence of the amplified products from the target nucleic acids was further confirmed with gel electrophoresis (FIG. 12F).

Example 15

Method for Digital PCR and Single Probe Imaging and Decoding

This Example provides exemplary methods for performing digital PCR using hybrid interpenetrated $SiO_2$—Pdots, and the single-particle imaging and decoding of the individual hybrid interpenetrated $SiO_2$—Pdots.

Figure 12G:
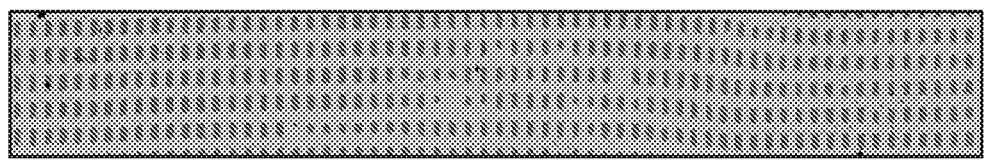
FIG. 12G shows the result of a digital PCR experiment in compartmentalized volumes using Pdot610-HPV18 $SiO_2$/Polymer-Pdot-DNA and with excitation at 473 nm in the detection of HPV18, in accordance with embodiments.
Figure 12G:
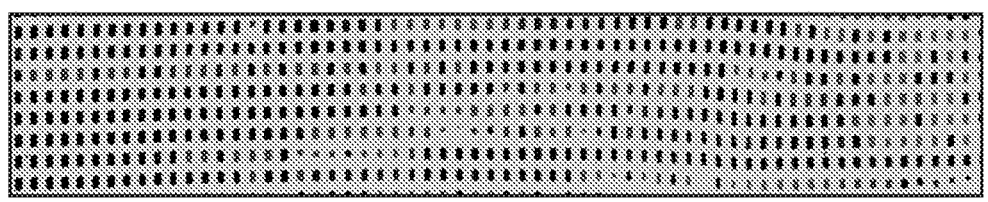
Figure 12H:
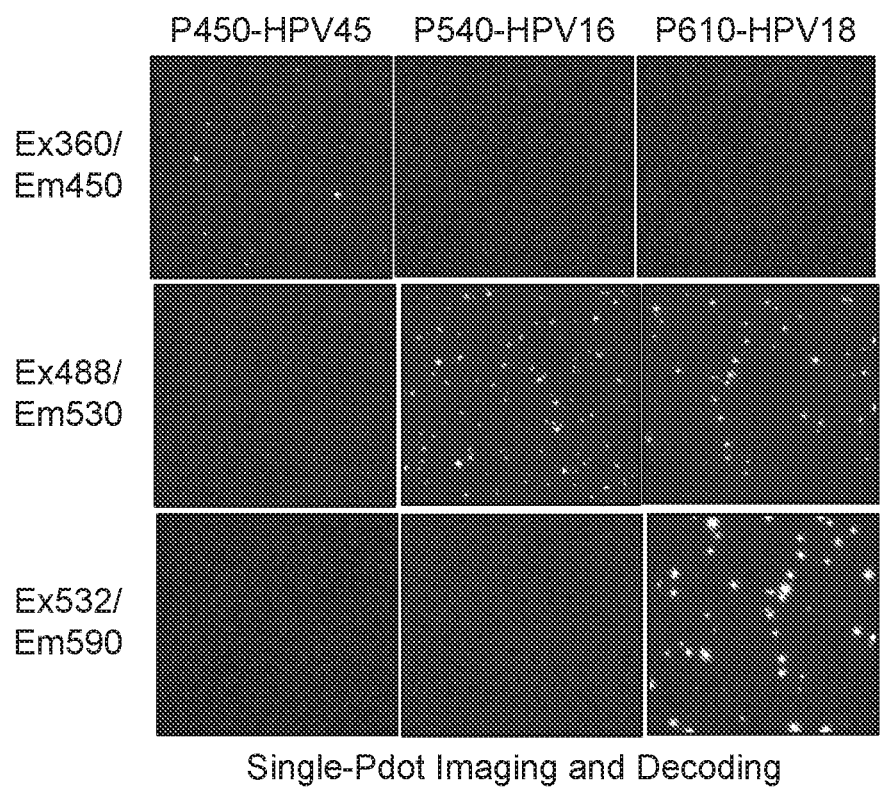
FIG. 12H shows the imaging and decoding of individual Pdots (Ex: excitation light used; Em: emission filter used), in accordance with embodiments.

Three different types of Pdots (Pdot450, Pdot540, Pdot610) each conjugated to three different nucleic acid sequences that were designed for the detection of HPV 16, 18, and 45 were prepared according to previous example. The three respective Pdots were: Pdot450-HPV45 (or Pdot450-45), Pdot540-HPV16 (or Pdot540-16), Pdot610-HPV18 (or Pdot610-18). These Pdots were subsequently used to carry out digital PCR, for which compartmentalized volumes were generated on a self-digitization (SD) chip after which the compartmentalized volumes were thermalcycled as described in previous examples. After thermalcycling, the SD chip was illuminated with 473 nm excitation light and imaged, where the darker volumes indicated target amplification (FIG. 12G). Additionally, each individual Pdots of the respective three different types of Pdots (Pdot450-45, Pdot540-16, Pdot610-18) were imaged at the single-particle level and decoded (FIG. 12H).

Example 16

Method for Multiplexed Digital PCR Using Inter-Probe Hybridization

This Example provides exemplary methods for performing digital PCR using inter-probe hybridization of Pdot-DNA probes.

Three different types of Pdots (Pdot450, Pdot540, Pdot610), each conjugated with a different DNA sequence (Pdot450 was conjugated to DNA 5'-ACA TGT ATT ACA C-3'; Pdot540 was conjugated to DNA 5'-TACTAACCGGTTTCG-3'; Pdot610 was conjugated to DNA 5'-ACA TGT ATT ACA C-3'), were utilized as a demonstration. In the presence of a crosslinking DNA sequence (i.e., 5'-ACA TGT ATT ACA CTA CTA ACC GGT TTC GAC ATG TAT TAC AC-3') complementary to nucleic acid sequences present in each of the DNA sequences conjugated to the Pdots, the crosslinking DNA sequence being present due to amplification of the analyte nucleic acid sequence, the Pdots were forced to co-localize and to form clusters. The Pdot clusters were easily imaged to detect the presence of the crosslinking DNA sequence.

To show inter-probe hybridization, single-particle imaging was performed using a wide-field fluorescence microscope, described as follows. A 405 nm diode laser was used as the excitation source. A Gaussian laser profile was observed at the sample plane, with full width half maximum of 54 µm. The excitation power density at the center of the laser spot was estimated to be ~100 W/cm² using a power meter. Pdot-DNA probes were immobilized on glass slides and imaged using a framerate of 10 Hz. The fluorescence emission from the three different color Pdots was filtered by 455±50 nm, 550±60 nm, 650±50 nm band pass filters, respectively. A CMOS camera (Hamamatsu, ORCA-Flash 4.0) with a gain factor of 0.48 electrons per count was used as the detector.

In control samples, the three color Pdot-DNA probes (0.1 ppm concentration) were mixed in PBS buffer without the cross-linking DNA present, and as a result, they were not colocalized (FIG. 13 Top Row titled "Control") at a rate higher than random chance.

Figure 13:
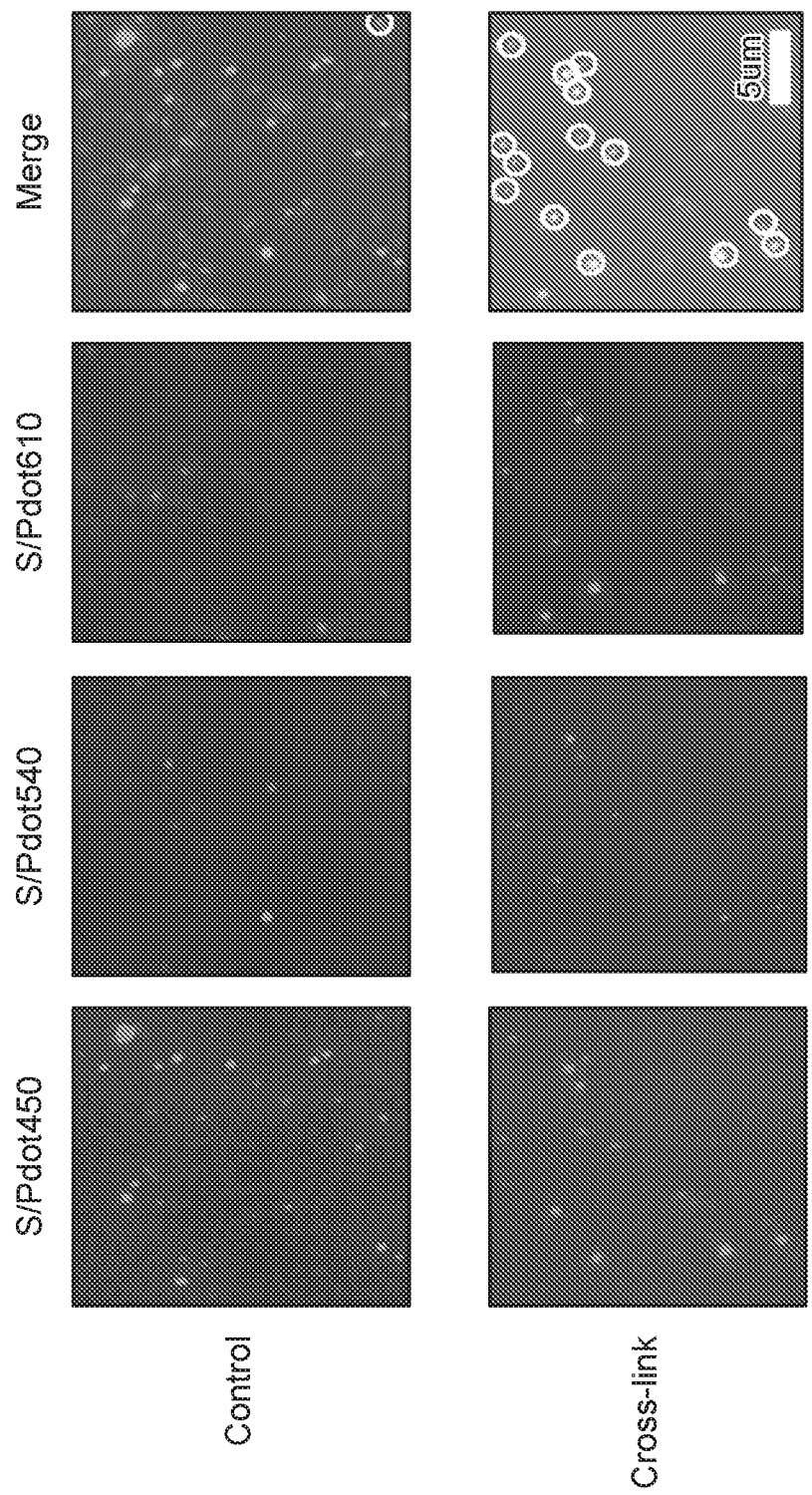
FIG. 13 shows individual and merged images of data obtained from three fluorescence color channels during inter-probe hybridization experiments performed under control and cross-link conditions.

In the presence of the cross-linking DNA (sequence: DNA 5'-ACA TGT ATT ACA CTA CTA ACC GGT TTC GAC ATG TAT TAC AC-3'), generated as a result of amplification of the analyte DNA molecules, the three color Pdot-DNA probes (0.1 ppm concentration) were colocalized at a very high rate (FIG. 13 Bottom Row titled "Cross-link"). Colocalized Pdot-DNA probes or events are emphasized in the Merged Image using circles to indicate the clusters that showed signal in all three color channels in the same location. The presence of inter-probe hybridization was thus easily detected and served as a simple readout for multiplexed digital PCR.

Figure 14:
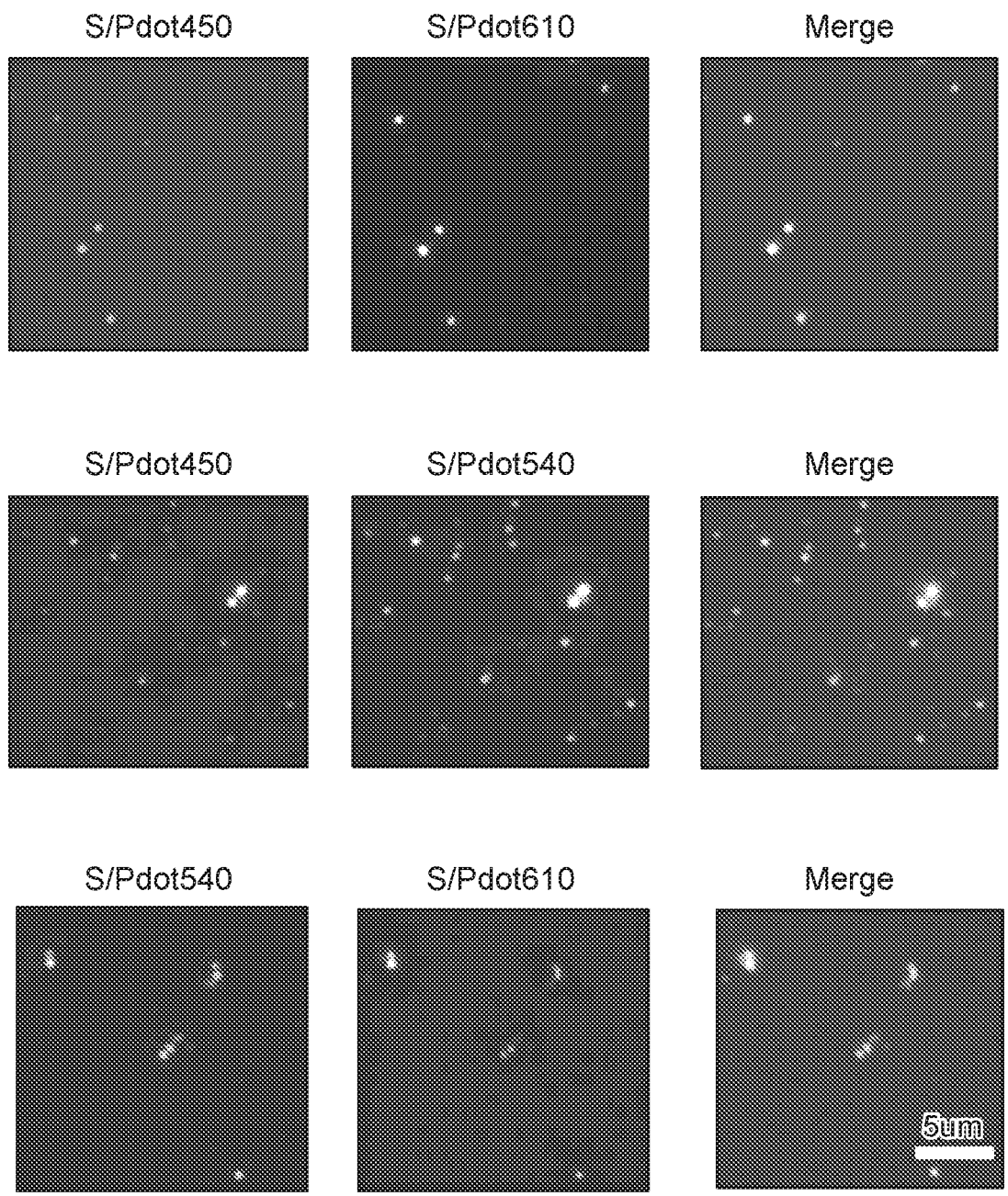
FIG. 14 shows pair-wise inter-probe hybridization of Pdot-DNA probes.

As an additional illustration of the flexibility provided by inter-probe hybridization for multiplexed digital PCR, we also performed experiments using multiple pairwise inter-probe hybridization of Pdot-DNA. All experimental conditions were the same as previously described, but here rather than causing inter-probe hybridization of three different color Pdot-DNA probes using a single DNA sequence (FIG. 13), we designed each pair of Pdot-DNA probe requiring a unique nucleic acid sequence to crosslink. This experiment shows each pairwise combination of Pdot-DNA probes became crosslinked only in the presence of the target nucleic acid sequence (specifically: Pdot450 and Pdot610 probes were cross-linked by 5'-ACA TGT ATT ACA CACA TGT ATT ACA C-3'; Pdot450 and Pdot540 probes were cross-linked by 5'-ACA TGT ATT ACA CTA CTA ACC GGT TTC G-3'; Pdot540 and Pdot610 probes were cross-linked by DNA 5'-TA CTA ACC GGT TTC G ACA TGT ATT ACAC-3'), which were generated as a result of amplification of the presence of the analyte nucleic acid molecules. These images (FIG. 14) show the co-localization in each color channel and the merged image. In separate control experiments, similar to FIG. 13 Control, the pairwise Pdot-DNA probes did not co-localize in the absence of the target nucleic acid sequence.

Example 17

Method for Varying Temperature of SD Chip for Spatial Meltcurve Analysis

This Example provides exemplary methods for controlling the temperature of the SD chip for spatial meltcurve analysis.

Figure 15A:
FIG. 15A shows fluorescent signal from a PCR amplified device at a temperature of approximately 39° C.
Figure 15B:
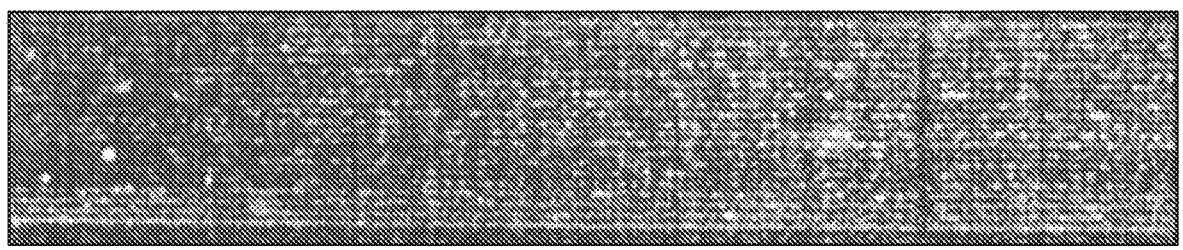
FIG. 15B shows fluorescent signal from a PCR amplified device at a temperature of approximately 55° C.
Figure 15C:
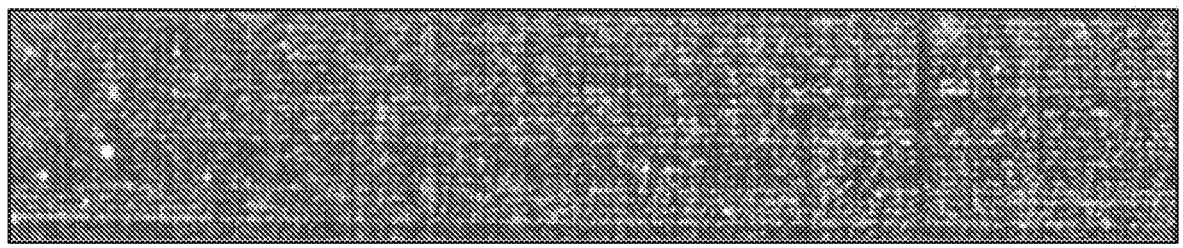
FIG. 15C shows fluorescent signal from a PCR amplified device at a temperature of approximately 72° C.
Figure 15D:
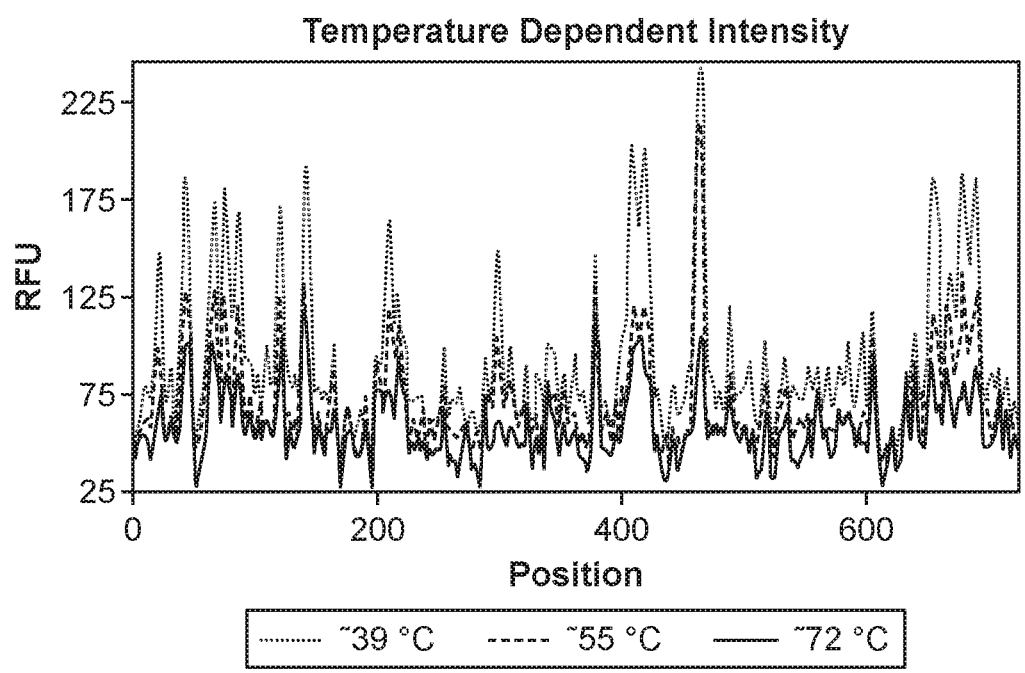
FIG. 15D shows a quantification of data obtained during spatial meltcurve experiments.

An SD chip device was digitized with a sample containing PCR reagents, Evagreen fluorophore, sequence specific primers, and a target template at a concentration where some of the wells would contain target template molecules and some would not. The SD device was amplified for 40 cycles between 95° C. and 58° C., after which the SD chip was placed on a heating element and temperature was adjusted to several different points. The device surface temperature was measured with a thermal IR sensor, then imaged using LED flood illumination at 470 nm and detected by a camera equipped with a 525/25 nm bandpass emission filter. Images were taken at IR temperature readings of about 39° C., 55° C., and 72° C. (FIG. 15). Processed images were further analyzed using a linescan to detect the signal changes as a function of temperature (FIG. 15D).

Figure 16A:
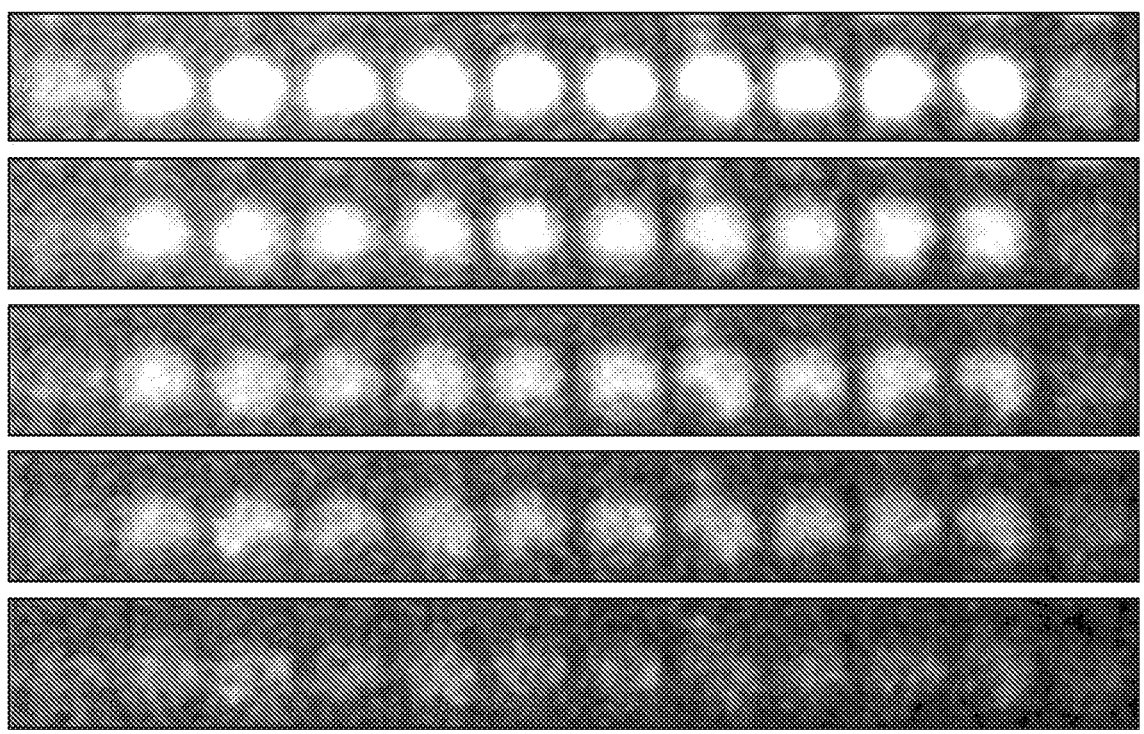
FIG. 16A shows fluorescent signal from a section of a PCR amplified device at (going from top to bottom), approximately 23° C., 39° C., 50° C., 59° C. and 73° C., respectively.
Figure 16B:
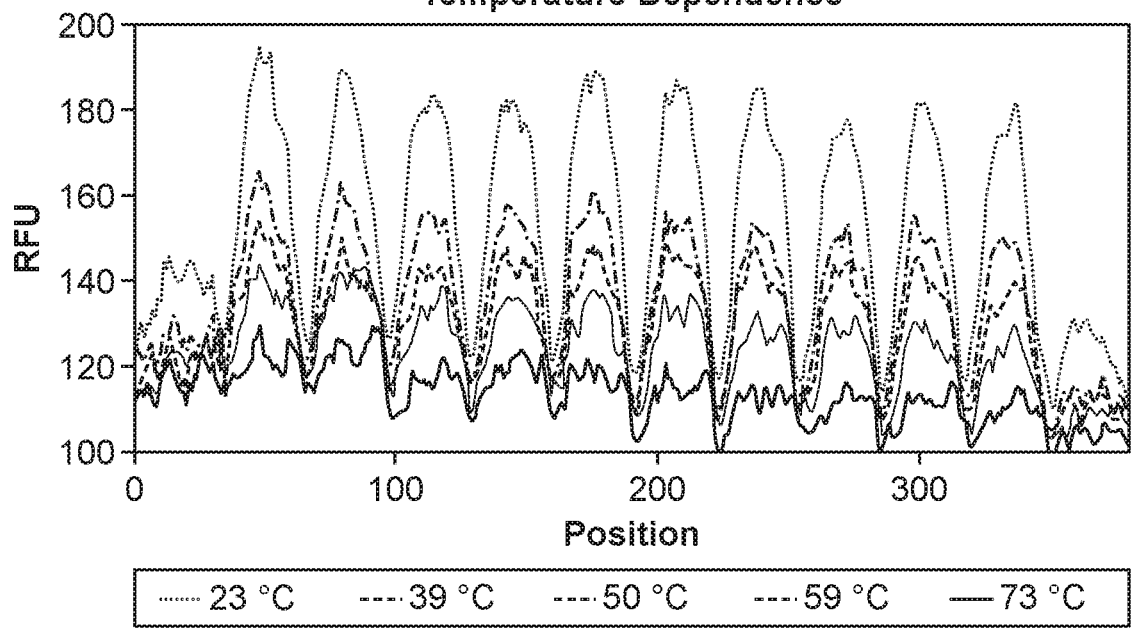
FIG. 16B shows an overlay of line scans of temperature profile images from FIG. 16A.

As a further example, FIG. 16A shows temperature profiles of the SD chip after digital PCR amplification from 23° C. (top), to 39° C. (second from top), 50° C. (middle), 52° C. (second from bottom), and 73° C. (bottom). The images were analyzed using line scans to quantify the signal changes as a function of temperature (FIG. 16B).

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of performing a digital assay, the method comprising:
providing a plurality of compartmentalized volumes, wherein:
each compartmentalized volume in the plurality of compartmentalized volumes comprises a probe, wherein each probe comprises an encoded particle comprising a plurality of distinct chromophores; and a plurality of binding nucleic acid molecules configured to bind to a target molecule or to a molecule that is correlated with the presence of the target molecule, and a plurality of quenchers, wherein each quencher of the plurality of quenchers is coupled to a quencher nucleic acid molecule configured to hybridize with the target molecule, an amplification product, or the binding nucleic acid molecule, wherein each quencher of the plurality of quenchers is configured to quench fluorescence from a chromophore of the plurality of distinct chromophores, and wherein the encoded particle has at least one dimension that is greater than 3 nm; and
at least some of the compartmentalized volumes in the plurality of compartmentalized volumes comprise the target molecule;
amplifying the target molecule; and
detecting an optically detectable code emitted by an encoded particle in the compartmentalized volume, wherein the detection of the optically detectable code indicates that the target molecule is present in the compartmentalized volume.

2. A method of performing a digital assay, the method comprising:
providing a plurality of compartmentalized volumes, wherein:
each compartmentalized volume in the plurality of compartmentalized volumes comprises a probe, wherein each probe comprises an encoded particle comprising a plurality of distinct chromophores; and a plurality of binding nucleic acid molecules configured to bind to a target molecule or to a molecule that is correlated with the presence of the target molecule, and a plurality of quenchers, wherein each quencher of the plurality of quenchers is coupled to a quencher nucleic acid molecule configured to hybridize with the target molecule, an amplification product, or the binding nucleic acid molecule, wherein each quencher of the plurality of quenchers is configured to quench fluorescence from a chromophore of the plurality of distinct chromophores, and wherein the encoded particle has at least one dimension that is greater than 3 nm; and
at least some of the compartmentalized volumes in the plurality of compartmentalized volumes comprise the target molecule;
amplifying a molecule that is correlated with the presence of the target molecule; and
detecting an optically detectable code emitted by an encoded particle in the compartmentalized volume, wherein the detection of the optically detectable code indicates that the target molecule is present in the compartmentalized volume.

3. The method of claim 2, wherein the optically detectable code comprises at least one of: (i) an emission peak wavelength; (ii) an emission peak intensity at a given wavelength; (iii) an emission peak spectral intensity; (iv) an emission lifetime; and (v) an absorbance peak wavelength.

4. The method of claim 2, wherein the compartmentalized volumes comprise at least one encoded particle that comprises an optically detectable code distinct from at least one other encoded particle present in the plurality of compartmentalized volumes.

5. The method of claim 2, wherein:
the plurality of compartmentalized volumes comprises a plurality of probes;
each compartmentalized volume of the plurality of compartmentalized volumes comprises at least one probe of the plurality of probes;
a first distinct probe of the plurality of probes comprises a binding nucleic acid molecule that is distinct from a binding nucleic acid molecule of a second distinct probe of the plurality of probes; and
the first distinct probe of the plurality of probes comprises an encoded particle capable of emitting an optically detectable code that is distinct from an optically detectable code of the second distinct probe of the plurality of probes.

6. The method of claim 5, wherein the optically detectable code of each distinct probe comprises a unique set of: an emission peak spectral intensity, emission peak wavelength, absorption peak wavelength, excitation peak wavelength, emission lifetime, or a combination thereof.

7. The method of claim 2, wherein the quencher reduces the intensity of the optically detectable code in the absence of the target molecule or prior to amplification of the target molecule.

8. The method of claim 2, further comprising increasing the distance between the encoded particle and the quencher during or after the amplifying.

9. The method of claim 2, wherein the amplifying comprises or is accompanied by cleaving the binding nucleic acid molecule of the probe.

10. The method of claim 2, wherein the amplifying comprises producing a plurality of copies of the molecule that is correlated with the presence of the target molecule.

11. The method of claim 2, wherein each compartmentalized volume in the plurality of compartmentalized volumes comprises a plurality of probes, wherein at least one probe comprises:
   a nucleic acid molecule configured to bind to the same distinct target molecule or to the molecule that is correlated with the presence of the same distinct target molecule as at least one other probe in the compartmentalized volume; and
   an encoded particle capable of emitting the same optically detectable code as the at least one other probe in the compartmentalized volume.

12. The method of claim 2, wherein each compartmentalized volume in the plurality of compartmentalized volumes comprises a plurality of probes, wherein each probe comprises:
   a binding nucleic acid molecule configured to bind to a different distinct target molecule or to the molecule that is correlated with the presence of a different distinct target molecule from at least one other probe in the compartmentalized volume; and
   an encoded particle capable of emitting an optically detectable code different from the at least one other probe in the compartmentalized volume.

13. The method of claim 2, wherein:
   each compartmentalized volume of the plurality of compartmentalized volumes comprises a circularized nucleic acid comprising a region capable of binding to the target molecule or to the molecule that is correlated with the presence of the target molecule; and
   the quencher is capable of hybridizing with an amplified product of the circularized nucleic acid.

14. A method of performing a digital melt-curve assay, the method comprising:
   providing a plurality of compartmentalized volumes distributed into a plurality of containers, wherein each compartmentalized volume in the plurality of compartmentalized volumes comprises:
   a probe comprising an encoded particle comprising:
      a plurality of distinct chromophores; and
      a plurality of binding nucleic acid molecules configured to bind to a target molecule or to a molecule that is correlated with the presence of the target molecule, and
   a plurality of quenchers, wherein each quencher of the plurality of quenchers is coupled to a quencher nucleic acid molecule configured to hybridize with the target molecule, an amplification product, or the binding nucleic acid molecule, wherein each quencher of the plurality of quenchers is configured to quench fluorescence from a chromophore of the plurality of distinct chromophores;
   wherein at least some of the compartmentalized volumes in the plurality of the compartmentalized volumes comprise a target molecule;
   applying a thermal energy gradient to the plurality of compartmentalized volumes to yield a plurality of assay temperatures varying over an area; and
   determining the melting temperature of the target molecule or of a molecule that is correlated with the presence of the target molecule by performing the digital melt-curve assay of the target molecule or of the molecule that is correlated with the presence of the target molecule in the presence of a temperature gradient.

15. A method of performing a digital melt-curve assay, the method comprising:
   providing a plurality of compartmentalized volumes, wherein:
   each compartmentalized volume in the plurality of compartmentalized volumes comprises:
   a probe comprising an encoded particle comprising:
      a plurality of distinct chromophores; and
      a plurality of binding nucleic acid molecules configured to bind to a target molecule or to a molecule that is correlated with the presence of the target molecule, and
      a plurality of quenchers, wherein each quencher of the plurality of quenchers is coupled to a quencher nucleic acid molecule configured to hybridize with the target molecule, an amplification product, or the binding nucleic acid molecule, wherein each quencher of the plurality of quenchers is configured to quench fluorescence from a chromophore of the plurality of distinct chromophores; and
   at least some of the compartmentalized volumes in the plurality of the compartmentalized volumes comprise the target molecule;
   amplifying the target molecule to produce an amplified molecule;
   applying a thermal energy gradient to the plurality of compartmentalized volumes to yield a plurality of assay temperatures varying over an area, such that when the assay temperature in each compartmentalized volume is:
   below a target molecule or amplified molecule melting temperature, at least 50% of the target molecule or of the amplified molecule is hybridized; and
   above the target molecule or amplified molecule melting temperature, less than 50% of the target molecule or of the amplified molecule is hybridized;
   detecting an optically detectable signal produced by a chromophore of the plurality of distinct chromophores associated with the hybridized target molecule or the amplified molecule, wherein the optically detectable signal is detected when the chromophore is associated with the hybridized target molecule or the amplified molecule; and
   determining the melting temperature for the target molecule or amplified molecule based on the presence or absence or magnitude of the optically detectable signal at each of the assay temperatures of the plurality of assay temperatures.

* * * * *